US012281336B2

(12) United States Patent
Nabel et al.

(10) Patent No.: US 12,281,336 B2
(45) Date of Patent: Apr. 22, 2025

(54) CHIKUNGUNYA VIRUS (CHIKV) VIRUS-LIKE PARTICLES (VLPS) COMPRISING THE C, E1, AND E2 STRUCTURAL PROTEINS

(71) Applicant: The United States of America, as represented by the Secretary, Department of Health and Human Services, Bethesda, MD (US)

(72) Inventors: Gary J. Nabel, Chestnut Hill, MA (US); Wataru Akahata, Kensington, MD (US); Srinivas Rao, Columbia, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/675,059

(22) Filed: May 27, 2024

(65) Prior Publication Data
US 2024/0307520 A1    Sep. 19, 2024

Related U.S. Application Data

(62) Division of application No. 17/850,706, filed on Jun. 27, 2022, now Pat. No. 11,992,523, which is a division of application No. 16/520,113, filed on Jul. 23, 2019, now Pat. No. 11,369,674, which is a division of application No. 15/145,483, filed on May 3, 2016, now Pat. No. 10,369,208, which is a division of application No. 13/131,287, filed as application No. PCT/US2009/006294 on Nov. 24, 2009, now Pat. No. 9,353,353.

(60) Provisional application No. 61/201,118, filed on Dec. 5, 2008, provisional application No. 61/118,206, filed on Nov. 26, 2008.

(51) Int. Cl.
| C12N 7/00 | (2006.01) |
| A61K 39/12 | (2006.01) |
| C12N 7/04 | (2006.01) |
| A61K 39/00 | (2006.01) |

(52) U.S. Cl.
CPC ............... *C12N 7/00* (2013.01); *A61K 39/12* (2013.01); *C12N 7/045* (2013.01); *A61K 2039/5258* (2013.01); *A61K 2039/55566* (2013.01); *C12N 2740/16043* (2013.01); *C12N 2770/36123* (2013.01); *C12N 2770/36134* (2013.01); *Y02A 50/30* (2018.01)

(58) Field of Classification Search
CPC ............ C12N 7/00; C12N 2770/36123; A61K 2039/5258
See application file for complete search history.

(56) References Cited

U.S. PATENT DOCUMENTS

| 7,947,822 B2 | 5/2011 | Nabel et al. |
| 9,353,353 B2 | 5/2016 | Nabel et al. |
| 10,369,208 B2 | 8/2019 | Nabel et al. |
| 2006/0216702 A1 | 9/2006 | Compans et al. |

FOREIGN PATENT DOCUMENTS

| EP | 1736538 | 12/2006 | |
| WO | WO 2008/026225 | 3/2008 | |
| WO | WO 2008/030220 | 3/2008 | |
| WO | WO-2008030220 A2 * | 3/2008 | ............. A61K 39/00 |

OTHER PUBLICATIONS

Akahata et al., "A VLP vaccine for epidemic Chikungunya virus protects nonhuman primates infection," *Nature Medicine* 16: 334-339, 2010.
Akahata et al. "A Specific Domain of the Chikungunya Virus E2 Protein Regulates Particle Formation in Human Cells: Implications for Alphavirus Vaccine Design," *Journal of Virology 86.16*: 8879-8883, Aug. 2012.
Chang et al., "Safety and Tolerability of Chikungunya Virus-Like Particle Vaccine in Healthy Adults: A Phase 1 Dose-Escalation Trial," *Lancet 384*: 2046-2052, Dec. 2014.
Gould et al., "Understanding the alphaviruses: Recent research on important emerging pathogens and progress towards their control," *Antivir Res. 87*: 111-124, 2010.
Huang et al. "Generation of Synthetic Severe Acute Respiratory Syndrome Coronavirus Pseudoparticles: Implications for Assembly and Vaccine Production," *Journal of Virology 78.22*: 12557-12565, Nov. 2004.
Intention to Grant for European Patent Application No. 098294 77 .0, dated Jan. 23, 2019, 5 pages.
International Search Report for International Patent Application No. PCT/US09/06294, dated Oct. 19, 2010.
Kim, Medical Molecular Virology, pp. 89-91, Science press, published on Feb. 2001 (evidence 1 cited in Official Action of related Chinese Patent Application No. 200980155476.X, dated Sep. 28, 2014, English translation of text from p. 90), 1 page.
Muthumani et al., "Immunogenicity of novel consensus-based DNA vaccines against Chikungunya virus," *Vaccine 26*: 5128-5134, Apr. 2008.
Notice of Allowance for U.S. Appl. No. 15/145,483, dated Mar. 19, 2018, 12 pages.
Notice of Reexamination with English Translation for China Patent Application No. 200980155476.X, dated Aug. 4, 2016, 15 pages.
Official Action for Australian Patent Application No. 2009320287, dated Dec. 11, 2014, 3 pages.

(Continued)

*Primary Examiner* — Jeffrey S Parkin
(74) *Attorney, Agent, or Firm* — Klarquist Sparkman, LLP

(57) ABSTRACT

The invention features compositions and methods for the prevention or treatment of one or more strains of Chikungunya virus, as well as other alphavirus-mediated diseases.

5 Claims, 118 Drawing Sheets
Specification includes a Sequence Listing.

(56) References Cited

OTHER PUBLICATIONS

Official Action (with English translation) for Chinese Patent Application No. 200980155476.X, dated May 14, 201, 20 pages.
Official Action (with English translation) for Chinese Patent Application No. 200980155476.X, dated Sep. 28, 2014, 20 pages.
Official Action for European Patent Application No. 09829477.0, mailed Jun. 4, 2012, 6 pages.
Official Action for European Patent Application No. 09829477.0, dated Mar. 9, 2015, 4 pages.
Official Action for European Patent Application No. 09829477.0, dated Jul. 22, 2016, 5 pages.
Official Action for European Patent Application No. 09829477.0, dated Sep. 28, 2017, 5 pages.
Official Action for Malaysia Patent Application No. PI2011002376, mailed May 15, 2015, 2 pages.
Official Action for Malaysia Patent Application No. PI 2011002376, mailed Mar. 31, 2016, 2 pages.
Official Action for Philippines Patent Application No. 1-2011-501012, mailed Jul. 25, 2014, 2 pages.
Official Action for Philippines Patent Application No. 1-2011-501012, mailed Oct. 10, 2014, 2 pages.
Official Action for Philippines Patent Application No. 1-2011-501012, mailed Jan. 22, 2015, 2 pages.
Official Action for Philippines Patent Application No. 1/2011/501012, mailed Apr. 14, 2015, 2 pages.
Official Action with English Translation for Vietnam Patent Application No. 1-2011-01662, dated Jun. 29, 2015, 2 pages.
Official Action (Restriction Requirement) for U.S. Appl. No. 13/131,287, mailed Jun. 4, 2013, 7 pages.
Official Action for U.S. Appl. No. 131,287, mailed Nov. 4, 2013.
Official Action for U.S. Appl. No. 13/131,287, mailed May 8, 2014, 6 pages.
Official Action for U.S. Appl. No. 13/131,287, mailed May 7, 2015, 13 pages.
Official Action for U.S. Appl. No. 13/131,287, mailed Nov. 6, 2015, 12 pages.
Official Action (Restriction Requirement) for U.S. Appl. No. 15/145,483, dated Sep. 25, 2017, 7 pages,.
Official Action for U.S. Appl. No. 15/145,483, dated Apr. 24, 2018, 13 pages.
Official Action for U.S. Appl. No. 15/145,483, dated Nov. 19, 2018, 10 pages.
Official Action for European Patent Application No. 09829477.0, date Aug. 6, 2018, 3 pages.
Pulmanausahakul et al., "Chikungunya in Southeast Asia: understanding the emergence and finding solutions," *International J. Infect. Dis.* 15: e671-e676, 2011.
Suhrbier et al., "Arthritogenic aphaviruses—an overview," *Nature* 8: 420-429, Jul. 2012.
Tan, Therapeutic Immunology, Science press, pp. 459-461, Mar. 2007 (evidence 3 cited in Official Action of Chinese Patent Application No. 200980155476.X dated Sep. 28, 2014, English translation of lines 4-5 and 18-22 of p. 460), 1 page.
Thiboutot et al., "Chikungunya: A potentially emerging epidemic?" *PLoS Neglected Tropical Diseases 4.4*: e623, Apr. 2010 (8 pages).
Wang et al., "Chimeric alphavirus vaccine candidates for chikungunya," *Vaccine* 26: 5030-5039, Aug. 2008.
Wang et al., "Chimeric sindbis/eastern equine encephalitis vaccine candidates are highly attenuated and immunogenic in mice," *Vaccine* 25: 7573-7581, Aug. 15, 2007.
Weaver et al., "Chikungunya virus and prospects for a vaccine," *Expert Rev Vaccines 11.9*: 1087-1101, 2012.
Weider, Science press, published on Jun. 2008, p. 234 (evidence 2 cited in Official Action of Chinese Patent Application No. 200980155476.X Sep. 28, 2014, English translation of text from p. 234), 1 page.

\* cited by examiner

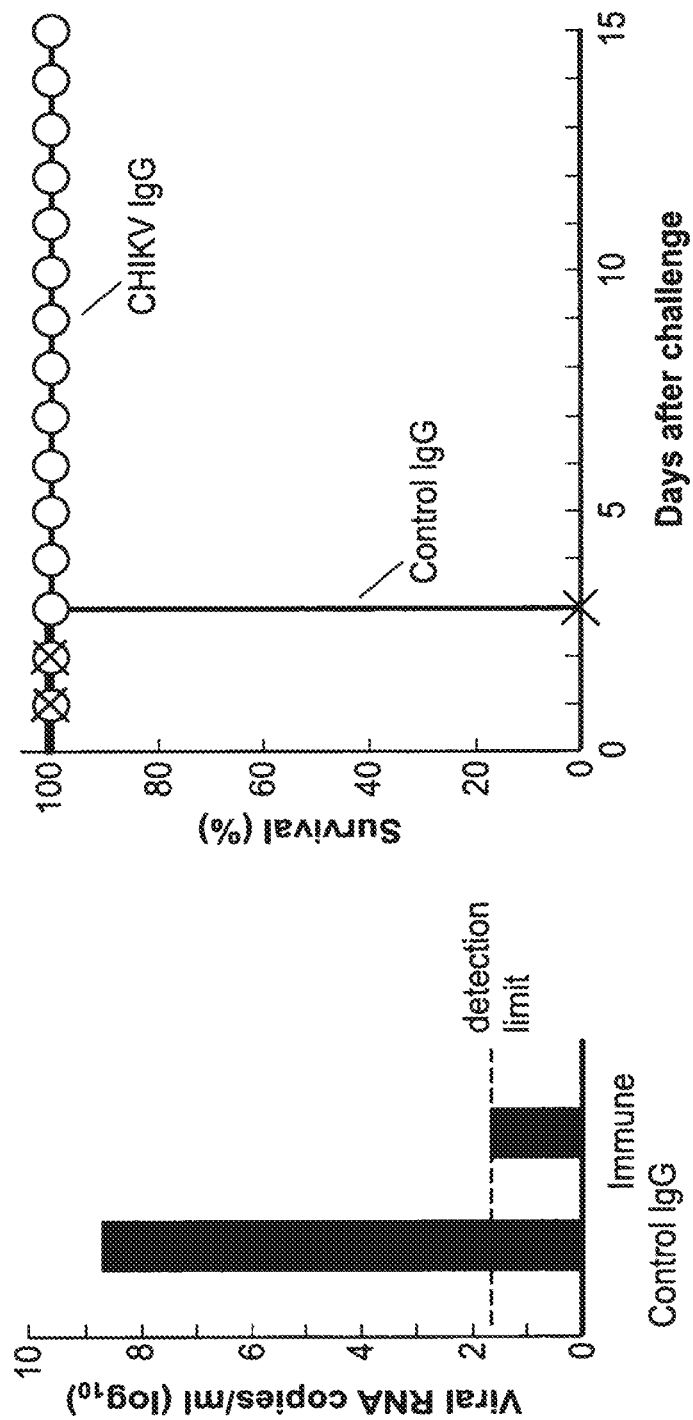

FIG. 7A

SEQ ID NO: 1
Insert C-E3-E2-6K-E1 (strain 37997)

atggagttcatccgacgcaaattctataacagaagtaccaacaagaagccctacaattcaagtaattagacctaga
ccacgtccacagaggcaggctggggcaactgcgccagctgatctccgcagtcaacaaattgaccatgcgcggtacctcaacagaagcctc
gcagaaatcggaaaaaacaagaggctgggcaggcgcgcgcaaaagccgcaaagaagcgcgaaaagaagcaaccaccacaa
aagaagccggctcaaaagaagaagaagaagaaccaggccgtaggggagagaatgtcatgaagagaaattgaaaattgatgcatcttcgaagtcaagcat
gaaggcaaagtgatgggctacgcgtcatgccgtggtgggataaagtaatgaaaacagcacatgtgaaggaactatcgacaatgccgatctg
gctaaactggcctttaagcgtgctcgtcaaatacgatcttgaatgttgcacagataccgtgcacatgaagtctcgaagttaccacga
gaaaccgaggggtactataactgcgacgagcagtcgtcagtattcaggaggccggttcactatccgacggagcaggtcaggccggg
agacagcggcagaccgatcttcgacaacaaatgacgggtgtgtggccatcgtcctaggagggagcggaagagtggaggccctgcgccctcccggtcttgtgctgttg
gcaaaacactacattcccgtctcagccgcgttgcacacccgtgctgactgcttctctcccacagacgcagtagtgccatgctgaggacaa
cgtgatgaccactacattaccagccgatactaccagtctcattgtcggagaagggcattcgtgccacagcctatcgcattggagcgatcagaaat
gaagcaacggacgctgaaaatcagtctctttgcagatcgcagcgagccgattgttgcttgaaggactcagcacgacaacccgcgacacggggacac
ttattctgccgatgccgaaagaggagagacgctgacagtggagttccactctgacaccacacatggaaagatcagcagcagatcagcagaatcagccacagtacttgcagcacgagctgcagatgcagcacc
atcatgaaccactgtgagagagatagaggtgcatatgcaagtgaacgcacgtgcggtggcaactgcaaacgacagtctggcaacgtgaagatca
cagttaatgcagacgcggtggtacaagttggtcactaatcacaagaattgcaatacaacaagaattgattgacaacgaatctccctttagtccgcaacgtgaactgaactattacgggaaccgta
aattgatcagtgcatgctgcagtcactaatcacaagaaacgtgacttgcagagtgccaaaagcaagaaacctacagtaacttacggaaaaaacc
aagtccatgcgtcactcgtatctgaccatccgacactctgtcttaccgtgagagctgctcactgggaagtgacatgggacaggaaccaaatacacgaggagtgggtgacac
acaagaagaggttaccttgaccgtcctactgaggtctgaggtcatgggcgaacaacaacatacaagaaccattacagactactagcacagagcacatacgatgct
acgaacctgctgctcatgcgtcacccacacagcagtgggataatcttgtactaattatgagctagcgtagtcagtcattgtgtcgtggcctgt
cgtgccttctgcgatggtgggcacagcagtgtgtgtcgcgcgcgcaaggcgcggagaatggtgctgcgcacggcattacccatatgaattaccacaggccac
tgttccctccctgctcagctgctgctgctgatgtgtcgtcagaacgaacgaccaaggcgggaccaccaagctgcggcatatctatgaagctgtgccgcatatctatgaaagcagcag

FIG. 7A (continued)

ccctgttctggttgcaggctcttatccgctggccgcctgatcgtcctgtcgtcaactctgtctgaaactcttgccatgtgtctgtgaagccctggcttttt
agccgtaatgagctgacatcggtgcccacactgtgagcgctgttgagatgagctggagagctgcttcacctcgtgaaccaacactgtcactgactacatcacgtgcg
tcaacagaccggttacagccgggtcatgtgttggagatgagctggagagctgcttcacctcgtgaaccaacactgtcactgactacatcacgtgcg
agtacaaactgtcatccctccccgtactgtgaagtgctgtgtacagcagaggcgtgcaaggagcaagagctacagacacagagtctgacagctgcaaggt
cttactgagtctaccattgtgggccaggccctactgctttgcgacgcgcgaaaatacgcaattgagcgaggcacatgtagagaaatctg
aatcttgcaaacagagtttgcatcggcctacagagccatcgcggaagctcgtcgtcctttaccaaggaaacaacatt
accgtagctgcctacgctaacggtgaccatgccgtcacagtgtcgtcaagttgtgtggccaatgctctccgctggacaccttg
acaacaaaatcgtggtgtacaaaggcgacgtctacaacatgaccgacgtctacaacatgaccggtctacaacaagaccagcagcagctacatgtaccatactctca
agtcgtaccaccggaaagtaaagactgctcaagtattgctgaaggaacgactgctcaacatgtccatcgacatctacataccgactttggcgtcgcactactctca
ggcaccactctggcttcaagtagttgcgtgtgggaacatcgacatctacataccgactttggcgcgtcgcactactctctggccttactatggttgtcatgcacctctgaacg
gtaagagctgtaaattgcgctgtgtgggaacctgcagctcacctgcgacttgggcgctcgcgcatcatcaaatacacagctagcaagaaggtaaagtc
gacatgtcatgcgaagtaccagctgcccgccgatgcgctagaagccgacgtagaagcgagcgagcgcaattatcttcaacgc
ctgcaaggcggatgttcgctcgtaactgcgcagcgccactgccgcatcgcgccagtgcatgtgttgggtgcaagattcttgggtgcaagaattacggggaggagtaggattaatt
gttgctgttgctgcttaatttaattgttgtgctatgcgtgtcgtttagcaggcactaa

FIG. 7B

SEQ ID NO: 2
CMV/R 37997 C-E3-E2-6K-E1 tcgcgcgtttcggtgatgacggtgaaaacctctgacacatgcagctcccggagacggtcacagcttgtctgtaagcggatgccgggagcaga
caagcccgtcagggcgcgtcagtggcgggtgtggctaactatggcgcattacatgtgcggtgtgaaataccgcacagatgcgtaaggagaaaataccgcatcaggcgccattcgccattcagg
tatgcggtgtgaaataccgcacagatgcgtaaggagaaaataccgcatcaggcgccattcgccattcaggctgcgcaactgttgggaagggcgatcggtgcgggcctcttcgctattacgcc
tacattttatggctcatgtccaacattaccgccatgttgacattattgactagttaatcaatttacggggtcattagttcatagccc
atatatggagttccgcgttacataacttacggtaaatggcccgcctggctgaccgcccaacgacccccgcccattgacgtcaataatgacgtat

FIG. 7B (continued)

```
gttccatagtaacgccaatagggacttccattgacgtcaatgggtggagtatttacgtaactgccactttggcagtacatcaagtgtatcat
atgccaagtacgccccctattgacgtcaatgacgtatggtaaatggcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctcacccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgttttgac
ctccatagaagacaccgggaccgatccagccctccatcgctctcgagcctccatcctcttcacgcgcccgcctacctgaggccgccatccacgc
cggttgagtcgcgttctgccgcctccccgcttctggtgcctcctgaacctgctccgccgtcaggtaagttaaagctcagttcgagaccgggcctt
tgtccggcgtccctggagcctacctagactcagccggtctctccacgctttgctgaccctgcttgctcaactctagttaacgtgaggcagt
gtagtctgagcagtactcgttgctgccggcgccaccagacataatagctgacagactaacagacgttcctttcatggtctttctgcagtc
acctgtcgtgacacgtgtgatcagatatcggaggcgctctagacaagagttcatccgccaaacttctataacagaaggtaccaac
cccgaccctgggcccacgccctacaattcaagtaattagacctaacagaagcctgcagaaatgtggaaaacaaagaagcaaaaggcaactccgcagtgatctc
cgcagtcaacaaattgaccatgcgcggtacctcaacagaagcctcgaaaaatgggaaaaaacaagcggctcaagaagagaaacaggcctaggga
gagaatgtgcatgaaattgaaaattgattgcatcttcgaagtcaagcatgaaagtgatgaagcaaagtgatggctacgcatgcctgtggggggataaag
taatgaaaccagcacatgtgaacactatcgacaatgcctcgatctgctaaactgcctttaagcggtcgtcaaatacgatcttgaatgtgc
acagataccggtcacatgaagtctgatgctcgaagttaccacgagaaaccgagggtcagagggtactataactgcatcacggagcagtgcagt
attcaggaggccggtcactatccgacgggtgcaggcaagcgggtgcagaccgatcttgacaacaaaggacgggtggtg
gccatcgtcgagggcaacgaagtgcccacgaaggtgccccggcctctccgtgctgacgtggaacaagacatcgtcacaaaattacccctg
agggagccgaagagtggagcctgccccggtcttgtgctgttggcaaaactacattccctgctctcagccgccttgcacacctgctg
ctacgaaaggaccgaaaggaacgacagcgagtggaggacaccttgccatgctgaggacaacgtgatgagccgatactaccagcagtactaaaagcatcgctgact
tgctctccccaccgccaaagacgggtcactatgccaagacagcagctatggagacgccatggaggaacgtgataaaaatgaagcgacgacgaacgtgaaatcaggtctctttgcagatc
aagggcattcgtgccacagatgccacagccgattgaccacaatggagacacttaatgtctatagcaacagccacaagaccatatctagctcattgtctgactgcgag
gggataaaagccgaagatgaacagggagcctgccattgagcgtgcatcagaaatgaagcaaacgacggaacgctgaaaatcagtctctttgcagatc
gtaaggactcagcacgtgcacgatcacagccacttattctcgccgatgcccgaaaaggagacacggagagcgtgacagtggatt
tacgacagcagaaagatcagcacagcaccgttccatcatgaaccaccgtgatagtgagaagaggagaggttcactctgacca
caacatgtaagagttaccttgcagcactttgagcagcacgtgcagacgtgcagagaccgctgcagcgacgtacgctgaggagaatagagaggttgcatatgccccagatactcc
```

FIG. 7B (continued)

```
tgaccgcacgctgatgacgctgcagcagtctggcaacgtgaagatcacagttaatgggcagacggtgcgagacgtgcaactgccgtggctca
aacgagggactgacaaccacagacaacagaaagtgatcaataactgcaaaattgatcagtgccatgctgcagtcactaatcacaagaattggcaat
acaactcccttagtccgcgcaacgctgaactcggggaccgtaaagaaagatccacatccattgcaaacgtgactgcaga
gtgccaaaagcaagaaaacctacagtaacttacggaaaaaaaccaagtcaccatgctgctgtatcctgaccatccgacactcttgtcttaccgta
acatgggacaggaaccaaattaccacgagagtgggtgacacacaagaaggaggttaccttgaccgtgcctactgagggtctggagtca
cttgggcaacaacaacataacaagtactggccgcagatgtctacgaacggtactgctcaccacatgagataatctgtactattat
gagctgtaccccactatgactgtagtcattgtcgtgtcggtggcctcgttcgtgcctctgtcgatggtgggcacagcagtgggaatgtgtgtgccgac
gggcgagatgcattaccatatgaattaacacaggagccactgttcccttcctgctcagctgtatgctgtcagaacgaccaaggcgg
cccacatattacgaggctgcggcatatctatgaacgaacagcagccctgttctgttcaggctcttatccgctgcaggcggcctgagctgctcgt
gcaactgtctgaaactcttgccatgtgccatgtgccgtgtaagagccctggctttttagccgtaatgagcatcggtgccacactgtgagcgctacgaacac
gtaacagtgatcccgaacacggtgggagtaccgtataagactcttgtcaacagaccggttacagaccgggattgttggagatggagctaca
atcagtcacctggaaccaacactgtcacttgactacacagtgccagtacaaaatgtcatccccccgtacgtgaagtgctgaagtgctgtggtacag
cagagtgcaaggacaagagcctaccagactacagtgcaaggtctttactggagtctaccattatgtggggcggcgctactgcttttgcga
cgccgaaaatacgcaattgagcgaggcacatgtagagagaaatctgaatcttgcaaaacagagttgcatcggcctacacagagcccaccgca
tcgggctcggcgaagctccgcgtcctttaccaaggaacggacgtagctgcctacgtaacggtgaccatgccgtcacagtaaagga
cgccaagttgtcgtggccaatgtcctccgctggacaattggtgacattcaaagtcgtaacaccggaaagtaaagacgtttatgccaacactcagttggta
ccaccttggccgcaggaagaccaggacacagtgccagaagccagagagctgtaaagcgctgtggggaacataccaattccatcgacat
ctacagaggccagcagcagcacgttcaggcgcgtcctttaccagcatgtccaggagagcttcaagattggctgggaagaacgaggagcatcgct
acagcacacggcacgttcgttcgtggccttactaggtttgccagattgccagcaccctgaccatgtcatgcagaagctgtaaattgcctgtggggaacataccaattccatcgacat
accggatgcgccatcatcaaatacagctagcaagaaagttaaatgccaagagctaccagccgcgttaccattcgagaagccgacgta
gctgcaggaactccgatgccaccccaaagaccacatatcctccaacagccatcaccaagccgccagtttcgctgcaagtgtccacacaagtaca
ctgcggcaggaactccgatgccaccccaaagaccacatatcctccaacagccatcaccaagccgccagtttcgctgcaagtgtccacacaagtaca
gaagtagaggccgatgccagaagatacgtgccttctagttgccagcctcgttgttgttgtgttgcccctccccgtgccttcttgacctgaaggccactccc
gcaatgtcttggtgcagaagatcagatctgctgtgactcaagtcgagatgcattgcatcgtgtcgttagcaggc
actaatgaggatccagatctgctgtgactcaagtcgagatgcattgcatcgtgtcgttagcaggc
actgtccttcctaataaaatgaggaaattgcatcgattgtcgagtaggtcatcattcttgtgtcgagggtgggtgggcaggacagcaaggg
```

FIG. 7B (continued)

ggaggattgggaagacaatagcaggcatgctgggatgcggtggctctatggtaccaggtgctgaagaattgaccggttcctctggg
ccagaagaagcaggcacatccccttctctgtgacaccccgtgtccagcccctgttctgttagttcagccgttcagccactcatagct
caggagggctccgccttcaatccaccgctaaagtactggagcggtctctccctccatgagccatcagccatcaaaactagcctccaag
agtggggaagaattaaagcaagatagcctattaagtgcagaggagagaagaaattccgcttcctccgctcactgactcgctgcgctcggtcgctgggcgagcggt
gaattttaaggccatgattaagcccatcatgcccttaatcttccgcttcctccgctcactgactcgctgcgctcggtcgctgggcgagcggt
atcagctcactcaaaggcggtaatacggttatccacagaatcaggggataacgcaggaaagaacatgagcaaaaggccagcaaaag
gccaggaaccgtaaaaaggccgcgttgctggcgttttccataggctccgcccccctgacgagcatcacaaaaatcgacgctcaagtcagag
gtggcgaaacccgacaggactataaagataccaggcgtttccccctggaagctccctcgtgcgctctcctgttccgaccctgccgctaccgga
tacctgtccgccttttctcccttcgggaagcgtggcgcttttctcatagctcacgctgtaggtatctcagttcggtgtaggtcgttcgctccaagctgggc
tgtgtgcacgaaccccccgttcagcccgaccgctgcgccttatccggtaactatcgtcttgagtccaacccggtaagacacgacttatcgccact
ggcagcagccactggtaacaggattagcagagcgaggtatgtaggcggtgctacagagttcttgaagtggtggcctaactacggctacacta
gaagaacagtatttggtatctgcgctctgctgaagccagttaccttcggaaaaagagttggtagctcttgatccgcaaacaaaccaccgctgg
tagcggtggtttttttgttgcaagcagcagattacgcgcagaaaaaaaggatctcaagaagatcctttgatcttttctacgggtctgacgctcagt
ggaacgaaaactcacgttaaggggggggcgcgcgcgccagcagttttgagctctttttttttaaattaaaaatgaagttttaaatcaat
ctaaagtatatagtagattgtctgacagttaccaatgcttaatcagtgaggcacctatctcagcgatctgtctatttcgttcatccatagttgc
ctgactccccgtcgtgtagataactacgatacgggagggcttaccatctggccccagtgctgcaatgataccgcgagacccacgctcaccggctccaga
tttatcagcaataaaccagccagccggaagggccgagcgcagaagtggtcctgcaactttatccgcctccatccagtctattaattgttgccggg
aagctagagtaagtagttcgccagttaatagtttgcgcaacgttgttgccattgctacaggcatcgtggtgtcacgctcgtcgtttggtatggc
ttcattcagctccggttcccaacgatcaaggcgagttacatgatcccccatgttgtgcaaaaaagcggttagctccttcggtcctccgatcgttgtcag
aagtaagttggccgcagtgttatcactcatggttatggcagcactgcataattctcttactgtcatgccatccgtaagatgcttttctgtgactggtgagt
actcaaccaagtcattctgagaatagtgtatgcggcgaccgagttgctcttgcccggcgtcaatacgggataataccgcgccacatagcagaact
ttaaaagtgctcatcattggaaaacgttcttcggggcgaaaactctcaaggatcttaccgctgttgagatccagttcgatgtaacccactcgtgcacc
caactgatcttcagcatcttttactttcaccagcgtttctgggtgagcaaaaacaggaaggcaaaatgccgcaaaaaagggaataagggcgacacgga
aatgttgaatactcatactcttcctttttcaatattattgaagcatttatcagggttattgtctcatgagcggatacatatttgaatgtatttagaaaaa
taaacaaataggggttccgcgcacatttccccgaaaagtgccacctgacgtctaagaaaccattattatcatgacattaacctataaaaatag
gcgtatcacgaggccctttcgtcttcaagaa

FIG. 7B (continued)

cccatataatcagcatccatgttggaatttaatcgcggcctcgagcaagacgtttcccgttgaatatggctcataacaccccttgtattactgtttat
gtaagcagacagtttattgttcatgatgatatttatcttgtgcaatgtaacatcagagatttgagacacaacgtggctttccccccccccatt
attgaagcatttatcagggttattgtctcatgagcggatacatattgaatgtatttagaaaataaacaaataggggttccgcgcacatttcccccg
aaaagtgccacctgacgtctaagaaaccattattatcatgacattaacctataaaaataggcgtatcacgaggccctttcgtc

FIG. 8B

SEQ ID NO: 3
Insert C-E3-E2-6K-E1 (strain OPY-1)

atggagtcatccaaccaaactttacaataggaggtaccagcctcgaccctgacccgcgcctactatccagtcatcaggcccagac
cgcgcccagaggcaagtgggcaacttgccagtgatctcagcagttaataactgacaatgcgcgcggtaccacaacagaagccac
gcaggaatcgaagaataagaacaacaggcgccacaaaaacaacacaaatcaaaagaagcagccacctaaaaa
gaaccggtcaaaagaaaagaaaaagaaagccggcagagagaggatgcagcagcaaagtaatgaaatcgaaaatgattgtattttcgaagtcaagcacg
aaggtaaggtaacaggttacgcgtgcctgtgtggggacaaagtacacagccgtgcacatgaaaccagtaccccgtgccgacgcttgaagttcaccatg
gccaaactggccttaagcggtcatcatgccggagctacaagtgcagtacagtactcaggagccgttcaccatcctacagtgctgcaaacca
gaaaccgagggtactacaactgccacgagcagtacagtacagtacagtgccgcgttcacatcctacagtgctgcaaacca
ggggacagcgcagaccgatcttcgacaacaaggacgctgtgtgcacagtgaagacgcgttcttaggaggagctaatgaaggagccgtacagccctc
tcggttgtgacctggaataaagacacattgtcactacaccccgaggggccgaagagtgagtcttgccatccagttgtctgttgg
caaacacacgttcccctgctccagcccccctgctcacgcctgctacaagcatccttaacatgttctcccacgaaaacctacgcatgcttgaggacaa
cgtcatgagaccggtactatcagctgctacaccatactactagtcgcgactgtggagaaggagcactcgtccatagtccgtagcactgaacgcatcagaa
ctataaagccacaagaccacatactagtccgacgctgaaaatccagtctccttgcaaatcgaataaagacgactgacagcggatgacacaagctgacaagctgcgtt
atgaagcgacagacggacgctgaaaatccagtctccttgcaaatcgaataaagacgactgacagcggatgacacaagctgcgtt
atatgggacaaccacgccagcagacgcagagagggcgggctatttgtaagaactcactgcacgagcacgctactgattactgacaatgggac
acttcatcctgccgatgtccaaaaggggaaactctgaggcggtgggattcactgacgagcacccctgctacacacacactccactagcagagccacagcagcac
ccgaccctcctgatagctcggagagatagaggtacaagtgcgtgtaaagaagcacacctgatcgcacatcagcacgacgtacgtgcaacgtaaagatc
gccgcaactaccgaggagcacgtgcggtacaagtgcgtgtaaagtgcagtaaaaagtgcagtataactacagaaagtgattaatactgca
acagtcaatgcgcggtcaaacgggacacaaaaatgcggtcaccaatcacaaaaaagtgcagtataactacctgtcccgctaatgctgaacttgggaccgaa
aggttgatcaatgtcatgccgcgttccgcgttcctgctgccaaatgtaacatgcaggtgcagtataactacctgtcccgctaatgctgaacttgggaccgaa
aaggaaaaattcaacatccgttcctgctgccaccaaatgtaacatgcaggtgcaggtgccacgtgcgtaaggaaccaccgtgactgtacggaaaaac
agtcatcatgctactgtctgtcgtgctaaccgtgccgactgccgagttcacgtgcgactgaggctgagagtcacgtaaactatcaagagagtggtgatgc
ataagaaggaagtgcgtgctaaccgtgccgactgccgagttcacgtgcgactgagataattctgtaatattgctaccctactactactgatctactgtattgtcgcagttatct
acaacgtacagccatgcccatgccacccgtgcggactgagataattctgtaatattgctaccctactactactgatctactgtattgtcgcagttatct
ttcatctctcgatgttcgatgtggtatgccagcggggtatgccacggcatcatgtgcacgacgcagatgcatcacaccgtgactgaactgtgcgcagatct

FIG. 8B (continued)

accgtcccttcctgcttagcctaatatgctgcatcagaacagctaaagcggccacataccaagagagctgcgatataccgtgcgatataccgtgtggaacgagcag
caaccttgtttgctacaagccttattccgctgcagcccctgattgttctatgcaactgtcgagactgttaccatgctgtctgtaaacgttggcttt
tttagccgtaatgagccgtcggtgccacactgtgagcgcgtacgaacagtgatccgaacacgtgggagtacctgtattacatcacgtgcg
agtcaatagacctgctacagcccccatgtgattggagatgaactactgtcagtcacttggagccaactatcgcttgattacatcacgtgcg
agtacaaaccgtcatccgtctccgtacgtagcttgctgcggtacagagagtgcaggagacaaaaacctaccgactacagtctaagtc
ttcaccggtctcaccatttatgtggggccggcctactgttctctgcgacgctgaaaacacgcagttgagcgaagcacgtgagaagtcc
gaatcatgcaaaacagaatttgcatcagcatacaggctcatcatacgccatcgcatcagctaagctccggctcctttaccagctaaataacatc
actgtaactgcctatgcaaacggcgaccatgcgtcacagttaaggacgcgtcacataccgccccttggcgcaggaagaccaggacaattggcatatctcag
acaacaaaattgtgtgtacaaagtgactgtctataatacaacactggtactgcagagaccggtctgtgggtacgtacacgtgccatactctcag
agtcgcacaccgagagtaaagacgtctatgctaaatacaaacgccgggggcggtcgctgcagcacacagccggcctccactaggtcgtgcgacgcccctcttaa
gcaccatctggcttaagtattggctaaaagaacgcgggcgtaaaagaacgccgcatccatccatctccagacttgggcgtcgccattattaaaatafgcgtcaaatctcagctgcaagt
gtgcggtgcattcgatgactaacgccgtcactattcgggaaggaagtcgagatagaagttgaaggaattcagctgcaaatctcttctgacggcc
ttagccagcgcctaccgaattccgcgtacaagtctgtttacacaagtacactgtgcagcgatgtcatgggtgcagaagatcacggagagtgtgggactgttg
ccgggcgtcacatacccctcgggcctcaggacacatccgctacggcgatgtcatgggtgcagaagatcacggagagtgtgggactgttg
ttgctgtgccgcactgatctaatcgtatgcgtgtcagcaggcac

FIG. 8C

SEQ ID NO: 4
CMV/R C-E3-E2-6K-E1 strain OPY-1 tcgcgcgtttcgtgatgacggtgaaacctctgacacatgcagctcccggagacggtcacagcttgtctgtaagcggatgccgagcaga
caagcccgtcaggcgcgtcagcggtgttggcggtgcttaactatgccatcagagcagattgtactgagagtgcacca
tatgcggtgtgaaataccgcacagatgcgtaaggagaaaataccgcatcagagattgccattgccatcgttatccatatcataatg
tacatttatattggctcatgtccaacattaccgccatgttgacattgattattgactagttataatgacggtcattagttcatagccc
atatatgagtccgcgttacataactacgtaatgggcctcctgactgccaacgaccccgcccattgacgtcaataatgacgtat FIG. 8C (continued)

```
gttccatagtaacgccaataggacttccattgacgtcaatgggtggtgggagtatttacggtaaactgcccacttggcagtacatcaagtgtatcat
atgccaagtacgccccctattgacgtcaatgacggtaaatggcccgcctggcattatgcccagtacatgaccttatgggactttcctacttggcag
tacatctacgtattagtcatcgctattaccatggtgatgcggttttggcagtacatcaatgggcgtggatagcggtttgactcacggggatttccaag
tctcacccccattgacgtcaatgggagtttgttttggcaccaaaatcaacgggactttccaaaatgtcgtaacaactccgccccattgacgcaaat
gggcggtaggcgtgtacggtgggaggtctatataagcagagctcgtttagtgaaccgtcagatcgcctggagacgccatccacgctgttttgac
ctccatagaagacaccgggaccgatccagcctccgcatcctcatcggtcgctcgactcgctccttcacgcgccgccctacctgaggccgccatccacgc
cggttgagtcgcgttctgccgcctgcttgcccgctccgtgtggtcctcctgaactgcgtccgccgtcctaggtaagtttaaagctcagttcgagaccgggcctt
tgtccggcgtccctggagctactagagactcagcgcggctctccacgcttgctgacctcgctccactctagttaacgttcatggtctttctcagtc
gtagtctgagcagtactcgttgctgccgcgcgccaccagataatagctgacagataacagactgttcctttcacaagactttacaataggaggtaccagcc
accgtctgacacgtgtgatcagatatcgcggcgccaccagcctagaacaggcccctcagaggcccaagctcggaacttgccagtgatctcag
tcgaccctgactccgcgcctactatccaagtcatcagggctaccaacagaagcagcaggaatcggacccacaacagaaagaagaaaaagcaaacagg
cagttaataaactgacaatgcgcggcggtaccacacaacaaatcaaaagaagcagccacctaaaagaaacggctcaaaagaaatgaaaaagaaccgggccgcagaga
ggatgtgcatgaaatcgaaaatgattgtatttcgaagtcaagcacgaaggtaagtaacagttacgcgtgctcgtggtgggggacaaagta
atgaaaccagcacacgtaaagggaccatcgataacgggacctggccaaactggccttaagcggtcatctaagtatgaccttgaatgcgc
gcagatacccgtgcacatgaagtcgacgcttcgaagttcacccaggcgaagttcaccagagagacaaccggagttgcaactgccaccacggagcagtaca
gtactcaggaggcggttcaccatccacctacaggtgctggcaaaccaggagcgcagcgcgccgcgactccgtgcaacaagaggacgcgtggt
ggccatagtcttaggaggagcaacgtaaatgaaggagcccgtacagccgtactgtgccctggcaaaccacgttccccgtccagcccccttgcacgccctgctg
aggggccgaagagtggagtcttgccatccagtatgccctgttggcaaacaacgtcatgagaccggtactgtctgtacaagcatcttaacat
ctacgaaaaggaaccgaggaaaccagcacgcatgctgaaagcaacaaccttaatgtctataaaagccacaagaccatactgagctcactgtccgactgtga
gttcccaccgtgcacgccgcgcacgagcagcaccaaggacaccaattcaatgtctataaagccacaagaccatactgagctcactgtccgactgtga
gaagggcactcgtgcatagtccgtagcactagtcgaacgcgactaagaaatgaaagcagcaagggaccgctgaaatccaggtcttgcaa
atcggaataaagacgatgacacgtgacgttgaccaagtcgttatatgaacacattgtcgaacatgccagcagcagacgcagagaggcgggct
atttgtaagaacatcagcacggtacgcgtattactgaccattactcggaacaatgggacactcatcctcggccgatgccgatgtcaaaagggaaactctgacggggg
attcactgacagtaagaagattagtcactcatgtacgaccccttccaccacgaccctctgtgataggtcgggaaaaaattcattccgaccgc
agcacggtaaagagctaccttgcagcactgtcagcacgtcgcaactaccgccaactaccgagagcaccgagagagagagaggaggaggaggaggaggaggaggaggaggaggaggaggagg
```

FIG. 8C (continued)

cctgatcgcacattaatgtcacaacagtccggcaacgtaaagatcacagtcaatggccagacggtgcggtacaagtgtaattgcggtggctca
aatgaaggactaacaactacagacaaagtgattaataactgcaagttgatcaagtcatgcccggtccaatcacaaaaagtggcagt
ataactccctctggtcccgcgtaatgctgaacttgggaccgaaaagaaaaattcacatccgttccgctggcaaatgtaacatgcagggt
gcctaaagcaaggaaccaccgtacgtgacggaaaaaaccaagtcatcatgctactgatcctgaccaccaccaactctgtcctaccgg
aatatgggagaagaaccaaactatcaagaaagtgggtgatgcataagaaggaagtcgtgctaaccgtgccgactgaaggctcgagtc
acgtgggcaacaacgagcgtgatataagtattggccgcagtccgcagtatcatacgagccgtacagcccatggccaccgcatgagataaattctgtattatt
atgagctgtaccccactatgactgtagtagttgtcagtggccacgttcatactcctgtcgatggtgggatggcagcggggatgtgcatgtgtgc
acgacgcagatgcatcaccgtatgaactgacaccaggagctaccgtcccttctgcttagccattgcatcagaacagctaaagc
ggccacataccaagaggctgcgatataccctgtggaacgagcagcagcaaccttgtttttagccgtaatgagcgtcgtgccacactgtgagcgcgtacgaaca
atgcaactgtctgagactctctgacatgctggtgtaaaacgtggctttttagccttagccgtaatgagcgtcctgtacaagccctattccgctggcagccctgattgtct
cgtaacagtgtcgaacagtgggagtcagagcgtaaagctgttgattacatcacgtgcgagtacaaaaccgtcatcccgtctccgtacgtaagtgcgtacgtgg
gtcagtcactttggagccaacatatcgtcttgattacatcacgtgcgagtacaaaaccgtcatcccgtctccgtacgtaagtgcgtacgtgg
cagagtgcaaggacaaaaaaccttaccagctgactacagctgtaagtcttcaccggcgtctacccattatgtgggcgcctactgcttctgcga
cgctgaaaacacgcagttgagcgaaggaagcacaggtggagaagtccgaatcatgcaaaacagcaaaacgtcatacaagggtcatacccgc
atctgcatcagctaagctccggtccttaccaaggaaaataacatcgtaactgcctatgcaaacgcgaccatgccgtcacagttaaggac
gccaaattcattgtgggccaatgtctcagcctgcaatgtcttcgacaacaaaattggtgtacaaaggtgacgtctataacgtgactaccc
gcccttgccgcaggaagaccaggacaatttggcgatatccaaagtgcacactggcgatatgctatgctaataacaactggtact
cagagaccggctgtggtacgtgggtacagtgcatgccatcaggcaccatctggcttaagtattggcaaaagaacgcgggcgtgctgca
gcacacagcaccattgctgccaatagcaaacaaaccggtaagagcgcgtaagaactgcgctagggaactgcccatccatcgacata
ccggaagcggcttcactagggtcgcgacgcagcagaaaggcaagcaagtgcggtgcattgatgactaacgccgtcactattcggaagctgagatag
gcgtcgccattataaatatgcagccagcagagaaagccaagcaagtgcggtgcattgatgactaacgccgtcactattcggaagctgagatag
aagttgaaggaattctcagctgcaaatctctttctcgacggcgcttagccgcctacccgcgtacaagtctgttctacacaagtacactgtg
cagccgagtgccaccccgaaggaccacatagtcaactaccggctcaactaccaccctcgggtccaggacatctccgctacgcga
tgtcatgggtgcagaagatcacggaggtggtcagccactgcttgccgcactgattcataatcgtggctatgcgtgtcgttcagcaggca
ctaatgaggatccagatctgctgccttctagttgccagcatctgttgtttgccccctcccccgtgccttccttgaccctgaaggtcaggaggca
ctgcctttcctaataaatgaggaaattgctgagtagtgtcattctattctgaagtaggtgcattgtcattctattctgaggggtggggtggggcaggacaggcaaggg FIG. 8C (continued)

gaggattgggaagacaatagcaggcatgctggggatgcggtggggtctatgggtaccaggtgctgaagaattgacccggttcctcggc
cagaaagaaggcaggcacatcccctctctgtgacacaccctggttcttagttccagcccactcatagaccactagcatagctc
aggagggctccgccttcaatcccaccgctaaagtactggagcggtctctcctcatcagcccacaaccaaactagcctccaaga
gtgggaagaaattaaagcaagataggctattaagtgcagaggagagaaaatgctccaacatgtgaggaagtaatgagagaaatcatag
aattttaaggcatgattaaggccatcatggcttcctgccttaatcttccgcttctcgctcactgactcgctgctcggctcgggcgagcggta
tcagctcactcaaaggcggtaatacggttatccaacaatcaggggataacgcaggaaagaacatgtgagcaaaaggccagcaaaaggc
caggaaccgtaaaaaggccgcgttgctggcgtttttccatagggctccgcccccctgacgagcatcacaaaaatcgacgctcaagtcagaggt
ggcgaaacccgacaggactataaagataccaggcgtttccccctggaagctccctcgtgcgctctctgttccgaccctgccgcttaccggata
cctgtccgcctttctccttcgggaagcgtggcgctttctcatagctcacgctgtaggtatctcagttcggtgtaggtcgttcgtccaagctgggctg
tgtgcacgaaccccccgttcagcccgaccgctgcgccttatccggtaactatcgtcttgagtccaacccggtaagacacgacttatcgccactg
gcagcagccactggtaacaggattagcagagcgaggtatgtaggcggtgctacagagttcttgaagtggtggcctaactacggctacactag
aagaacagtatttggtatctgcgctctgctgaagccagttaccttcggaaaaagagttggtagctctgatctctgatcgggtctgacgctcagt
ggaacgaaaactcacgttaagggattttggtcatgagattatcaaaaaggatcttcacctagatccttttaaattaaaatgaagttttaaatcaat
ctaaagtatatatgagtaaacttggtctgacagttaccaatgcttaatcagtgaggcacctatctcagcgatctgtctatttcgttcatccatagttgc
ctgactcgggggggggggggcctgagctgcctgctgagtgtgctgactcatcaccagccccatcatccagccaga
aagtgaggagccacggttgatgagagctttgttaggtggaccagttgcttgccacgaacggtcgttgtcggg
aagatgcgtgatctgatccttcaactcagcaaaagttcgattattcaacaaagccgccgtccgtcaagtcagctctgccagtgttac
aaccaattaaccaattctgattagaagaaaactcatcgagcatcaaaatgaaactgcaatttattcattcatcaggattatcaatacatatttgaaaaa
gccgtttctgtaatgaagagaaaactcaccgaggcagttcctccatagggatgcaagatctgcgaagatcggtctgcgatgcgtcgacgatc
aatacaacttaatttccctcgtcaaaaataaggttatcaagtgagaaatcaccatgagtgacgactgaatccgtgagaatggcaaaag
cttatgcatttctttccagactgttcaacaggccagccattacgctcgtcatcaaatcactcgcatcaaccaccgttattcattgattgcgc
ctgagcgagacgaaatacgcgatcgctgttaaaaggacaattacaaacaggaatcgaatgcaaccggcgcaggaacactgccagcgcat
caacaatattttcacctgaatcaggatatcctaataccgataccgtttccgggatgcagttgagtaacatcattggcaacgctaccttt
acggataaaatgcttgatggtcgggaagaggcataaattccgtcagccagtttagtctgaccatctcatctgtaacatcattggcaacgctacctttt
gccatgtttcagaaacaactggcgcatcggctgagcttccatacaacaatcgatagattgtcacctgattgccacctgatgccgagcccattata FIG. 8C (continued)

cccataaatcagcatccatgttgaattaatcgcggcctcgagcaagacgttcccgttgaatatggctcataacacccttgattactgtttat
gtaagcagacagttttattgtcatgatgatatttatcttgtgcaatgtaacatcagagatttgagacacaacgtggctttcccccccccatt
attgaagcatttatcagggtattgtctcatgagcggatacatattgaatgtattagaaaaataaacaaataggggttccgcgcacatttcccg
aaaagtgccacctgacgtctaagaaaccattattatcatgacattaacctataaaaataggcgtatcacgaggccctttcgtc

FIG. 9B

SEQ ID NO: 3 tcgccgcgttcgctgatgacggtgaaaacctcgacacatgcagctcccggagacggtcacagcttgtctgtaagcgtgatgccggga
gcagacaagcccgtcagggcgtcagccggtcggtcggtgttggccggtgtcggcgtgtcggttggtcgctaactatgccgatcagaacagaattgtactg
agagtgcaccatatgcgtgtgtgaaatacgcacagatgcgtaagagagaaaatacgcatcagattggcattggtattggccattcgttg
tatccatatcataatgtacattattggctcatgtccaacaatatccgccatgttgacattgattattgactagttattaatagtaatcaatta
cggggtcattagtcatagccatataggagttccgcgttacataactacggtaaatggcccgcctggctgaccggcccaacgaccccc
cgcccattgacgtcaataatgacgtatgttcccatagtaacgccaatagggactttccattgacgtcaatgggtggagttacggtaaa
ctgcccacttggcagtacatcaagtgtatcatatgccaagtacgcccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattggcagtacatcaagtgtatcatatgccaagtacgccccctattgacgtcaatgacggtaaatggcccgcctggcattatg
gctcgtttagtgaaccgtcagatcgcctggagacgccatccacgctgttttgacctccatagaagacaccgggaccgatccagcctcc
atcggctcgcatctctcttcacggctcgcatgccgcctcaggtaagttaagctcagtcgagaaccggcctttgtccgggcagtgtgagcagtact
acgttgctgcgcgcgtccgggccgtgccgcagttccgggcgctctaggtaagctcctgctcaacctagtcaacatagtctgctcactggtcttcctttctgcagtcaccgctgtcg
acacgtgatcaatgaattacatacctacgccacccgtgccgtgccgtggccgatggcgtcctcgcccgatggcgtcctcgccccggggtcgc
tccaccaccgtatactatcccacccgccacccgtgccgtgtccaaccctgaccgccaagccgcagcaaatgcaacaacttattgctgcgtcaat
acgctgctaaaggtcagatggcacccgaacatgcaacctgacaacaacgaaggaaacgtcaatcaaacaacaagaggaaacag
acacccccgaagaaaacagaacccggctgaaaacaaagaacaagcagaaaacgcagcaaccagcctaagaaacggaaaacggg
caaggagagaaaggaaaatgcatgatgaagatagagaacacgtgaaagaagtcatagaagagtcatatcgaggtcaagctgaagctcactggtacgctgcct
ggttaggagataaacttgagtgtgcgcaaattccgtccacagaagtcctcgcagttcaccacgaagtgtaagctctggtaagctagctttaagaaatgagc
aagatgaccttgagtgtgcgcaaattccgtccacatgaagtcagtagttcaccacgaagtgtaagctagctttaagaaatgagc
actggccaccaatgtctcagtacaatacctgaacgggaagattaccatcccgacaggtgctggtaagccagctgacactgcagcgcgtaggcct
atctttgacaacaaggtcgctgtagttgccattgtctgtggggtgccatttgtctggggaggacgcgaggtggtctatcggttgtcaccctgg
aacaaagcatgttgactacgcctgccactacgtgccccttgccctgctatgaaaaagcacgagagtggtgtacaactcggtgtacctgagcactga
actttcgatgtgcagccctgatccctgtcgatcatcaagtgtgaccactgactgcacagcggcagcggtcgcgccaatctg
gataacccccggcactacgctcctgctgatccccatcgtgaccagcagcgcgtcgccaatctgagcggcagcgctaacctgagcatctg FIG. 9B (continued)

ctacggaggcttataaactcactaagccgtacatagcctattgctctgactgcgggaacggacagtttgctacagcccgatagctattga
gaagtcaggacgggaggcatccgacggaatgctaaagatacagatctgcaaaatagccctgcaggtgacggagctcatgcgt
ggacgaaaatcagatacatgaaaggccaccgacgtgagtgacacagacagaactcactgaaggtgttcaccaccggagagtgtac
ggtccatggcaccatggccattcatcgtagctacatgcccgaaggtgactcttgacagttgacagtggcgttcgttgacaaacataaggtca
ggcacgcgttgcaggatagcgttgtccccgtattggccagaagagcacttacggctacggcccacatcatggagtagaatt
gccatgcaccacgtacgccatgagaacatcagtgcactaccgaagaaatagaaatgcacgtggcgcatgacgtgccgacaacacctt
tctatccaaagaccggaaataaagttgaagataaacgccaaaagccacgtattcgctacaactgcacgtgtgtcttaaggagaggcggt
gtcacaaagcaagacaaagaatttgacaactgcaggtctcaggcaaagaaagaatcacactgtaccccttccactgagccgataagtggcagttaact
ctccttatgtccctaggcaggtctcaggcaaagaagaatgaatcacactgcagttgcatccgtgccccgacgctaacctacgcacgc
gcggcttttaccgaacacaccatcccggcaaagaatcacactgcagttgcatccgtgccccgacgctaacctacgcacgc
tcggagagaaaccagaaaacaccagaacgtggatatcagaagtgcgaacgtacacactccctgtacctgaggaggtggagtac
acatgggccaatcacgcccctgtgagactgtggcacaacgtgacgactaaggttcagccagatgccgacgaaatctctcat
attactatggattgtaccctgccacgacggttcagttgcagttgcgtggcctagcgtgtgtgatcttgtcctgtgcctgctgcct
gtcgtgtcagcggaggccaagtgcttgaccccgtacgcgttgacgcaggagccgtggtgccgttgacagatcctgtctgcactttgagcttattgtgctcg
cccccagagccaagcgccaacgtttgcgagaacagccgcatatctatggacagagccgccacttgatgctgtctgtagggatgccactgtctgatgcaattcgca
atccccgtagcatgctttatgatagtgacatatttcctgccaacgcgttgctgctgtaggaccgcttcttcttagtgcagtaagcctg
ggaatgggggcgaccaggcgtccatatggaggtagtctccactagcctggaggtgcacaccagcaaaaagcgactttcaatgtaaagtctac
accggctgctgcctgcctaaggtcacctgtgccgcctactgctttgcaattcgaaacactcagctgcagcgaagctatgttgagcggagc
gagtgtgcaaaacacgatcacgcagcggcgtatcgctcataccgcgaattgaagctaaaatcagtgacctacggttccacg
aacgggacggctgagcgcgtttgaccccaaagatcgtcgctcacaagagaccacgcaagagcgaattatcacctaccacgcaagcggt
gtgagcccctttgaccttgcactgcctacaagagagagcacgaaagacgaagctaccgttacaagctgcctctaaacatcgccaacaaccgggt
agatttggggactaacagagcaggtcgcatgaaatgcagacaaggagagtaacgagtgtacgccaatctgcactgaagctgctgcgcccattgccggc
acggttcacggttccatatacccagaacgccagcgccagcgcctcccggtttaagttattggctaaaagaaaaaaggggacgcattgaaccacaagctcctt
cggctgcatcatcgacgtagtcgacgacgacccatgcaccatgcctagacggctaacctgcctagacactcccgacgcggc
tttacacgctagtcgacgacgacccatgcaccatgcctaacctgaagtgcgagttgcgactgcagcactcatccgacttggaggcactt
tgtgtgctggagtacaagacgaacgaaaagtggggacgtgcgccgtccactcagaatccaacacggtcgttatgcaggagagctgt FIG. 9B (continued)

FIG. 9B (continued)

cagccattacgctcgtcatcaaatcactcgtcatcaaccaaaccgttattcattcgttgattgcgcctgagcgagcgagacgaaatacgcgatcg
ctgttaaaaggacaattacaaacaggaatcgaatcgaaccggcgcaggaacactgccagcgcatcaacaatatttcacctgaatcag
gatattcttctaatacctggaatgctgtttcccgsggatcgcagtggtgagtaaccatgcatcatcaggagtacggataaaatgcttgat
ggtcggaagaggcataaattccgtcagcagtttagtctgaccatctcatctgtaacatcattggcaacgctaccttgccatgtttcagaa
acaacctggccatcgggcttcccatacaaatcgatagattgtcgcacctgatggcccgacattatcgcgagcccattataaccatataa
atcagcatccatgttggaatttaatgcgcctcgagcaagacgtttcccgttgaatatggctcataacaccccctgtattactgtttatgta
agcagacagtttattgttcatgatgatatatttttatcttgtcaatgtaacatcagagatttgaagacacaacgtggctttccccccccc
cattattgaagcacattatcaggttattgtcatgagcggatacatattgaatgtatttagaaaaataaacaaataggggttccgcgcaca
tttcccgaaaagtgccacctgacgtctaagaaaccattattatcatgacataaaaataggcgtatcacgaggccctttcgtc FIG. 10B (continued)

SEQ ID NO: 6 tcgcgcgttcgtcgttcgtgatgacgtgaaacctctgacacagcagctcccggagacggtcacagcttgtctgtaagcggatgccgga
gcagacaagcccgtcaggcgtcgtcagcggtgtggcggtgtgcggtgtccggtgtccggtgctgcttaactatgccgcatcagagcagattgtactg
agagtgcaccatatgccggttgaaatatccgcacagatgcgtaaggcgtaaggagaaaatatccgcatcagattggctattggccattgcatacgttg
tatccaatatcataaatgtacattattattggctcatgtccaacattaccgccatgttgacattgattattgactagttattaaatgtaatcaatta
cgggggtcattagttcatatagccataatggagttccgcgttacataactacgtaaatggccgcctgctgaccgcccaacgaccc
cgccattgacgtcaataatgacgtatgttccatagtaacgccataggactttccattgacgtcaatgggtggagtattacgtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acggactttccaaaatgtcgtaacaactccgccccattgacgcaaatgggcggtaggcgtgtacggtgggaggtctatataagcaga
gctcgtttagtgaaccgtcagatcgcctggagacggtgagcgcggcctctgcttgtccgccctggcctggactatagacacctcagcgctctc
atcggctccatctctcctcttcacgcgctcgctcggccgtcgttggtaagctcagtcgagaccgggcctttgtccgcgctcccttggagcct
tgtggtgccctcctgaactcgtcgcctcgcctgtagtaagttaaagctcaactctagttctcaacagagtatagcgcctcgagcagtact
acctagactcagccgcggtctccacggttcctgacctgcttctcaactctagtgaaggtgaggcagtggtgtcgagcagtact
cgttgctgccgcgcgcgaccagacataatgctgacagactaacagactgttctttccatgggtctttctgcaggctcagcgtcgtcg
acacgtgatcagatatcgcggcggggccgccaccatgttccatcaactagctacgactacatgggaagcagtctggtgccgtctg
tggctctcgaaccagatcagccgtgcccgccgcccagctgtcccagcgtgctggacctgcccggagacttgccggccaaggccaagctggatggccaagctgtattgctgcc
ctcggccgaaccagatgagcggctgtccagctgacgttgccagcgtgctggacttgcccggagacttgccaaggctgaccggtgtgacc
tttcagaaaaccaagcagaagaagaactctctcaacggagaaaaacccaaggagccccggcgaagaagcggaaggtaaggatctctgtaaagcgccg
agaaaggagcggccggtgaaaaagccgagccgccagcgagagcggccgcaagagcggaagggtaaggatccgctgaagcaagcggggcgcg
acagacccttcccggtgcacaccgcgaactgcggtgcccatatccgctagtccaagggtcgcctatgccggatgtgctgatgccatggacctcgttaagccagccagcagcagcggggc
acacctcaagcggctcgtgcccatatccgctatgcggttcaagtcgccgaggtcatgccgagggtcaagtggacagtggacagtggatg
aggtaagttcgacaccgaacttgccgtgcaagcagccagaagcggggcgttgacgtccaggagtccgggaggcaatattcaggacatttccgg
tcatcgcgaacagatgagcggctgaacagcgggcatgagagtcgccgaggtcatcgccgaggtcatgagacagtgacagtcgaaagtgtcggtat
aattgtgattcgatgccgaggcagagagagcggcaagaagcggcagccaatcaaccgcaaactccgacaactccagaaagttgtcggtat
cgtcccgaagaggcaccccaacgatgttgcacagtccgggccacaacgtctctcgtgctgctatcgctatgtgctatctctctctccagaagcgtgatctgaaggccagaagatcgctcct
aaggggcgccatcccctggacacgcgcggcaccagccgcggcgcacagctctgctcctgccctcgcctacacctccccaccaatctccaatacttgatt
gtccaaaaccgcctgccaggttgcattacgtgaacaaccgctgaccatgactctgaaagaaggccatatgacgactacactgcgaaaagcccgaa FIG. 10B (continued)

ctactggaccgctcattgcctgctcaccacctgcagttcgccgaaaaagaggggctgtgtctacgtcgccgtgccgttacgaca
cacaaattctgcgcccacgcagtcgcctcccgtataggcgcccgattgtgacggaactgcctgcatctgccgatagc
tatcgacgaggtggttaagtaggtggtagtgaccacgtccttcgcatctggtcggtctcaatcgggagtgaccgctaaagcgggtgc
ggcgggtgaaacctctcgcgatacctggaaggagacggtaaggttacgccgcgacaacacgcggctcgtcgtgtccgccaccactg
caaagtgtgacggctgcggcatcaatgcaccacggtttcgaactgccactactttcgccaactgccagtgggcagagttcacctgtgcggccacactgg
acggtaccccggctgcgcatcaatgcaccacggtttcgaacatcaagtaacggagaagttcacaagagaaacgcagcaagccaccacctg
tccgatctgaccaagaaatgcaccagttctccaccaccgaaagaagttccgctctatctgttgattgttgatgatgtctgccgact
tctgtagagatcagcaccgtggtgacatgcaacgaagacagtgcacagtgaggtgccacccggtaccacagtgaaattcgataag
aggtgcaagaacgtgccaaagagacccgtcacctttcaccagcgactccagagcgttacgtccgaggagccggtcctaacggccgc
cagcatcacccaggcaaggccaacaccatcagtgtgcccagtgaggagccaaagagtgaaagcgaggaattcattcccgt
tcccgccagagactgcgactgcgagtgagaatcgcccccactgccatcgattacctatgaagaaacgatgttctgctgccggac
tgcgaaatacccggctgctaactacacggaaacctgttccatagcaacgccacgctgcactctgtcatctgcaggtaccgcgcc
gcatcccggtcacgcgcccaaggattgaactaatgttggaaaacaacgcaccgctgcactctgtcatctgcaggtacgcatctgg
agacgccgacgcgtgaccctgggaacttctgcgtgcaccatcaagccgagtacgcggtgcgtttgttaggaggtcatgt
gccctgcggggtcgcaatgcagcattgttcgcgtgcactgcagtgcaggcgtgcgtactctctgtctccaacacgttcaacccgaacc
cacaccattgacccgactgactgctgcagcattgtgctgcatacctgggcgtcgcggatcaacctacctgacatcattgcactactgt
ggaccaacagcaaagtggccttcggcgtgcaatgcggcctcggcggtcggcgtctgtggcttgcatgcctcatcgttactatcgcctttagacattgcag
attgtcaattcttttttaggggtaagaggtgtcggtctgctgtgtcatctgcgtatgtacagacgtcaaggcgtacgaacac
accggtggtcccaatgatccagaaccgctgctacgagggggtgataaaccgaatggtgtaccccgaagcttaccatc
gcagtgaacttaccgtcatccaccaactacggcctctgcagaatactggacctgcaggagtccctgctgcgagccccgcccatgtggg
ctgctgaactgcacgtcagtgttcctgcccctcgacctctcacgcgtcacgcgttccactgcggtccaaaacgacgcagtcagcgtgcgatgtg
cacacgaacgtgtaccccttgttgtgggactcagagcgccgcgagcggtcagcgcgttcactgccgttcagcggcgtgtgccgccaccgt
tctgagttctgtctcaggactgtcaggacgttacgtgacgggtccaacatcagcagcgttaccgacctcaagatcgtggctgccaata
gtgaagtggtgacggtccaacgttacgtgacggttcctcggtaccggggtaacatcagcagcgggtaccgacctcaagatcgtggctgccaata
acaactgactactccccgtttgaccgcaaagtagtcgtatcgcgaagagagttctataattaccgacggcctcattacgactgccctgtcg
accaggcacactggaggacattcaaggaccgtaccgtgttcaaccaactatgtcaaaccaatgatcgtacgggacatcgaattgaagtactg
cagcggactaatcgacaccgcgttgaagcttaacgaccctggggcctccatcgattgggttgctgcgttgtgggtggtgcgaatgcctccgaaaccactca
gtcagcaccgcgttgaagctaacaagcgctaaccccgctcggcctgcctgattgggcctccattgggcgtgcgcctcccatgtccatcaaac
attccggacgcgaagttcaccgacctaaagaccgaaacttcggcccctgaaatgcggtcctgacatgcgagtacgsggt FIG. 10B (continued)

FIG. 10B (continued)

atggcaaaagctatgcattcttccagacttgtcaacaggccagccattacgctcgtcatcaaaatcactcgtcatcaacaaaccgtta
ttcatcgtgattgcgcctgagcgagcgatcgagacgatcgcgtaaaaggacaattacaaacaggaatcgaatgcaacgggatcgcgca
ggaacactgccagcgccatcaacaatatttcacctgaatcaggatattcttctaatacctgaatgctgttcccgggatcgcaptgct
gagtaacatgcatcatcaggatcgcggatcttgatgtcggaagaggcataaaattccgtcagccagttagtcgtgaccatctc
atcgtaacaicaatggcaaacgctacctttgccatgtttcagaaacaactctggcgcatcggcttcccatacaatcgtaagatigcca
cctgattgcccgacattatcgcgagcccattatcgcgagccatcatcagcgatcatgtttgaattaatcgccgcctcgagcaagacgtt
cccggtgaatatggctcataacacccctgtattacgtttatgtaagcagacagtttatgttcatgatgatatttatcttgtcaatgta
acatcagaagattgagacacaacgtggctttcccccccccatattgaagcattatcagggttattgtctcatgagcggatacatatt
tgaatgtattgaaaaataacaaatagggttccgcacattccccgaaaagtgccacctgacgtctaagaaccattattatcatg
acattaacctataaatagcgtatcacgaggcccttcgtc

FIG. 11B
SEQ ID NO:7 tcgcgcgttcgtgatgacggtgaaaacctcgacacatgcagctcccggagacggtcacagctgtcgtgaagtggatgccgga
gcagacaagcccgtcaggccgtcagccgtggaaatacccgacacagatgcgtaaggacgtaaagagagggtcgcttaactatgccgcatcagagccagattgtactg
agagtgcaccatagccggtgaaatacccgacacagatgcgtaaggagaaaataccatcagattggctattgccattgcatacgttg
tatccatatcataatgtacattatattggtccatattacggcgcagttgacattgattattattagtaatcaatta
cgggtcattagttcatagcccatataggagttccgccgttacataacttacggtaaatcggccgctgctgaccgcccaaacgaccc
cgccattgacgtcaataatgacgtatgttcccatagtaacgccaatagggactttccattgacgtcaatgggtggagtatttacgtaaa
ctgccactggcagtacatcaagtgtatcatatgccaagtacgccccctattgacgtcaatgacggtaaatggcccgcctggcattatg
cccagtacatgaccttatgggactttcctactggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgtcaatgggagtgtactggtgtaccgcctgcggaagtctatataagcaga
gctcgtttagtgaaccgtcagatcgcctggagacgccatccacgctgttttgacctccatagaagacaccgggaccgatccagcctcc
atcggctcgcatctctccttcacgctcacgctcacgctaccgtcctgagttggctgactctctagtgggtcctgagccagcgtagttgagcagtact
gttggtgcctcctcgaactgcgtccgccgtctaggtagttaaagtcgggtgcctgctccaactctagttaacggtcgaggcagttagtgcagtact
acctagactcagccgccgctctccacgcttgcctgaccctgagcagtaatctgagccatggttaaagtcgagtctgctcaagtcgtcagtcaagtcccat
gttgctgcctcaagctgtcgtccgccaccagacgcttaagcagtccacgcgccgctccaccaccaccgcgccgttgcgaccacgccttgcgaccacgcctcaag
cgttgctgcctcaagctgtcgtccgccaccagacgcttaagcagtccacgcgccgttgcgaccacgccgttgcgaccacgccatccagatactccgtcagccatggcgcct
acacgtgatcaccatgaattacattccaacactcaaacctttacggacgcgttgcgaccacgccgttgcgaccacgccgtacctacgccgtcatgcc
gatgccgtgatcagccggtgccaccagacagttcattccaacactcaaacctttacggacgccgttgcgaccacgccgttgcgaccgcctacctacgccgtcatgcc
ggcagtttctgcccgacgaccagcacactggataagtgataagtgaacctcgagtgctgaaaatccatcgagtgaacagcgaaagaaatccgctaagccgagatatcgagtgcaagccgaaagaatccgctagatcg
tgcagtttctgcccgacgaccagcacactggataagtgatgagtgaagcaccaccaggcgaagaaatccgctaagccgagatatcgagtgcaagccgaaagaatccgctaagcctagtcgg
aacgaacagcaaagaagaacgagagagaagatagagaagaaatccgctaaagcaagcagaagaaatccgcccgctaagcagaaagcgaagaaaccaggaaaaaatg
ggaacgcatgtcagtgacgccgtgtgcggggtcattgtcctcggaagggtcgccacagacgagaaggagccaggaactgcccatcgccctacaacagtcaagtcgtaagt
gataaagtgatgaagcgacagccacagtgcatgcagccaggtcacaagtgcaagaatcccacacccatgaaaatacaccaggaagggcacatacaatgg
gacctgagtgcccagatacccagtgcacatgaagtcagatgtcaacatcccgacagcttcaaaagtacaccatgaaaaaccaggaagggcactacaattgg
catcacgtgcagtccagtgccggttccagttccagttgccagttcctgcagtccgaccttccaggtaaaccaagccaaaccaggacgcagcgcgccgatct
tcgaacaaaggaccgtgtggtgccattgtcctgggagccgtcgtgcaggaaggcccaggacatgcccccatcagttccacatcccgtgtcagtcgtgaccctgag
caagacaatggtcagagcccagctgtcacccagaacagagaagaatgtccgccgcctgatgtggtcttcaccgtcactcaccggaactaaagcgtagcttgacg
ccatgctcagagccccgctgtcaccctgttcatgaaaaaccagagacactgaggtgtttagaggacaacgtagaggacaacgtagaccgcatcagtactac
cgcggctactacgactctgcgaccgtgacggtaaaatgcacgtgacgtcaccgtcccggtgcaccgtgcagtgaccgtgcagtgaccgcatcaagtc FIG. 11B (continued)

```
tacaaggccacgaaccgtatcgtattgcgccgactgccggagacgggccgcagttcgttacagcccggtggcctataagaaaaatta
gggatgaggcttccgatgcatgataaaatccagttcgcagccgcaaattgccagccgaacacgaacgaacacgaacaacaaa
atcagtacatgccgggacatgaaagaggcatgaaacactcggagacttcttacaagtccatactccgtgtgtgccatcgaagca
cgatgggccacttcatcgtgccgactgcctactgccggagacgaactaaagtccagtccaagatgcagaatcgcacaccaggct
gcaaagtcaggtacaaacacgcacggcccagtaggagagagagatcgacatgcatacccaccggatatccagacataacgttcgtcg
acaacgaccagctgactaccgcaccgacggaggaagagagatcgacatgcatacccaccggatatccagacataacgttgctgcg
cagcagtcaggtatgtaaagatcaacagcaggaggaaaaaccatcagatacaacagtcacgtgttgatgtggccactggcaccac
cagtagccgacaagactactcaattgtcaaaatagcacagtcacgtaaagtcacgtactttccctgaccaactccacatgccacgtgtgca
tttgtccctagagccgaccagttgtctgcaaagagagagtggataggagactgaaactgacagtgaaactgcaccggaccgatcaactgcgagcta
cgtgccaccagtcagtcacatacgccgctatgagagagtggataaccgctagagacacgagatcatccacgtcgttgaccgttgaccggagctcatgga
gagcagatccgccgttacaaccacccgtgccgcttgtggccgtcagcagttgaaaactgcacccagatcatccacgtcgttgaccgagcagatgcagga
gatgggaaacaaccacccgtgccgtcagcagttgaaaactgcaccatggggtgcgcacgagatcatactc
tattactatggctataccaacagcaccgcgtcaatcatactcgcggtctcagctgcagtgctgtactatcgctgctggtcatgttac
atgtcgccactgcacgcgcaagtgcctgaccaagtgcctatcgcggcgtaaatctgatgcggtcgtgcctgagctgtcgtccgggtaactactaggagtactatgct
gtccaccacgagccgcatgcgcgtcattgccagcagtgccgtcagcagtagccggccggttcctgctgcatcttgctcaacactgttttgctggagctgca
acgcccgtcgtcgcgtcgtaaatcttacgaacacacccggaatctatggcgtcagcagtgaacggaacgcatgccgaatgccgtctgaaaccgcagtagaacactg
gactcccgtgatgaccgttacaagttgaagtcctgccgaatgcgcaacgatcccgaatgtgttggtgcgattccgtaaactgtgaatacaaga
gctcctccccgatgaccgttacaagttgaagtcctgccgaatgcgcaacgatcccgaatgtgttggtgcgattccgtaaactgtgaatacaaga
cagtcgtgccatcaccttatatcaagtgctgcgggacagagtcatgagcgccccgactatcaatgccagtctctac
aggagtgtaccacttatggcgcgccatactgcttcgtgacactgcttctgaacacccagctgagtgacacatacgttgatagtcg
gactgtaccaagcacgaccatgccgcctacaaaggccgcataccgcggcaagcgcatatgtgcaatgaaaagccacatccgaatagctacggaacct
caatcagacacaacaacggcgttcgtcaactggaggagcacaacgacgtctacacagctccacccacggctcaggcagcaaccaggt
tgaagccttcgaacaaagatcgtcgtctacaagaacgacgctacaaaccaggactccccaccacccggtcaggacacaaccaggt
aggttgagacatccagaggacggtagaaagagctagaaggacagctaaggaccctcgcttaagtacttcttcaagacttcgtccgt
actgttcacgtcctgcctacacacagaccccttctgccttaagtatactggatgataaaaagaagatgcccgtctgctgaatgacaaggctccctt
agggcgtaatcaccttatcaagtgccgccgtggcgcttgcaacactccagtccacggtgcacgtccactcatccagtccactcatccatgcaccatcggacgcacgt
gttcacgccgtcgtgattgtgcacctgccgtcacaaacctgggtgtaagccaatgccgctgcccactcatccggaattcggcgatc
gcgactctgactttcaaaactgacaaaccggaaaaaatgtgctgtccatcgtctcattcgaacgtagccatacgtagccagcagctgga
```

FIG. 11B (continued)

```
catcaaaacagatggcaagtaacccigcatcttacagcatcagcatcccggcaicagatgigigigcagigcaaaacga
catgcatggcagcgtgagccgccgaaggaccacatcgtccctatggggcgagccataacaaccaagttttcctgacatgtctgg
cacgcaatgacatggcggcagcggtagccggggcctaactccgccgcagtggcagtactatactgtgtgacgt
gtgtgactatgccgcgctaatctagaccaggcccctggatccagatctgictgcccttcctttagttgccagccatctgttgttgccctccc
cgtgccttcctigaccctggaaggtggccactccactgtccctccaataaaatgaggaaattgcatcgcattgtcgagtaggtcatt
ctattctgtgggaggtggggtgggcagtcaggacagcaagggggaggattgggaagacaatagccatgcgggatgcggtgggct
ctatgggtacccagttgctgaagaattgacccggttcctcctggccagaaaagcaggcactccttcaatccaccccgctaagtactt
ccaacgccccctggtcttagttcagccccactcatagacactcagtcagccttcccggcctcaatccaccccgctaagtactt
ggagcggtctctcccctcatcagccaacatgtcggaagtaatgagagaaatcatagaattaaggccatgatcaggcatcatgg
tgcaggaggagaaatgcctcactgactgctgcaggaacatgtgcagaaaaggccaggaacatagagtatcagtcacctcaagggcgtaata
cggtatcgcacagaatcaggggttcctccggacccgctcctgtccgacccttcgttagagccttaccggataccgtccgcc
gcgttgctggcgtttccgaggcgttcccatagctccatagcgctgcctatcagcgtgagtatctcagttcgtgtaggtcgttgctctcaagctggctgt
ttctcccttcgggaagcgtggcgtttcccatagctccatagcgctgcctatcagcgtgagtatctcagttcgtgtaggtcgttgctctcaagctggctgt
gcacgaaccccgtcagccgagcagccgttcagcggattagccgctgcagagccggtgtatgtaggtgctacacagagtttcttgaagtgtggccttaactcagcagct
cgtggcagcagcactgaacagattagccgctgcagagccggtgtatgtaggtgctacacagagtttcttgaagtgtggccttaactcagcagct
acactagaagaaacagtattgttatcgcgctcgtgaagcagttaccttgctgaaaaaaggatctcaagaagatcttgatcttctacg
ccacgcgctgtagcggtggttgttgcaagacagcagattacgcgcagaaaaaaggatcaagaactcaagaagatcttgatcttctacg
gggtctgacgctcagttggaacgtgaaactcacgttaaggaattttgcatgacagttaccaatgcttaatcagtgaggcacctatctcagcgat
ctgtcatttgttcatccatagttgcctgactggggtgcacactttatatgaagtaacttgtcgtcgtgactcacgtgaagcacctatctcagcgat
ggcctgaatcgccccatcgtccacgaaacgtgcgttcccggaagcgccacgagctgagcaaagccgttcgtgagagcttgtgccagctgtgatttga
actttgctttgccacgaacgtctgcgttgtcggaagatgcgtgatcgattgctccttcaactcagcaagcgttattcaacaagc
cgccgtccgtcaagtcagcgtaatcgcactgctctgcctagtctgccacactgcaaaagccgtttctgtaatgaaggagaaaactcaccgaggcagtca
actgcaattaicatatcaggattatcaatacatattttgaaaaagccgtttctgtaatgaaggagaaaactcaccgaggcagtcagtatca
ggggacaatatcaggatcgctgcgtcgacctcgtccaacatcaatcaacctattaattccctgtcaaaataaggttatca
agtgagaaatcaccatgagtgacgactgaatccgtgagtatgcaaaaagccagtgattcatcttccagactgttcatcttccagactgttcaacaggccagcc
```

FIG. 11B (continued)

attacgctcgtcatcaaaatcactcgcatcaaccaaacgttattcattcgtgattgcgcctgagcgagacgaaatacgcgaatacgcgatcgtgta
aaagacaattacaaacaggaatcgaatgcaaccggcgcaggaacactgccagcgcatcaacaatatttcacctgaatcaggatatt
cttctaatacctggaatgctgtttcccggatgcagtgctgagtgctgagtaaccatgcatcatcaggagtacggataaaatgcttgatgtcg
gaagaggcataaaatccgtcagccagttagtctgaccatccatctgtaccatcattggcaacgctaccttgccatgttcagaaacaaac
tctggcgcatccatcggcttcccatacaatcgatagattgtccgcacctgattgccgacattatgccgagccataatcgagaacgctacgtttatgttatgatatactgtttatgagctatacgttatgtatgcag
acagtttattgttcatgcatgatatatttttatctgtcaatgcggatacatattgaatgtatttgaaaaaataaaacaaataggaggtccgcgcacattccc
cgaaaagtgccacctgaccgtctaagaaaccattattcatgacataatggtcacgaggccctttcgtc

FIG. 12A

Plasmid map: CMV/R Venezuelan equine encephalitis virus VLP, 8186 bp

Labeled features:
- CMV/R Backbone
- ApaLI (178)
- CMV IE Enhancer/Promoter
- NcoI (697)
- HTLV-1 R Region/Splicing Donor
- CMV IE Splicing Acceptor
- NcoI (1317)
- PstI (1334)
- XmaI (2323)
- AvaI (2323)
- SmaI (2325)
- NcoI (2712)
- XmaI (2887)
- AvaI (2887)
- SmaI (2889)
- ApaLI (3037)
- PstI (3075)
- structure
- XmaI (3642)
- AvaI (3642)
- SmaI (3644)
- PstI (4306)
- PstI (4482)
- BamHI (5162)
- Tbgh
- ApaLI (6190)
- AvaI (6766)
- HindIII (7328)
- Kan.
- XmaI (7574)
- AvaI (7574)
- SmaI (7576)
- ClaI (7757)
- AvaI (7848)

FIG. 12B
SEQ ID NO: 8 tcgcgccgttcggtgatgacggtgaaaacctgacacatgcagctcccggagacggtcacagctgtctgtaagcggatgccgga
gcagacaagccgtcaggcgtctcagccgcggtgtcggtgccggctggcctggttaactatgcggcatcagagcagatgctactg
agagtgcaccaatgcggtgtgaaataccgcacagatgcgtaaggagaaaataccgcatcagattgccatggccatatgcgttg
tatccatatcatatatgcattaattgcgttgcgctcactgcccgctttccagtcgggaaacctgtcgtgccagctgcatta atca atta
cggggtcattagttcatagcccatatatggagttccgcgttacataacttacggtaaatggcccgcctggctgaccgcccaacgacccc
cgcccattgacgtcaataatgacgtatgttcccatagtaacgccaataggggactttccattgacgtcaatgggtggagtatttacgtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatcagcctcc
atcggctccgcatctcctccttcacgcgcccgccgccctacctgaggccgccatccacgccggttgagtcgcgttgcgccgctccgcc
tgtggtgcctcctgaactgtgtccgccgcgtctagttaaagctcctggtaagtttccttaaggtttaacgcgaactctggtgctgagcagct
acctagactcagccgccgccgccacagacaataagctgacagagcataacatggctttcactgctagtgcagtcagcagtact
cgtgctgccgccgccgcgggcgcccagagagcagccagccatgtatccccagagaaccgaccccttttctgccgatgcagtgcatgcagg
acacggtgatcagatatcggcgcgcccacagagcccatgccaccatgtatctgatcttgatgatgtcagcagcagagtagtcgcagtact
cggcccccgccagccgccgcccacctggagaccgcgagggccacctgctaagaaaccttaagaggaaggggaatttaccgctaactga
cgttcaagccaaaccgccggagacgcccacctggagacgccccggaagaaccttaagaggaaggggaaccgctaatcgacaagcattccaattgctg
gctaggccaagaagaagccaagcaccagagaaccaagccagagagcgagagagagagagagagcaagaggccactaatcgacaagcattccaatatgctg
aacagagaggcacaaccagaagagaaacaaaccaggcaagcatgtcatgaaatgcacaagacatcccaattatgctg
gaaggaagattaaccgcgtacgctcgcgtgcagccagcagcagcagcagcaagcagacacgt
tctggccgcactaagacgaagaaacgtccaaatatgatcttgagtgtcagaagcatgccagagatgccagcgccgatacattcaagt
acaccatgagagaagcccccagcttgctcgtattacagctggcatcatggagcgtcatgaactgaaaaatggcgttcacgtggtgccaaaagaggg
tcagaccaagcagaagacagcggaagaacgcagcagaagcagcagcagcagcatgcatgtccgaagctgtggttgctgggaggtgtgaatgaaggat
ctaggacagccctttcagtcgtcatgtgaacaggaggagagaggtaactgtgaagctataccgaaggtgtggttgctggagaggtggtgaatgaaggat
gaccacatgtgcctgctctgacgttccgccaatgtgactgacgttccgaacaccaatgactgcatacgacgacagagacagagacttggcca

FIG. 12 B (continued)

```
tgctcagcgtaacgttgacaaccggctacgatgagcagctgttaagtcccgaagaaaaggagatctaccg
aggagctgttaaggagtataagctaacgcgccatcagcgcccctacacggcgccatcatcagatgtgcctggagctgccatagtccaatagca
attgaggcagtgaagcgacgacggccacgacggctatgttagactcctcgcagtatggcctggcagtatcctcgcaacttaaa
gggaaggactatgcggtatgatatgcacggaaccattgaagagatacacctaccactacatcaagtgtcactccacatctcgccgtcac
attgtggatggcgcatggttattttctgttgtccggcgtagtgcccggcaggagcaactccatccatgggaattaagaaggttcagtcacacact
cctgctcagtcgtgcctatgaagtgaaattaatccgtagccagagaactccacactcatccaccagaaccaggagcagagcagcgtg
ccaagtctaccgcgcacgatcgcacgatgcacagagagagcttatgtcgagatgcacctccggctcgtcgaagtggacagcagttgatttcc
ttgagcggcagttcagtcaccgttgacaccttcgtcggagtagcgcctgttgtgaaatgcaagtgcgggcgcacaaagatcctcgaa
accatcaacaaggcaaaaacagttcagccagttgcacgttgcacaaagaagagagcagtgcatatcgactgcagaatgacaagtggtgta
taattctgacaaactgccaaagcagcgggagccaccctaaaaggaaaactacacgtccgttcttgctgcagacgcaaatgcac
cgtgcctcagcaccggaacctagtgataaactcgtgttccgatcagtgtcactgaaactgcacctaagaatccacatcccacatatcgaccact
cgccaacttgctgatgagcctcattacacgcacgagctcatatctgaacaccagctgttaggaatttaccgtcactgaaaagggtggga
gtttgatgggaaaccatcgccgcgaaaaggtttgcacaggaaacagcaccggaaatccacatggctgccacatgaggtgat
aactcattattaccacagatacccttgtccacctatgcctaactccttaccggctaacgccttcgtcggtgcagcgtccacctg
gctgttttgcaaatccagagttcgtgcctaactctcttacggctaacgccaggatgccgctttgccctgtgccgctggctgctgc
gcccgcactgcccggccgagaccacctggagtcttggatcacctatggaacatataaccaacagatgttctgattcaattgcgat
cccctgccgcctgattgtaggctgaccggctcgccgctcaagtgctgtgtagtgctgtagtaccaccatagtcaacagagcaggctaccgcgcca
ctccctatcagcataacacaaagatcaagctgcgagccaactcaagctgaactcgagtacctgcactgccactacaaaacaggaatgg
attccaccagccatcagtcaaatgctgcggatcctcaggaattgcttttgcgacacaggctcaactaccaggcctgatgaacagtgcaaagtcttcacaggggttac
ccgtcatgtggagagtgcatattgcttttgcgacacaggctcagtcagcaggcctacgtaatgaaatctgacgactgcctt
gcggatcatgctgaagcactacaaaagcgcacacaggccctcagtgccaggcgttcctcaactcacagtgggcgaacactctattgtacc
accgtgtatgttggaatggagaagtccgtgaacttcaaactaactaagggtcaaactaactaacctagtgcagctgtgacacccttgac
agaaaaaatgtgcagttgccggaagtatgccggagatctgagagatctataattacgatttcctgagtatggggcaggaccaaacaggagcattggaagacataca
atccagaacagtctcaagctcagatctgatctgtatgccaatccaaccactagtgtcgagagaccaaagcaggagcgatcatgccatac
actcaggcaccatcggtgtttgagcatcggaaatgaagaagataaagctcgtcattgaaattcaccgccccttcggatgcgaatatataca
aacccattcgcgccgaaaattgctgtaggtgtcaattccattagcctttgacattccgacgcctgttcaccaggggtgtcagaaaca
```

FIG. 12 B (continued)

```
ccgacactttcagccggccgaatgcactctaacgagtcgtgtattcatccgactttggcgggatcgccacggtcaagtattcggccag
caagtcaggcaagtcgcgcagtccagtgccatgtgccatcaggactgctaccctaaaagaagcagtcgagctaaccgagcaaggtcg
gcgaccattcattctcgaccgcaaatatccaccggagttcaggctccaaatcacatatgtcacgtcaaaaggtgattgcac
ccccgaaagaccacattgtgacacaccccagtatcacgcccaaacattacagcgcggtgtcaaaaaccgcgtggacgtggtta
acatccctgctggaggatcggccgtaattattataattgcttagtgctgcctcagttgccagccatcgttgtggccatcgttgcccctcccccgtgccttccttga
ataatgatctagaccaggccctggatccgatccagatcgctgtgcctctagttgccagccatcgttgcctattctgagtaggtcattctattctgggggt
ccctgaaggtgccactccactgtccttcctttctaataaaatgaggaaattgcatcgcattgctgagtaggtggctctatgggtaccag
ggggtgggcaggacagcaagagggagaggattggaaagacaatagcaggcatgctgggaatgcggtgggctgtccacacccctctgtgacacaccctgttcacgccctggt
gtgctgaagaattgaccccggttcctctgggccagaagaagcagccacatcccctctgtgacacaccctgttcacgccctggt
cttagttcagccccactcatagacactcatagtccatcaggaggctcctcaatccacccgctaaagtactgagcggtctc
cctcccatcagccccatcatagaccctccaagagctggtgggaagaattaaagcaagataggctattaagtgcagaggaga
gaaaatgcctcaacatgtgaggaagtaatgagagaatcatagaatttaaggccatgattaaggccttaatcttccgct
tcctcgctcactgactcgctgcgctcgtcgtcggctgcgcagcagaagccaagaacgtaaaaagccgcgttgctgcggtt
atcagggataacgcaggaagaacatgtgagcaacagccagagccaaaaggccagactcagagaggtggcaaacccgacagactataaagatac
ttccataggctccgccccctggaagctccctcgtgcgctcctcctgttccgaccctcgttaccggatacctgtccgccttctcccttcggaa
caggcgttccccctggaagctccctcgtgcgctcctcctgttccgaccctcgttaccggatacctgtccgccttctcccttcggaa
gcgtggcgctttctcatagctccatgctgtagtatcgttgagttcggtaggtgttcgctcaagctggtgctgcacgaaccccg
ttcagccgaccgctgcgccttatccgctaactatcgtcttgagtccaacccgtaagacacgacttatcgccactggcagcagccact
ggtaacaggattagcagcagccaggtagcgaggtatgtgctacagagttcttgaagtggtggcctactacgctacactagaagaaca
gtattggtatctgctcgtgctgaagccagttaccttgctgcagtttgagcctcttgatccggcaaacaaacccgctggtagc
ggtggttttttgttgcaagcagcagatttacgcgcagaaaaaaagatctcaagaaagatcctttgatcttctacgggtctgacgtca
gtggaacgaaaactcacgttaagggatttggtcagcatgatttgtcatgacagttgacagttgacaaagttgactacgatctgtcgtattcgttca
atcaataagtatatatgatgtagtaaacttggtctcgacagttgacagttgaagaaggtgtgctgatcaacaagttgacttttggcca
tccatagttcctgactgggggcgctgagtcgctgagtggtcgctcgtgaagaaaggtgtgctgactcataccaggctgaatcgcc
ccatcatccagccagaaagtgaggagccacggtgatctgatccttcaactcagcaaagttcgattattcaacaaagccgcgtcccgtca
ggaacgtctgcgtgtcggagaagagtgcggagagcgtgatcgatctctccatctctcaactcagcaaagttcgattattcaacaaagccgcgtcccgtca
agtcagcgtaatgctctgcagtgttacaaccaattaacaatctgattagaaaaactcatcgagcatcaaactgaaactgcaatttattca
```

FIG. 12 B (continued)

tatcaggattatcaataccatatttgaaaaagccgttctgtaatgaaggagaaaactcaccgagcagtccataggatggcaagatc
ctggtatcggtctgcgattccgactccgtccaacatcaaatacctattaatttccctcgtcaaaaatagttatcaagtgagaaatcac
catgagtgacgactgaatccggtgagaatgccaaaagcttatgcattcttccagacttgttcaacaggccagccattacgctcgtcatc
aaaatcactcgcatcaaccaaacgtattcatcgtgattgcctgagcgagacgaaatacgcgatcgcgtgtaaaaggacaattaca
aacaggaatgaatgcaacggcagcagaaccggccagcgaacactgcccagcgcatcaacaatatttcacctgaatcaggatattcttctaataactgga
atgctgtttccggatcgcagttgtagtaaccatgcatcatcaggagtacggataacatgcttgatgtcggaagaggcataaat
tccgtcagccagtttagtcgaccatctcatcgtaacatcattggcaacgctacctttgccatgtttcagaaacaactctggcgcatcggg
cttccataacaatcgatagattgtcgcacctgattgcccgacattatcggagccgcccattatacaccccctgtattactgttattgtaagcagacagtttatgttcat
taatcgcggcctcgagcaagacgtttcccgttgaatatggctcataacacccccttgtattactgttattgtaagcagacagtttatgttcat
gatgatatatttatctttgtgcaatgtaacatcagagatttttgagaacacaacagattttgaaaataaaacaaatagggttccgcgcacatttcccgaaaagtgccacct
gttattgtctcatgagcggatacatatttgaatgtatttagaaaataaacaaataggggttccgcgcacatttcccgaaaagtgccacct
gacgtctaagaaaccattattatcatgacattaacctataaaaataggcgtatcacgaggccctttcgtc

FIG. 13B

SEQ ID NO: 9 tcgcggcttcggtgatgacggtgaaaacctctgacacatgcagtcccggagacggtcacagctgtgtctgtaagcggatgccgaga
gcagacaagcccgtcagggcgtcagcggtgtggccggtggccatcagagcagattgtactg
agatgtgcaccatatgcgtgtgaaatacgcacagatgcgtaaggagagagatacccatcagtcctaactatgcggccattggccattgccattccatacgtg
tatccaatatcatatatgtacattatattgctcatcatgtccaacatattaccgcccatgtgacatgttgatatgaccgttagttattaagtaatcaatta
cggggtcattagtcatagcccccatatggagtccccgttcatacatatactacgtaaatgccccgcctgctgaccgcccaacgaccc
cgccatgacgtcaataatgacgtatgttcccatagtaaccgccccatattgacgtcaatgacggtaaatggcccgcctggcattatg
ctgcccactgcccagtagtacatcaagtgtatcatatgccaagtacgccccctattgacgtcaatgacggtaaatggcccgcctggcattaa
cccagtacatgaccttatggactttcctacttggcagtacatctacgtattagtcatcgctattaccatggtgatgcggttttggcagtaca
tcaatgggcgtggatagcggttgactcacggggatttccaagtctccaccccattgacgtcaatgggagtttgttttggcaccaaaatca
acgggactttccaaatgtcgtaacaactccgccccattgacgcaaatgggcggtaggcgtgtacggtgggaggtctatataagcaga
gctcgttagtgaaccgtcatctctcctggagacgccatccacgctgttttgacctccatagaagacaccgggaccgatcagcctcc
atcggctcgcatctctccttcacgtcagatgcctagtcagctcaattgtcatcgtcagctcctactgagtcgagaactcagtctagagcct
tgtggtgcctctgtcgtgtgcgccgtctagttcctgctagcccgttaactaaagtcgagcagtgtggaggcagtgtagtcgagcagtact
cgttctgccgcggcgtgccaccagaacataatgctgacagactgtccatcccctcgaacttccaccagttacctacaatccgatgccttac
acacgtgtgatcagatatcggcgtccgccaccagaacatgctcatacccctcagctgaacttcctcatcccctgggctcaaatcgatgccttga
cgagatcaaacccctcagccgccgctggaaggccgttcggcctcgtgtcaaatcgaagatctagagtcgatagc
aacttgactttaaacaacgatcactactattccgccgccaagcagaacaagaagaaggtcctaagccaaaacctctc
agcctaaaagaagaagcagccaagagccaagccgccaaggaagcagggaaacgaacgctatgtgatgaagttgga
gtcggacaagacattccgatcatgctgacaattgccgtcaattgcgccgtgaatgacctgacgtcaaggatatgcctgccgttgtcgaggaacgaagccgcgacgcctccac
gttgaaggaaaaattgataatgacaagccaccagcgggacgacaaaccgaccgacttgtggcatcctctactactgtgcaggcgaggcttcctacaactgccaccacggcggcagtccagatgag
agaacatgaagattaccgtaccgaggaatggcgggaagtgcggggagaccgaggagagaccgatccaggtcacttggaaccagaaaggtgacaacagaggcagagtgtg
aatggagagattctaggtcagaaatgacaaatggccacgtcactggcgcatgcgcatggtcagtgcgtgcttcagtgaatgaaccggcgcgttccatgggaagttcatcacgttgcttggaaccagttccatcagcacgttgacaacaaccaccgtgtgct
ccccgaaggctgaacgtgtcacgtagttacagcgccatgcgccagcggcgcatgcgcatggtcagtgcgtgcttcagtgaatgaaccggcgcgttccatgggaagttcatcacgttgcttgaaccagttccatcagcacgttgacaacaaccaccgtgtgct
attcactgaccgccagaacgaacactcgacgtctcgaagagaacgtcgacaattacgacaatccaaattacgacacgctgagaacgtcttga FIG. 13B (continued)

aatgtccatcacgccggcccaaacgaagcattacgatgacttcacactgaccagtccctactgggttctgcccgtattgcagacac
tcaacgcgtgtttaagcccaataaaaattgagaacgtgtggacgaatctgatgatgatcgattagaatccaggtctcggcacaattc
ggctacaatcaggcaggcactgccgagtcaccaaattccgttacattcgaccagccatgaccatcaagactacatcaaggaagacagtatgg
agaaaatagctatoagcacatctgaccctggaccgtgcgctgctgtcgttggccacaaagggtacttcctgttagctcaatgtcctccaggtgacagtg
taaccgtcagtatcacgagcggagccatctgagaattcatgcaccgttacgcacgttacgatcacttgaaggacgctgccgggtacataaccatgcac
actgtgttcccaccgtccatggaaagctgtaaagtgccacgttacgatcacttgaaggagacgctgccgggtacataaccatgcac
agccaggccacacgcgtataagtcctatcggaagaagcgtcaggcgaagtgtacattaaccaccctctggcaagactcacc
tacgaatgtaagtgtgggacgactacagcacagttgtgagcaaggcgaacgcgaagatgaacgtgcactaaagcaaaacagtcacc
gcctacaagagcgaccaaacgaaatgggtcttcaactcgccgatcttattaggcacacagaccactcagtgcaaggtaaattgcaca
ttccattccgcttgacaccgacagtcgccggttccgttagctcacacgcctacagtggttcaaaggcatcaccctccacc
tgactgcaatgcgaccaacattgctgacaacgagaaaattgggctgcagcagcaacagcaacagaatggattaacagggtctacat
caaggaaattttctgtggcgagaaggccgcatgagatcaatcacattatcatcgatcaactgtcactgtcgtgtcg
caggcgaccacatgaggccgcatgagatcagagcttgggtaaccatgaaccatcagagctcgggccagagtcggcac
ctcttgccatcctgtgtagcactgcatcatcagacgcattagcggttgctgcatcaagagactgcctgacgcaaatacgcgctgcaac
gaacgcaaacaccggtaccacagcgttctctgggcacagttgtgccattcctctggacagttgcgccaaccactgtgccaactgccttcatgctgcattgaacatcgt
ggttaacaacaaccggtctgcctgggaagtagagccacttaaccttggacacagatcacgtcgttccgccaaatgtccggatccgtaaaggc
tatgttgcagcgtcgtccaaattccacacagttacgcatccttccaccacaagtaaatgcgggtccctcgagtgcaagcactgagaacacaactgagtgagc
acatgcgcgtgtttggcgtcctccagactgcactattagaatcacgcagtcgcactaagtttcagaagtgcgcgcctgcgtaaag
gtacgctcgagtgctcagactgcactattagatcacgcagtcgcactaagtttcagaagtgcgcgcctgcgtaaag
tatacggcaacaccacggcgcaccctgaccttgacccttgtcaatggcgtcagccagttccacgggaactgaagctcataggagcggc
cgatatcagccgctttcaccttgaccatcaagtgctcatcaaaggctgttaccactacgactccgagtatggagatgg
aaaccaggagcggtggccaacatcctggcgtattcaagcatcctgctgatcagagtacataggtcagagacattagccgtaacggctgcgaagcttc
tgtcaagaacatccagcgtcccctacacgtaccctaagcagtaataggtatgaaatgtgaagaacaactcaggacgcgaaccctgcaagaaac
agcaccaattggatgtaaattgaaggagccctcgagcgtctaactgcttacggcttacgcgcatcctatcgatgacatccgat
gcagcatttgtgagatcatcagaatcagaaacaacaatttagaagtagctgaacgtaacgtagcagactgcagaactgcattattctgcagactttggttct FIG. 13B (continued)

FIG. 13B (continued)

cgtcccgtcaagtcagcgtaatgtctgccagtgttacaaccaattaaccatctgattagaaaaactcatcgagcataaatgtaaactg
caattaattcatatcaggattatcaaatacatatttgaaaaagccgtttctgtaatgaaggagaaaactcaccgaggcagttccataggat
ggcaagatctggtatcggttctgcgattccgactcgtccaacatcaatcaactattaattccctcgtcaaaaataaggttatcaagtg
agaaatcaccatgagtgacgactgaatccgtgagaatggcaaaagcttalgcttcattccagactgtttaacaggccagccatlsc
gctcgtcatcaaaatactcgcatcaaccaaacgtatcattcgttgatgcgctgagcgacgaaatacgcgatcgctgttaaaag
gacaattacaaacaggaatcgaatgcaaccggcgcaggaacactgccagcgcatcaacacatgtaatccacgatcaggatattcttct
aatacctggaatctgtttccgggatcgtgagtaactctcactctaacatcataaggagtacggataaaatgcttgatggtcggaag
aggcataaattccgtcagccagttagtcgaccatctcactgtaacatcatgccaacgctaccttgccatgtttcagaaacaactcg
gcgcatcgggcttccatacaatcgatagattgtcgcaccgtgatgccgacattatgccgagccattatacacccatataaatcagcatc
catgttggaattaatcgcggcctcagcgagcaagacgttcccgttgaatatgctataacacacccctgtattactgtttatgtaagcagaca
gtttattgttcatgatgatatatttatctgtgcaatgtaacatcagaatttgagacaatcagatttgaaaaataaacaaagggttccgatatgaa
gcattatcaggttattgtctcatgagcggatacatattgaatgtatttagaaaaataaccataacattaaaaaataggctatcacgaatgaa
aaagtgccacctgacgtcaagtcaaaaccattatcatgacatlaacattaatcatgacattaatcatattaaaaataggctatcacgaagccccttcgtc

FIG. 14A

Plasmid map: CMV/R Eastern equine encephalitis virus VLP, 8144 bp

Labeled features and restriction sites:
- CMV/R Backbone
- ApaLI (178)
- CMV IE Enhancer/Promoter
- NcoI (697)
- HTLV-1 R Region/Splicing Donor
- CMV IE Splicing Acceptor
- NcoI (1317)
- PstI (1334)
- BamHI (1441)
- NcoI (1942)
- BamHI (2075)
- NcoI (2153)
- ApaLI (2710)
- EcoRI (2732)
- XmaI (2852)
- AvaI (2852)
- SmaI (2854)
- AvaI (3069)
- structure
- BamHI (3813)
- HindIII (3825)
- HindIII (4137)
- PstI (4213)
- ApaLI (4466)
- PstI (4884)
- BamHI (5120)
- Tbgh
- ApaLI (6148)
- AvaI (6724)
- HindIII (7286)
- Kan.
- XmaI (7532)
- AvaI (7532)
- SmaI (7534)
- ClaI (7715)
- AvaI (7806)

FIG. 14B

SEQ ID NO: 10 tcgcgcgttcgtcgtaatgacggtaaaactctgacacatgcagctcccggagacggtcacagcttgtctgtaagcggatgccgggag
gcagacaagccgtcagggcgcgtcagcgggtgttggccgtcgggcggctgctaactatgcggcatcagagcagattgtactg
agagtgcaccatatgcggtgtgaaataccgcacagatgcgtaaggagaaaataccgcatcaggcgccattcgccattcaggctgcgcaactgttgggaagggcgatcggtgcgggcctcttcgctatattacttgacggtgccgccatgtaatgtaatta
acgaatcgttcataatatgacgtatcccatagtcctgttcccataagccacgtatcccataatccgtccaaatcccgtccagcgtatattacgcggtccgcaatttgtacttagggcaatgagccgcatgtgcctgtgaccgctgatattagcgcaaaagcatagcgctaaaacacgaatcgctcccatttgctaaagtgtgaagggtgactaaaatcgaatctcattggtgtgctgactacagatgtggagggcgtcattccaacagttaccccatcatactgcagctgctaagctaggttgccacaaacagttgcccccataagttgcatctgttgcagagggggagcctcatgccacacccctaaaaatcccatgccctgcccaaagttgaacactcaaattgccaaagcagatcactacgaaagcacagcagaaggtgggtccccactttgtttgctggtttctgcactaacagcagttgtgctgctgttaaagcaacttgaatctagcctgatttacacatgttgggactgaactgagatcttctaacccacagtagcgtgctctttcctgccagcgagcgctcacgtcgtgtcgcagaagtcgatccagtagctaagtcagtcgaggcgcgattccatggtcttatcccacgacgactttacccggcagtggccggctctgtgcagctgcacatggcgcaggcaaggacggccattctgaacccgccgccgctcgccctaagttcggcatgtggcagactgcaaccaaatgaaagctgcccaaggaccacgctaccatgccggacacgaaggcgacaggttggtgaagcccctccgaccagaaaatgcaaaccagcagccaaacgacagcgaatgtgatgaagcttgcctggtgatgcactgaacacgcatgaggagggcctatgtaccacttgttcgacgacggctaaaagccagcatggtctgttgaagtcagcagatatcagctagaaggcagatgcaaactgcctgtatgggcttgcacgacacagcaggtgatgatcatgtgaaatgccgccatcaagctgccaatcttgaaggaaagtgtccgggtactgagcaactgtgatcgtagtcagtaatgcaatatcagctgccatcaacactggctctcgccacactcatgctcgaaagctacagcggagcgcgtaccagatcgcaccaccccttttctgcagaatccaaagagccacagcgtggctcggcctatgggaagccggaagtgaggcacatcacagagtcgttctgtgagggcgccattcacagttaccgatagcgcctgaaattgcacaacgaccaacgcagcgtgcaacaactatgggtcatgttgcacatcgcaagggcgtctgcctatatgcgcaactagctgcagagcaggctggcaaatcctgaggcttgaagaggaactaagcgcatgtaactagcctgatttgtcatgtgctctgccctgtcctgccaatatcacgttcatgtggtgacatgctgcaaaactgccaattgccaatctcctgaaacaacacagctgactcgtgcctgcctacttcactgaaaggtgggacacgccaaccacccctgtcctgatcaaccatcacgttcctgtctcaacccctgtctggaacactcactcacaactcacggaaccacagcctatgccaactgaatccactgcaccaccaccccagcctatgccgagcctatgcaggatac FIG. 14B (continued)

gcagtccataggatggcaagatcctgtatcggtctgcgattcgactcgtccaacatcaatacaacctattaattccctcgtcaaaa
ataaggttatcaagtgagaaatcaccatgagtacgactgaatccgtgagaatgcaaaagcttatgcatttcttccagactgttcaa
caggccagccattacgctcgtcatcaaaatcactcgcatcaaccaaaccgttattcattcgtgattgcgcctgagcgagacgaaatacg
cgatcgctgttaaaaggacaattacaaacaggaatgcaaccggcgcaggaacactgccagcgccatcaacaatatttcacctg
aatcaggatattcttctaatacctggaatgctgttttcccggggatcgcagtggtgagtaaccatgcatcatcaggagtacggataaaatg
cttgatggtcggaagaggcataaattccgtcagccagttagtctgaccatctcatcgtaacatcattggcaacgctaccttgccatgtt
cagaaaacaactctggcgcatcggcgttccccattacaatcgatagattgtcgcacctgattgcccgacattatcgcgagccattatacc
atataaatcagcatccatcgttgaattaatgcggcctcgagcaagaacgttcccgttgaatatggctcataacaccccttgtattactgtt
tatgtaagcagacagttttattgttcatgatgataatatttatcttgtcaatgtaacatcaggagatttgagacacaacgtggctttcccccc
cccccattattgaagcattatcaggggttattgtctcatgagcggatacatatttgaatgtatttagaaaaataaacaaataggggttccgc
gcacattcccgaaaagtgccacctgacgtcaagaaacccattattatcatgacattaacctataaaaatagggcgtatcacgaggccctt
tcgtc

FIG. 15B

SEQ ID NO: 11 tcgcgcgttcggtgatgacggtgaaacctctgacacatgcagctccggagacggtcacagctgtctgtaagcggatgccggagcagacaagcccgtcaggcgcgtcagcggttgcgggtgttgccggtgtcgggtcttaactatgcagattcggcatcagagcagattgtacigagagtgcaccatatgcggttgtgaaataccgcatcagatggccattggccattgccatacgtgtatccatatcataatatgtacattatattggctcatgtccaaacattacgccatgtigacattgattattgactagttattaatagtaattacggggtcattagttcatagcccatatatggagttccgcgttacataacttacggtaaatggcccgcctggctgaccgcccaacgacccccgccattgacgtcaataatgacgtatgttcccatagtaacgccaatagggactttccattgacgtcaatgggtggagtatttacggtaaactgcccacttggcagtacatcaagtgtatcatatgccaagtacgccccctattgacgtcaatgacggtaaatggcccgcctggcattatgcccagtacatgaccttatgggactttcctacttggcagtacatctacgtattagtcatcgctattaccatggtgatgcggttttggcagtacatcaatgggcgtggatagcggtttgactcacggggatttccaagtctccaccccattgacgcaaatgggcggtaggcgtgtacggtgggaggtctatataagcagagctcgtttagtgaaccgtcagatcgcctggagacgccatccacgctgttttgacctccatagaagacaccgggaccgatccagcctccgcggccgggaacggtgcattggaacgcggattctccgtgggaacaaacggcggattctccgtgggaacaaacggcggattcggtcgacggatcgggagatctcccgatcccctatggtcgactctcagtacaatctggacctgcctcgaactcagcctgggctctctccacgctttgcctgaccctgcttgctcaactctagttaacgtcgaggtaactctagatgatgaagagcagtgatctgagcagtactcgttgctgccgcgcgcgccaacagatatatcgcccaccgagcagatctatagacagtcttgctccttccatggttctcagtggtgtctgcagtccgtcgcacacgtgatcagatatcgcggccgcctaccatagagcgaaggggcagccatggaccccgatcccagttcgagcttgaccccccactgcctgcctcccgccaggccccaacctctcatcagcaaatcagcaaatcagcaaatcagcaaatctgaccgcgaagaaagagacccagtgtcggtatatggggaggagggccaggtcattgccgacaggtaaactggacaggaacaactggacaaactcccgcaacagaggaagctgctgccagccagcttaggtggacaggaagtaggaagaggaagaagaacctgcaaacctgaaaaaccggaaagagacagcgaagcatggcatggagttcgacgacgacagttgactgccgacagattgttcgacgtcaaggacgagctgtatcaaggttcatcggcacgtcacgtacgcaccaatatccacaatgtcctctccatgtatctcaactggttccgactctgatcaagactcacaaaccgtaaaaatcgctcacttaccggacaggtaccgagagccctgctatcaagctgaaccaccccgagagatcataactacgacgaggagttcgacagttgccagtccaacatgagaggcattcacctcacccaccagtgaaccggagttgtccgcacgaggtccgaggttccgcagccgaaatgccgctatgcagcgaaccaccagtaggagccagtaggagccagtaggagccagtaggagcagtaggagcagtaggccaatgccggcaccacgagctccgttgtcgcagtgctcgcgatgaaggaacacgaaccggacacgcccttttccgtcgtcacagtgctggtctcgacgagaaccggcaaatgttgctcggattctataactgtaaaggggcagaaggccgtcggttgcgatagtcctcgatagtcctcgatagtcctggttgcgatagtcctcgatagtcctcgatagtcctcgatagtcctcgatagtcctggttgctgctctaggtaaaggggaagcttccatgatgcgagaagaactcaaggcactgttcgccaacctgatgaagacggcttcccacacctcaggcacacttcaggcgctataccgctaaaaaacttgaagagaacgtgaacc FIG. 15B (continued)

atggcctacgtaccctgctcaatgcctatttgcgtgctggatcgctctgcgtaagcaaaagaagcgtcattgacgacttacctg
accagcccctactctggcacatgctcgttactgccaccatacgtaccgttcagccgttaagatcgagcaagtcgaagtcggacgaagc
ggacgataaccatacgcatacagacttcgccagtttggatacgaccaaagctgagcagcaaagcgcaaacaagtacgctaca
gtcgcgttaagcaggatcacacgccgttaagaaggcacctatggatacgatcaagatagccctcaggacgcgtagaaggcttagcta
caaaggtacttctctctcgaaaatgcctccagggagcacagctaaccagcgtaacggtagctcatagcaagctgatgtaca
ctggccgcaagtataaaccaaaatcgtgggacggaaaaatatgatctacctccgttcacgtagtagcaactgtaaaaaattcttgcacagtgta
cgaccgtcgaaagaaacaactgcaggctacatcactagtcacaggccgagaccgcacgcttatcactacctgaagaatcatca
gggaaagttacgcaagcgccccatctggaaagaacattacgtatgagtcaagcgaccaaaacgaaggtgggctcaactcacggac
cgcaccgaaatactgttgcacgccatcacacggccccaaggcagtgcgtgcctataaagagcgactacataacgaagtgggtcttcaactcaccgac
ttgatcagacatgacgaccaccaccatcgcttaaacacatcagcctcaattagatacagatgatcaagttgatcccgagtacctgcatgccccac
gcgccgaatgtaaatacatggctttaaacacatcagcctcaattagatacagatgatcaagttgatcccgagtacctctcaccaccagagactaggggc
aaacccggaactgaaccaactgaatgaatggaatcgtcggaaagagctcagcgtcgaatcatcagctccgtggcgatgatcgaccgagatggccacgatgccaaatagtacagcattact
gaaatcatgagccagtgaggtctatgcctcgtgtacaccatcttagccgtgcatcagcagccgtggcatgatgattggcgtaacttcgctgtgcagttgcagttgcagttatgtcctg
accatcgcccatcgtgtaccaccatcttagccgtgcatcagcagccgtggcatgatgattggcgtaacttcgctggcactctgctgctgcgttagg
taaagcgccgtgagtcctgacgctcatacgcctggccgtaatccaacttcgctggcactctgctgctgcagttgcagtcgttgcataacttcggtcataacctttgg
tcggccaatgctgaaacgttcaccgagaccatgagttacttgtgctgaacagtagaacagtcgcgttctctcgtcagttgtgcataacctttgg
cccgcttcatcatcgttctaaatgcctgtctcctgctgcctgcctgctgctgcctttttagtggttgccggcgcccttgcgcgcctactggcgaaggtaggaccgcctacga
acatgcgaccactgttccaaaatgtgcctccaaaatgtcgacagataccgtataaggcactgttgaaagtcagggcaggtatgccggctcaattggagatca
ctgtcatgtcctcggagttttgcctccaccaagtacattacctgcaaattcacactgtccaaattcacactgtcctcccaaaaatcaaatg
ctgcggctccttgaattgcgacagtcagcgccgctcatgcacacagagtaagctcagagaaggttcagaagcgcgtacagaggactatacctgcgaggtcaagtcagagactctcgaggtctcgaagtcagctactaccctttatgtggggagga
gcggccaatgttttgcgacagtcagcgacagtgaacagtcagcgggctatggaggctacgtcagagattgcagcagattgcgcgtcgaccacgcgcag
gcgattaagtgcacactgccgcgatgaaagtaggaactgcgattgttacggaacactaccagttcctagatgtgacgtaacgg
agtcaccaaggaacgtcaaagactcatagcctggaacaattcagcatcgttacgccattcgatcataagtcgttatccat
cgcggccctggtacaactcatcgccacacagacattaggctactcaagcgttgagaaccaagacgcgttggagacattgaagacattcgttgacgtttggagacattcaagctactcctttgactag
caagatcatcgccagtgccagcacagacattggctactcaagccttccgccaagaaccgccacctttggggtaagatttgcagtaagatcgccgaccg
attgagatgtgaaaaacaactcagcaccgccactcagcgccgaaaccgcgaaaatccgcagaaatccgccgagccg
gtggactacttcatacgaacattcccattctattgacatccgaacgctccttatcaggacatcaggacacgatcaggtctcaacag FIG. 15B (continued)

```
tcaaatgtgaagtcagtgagtgcacttattcagcagaacttcggcgggatgccacctgcagtatgtatccgaccgcgaagtcaatgc
cccggacattcgattccagcgaacttatcgtatcgtcgtgtggaagaagcaacatgcgccatcaaaacatcatgagttggctgtgttgccttcggtcg
cgtcgaccccgcacaaaaatgaccagaattgcttgctgcagcatgatgatttgcttgctgcagcaatgatgcacaccactgcacacagtgaccata
cctgcgttcgctattaattataggcttagttgccatcgtgttgcccctccccgtgccttccttgaccctgaaggtgccactcccactgtcctt
agatctgctgtgcttcagtgccatcgtgtgtcatcatctctggggtgtcgggggggggcaagggttggggcagggg
tcctaataaatgagaaattgcatgctcggaatgccatggtcctataagaaagtgaaccacctgattttcgaagaattgaccccactggcacttagca
aagattggaagacaatagcaggcatgctgggaatgccggtggggtgaccaggtcgcttagtccagcccactcatcataggaca
gggccagaagaaggcaggcacatcccctccgcccttaaatccaccgctaaagtacttgagcgtctctcctccctcatcagcccaacaaacaaa
ctcatagcctccaagagtgcggaagaattaaaagcaagaggcctataaggctattaagtgtcaggagggggagaaatgcctccaacatgtgaggaagt
aatgagaaatcatagaatttaaggccatcatcttccgcttctcgctcatgactcgctgctcgg
tcgttcgctgcgagcgtgtatcagtcactcaaaagccggttatcacagaatcaggggataacgcaggaaagaaaca
tgtgagcaaaaggccagcaaaaggccaggaaccgtaaaaaggccgcgttgctggcgtttttccataggctccgcccccctgacgag
catcacaaaaatcgacgctcaagtcagaggtggcgaaacccgacaggactataaagataccaggcgtttccccctggaagctccctc
gtgcgctctctcgttccgaccctgccgcttaccggatacctgtccgcctttctcccttcgggaagcgtgcctttctcatgctcacgct
gtaggtatctcagttcggtgtaggtcgttcgctccaagctgggctgtgtgcacgaaccccccgttcagcccgaccgctgcgccttatcc
ggtaactatcgtcttgagtccaacccggtaagacacgacttatcgccactggcagcagccactggtaacaggattagcagagcgaggt
atgtaggcggtgctacagagttcttgaagtggtggcctaactacggctacactagaagaacagtatttggtatctgcgctctgctgaagc
cagttaccttcggaaaaagagttggtagctcttgatccggcaaacaaaccaccgctggtagcggtggtttttttgtttgcaagcagcagat
tacgcgcagaaaaaaaggatctcaagaagatcctttgatcttttctacggggtctgacgctcagtggaacgaaaactcacgttaaggga
ttttggtcatgagattatcaaaaaggatcttcacctagatccttttaaattaaaaatgaagttttaaatcaatctaaagtatatatgagtaaactt
ggtctgacagttaccaatgcttaatcagtgaggcacctatctcagcgatctgtctatttcgttcatccatagttgcctgactccggggggg
gagggcgctgaggtctgcctcgtgaagaaggtgttgctgactcataccagccggaatcgcatcagcagtcgcagccatcaccagccagaaggtaggga
```

FIG. 15B (continued)

gccacgttgatgagagcttgttgtaggtggaccagttggtgatttgaactttgcttgccacggaacggtcgcgtgtcggaagat
gcgtgatctgatccttcaactcagcaaaagtcgattattcaacaaagccgccgtcccgtcaattattcatatcagattgaa
aaccaattaactcattctgattagaaaaactcatcgagcatcaaatgaaactgcaaattattcatatcagattatcaataccatattgaa
aaagccgttcgttaatgaaggagaaaactcacgaggcagttccatatggcagatccgtatcggtctgcgatccgactcgt
ccaacatcaatacaaacctattaattccctcgtcaaaataaggttatcaagtgagaaatcaccacgagtgacgacgatccgtgaag
aatggcaaaagcttatgcattcttccagacttgttcaacaggccagccatacgctcgtcatcaaaatcactcgcatcaaccaaccgtt
attccatcgtgattgcgcctgagcgagacgaaatacgtcgttaaaagacaataacaggaatcaggaatgcgaacggcgc
aggaacactgccagcgccatcaacaatattcacctgaatcctcctaatacctggaatcggtttccgcgggatcgtagtgg
tgagtaaccatgcatcatcaggagtacggatagaatgctgatgtccggaagaggcataaaattccgtcagccagttagtctgaccatct
catctgtaaacatcattcaaagctaccttgccatgttcagaaaacaactctgccgatcggcttccatcaaatcgatagattgtcgc
aactgattgccgacatatcgcgagcctcaatcatcaaatcaatcagcacccatcatgttggaattaatcgcctcgaccaagacgtt
tcccgttgaatagtcataactgtttatgttattactgttcgtttatgtcatgatatatttcatcttgcaatgta
acatcagagattagaaaaatacaaatagggttccgcgcacattcccgaaaagtgccactgagcgtcagcggatacatatt
tgaatgtattagaaaaataaaaataggcgtatcacgaggccctttcgtc

FIG. 16B

SEQ ID NO: 12 tcgcggcgttcggtgatgacgtgaaaacctctgacacatgcagctcccggagacgtcacagttgtcgtaagcggatgccgga
gcagacaagccgtcaggagcgtcagcggccgggtgttggccggcggagtgggtgccatcactagccatcagagccagattgtactg
agagtgcaccatgcgttgaaatacgcacagagatgcgtaagagagaaaatacgcatcagattggccattgccattgcatacgttg
tatccatcataatatgtacatttatattggtcatgtcagtgtccaacatattcgccaacatgtgacatgttgacattgactagtaattaatagtaatcaatta
cgggtgtcattagtcatatgaccataatgacgtatgttccatagtaacgccaaatggacttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatcagcctcc
atcggctccatctctcctcctcacgcgtctcgcgtctagtaagttcacgctgcctgagccgtcagtactctcaactctagttaagctcaactctagt
acctgtgccgcgcgcgtccgccaccagacatatgactgccccacatgaattacatcccctacgcaaacgttttccttctcatgcgtttacggccccagcaaaga
aacacgtgtgatcagatatgccgcggttgcaggcactcggccgccgccagacttgctcctgcctcggtgtctccctcactctgtcg
ggccgctcctggccgtagcaatgacgaacatgacagaacagatcaacagcagcaatccgtccgccgggtgccccgccgccgcgc
cgtaaatgcgtgacaatgaccacagtagacaacgcaattgctcctgcctcccaaaccaaagaagaaagccgacaagaagagaa
acccggaaaagagaagaatgtgcgcacaagatcaatgcagcaggcttttgcattgaaaagcaaaaagccgaagaaggtactgcgc
ctgcctggctggccacccgggacaactgccactcactccactaacgctgcagttatctgcctgttggctaagaggacctcacgcagcgtggt
ggcacccacagttcccctgtggggtctcaacaaggggtgccagcagtcgcgccccctgttactgcactctgcatgtgtggt
cctggcccaatgctacctcccgtttccagccccctgtgtacttgctgctgtctgtttgaaaacaaacgagccaactacggatgctcg FIG. 16B (continued)

catcaaatgaaactgcaattattcattcaggattcaataccatattttgaaaaagccgttctgtaatgaaggagaaaactcaccgag
gcagttccataggatggcaagatcctggtatcggtctgcgattccgactcgtcgtccaacatcaataacctattaattccctcgtcaaaa
ataaggttatcaagtgagaaaatcaccatgagtgacgactgaatccggtgagaatgcaaaagctatgcattcattcttccagactgtcaa
caggccagtccattacgctctgtcatcaaaatcactcgcatcaaaccgttatcattcgtgattgcgcctgagcgagacgaaatacg
cgatcgctgttaaaaggacaattacaaacaggaatcgaatgcaacgcgaggaacactgccagcgcatcaaacaatatttcacctg
aatcaggatatcttctaatacctgaatctgttttccccggaatcgagtgagtaaccatgcatcatcaggagtacggataaaatg
cttgatgttcggaagaggcataaattccgtcagccaggttagtctgcaatccgatcatcatcgtaacgtaccttcgcacttcgcatgtt
cagaaacaacttctggcgcatcggcgcttcccatacaatcgatagattgtccgcacctgattgcccgacattatcgcgagcccattataccc
atataaatcagcatccatgttggaatttaatcgcggcctcgagcaagacgtttcccgttgaatgcaatcagagagatttttgagacaacacgtggctttcccc
tatgtaagcagacagttttattgttcatgatgagcattaatcaggggttatgtctcatgagcggatacatatttgaatgtatttagaaaaataaacaaataggggttccgc
ccccccattattgaagcatttatcaggcattaatgccggcgtaagcggccgatcattaccttactgacattaaccacttccccgcacttccccgtattcacgaggccctt
gcacattccccgaaaagtgccacctgacgtctaagaaaccattattatcatgacattaacctataaaaatag
tcgtc

FIG. 17B

SEQ ID NO: 13 tcgcggcttccggtcggtgatgacggtgaaaacctctgacacatgcagctcccggagacggtcacagcttgtctgtaagcggatgccgga
gcagacaagccgtcaggccgtcagccgggtgttggccgggtgtggccgatattgacgaggcgcatgaatgccatcagagcagattgctactg
agagtgccaccatatgccggtgaaatacgcacagatgcgtaaggagagaaaatccgcatcagatggccatgcatcagagcagattgctactg
tatccatcatcatatatgtacattattggctcatgtccaacattaccgccgtcattgacatgtcagattatgtactagttattaatagtaatcaatta
cgggtcattagttcatagccatatagcgatgtccgcgttacataacttacggtaaatggccgcctgctgaccgcccaacgacccc
cgcccattgacgtcaataatgacgtatgttcccatagtaacgccaatagggactttccattgacgtcaatgggtggagtatttacgtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttgacctccatagaagacaccgggaccgatccagcctcc
atcggctcgcatctcttacgcgtccgccccgctaaggcttcctcaactctagttaagctcgttaaatcagcctgagcgccgatcagcctcc
tgtggtgcctgcttcttcctgctctccacgctctccacgcttgcctgaccctgctctcaactctagttaaagctcgtcaactctgctggcctg
acctagctcagcctggcgccgcgtctagttgcctgaccctgctaactctagttaaagctcgtcaactctagttaagctcgttgagcagtact
cgttgctgccgccgccgcgggagcacagaataagctgacagagactgttccttccctgagccaccatcagccccatcagcctcgccgtcg
acacgcggatcagtagcgccgcgcacggccgcaaacgccagatgagccaaacctggccaacagcggccaactctgggctcc
tccccggaggccagcaagtaccacgcgtccagttgcaggtactgcaggtgacctgccgcaagccgtgaccgccgtgggcaagacgtgtc
gcgaaccagatgagtgcgctccagttgcaggtagctgacttgccgccgcaagcctggccagaacacaggagaag
agaagaacaagcagagaagaacaagaacttccaaacggagaaaaaaccgaccgggaagaaagaagaaacaacaggagaag
aagggaagccagcgaaaagtcggcagaagagactagaacggagaaggtaggaaggaaggtaggtaaggccgaagtgcgcgacag
agcacttcccgtaccacgaagtgctatatccgctacgctgtctgattgcgtatcgcgtattcaagccggcacacgtgaagg
taagatcgaccaccccgaactgcagcagacatcaagttccaggtgccgagggacatgaccctcgaagcagctcgtaccgtgaagaca
tgccggagcaagcaagtggtgaacggcagcgggagtacaagttccaaatggagagtatggcactatcaggagtgagatatgtc
ataatcgacgacgggtgtaggcgtcatgccgatggcaagccgggcaagccgggtgacagggccatcaccggacaactctgggaagatcc
cggaggagaccgatgccgatggccgcacacgccctccgtgataggtttcgaccaagaagatgaaggctaggagatcgcctacagt
gatgccatacctggacacgcggtccggcagcctcggcctgtctgccactcacagtgtcttatgttgtcgaccccctgtatgttggaaagtcct FIG. 17B (continued)

cggttgatgagagcttgttgtggttggaaccagttggttgattgaactttgcttgccacggaacgttcgcgttgtcggaagatgcgt
gatcgatccttcaactcagcaaagttcgattattcaacaaagccgccgtccgtcaagtcagtctcgccagtgttacaacc
aattaaccaattctgattagaaaaactcatcgagcatcgaaatgaaactgcaattattcattcaggattatcaataccatatttgaaaaaag
ccgttctgtaatgaaggagagaaactcaccgagccagtccatagggaatggccaagatccctggttatcggttcggatccgactcgtccaa
catcaatacaaccttattaattccccatcgtcaaaaataaggttatcaagtcaagttgacgactgaatgacgctgaatg
gcaaagcttatgcattcttccagactgttcaacagtccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccagccag

FIG. 18B
SEQ ID NO: 14

```
tcgggcgttcgtgatgacggtgaaaacctctgacacatgcagtcagtgagagcggtctcgtaagcggatgccggga
gcagacaagcccgtcaggccgtcagccggttgtcgccggttgcggtgtcggggctgcttaactatgggcatcagagcagattgtactg
agagtgcaccatatgcggtgtgaaatacggcacagatgcgtaaggagagaaaatacgcatcagatgcattggctattggccatacgttg
tatccatatcatatatgtacattatattgctcatgtccaagtcgccatgtgcaatatcgccatgtattatgactagttattaatagtaatcaatta
cgggtcattagttcatagcccatatgcggtagccccatatagcggttccggttacataactactacgtaatggccccgctggctgccaaccgaccc
cgccattgacgtcaataatgacgtatgttccatatgggactttccatatgacgtcaatggagagtattacgtaaa
ctgcccacttggcagtacatcaagtgtatcagttatatgcccagtacgcccccctattgacgtcaatgacggtaaatggcccgcctggcattatg
cccagtacatgaccttatggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcatctcctcggctgccatcgctccaactgctgagcgcgcctccatccacgccgttgagtccgcgttctgcgctcctttggagcct
tgtgctccgtccatctcctgaactgcgtcgcgctcaggtaagttttaaggcctgtccctgaccctgccgtgcaaactctagtaacgctagtagtcgagcagtact
cgttgctgccgcgtcgcgccaccagatcagccgcgacagcgcatctgcgacatctgcgaactacagactaacagatctaggttcctcccatggtcttctcgagtcagtctcagctctccgccgtgtcgcg
acacgtgatcagatatcgcggccgcgcatgaattacatacatgcgaactacttttacgagcgcgttgccggcctcgaaccgaaccgccgccttcc
gtccatggcaggtcgcgatgccagcaacggatcgaatcgcgacaccctatgttacacccaagtgcaccagaatcaacagatgcaac
aactgatcagccgcagtctgcactaaccaccaaaaacagaagtgaaagtaaagcaccaaaaggcaaccgaaacagcaaaccaaagaaccagaaaagagaagagaaagagagagaagaggaagagtgcataaaagccgcagcattccccagtaccggttgccaagtgaacgaagatgactgcatatctgaggtctaaactgaggtccaaggttaccgg
ctatgcggtcctagtcgagtcgagtaaggtcatcgagccgcccaagtcgagccgcccgtgaaaggcacaaatgtataaaccagaccttgcgaagttgactacac
agaaatccagtaagttaagcctcgaatcgcccagatcccagtcacgtcacaagccaccagaagttaccatcccacaccaggcaagaagcccg
aaggtcattacaattggcaccatgtgaccccgagcagtgcgtcacagcgnngggaaggtttaccatcccacaccaggcgcggcaacccagagat
agcggtagccgtggacaacaaggcgagtngtggccatcgtgtagccggggccaacgaagtgtggcgccgatgatgatgcctgtct
gtggttgacgtggacgtcgagacaaaaacatgtcactcggtaacgccgaaggaaccgaagtggtcgccgcgcgatgatgatgcctggaag
gccaacaacctcttccatgctcgtccctcccgctcacctgaaaaacagcagagaacagacactgcggactgcgaactgcctggaag
```

ctgcaattattcatatcaggattatcaataccatattttgaaaaagccgtttctgtaatgaaggagaaaactcaccgaggcagttccatag
gatggcaagatcctggtatcgcgtatcggtctgcgattcgactcgtccaacatcaatacaaccctattaattccctcgtcaaaaataaggttatcaa
gtgagaaatcaccatgagtgacgactgaatcgcggtgacgaatgccaaaagcttatgcattctttccagactgttcaacaggccagccat
tacgctcgtcatcaaaatcactcgcatcaaaccatcgtgattgtgccgagcgagacgaaatacgcgatcgctgttaa
aaggacaattacaaacaggaatcgaatgcaaccggccgcaggaacactgccagccatcaacaataattttcacctgaatcaggatattc
tctaataacctggaatgctgttttcccgggatgtaagccagtggtgagtaaccatcatcaggagtaccggataaaatgcttgatgtcgg
aagaggcataaattccgtcagccagttagtctgaccatctcattgaacgctacctgctacttgccatgttcagaaacaact
ctgccgatcggtcctccatacaatcggatagatttgtcgcacctgattcgccacctgattcgccacatatcgcgagccacattaccccatataatcagc
atccatgttgaatttaatcgcggcctcgagccaagacgtttcccgttgaatatggctcataacaccccgttcccctgtattactgttatgtaagcaga
cagtttattgttcatgatgatatatttatctgtgcaatgtaacatcagagatttgaagacacaaccgtggcttccccccccccattattg
aagcattatcaggtattgctcaatgagcggatacatattgaatgtatttagaaaatataaacaaataggggttccgcgcacatttcccc
gaaaagtgccacctgacgtctaagaaaccattattatcatgacattaacctataaaaatagggcgtatcacgaggccctttcgtc

SEQ ID NO: 15 tcgccgcttcgctgatgacgtgaaacctctgacacatgcagctcccggagacggtcacagcttgtctgtaagcggatgccgga
gcagacaagccgtcaaggccgctgcgtcagtcgcttggcgggtcgcagccttaactatgcggcatcagagcagattgtactg
agagtgcaccatatgccgtgtgaaatccgcacagatgcgtaagagagaaaaataccgcatcagattgccattgccattgcatacgttg
tatccatacatatatgtcattattggctcatcatgttgcaaaacattaccgccatgttgacaatgatattgactagttattaatagtaatcaatta
cgggtcattagtccatatagtccatatgagttccgcgttactaacttacgtaaatggcccgcctggctgaccgcccaacgacccc
cgcccattgacgtcaataatgacgtatgttcccatagtaacgccaatagggactttccattgacgtcaatgggtggagtatttacgtaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatcagcctcc
atcggctcgcatctctccttcacgcgctccgccagccgccggcgctgatccatccacgccgcttgagtcgcgttctgccgtctccgcc
tgtgtgctcctgaactggtcgccgtctagttaaagctcaagtgtctcgtccgctttgcctgctgttccggctccctggagcct
aactagactcagaccgctctctccacgcttcgttgcctgaccctgcttctcaactctcagtgttaacgctctagttgtgaggcagtagctgagcagtact
cgttgctccgcgccgccaccagacataatagctgacagactaacagactgttcctttccatggtctttctgcagtcaccgtcgtcg
accaccatggagttcaataccaagccaccagacataagaactgctacacctcgttcactagaagctagcttactgcttcgtgtggtgat
caggccaaaaccacgccgagaccgcctgaagaagaaggcctgcaggaacaactcgcacaactgatatccgacactgctgtacagttc
cccagaaaccacgccgagaccgaaaatttaagacaaagaaagagaacaaggcaagtaaagcaaacagagtactacgaaccagaagaaaa
aggcgaaaacaaaacagacaaagaaaaaagagaacagaggaaagatgtgcatgaagattgaaaatgactgca
tcttcgagagtcagacatcagaaggaagaatgggaactagccgggtatgcatgcctagttagtgcataagacaaggaaaggaa
ctattgacaacgcagaccctagccgaagttggcgttcaaaagatcatccaaaaatatgatcctagagtgcgcacagtaccagtgcacatgaaa
tcggacgccctcaagaaggggttccccatgaaaaaccagagaaggctatccagctcatcacgcgagcagtacagtactctggaggagtca
cgatcccactacaggcgccaggaaaagcctgggacgaggcggaagaacaatcttgacaacaaggcgtgctggctattgttctaggcg
gagcaaacgaaggaaccagaggaactgcagctcgtagtgacttgactggaataaagacatggaataaaatccaccaaaatcacaccagagggtcagttg
aatgaagccttgccctccccgtcatgtgcctgttgccgaagacaacaacctccccatgtttcccaaacgcttgccgccgtctgctacgaaa
agaaaccggaagaaacccttgagaatgctggaagaactgagaagcaaccaggatattaccaggacaccaggatattaccaggacaccgattaccagttactccagttactactcagttcgattcagattcaggccattcagattgctc FIG. 19B (continued)

FIG. 19B (continued)

tcatctgattttggagtgccgcagtcagtaaagtacacagtagtaaaaaggaaaaatgccgtgcactctgtaacaaatgcggtcac
tatccggaacctaacgtagatgtcaaggagaacagcacaattgcaaattgccttctcgaccgccactagctagtgcggaattcaaggtgc
agatctgctccacactggtacactgtcagcgactgctgccatcctcctaaagaccatagtcaattaccgtcacctcaccactag
gagtgcaggacatttcaagacagacagtatgctcttggtcagacactagcggccgtctagacactagcggagttgacctcggttgcttgatct
taattatagttctctgctatcattagcagacactaggaggactcctgagaccgtcagatgcgtgtctctagttgcc
agccatctgttgttgccctccccgttccctctttcctgaccctgaaggtgccactcccactgtcctctaataaaatgaggaaattgca
tcgcattgtctgagtaggttgtcattctatctgggggtgggggggggggacagcaagggaggattgggaagacaataggcagg
catgctggaagcggttggctgctctatggtacccagtgctgaagaattgacccgttcctctctgggcagaaagaagcaggcacat
cccttctctgtgacacaccctgccacgcccctggttcttagttccagccccactcatagacacactcaggaggctcgcct
tcaatccacccgctaaagtactttggagcgctctctccctcatcagtcctccaacatgcctccaagagtgggaagaa
attaaagcaagatagatagctattaagtgagaggagagaaaatgcctccaactgtgaggaagtaatgagagaaatcatagaattaa
ggccatgattaaggccatcaaggccttaatctccgcttcctcactgactcgctcgctcgtcgtcgcgcgagcggta
tcagctcactcaaggccgtaatacggttatccacagaatcaggggatacgcaggaaagaacatgagcaaaaggccagcagcaaa
ggccaggaaccgtaaaaaggccgcgttgctgctttttccataggctcgcccccctgaagctcccctcgtgctctcctgttccgaccctg
tcagaggtggcgaaacccgacaggactataaagataccaggcgttccccctggaagctccctcgtgcgctctctcatagctcaccgctg
ccgttaccggatacctgtccgcctttctcccttcgggaagcgtggcgctttctcatagctcacgctgtaggtatctcagttcggtgtaggt
cgttcgctccaagctgggctgtgtgcacgaaccccccgttcagcccgaccgctgcgccttatccggtaactatcgtcttgagtccaacc
cggtaagacacgacttatcgccactggcagcagccactggtaacaggattagcagagcgaggtatgtaggcggtgctacagagttctt
gaagtggtggcctaactacggctacactagaagaacagtattggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctc
aagaagatcctttgatcttttctacggggtctgacgctcagtggaacgaaaactcacgttaaggggattttggtcatgagattatcaaaaag
gatcttcacctagatccttttaaattaaaaatgaagttttaaatcaatctaaagtatatatgagtaaacttggtctgacagttaccaatgcttaa
tcagtgaggcacctatctcagcgatctgtctatttcgttcatccatagttgcctgactccccgtcgtgtagataactacgatacgggagggctta
ccatctggccccagtgctgcaatgataccgcgagacccacgctcaccggctccagatttatcagcaataaaccagccagccggaagggc
cgagcgcagaagtggtcctgcaactttatccgcctccatccagtctattaattgttgccgggaagctagagtaagtagttcgccagttaa
tagtttgcgcaacgttgttgccattgctacaggcatcgtggtgtcacgctcgtcgtttggtatggcttcattcagctccggttcccaacgatcaag
gcgagttacatgatcccccatgttgtgcaaaaaagcggttagctccttcggtcctccgatcgttgtcagaagtaagttggccgcagtgtt
atcactcatggttatggcagcactgcataattctcttactgtcatgccatccgtaagatgcttttctgtgactggtgagtactcaaccaagtc
attctgagaatagtgtatgcggcgaccgagttgctcttgcccggcgtcaatacgggataataccgcgccacatagcagaactttaaaag
tgctcatcattggaaaacgttcttcggggcgaaaactctcaaggatcttaccgctgttgagatccagttcgatgtaacccactcgtgcacc
caactgatcttcagcatcttttactttcaccagcgtttctgggtgagcaaaaacaggaaggcaaaatgccgcaaaaaagggaataaggg
cgacacggaaatgttgaatactcatactcttcctttttcaatattattgaagcatttatcagggttattgtctcatgagcggatacatatttgaat
gtatttagaaaaataaacaaataggggttccgcgcacatttccccgaaaagtgccacctg FIG. 19B (continued)

caaagtcgattattcaacaaagcgccgtccgtcaagtcagcgtaatgctctgccagtgttacaaccaattaaccaattctgattag
aaaatcatcgagcgagccagtcagtccatagcgcagtcaattatcatatcagcgattatcaataccatattttgaaaaagcgttctgtaatgaagga
gaaaactcaccgaggcagtccatagcagtccaagatcctggtatcgtctcgactcgtccaacatcaatacaacctattaat
ttccctgtcaaaatagttatcaagtgacgtatgacgactgaatccggtgagaatggcaaaagcttatgcattctt
tccagacttgtcaacaggccagtcatcgctcgtcatcaaaatcactcgtattcatcgtgattgcgctgaggc
gagcgaatacgcgatcgctgtaaaggacaattacaaacaggaatcgaatgcaacggcgcaggaacactgccagcgcatcaa
caatatttcactgaatcaggatatcttcttaatacctgaatgctgtttccggaatcgcagtgagtgagtaactatgcatcatgcaacgc
gtaccgataaaatgcttgatgtcgaagaggcataaattccgtcagccagttagtctgaccatctcatcgtaacatcattggcaacgc
tacctttgccatgtcagttcagaaacaactcgccgctccatccggcttccatatcggcactaatgcgatagattgtcgcacctgattgccgactatcgcg
agcccattatacccattaaaatcagcacatccatgtcggattaatcgccctcgagcaagacgtttccgttgaatatgcctcataacac
ccttgttactgttatgtcagacagttatgtcatgatgatatttgtctcatgagcggatacatattgaatgtattagaaaaataaaca
gtggcttccccccccccattattgaagcattacaggsttattgcttcatgacggatacattatcatgacattaacctaaaatatogcg
aataggggttccgcacattccccgaaaagtgccacctgacgtcaagtgaacattatcatgacattaacctataaaatatggcg
tatcacgaggccctttcgtc

SEQ ID NO: 16 tcgcgcgttcggtgatgacggtgaaaacctctgacacatgcagctccggagacggtcacagctgtctgtaagcggatgccggga
gcagacaagcccgtcagggcgcgtcagccgggtgttggcgggtgtcgggtgtgcttaactatgccggtgcttcgggcatcagagcagattgtactg
agagtgcaccatatgccggtgaaataccgcacagatgcgtaaggagaaaataccgcatcagattgcactattggccattgcctattggccatgcgttg
tatccatatcataatatgtacattatattggctcatgccaacattaccgccatgttgacattgattattgactagttattaatagtaatcaatta
cgggtcattagttcatagcccatatatggagttccgcgttacataacttacgtaaatggcccgcctggctgaccgcccaacgacccc
cgccattgacgtcaataatgacgtatgttcccatagtaacgccaatagggactttccattgacgtcaatgggtggagtattacgtaaa
ctgcccacttggcagtacatcaagtgtatcatatgccaagtacgccccctattgacgtcaatgacggtaaatggcccgcctggcattatg
cccagtacatgaccttatgaccttacggtaaatggcccgcctggcattatgcccagtacatgaccttatgggactttcctacttggcagtacatctacgtattagtcatcgctattaccatggtcgaggtgagtttgttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatggcggtaggcgtgtacggtgggaggtctatataagcaga
gctcgtttagtgaaccgtcagatcgcctggagacgccatccacgctgttttgacctccatagaagacaccgggaccgatcagcctcc
atcggctccatctctcttcacgcgtcgtcgccaccagagatcagccggcctctaggtaagttaaagcttcagctcccatctgttgactccaagt...

gtgtctacatgcacgccactcatcggatttggcggatcgctgtacttcctacaagtcgtggaaaatcaggcaggtgcgacatccatca
cattcaaacgtcgccgtactccgtagtcggcacgttccatcgagacagagaagttccatcgagacgatgagtcgatcgatccactctcaaccgcatcagctcccccttcc
ttcgtagttctgtttgtttgtagttcgcgtcgtgctacgtgccacagccacactgcaacagcgaaatgtgaaccaccgttgtaacatccagcaaatcataa
cgggtaacttgccagaacttatctagcactgccatgacgcgtggccacaacatcttgccgggcggagttggagttgctgtatagctgcgg
tgctaattctggtaatagttaactggtgatagatttgagaaggtaagatgcagatccagatcgctgtgcctctagttgccagctgcatgtttgccc
ctccccgtgcctcttgacccgtgaagtgccactccactgtccttcctaataaaatgaggaaattgcatcgcattgctgtctgagtaggt
gtcatttattcgggggtggggcaggacagcaaggggagattggagaagacaatagcaggcaatgcctggagatgcggt
gggctctatggtaccccagagtgctgaagaattgaccggttcctcctgggccgaaaggaaggaggcaggcacactccccttctcgtgacaca
ccctgtccacgccccgtgttcttagttccagcccctcatcagtccacactcatagctgaggacactcagttcctccaagtcggaaagaaatcatatagaattgaaggccatgattaaggcca
agtacttggagcggtgtcctccctccgtcactgactgctgccgtcgttcgcgctgcggagcgaggtatcagctcagcctcactcaaagcg
tattaaggcagaggagaggagaagaaatgcctccaacatgtgaggaagtaatgagagaaatcatagaattaaggcatgattaaggcca
tcatggccttaatcttccgctcctcgctcactgactcgctgcgtcggtcgccgagcggtatcagcctcactcaaagcg
gtaatacggttatccacagaatcaggcggttttccataagccgttgtcaggaaagaacatgtgagcagaaggccagaaggccagaaccgtaaaa
aggccgcgttgctggcgttttccataggcctcgccccctgacgagcatcacaaaaatgcacgtcaagtcagaggtggcgaaacc
cgacaggactataaagataccaggcgtttccccctggaagctccctcgtgcgctctcctgttccgaccctgccgcttaccggatacctgt
ccgcctttctcccttcggaaagcgtggcgctttctcatagctcacgctgtaggtatctcagttcggtgtaggtcgttcgctccaagctgg
gctgtgtgcacgaacccccccgttcagcccgaccgctgcgccttatccggtaactatcgtcttgagtccaacccggtaagacacgactat
cgccactggcagcagccactggtaacagatttggtatctgcgctctgctgaagccagttaccttcggaaaaagagttggtactcgctaact
acggctacactagaagaacagtattggtatctgcgctctgctgaagccagttaccttcggaaaaagagtggtactcgcctaact
aacaaaccaccgctggtagcggtggtttttttgttgcaagcagcagattacgcgcagaaaaaaaggatctcaagaagatcctttgatctt
tctacggggtctgacgctcagtggaacgaaaactcacgttaagggattttggtcatgagattatcaaaaggatcttcacctagatcctt
taaattaaaaatgaagttttaaatcaatctaaagtatatgagtaaacttggtctgacagttaccaatgcttaatcagtgaggcacctatctc
agcgatctgtctatttcgttcatccatagttgcctgactccccgtcgtgtagataactacgatacgggagggcttaccatctggccccagtgctgcaatg
ataccgcgagacccacgctcaccggctccagatttatcagcaataaaccagccagccggaagggccgagcgcagaagtggtcctgcaactttatccgcc
tccatccagtctattaattgttgccgggaagctagagtaagtagttcgccagttaatagtttgcgcaacgttgttgccattgctacaggcatcgtggtg
tcacgctcgtcgtttggtatggcttcattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtc FIG. 20B (continued)

ttccataggatggcaagatcctgtatcggtctggattccgactcgtccaacatcaataacctattaatttccctcgtcaaaaataag
gttatcaagtgagaaaatcaccatgagtgacgactgaatccgrtgagaaaggcaaaagcttatgcattcttccagactgttcaacaggc
cagccattacgtcgtcatcaaaatcactgcatcaaaccaaaccgttattcattcgtgattgcgcctgagcgagacgaaatacgcgatcg
ctgttaaaaggacaattacaaacagaaatcgaatgcaaactgccagcgcatcaacaactgccaacatcaacaatattttcacctgaatcag
gatattcttctaataacctggaatgctgtttcccggsgatcgcagtggtgagtaaccatgcatcatcaggagtacggataaaatgctgat
ggtcgaagaggcataaattccgtcagccagtttagtcgaccatctcatcgtaacatcaattggcaacgctaccttgccatgtttcagaa
acaacctgccgcatccggcttcccatacaaatcgatagattgtcgcacctgattgcccggaatatgcgagccattatacccatataa
atcagcatccatgttgaattaatcgcggcctcgagccaagacgtttccgttgaatatgctcataacaccccttgtattactgttatgta
agcagacagtttattgtcatgatatattttatctfgcaatgcaatcagagatttgagacacaacgtggctttcccccccccc
cattattgaagcagttatcaggttattgctcatgagcggatacatatttgaatgtatttagaaaatataacaaatagggttccgcgcaca
tttccccgaaaagtgccacctgacgtctaagaaaccattattatcatgacattaaccatataaaaatagggttcacgaggcccttcgtc

SEQ ID NO: 17 tcgccggtttcgtgatgacgtgaaaacctctgacacatgcagtcccggagacgtcacagcttgtctgtaagcggatgccgggag
gcagcaagcccgtcaggcgcgtcagcggcgtgttggcggtgtcgaggctgcttaactatgccgcatcagagcagattgtactg
agagtgcaccatatgccggtgaaataccgcacagatgcgtaagcagatggagaaaataccgcatcagattggctcattgcatacgttg
tatccatacataatatgtacatttatattggctcatgtcatgatgttgacatttgacattgattattgactagtaataagtaatcatta
cgggtcattagttcatagcccatatatggagttccctagtccgcgttacataacttacgtaaatggcccgcctggctgaccgcccaacgacccc
cgcccattgacgtcaataatgacgtatgttcccatagtaacgccaataggcactttccattgacgtcaatgggtggagtatttacggtaaa
ctgcccacttggcagtacatcaagtgtatcatatgccaagtacgccccctattgacgtcaatgacggtaaatggcccgcctggcattatg
cccagtacatgaccttatgggactttcctacttggcagtacatctacgtattagtcatcgctattaccatggtgatgcggttttggcagtaca
tcaatgggcgtggatagcggtttgactcacggggatttccaagtctccaccccattgacgtcaatgggagtttgttttggcaccaaaatca
acgggactttccaaaatgtcgtaacaactccgccccattgacgcaaatgggcggtaggcgtgtacggtgggaggtctatataagcaga
gctcgtttagtgaaccgtcagatcgcctggagacgccatccacgctgttttgacctccatagaagacaccgggaccgatccagcctc
atcggctcgcatctctcctgaactctgaactgcgcgcgccgtcagttaaagtcagctgagtgttgagctgccttgtccgcggtctcccctggagcct
tgtggtgccctcctgaactctgaactgcgtcgtgcagctgagtttgactgccgctctaacgttcgcggcgtcagtcctggagcct
acctagactcagccgccgccgccaacaggacataaatagctgacagacgaccaggcccctgatctctcaactctagttactgcctgactaaacagctgtcagctgtcagtctgcagtcatcgccagcagtcgtgttctttcatggtgctagtgtcgcagtgcgtcgtg
cgttgctgccgcgcgccgcggccaacaggacactgcggccgcgtcaccatcagtgacccgccctcaactacaacccagcaccaccacccccaaaaccaaccacccagagtgtggaattcccagcaccaccaacccccaaaccaaccagagaagcaacattttgagatttcagccgcccaaagccaagtgctggctctcactcatgtgtgagacgatg
gagccagagcaaccaagtccagagaactccgcactagcctacactcacttgggccgctagccatcccccacccctgtaagagaggaagagacctccaatctcaactccca
cagcttgctgctgcattggccgccactagctctacaaaacccaggcctaaagccacaaccccaagaagtccaaaccccgccaaacgtatgcgtaactgcat
gaagatggaagatgactgcatcttccggtgatgctgctcgatcgatgtctggtgaaagcttaacggtgcttgctttagtgggatataagtcatgaaac
cagtccatgtgaaggcacggcacgatcgacaatcagaactagccaacattcaagaaaatcagcaagtatgatcagaagtgtcaa
gtccgggtgcatgaatcagacgcatccacaaggcatcagaagaaccagaaggagctacccatgcgccatggcaccatgggccagtgcaa
ttagccaatgcgtaggagttaccattccgacgcgtctccggcgtcctctggcaactcggagacagccatccgctgtcaccgtgtcaccactggcctgcgtctgcgaaataaaggaatatggtgaccgcaacg
gcccaatgtcatgcatgagcaccagtcatccgacagccatggcccatccttgcaaactggccgacagtcactattgtcctctcaaccttgtcgtgtcactacggacactactcacgtcatgcactgggctgcgtaagaagtactatcagcaactatcgttccgtgtcgtgtcaccactggagctgtc
acctgaagaatcagtggaggtcgccgccgcgccgctcggctgacgcgcgcactgtataaacgcactactgtctctccgaacttatcgtcttccgtcgtcgtgtcacgagcaataacac
caccatgtgcaccatgcccgtgtcgaaagagccctgcggaaaagaagaagaccctgcgttcgtcgtgaaatggtgtgtctgatgacgaagttccgccgtaacttgtcgtgtcaccactgctaagattgtgtctgaccaccaagattgtgtctgaccactgacaaccactactaccaacccaagttgtcgtgtcaccactgctaagattgtgtctgaccaccaagattgtgtctgaccactgacaaccactactaccaacccaagaagttattatgaat FIG. 21B (continued)

FIG. 21B (continued)

```
catcggattggcggagtagcggagtagccacatcctacacatcaataagtagtaagtgtgccatcacagccactccgaactccgcaacg
atgaaggatctgcaggatgtgccaggaaagcggcgccttgtcgcttgtcttgcgacttcctgtctcgagccgaacttcgtggtccaag
tgtgtaacgccgcggatcacttgccatggatcagcactgtgaaccaccgaaagaccacatcgtaccatacgcagccaaacacaacgacggcg
agttccatccatccatcctactacagctgccaatggtcaatggtggcaatggtggcaactcaaggccactacactctgtggtagccattatagtcgtt
gtgagtatccattgagtatgtagtcagacactagagatcgtcctttctaataaaatgaggaaattgcatcgcattgtcgtagtagtgtcattcatcgaa
ccttgaccctggaaggcgtgccatccctactgtccttcctaataaaatgaggaaattgcatcgcattgtctgagtagtgtcatctatctgaa
ggaggtggagggtggcaggacaagcaagggaggatggaagacaatagcagcatgtgggagatgcgtgtggagctcatgggta
cccaggtctgctgaagaattgacccggttcctcctggacactcatagctcaggagaggctcgcctcaaatcccaccgtcaaagtactggagtggt
ctgtccttagtcctcatgagtctcaggacactcatagctcaggagaggctgcctcaaatcccaccgctaaagtactggagtggt
ctctccctcgtcatcagcctcaatgctctcaacatgtgaggaagtaatgaggaagatcaatataggaaggcatgttaaggccatgtcattaagtgcagagg
gagagaaatgctctcaacatgtgaggaagtaatgaggaagatcaatataggaaggcatgttaaggccatgtcattaagtgcagagg
ccgttcctcgctcactgactgctgctgctcgggtcgtcggagccgtatcagctcgggatcacagtcgggtatacgctatac
acagaatcaggggatatacgctccgccccctgacgaaagaacatgtgagcaagagacgctcaagtcagcaggaggtggcgaaaccgacgacaggactataa
gcgtttccatagggcgtgcccccctgacgaaagaacatgtgagcaagagacgctcaagtcagcaggaggtggcgaaaccgacgacaggactataa
agatccaggcgttcccctggaagcgtttcatagctccacgctagtagtaccgtcagttcgtgtaggttcgtgctccaagctcggctgtgtgcacgaac
cggaagcgtggccgacgctggccgctatccgccattcacgctagtagtaccgtcagttcgtgtaggttcgtgctccaagctcggctgtgtgcacgaac
ccccgttcagccgaccgctggccgctatccgccttaatctcgggtatgtggccttgaagtggtggcctaactaggctacactagaa
gccactggtaacaggattaggcaggcggagcggctatgtaggcggctcactagagtgtggctacactagaa
gaacagtattggtatctgcgctctgccttgaagccagtatccggctaccttcgggaaaagagttggtgggtgctactttgatctgatccgggcaaacaccgctg
gtagccgtgtgtttgtttcagcagcagatccgcgcagatccgggaaaaaaggatccaagaggatccaagaggatcttacctaccgggtctgaac
gtcagtggaacgaaaactcacgttaaggattgctcatggattgtcatggagtcacactcaccctcaactagatccttaattaaaatgaaagaag
tttaaatcaatcaatctaaagtatatatgaaactcgctctgacagtaacctcgctttaatcagtgaggcaccatcagcgatcgtctatttc
gttcatccatagttgcctgactcgggggggggggggtggctcgagtctgcctcgggtcgctgaagaagttgtgcgatcatccagcctgaat
cgccccatccagcaatctcgcgttctgggaagatgcaagaagccagttaaccttcaactcagcaaaagtcgattgtgattgaactttgcttt
gccacggaacggttcgttgtcgggaagatgcgtgtatctgatccttcaactcagcaaaagtcgattgattcaacaaagccgctc
cgtcaagtcagcgtaatgctgtaacatcgggtaagagcaagaactcgattcaacaaagccgctcgattttgaaatgaactgcaat
tattcatatcaggattacaatctcaattcgttctgtaatgaagaagaaaactgacaatctgataagaaactgacaagccgtcgaatcaatagccgttcgaagcagtccagcg
```

FIG. 21B (continued)

agatcctggtatcgattcgatccgattcgatgattgcaacatcaatacaaccatataattcccctcgtcaaaaataaggttatcaagtgagaa
atcaccatgagtgacgactgaatccggtgaatccgggtgaagcttatgcaaaagcttatgcatttcttccagactgttcaacaggccagccattacgctc
gtcatcaaaatcactcgcatcaaccaaaccgtattcattcattgcctgagcgagacgaaatacgcgatcgctgtaaaaggac
aattacaaacaggaatcgtaatgccaaccggcgcagtaagcgccatcaacatatttcacctgaatcaggatattctcaata
cctggaatgctgttccgggatcgcagtgctggagtaaccatgccatcatcaggagtaccggataaaatgcttgatgtcggaagagg
cataaatccgtcagccagttagtctgaccatcatcgtaacatcattgccaacgctaccttgccatgtttcagaaacaactctgccg
catcggcttccatccatccgatagattgtcgcacctgattgcccgacattgccgagccagcattataccccctgtattactgttattgtaagcagacagtt
gttggaattaatcgtcggcctcgagcaagacgtttcccgtttgaatatgctcataacacccgtggctttccccccccattattgaagca
tattgttcatgatgatatatttttatcttgtgcaatgtaacacatcaagaatttgagacacaaacgtggcacactgggttccgcacattcgtc
ttatcagggttattgctcatgagcggataacactattgaatgtatttagaaaaataaacaaatagggttccgcacattcgtc
gtgccacctgacgtcaagaaacttattatcatgacattaacctaaaaaaatggcgtatacgagccettcgtc

FIG. 22B

SEQ ID NO: 18

FIG. 22B (continued)

```
gttctgctggacgctgctctgaggtgctgcacgaggcacgtcagaatcaagccacgatgactcactctcacagcaccgtacc
tcggcttgtcacagatgtaagacgatgaacatgcctacacccttataaaatcgaaaaagtgtggatgatgccgatgacggagt
ctccgtatcacaagtaagtcccagttaagtacaacagagcgggcactgcagtcagctagcgccgccgatccgttcatgggcggaggagt
gcctccggaaatccaagaggagaacaatgcaatgcagatttaagtcttcacgtccaaaccatgttacaccatccaatcacataaaggatactttgtc
attgtcaagtgccctctgttgatagatgattacaacatcattgaaagtcatgcatgctcggatcaaaaaccttgccatgatcacaacttgcaatcaatgcgagtaggtt
acaagtctgtaggcaggaaaaatatactctgccaccaaatgcatggagacaaaatacctgcttactctacgaaaggacacgagaga
aaagtcaggatacgtgaccatgcatcgtccccgacaacaatccataacatcgtgatggaagaagcggaggaggtacgta
caaccgacagtgccgaacagtcactcagtcacctacgagtgtaaatgcggagctgtaaactggggactgtcactgcgcactaaaatagac
ggctgtacagaaagggaaaacaatgcattgcgatttctgccgaccacgtcaaatgggttaactccctgactgatcaggcataccga
ccaacacagcccaaggagttgcatacctactaccatccgctacagcagtcaatgtacagtactaccccattgccgccacccttccaggcgtaag
catcctacgcagatgtctctgacactgcaggtcacgctgagctgctacaccgccatctgagtattctggaaatcagaaaccggtccga
cagaatgcggtgttcggagtggtaactggccaccgtgaatctcgaaatcatcatgctgccaatcgtacgccatactggaaatcgaccacctccagccactg
gtgtacgccgcaggaatcgcacctgaatcctgtcaatccatcatggctgccacatgaaatgtacgccattactacaccacctctatccttcctaccac
gttacagtgctgagcggagcggaggactgccatggccatatgcgctagtgtcgatcagattatgcgtcgcaaagcaagaagggattgccta
acaccctaccaactggccgccgaacgctacgtaccgtaccattctggtactaacaattgttgtcttgcaacgacctcaggcgacttacggatgaattaccg
ataccatggtacctatgccaacacagtcaaacatgtctgatacaaagggacgccctactacgatcactactgtcccaaatgcgccgtt
tgctcctgtgctactctttttattggttgccagtcggaactgctcctaacaaagcggacgcctacgaacatcacgatcatgtcatgaaccagatcataccatcgg
gaactcgtaaagtcactagtggaacggcctggtatgcccccttgaatcttgaagtcatggttgcgaactgtcgaatgcccgaaaggtg
ttaaacgtaataaataccgcagttacctgtgtcaccgttcttcaccgcagattaaatgttgcggaactgtcgaatgcccgaaaagtc
aaaaagcagactataccctgcaactagtcgaacctgcagttgtcgtaccacaccgttgtgtcgaaccagatgttggactccgaaaacagtc
agcttagcgacaagtacgtcgaactcacagagcacagagagcaccacccccagctcgtcagagtcacacgctcggtgatcgtgaat
cacagcctccgaataaacctacgggaactccacacagacgtagtcaaacctgtgtactccagccaggagcaaagagacaga
aattgataggcgccccattactactaccatttcccgttgataataagtcattatataatcatgggaaaagtctatacatagtgactccgga
atttggcccgaagaacactggagcttcggagatgtccaagcgtcatccaccaaccgcggttcgaattctggaagaataacagcggtcag
gcaagagcccggagccggagaccagaaaacactacctcccgtacaacccaagcaggtccaagcaagtccgtcagacaagtgtgccgtggatcatcccgatatcc
ccttatctgacactgcccctttccgatcaaagtcaatgcaagtcagtcaacggtacgtcagaacaagtgtgccgttaagtgcaccgttactagttgcacatactcta
gtggatataccggcgctgcattacacgcgtatccgagcccctgccatcactgcttaagtgcaccgttactagttgcacactactcaca
```

FIG. 22B (continued)

gactatggcggagtgctcgttgacatacgagtcgattcgcggggcaatgcgctgtacactcgcatcatcaacagcgtactgc
gagcccatcggtatacgtcgagagcactgcaatgccaatgcaactgaaggagccagagagagacttcgaggtatcgatg
tgcggaacggagaactcactttgccatgccatcatgcaactgcaaccacccaacggaacacgcgttatgacagaccccagaagtgactccagactc
tcctcagtcgatatccaaacatcatggaactgcgattacagcgcttatgggaattccagtagctgctatagccgcaatgtgctg
gtcatagcattagctattacagcacaacacagatgatcgaacagagccccgtcctgaccgcagtctgctgtccttcagtgccagtcatcg
ttgtttgccctcccccgtgctgtccttcgtgaccctgaaggtgccactccccactgtcctttccaataaaatgaggaaattgcatcgcattgtc
tgagtagtgtcatcttatccggtgaaggagtggggcaggacaagaggattgggaagacaatagcagcagccatgctggg
gatggtgggtcctcatatggtaccccagttgctgaagaattgacccggttcctcctgggccagaaagcagtctcccgcttcaatcca
gtgacacacccgtgtcccacgccctgttcttctagttcccctcccatcagcactatagggacactcatgcctcaggagtccctcgcttcaatcca
cccgcttaaagtacttggacggtctcctccccctcatcagccctccccaaaccagcctcagagagtcctccaagagtggaagaaattaagca
agtaaggcattaagtgcagagagagagaggaagaaaatgcctccactgactcgtcgtcgctcctcggtcggcgtgcgaggcggtatcagtcact
taaggccatcatggccttaaactccgcttcctcgtccactgactcgtcgtcggtccggtggtaacgcggggtgcacatgaggaaaagccagga
caaggcgtaaaacgccgttgctcggcgttttccatgaggaataacagaggaaaggtcagggaaaaatgacgctcaagtcagaggtg
acggaaaaaggccgccgttgcctcggcgtttccatgaggatacccaaaccccccctgaaggcctccatgctgcgctcctgtccatcctctgtccgaccctgccgcttacc
ggaaaccgcgacaggactataaaagataccaggcgtttccccctgaaggctcctgtccgacctgttcagtcagtcgctctcgtaccctgcgcttacc
ggaaccctgtccgcctttctccttcgaaccccccgttcagccccgaccctatccggaagctgtaggtatcgtcagttcgctgtagtgcgttcgctc
caagctgagctgtgtccaaccgtccctcagtcgagcagttgccgttgtcggccgttattgagcctgaaggtacctccaacccggtaa
cacgactgaccactatcagcctgcagcagcacctgatcaagagattggcagcaggaagcagcagattacgccgcagaaaaaaaggatctcaagaaga
tgcctacactaggctcagcgatcctgaagaacaggcgtctggtccatttggtactcctgaaagccagttactcggaaaaaagatgggtctct
tccttcgatctttcctacgggctgctcagcgtttaactaaatcaaagatcaaaaggatcttcacctggaaaactcactcaagaaaggatcttca
cctagatcctttaaattaaaaatggaagttttaaatccaatcaaagagttggcgctgactgcctgactgctgcggcaagatgcagtgaagat
ggcacctatcctatccagcatcgtgctattgctatttgctcatccctgcccactgctctgccaatgcccagcgttgcgatgcctgccctgtgaagag
gtgttgctgactataccaggtccgcgtccgtaatgcgcgcagtgcgtaatctcgccagttccagttacaaccaattctgattagaaaact
gaccagtggctgatttgaacttgaacttgcttgccaacgacttgcgttgtcggagaaagaatgctgacctgatccttcaactcagcaaaagtt
tcgattattcaacaaagccgccgtcccgtcaagccgtaatgcgttacaaccaattctgattagaaaact
catcgagcatcaaatgaaactgcaattatcaggattatcaatcaggattatcaatccattttgaaaaagccgtttctgtaatgaaggaaaact FIG. 22B (continued)

caccgaggcagttccataggatggcaagatcctgtatcggtctgcgattcgactcgtccaacatcaatacaacctattaattccctc
gtcaaaaataaggttatcaagtgagaaatcaccatgagtgacgactgaatccgtgagaatggcaaaagcttatgcattcttccagac
ttgttcaacaggccagtccagccattacgctcgtcatcaaaaatcactcgcatcaaaccgttattcattcgtgcgcctgagcgagacg
aaatacgcgatcgctgttaaaagaacattacaaacaggaatcgaatgcaaccggcgcaggaacactgccagcgcatcaacaatattt
tcacctgaatcaggatattcttcaataccctggaatgctgttttcccgggatgcgcaggatggtgagtaaccatgcatcatcaggagtacgga
taaatgcttgatggtcggaagaggcataaaattccgtcagccagttagtctgaccatctcatcgtaacatcattggcaacgctcacttg
ccatgtttcagaaaacactctggcgcatcggcttcccatacaatcgatagattgtcgcacctgattgcccgacattatcgcgagccatt
tataccatataaatcagcatccatgttggaatttaatcgcggcctcgagcaagacgtttcccgttgaatatgcctcataacaccctgta
ttactgtttatgttagcagacagttttattgttcatgatgatatattttatctgtgcaatgtaacatcagagatttgagacacaacgtggcttt
ccccccccccattattgaagcattttcaggttatgtctcatgagcggataacattgaatgtatttagaaaaataaacaaatagg
gttccgcgcacattcccgaaaagtgccaccgactgctaagaaacgctaagaaacaccattaattatcatgacattaaccttatgactcacga
ggcccttcgtc FIG. 23B (continued)

SEQ ID NO:19 atgagcctgcccctccgtcttgtgcctgttggcaaacactacattccctgctctcagcgcgcttgcacacccctgctgctacgaaaaggaacc
ggaaagcaccttgcgcatgctgccgttgaggacaacgtgatgagaccgatactaccagtactaaaagcatcgtgacttgctctcccacgcc
aaagacgcagtactaaggacaatttaatgtctataaagccacaagaccatatcagtcattgtcctgactgcggagaaggcattcgtgcca
cagccctatcgcattggagcgcatcagaaatcaggagctctttgcagatcgcaggataagacagat
gacagccacgattggaccaagctgcgtatatggatagccataccgcggaaaggagagagcgtgacagtgggatttgcttgtaaggacttcagcac
cgtgcacgatcaccgggacaatgggaccactttattctgccgatgccgaaaggaagagagcgctgacagtgggatttacggacagcagaaa
gatcagccacactgcacacccgttccatcatgaaccactcgtgataggtaggaagagttccactctgaccacaacatgttaaagagt
tacttgcagcacgtacgtgcagagacaccgctgcagtgctgagggaagtgcatatgccccagatactcctgaccgcacgctgatg
accgcagcagtctgcaacgtgaagatcacagagtgggcagacagtggtgcgtacaagtgcggtggctcaaacgaggactgaca
accacagaacaagtgatcaataactgcaaaatgatcagtgccatgtcagtcgcaataacaagaattggcaataacactccccttagtcc
cgccacgctgaactcggggactgtaaggaccgtaagaaagatcaccatggcaaacgtgacttgcagagtgccaaagcaagaa
acctacagtaacttacgaaaaaaacaagtcaccatcgctgctatcctgaccatcgacactcttgtcttaccgtaacatggagacaggaac
aaattaccacgagagtgggtgacacaacaagaggagtacttgaccgtgcctactgaggtctgaggtcacttgggcaacaacgaa
ccatacaagtactgccgcagatgcctagggcctcttgctcatgtcaccacacagagtaatcttgtactattatgcgcacggccagatgcattaca
actgtagtcattgttgtgtggcctctgtcgtctgtcgatggtgggcacagcagtggaatgtgtgcgcacgcgcagatgtcattacgaggctg
ccatatgaattaacaccaggagcgaacagcagccctgcgcctctcagcgctatgcagcgctcttatccccgctggcagcctcttgtaactttgaaactctt
cggcatgctgctgtaagaccctgcttttttagccgtaatgagccatcgggtgccgcgtgagcgcgtacgaacacgtaacagtgatcccgaac
gccatgcctgctgtaagaccctgtataagactctgtcaacagcaccggttgcaaaactgtgttgagatgagtgctgtggtacagcagagtcaaggacaag
acgtgggagtaccgtataagactctgtcaacagcaccggttgcaaaactgtgttgagatgagtgctacaatcagtcacttggaacca
acactgtcacttgactacatcacgtgcgagtacaaactgtgagtctgcaaaacagagtttgcatcggcctacagagcccacacgagccatcggctcgtcggcaagctc
ageggaggcacatgagagaactacagctggtcaaagtctgaattcgcaaaacagagttgcatcggcctacagagcccacacgagccacgagccatcggctcgtggc
cgcgtcctttaccaagaaaacaacattaccgtagctgccctaacgtgaccatgccgtcacagtaaaggacgcaagccaagccaagccactcctttggctgtgggc
ccaatgtcctccgcctggacaccttttgacaacattcaaagtcgtacaccgaaaatcgtacaaaggcgactaccaccaccagttggcgcaggaa
gaccaggaccaattggtgacatgtacaatgaccatctcagcaattggctcaaagctgacattggctgaaggaacgagagagcatcgtacagcagca
ggcacggtactaccatctctcagcacgtgcttcaagtgtattggcaagtgaaggaacgagaggcacacgagagcatcgtacagcagca
ggcacggtactaccatctctcagcagccaccatcgctggcacatcgcttcaagtattggctgaaggaacgaggagagcacacgagagcacgcaccgtt FIG. 23B (continued)

cggttgccagattgcgacaaacccgtaagagctgaagagtgtaaattgcgctgtggggaacataccaattccatcgacataccggatgcggccttact
aggtttgtcgatgcaccctcgtaacgacatgtcatgcgaagtacgaagcctgcactcactcctccgactttggggcgtcgccatcatcaaata
cacagctagcagaagtaaatgtcagtacattcgatgacgccgcagcctgccgttaccattcgagaagccgacgtagaagtagagggaactc
ccagctgcaaatatcctctcaacagccctgcaagcgccgagttttcgtgcaagtgtctccacacaagtacactgcgcagcccatgcca
ccctccaaaggaccacatagtccaattaccagcatcacacaccacccttggggtcaggatatatccacaacggcaatgtcttggtgcaga
agattacgggaggagtaggattaattgttgctgttgctgcctaatttaattgtggtgctatgcgtcgtcgtttagcaggcac SEQ ID NO: 20
atgagtcttgccatcccagttatgtgccigtgtggcaaacaccagttccctgctccagcccttgcacgccctgctgctacgaaaggaacc
ggaggaaacctacgcatgcttgaggacaacgtcatgagaccttgggtactatcagtcgtacaagcatcttaacatgttctcccacccgcca
gcgacgcagcaccaaggacaacttcaaatgtctataagccaccatactttagctcactgtccgactgtggagaaggcactcgtgcc
atagtccgtagcacggcatcacagaaatgaagcgacagcgggacgtgaaaatccagtgtcctgcaaatcgaatcggaataaagacgg
atgacagccacgattgaccaagtcgcgttatatgacaaccacatgccagcagacgcagagaggcggctattgtaagaacatcag
caccgtgtacgattactggaacaatggacacttcaccagccgccgatgtccaaaaggaaactctgacgtgggattcactgacgtagg
aagattagtcactcatgtcacgaccactttcaccagaccctctgataggtcggaaaaaattccattccgaccgcagcacggtaaagag
ctaccttgcacgtacgtgccaacgtaaagatcacagcctgaaggatagagaggtacacatgtccccagacacccctgatcgcacatta
atgtcacaacagtccgcaacgtaataactgcaggtcattgatcatgcaagtgttacagttcggtgctcaaatgaaggactaa
caactacaaaggattataatgattcaaggttgcagtgaaaaccagtagcttccgcgtaacatgtaacatcagggtgcctaaagcaagg
cccgcgtaatgctgaacttgggaaccggaaaaggaaaaacccagtcatcatcatgctactactgtatcctgtcaccgagatgggagaaga
aaccccacgtgacgtacgggaaaccgtaagcataagaggaagtcgtgcaacctgccgactgaagcgtcgaggtcacgtggcaaca
agaaactatcaagaagattattggccgcagttatctcacaaacgtagccatgccaccccgtgcgcaccccatgagagatatctgtattattatgagctgtaccc
actatgactgtagtagttgtcagtgccacgctcatactcctgtcgtgatggtggatgcgaccgccgatgtgcacgacggcagatgc
atcacccgtatgaactgaccaccaggagctacgcgtccttcctgctacctaaagccttgtttggctacaagccctattccgctggcagccctgattgttcatgcaactgctga
gaggcgtgcgatatacctgtggaacgtggaacagcagtcgtggccaacacgtgccgccacactgagcgcgtacaacagcggccacataccaa
gactcttaccactgcgctcgtgaaaacgttggcttttttagccgtaatgagcgtcggtgccacacgtgagcgctacagtaacagtagatcc
cgaacacggtggagtaccgtataagactctagtcaatagaccttggctacagccccatggttattggagatgaactgctcagtcacttgtga FIG. 23B (continued)

gccaacactatcgcttgattacatcacgtgcgagtacaaaccgtcatccgtccgtcgtgaagtgctgcgtacagcagagtgcaagga
caaaaactacctgactacagtcgtaagtcttcaccgggtcaccggtgtcaccatttatgtgggggcgcctactgcttcgcgacgctgaaaacacg
cagttgagcgaagcacacgtggagaacacgtccgaatcatgcaaaacagaattgcatcagcatacaggtcatacaggtctatacgcatctgcatcagctaa
gctccggtccttaccaaggaagaaataacatcactgctactgccatgcaaacggcgaccatgccgaccatgccgtcacagttaaggacgccaaattcattgtg
ggccaatgtcttcagcctggcgacaccttcgacaacaaaattggtgtacaaagtgactgtctataaacatgactacaactgtactgcagagaccggc
gaagaccaggacaatttggcgatatccaaagtcgcacacgtccgagagtaaagacgtctatgctaataacaagcgggcgtcgctgcagcacagtacc
tgtgggtacggtacacgtgccatctctcaggcaccatcgcctttaagtattgctaaaagaacgcgggcgtcgctgcagcacagtacc
atttggctgcaaatagcaacaaccgtaagagccgccctctttaacgacatgtcgtgcgaggtaccagctgcaccattcctcagacttttggggcgtcgccattat
cttcactagggtcgtcgacgcgcgcctcttttaacgacatgtcgtggtcattcgatgactaacgcgtcactattcggaagcgtgagatagaagttgaagg
aattctcagctgcaaatctcttttctcacgcgcgcctttagccagccgggtcactactaccggtcacataccacctcgggatccaggacatccgctacggcgatgtcatgggtgc
cacccccgaaggactgggaccacatagtcaactaccggtcacataccacctcgggatccaggacatccgctacggcgatgtcatgggtgc
agaagatcacggaggagtgtggggactggttgctgttgctgccgcactactgtgtgctatgcgtgtcgttcagcaggcac SEQ ID NO: 21
Atggagttcatccgcgaccgcaaacttttctataacagaaggtaccaacccgaccctggcccaccgacccctacaattcaagtaattagacctagacca
cgtccacagaggcaggctgggcaactgggcactgctcccgcagtcaacaaattgaccatgcgcggtacctcaacagaagcctcgagaa
atcggaaaagacaagaagcaggcgccgcaaaacgaccaaagcaaaagaacaaccaccaaaagaagccggctc
aaagaagaagaaaacaggccgtaggagagagagaatgtgcatgaaagtgcaagcacagtgatcttcgaagtcaagcaagtgatggg
ctacgcatgcctgtggggataaagttgcacagataccggtgcacatgaagaactatcgacaatgccgatctggctaaactggcctttaagcggtc
gtctaataatacgtgtgaatgtgcagtattcaggagttcctgaagttacccagagccaagcaggagaacaggagaccggagggtactataactgg
catcacgagcagtcagtgccgttcactatcccgacgggcaagcggtgcaagcagcggcagaccgcgatcttcgacaac
aaaggacgtggtggccatcgtcctaggagggggccctagagcagcgaacgaaggtgcccgcacggcccctccgtgtgacgtggaacaaagacatcgtcaca
aaaattaccctgagggagccgaagagtgg

FIG. 23B (continued)

SEQ ID NO: 22

Atggagttcatcccaacccaaacttttacaataggaggtaccagcctcgacctgactccgcgcctactatccaagtcatcaggcccagaccg
cgccctcagagaggcaagctgggcaacttgccagctgatctcagcagttaataaactgacaatgcgcgttaccaacagaagccacgcagga
atcggaagaataagaagcaaaagcaaacaggcgccacaaacaacaaatcaaaagaagcagccacctaaaagaaaccggctcaa
agaaaaagagccggggacaaagtaatgaaaccagacgcacacgtaaaggggaccatcgcgataacgcctggccaaactgccttaagcggtca
cgcgtgcctggtgtggggggacaaagtaatgaaaccagacgcacacgtaaaggggaccatcgcgataacgccgacttggccaaactgccttaagcggtca
tctaagtatgacctgaatgcgcgcagatacccgtgcacagaagtccgacgttcgaagttcaccatgagaaccggaggggtactacaactgg
caccacggagcagcagtacagtcttaggaggagctaatgaaggagccctacagcccctctcggtggtgacctgaataaagacattgtcactaa
aagggacgcgtgttgccatagtcttaggaggctaatgaaggagccctacagcccctctcggtggtgacctgaataaagacattgtcactaa
aatcaccccgaggggccgaagagtgg

FIG. 24

Seq ID NO: 23

```
   1 atggctgcgt gagacacacg tagcctacca gttctactct gctctactct gcaaagcaag
  61 agattaataa cccatcatgg atcctgtgta cgtggacata gacgctgaca gcgccttttt
 121 gaaggccctg caacgtgcgt acccccatgtt tgaggtggaa ccaaggcagg tcacaccgaa
 181 tgaccatgct aatgctagag cgttctcgca tctagctata agcaggaaat
 241 tgaccccgac tcaaccatcc tggatatcgg cagtgcgcca aaactaatag agcaggagga
 301 caggaagtac cactgcgtct gccgatgcg cagtgcggaa gcaaggagga tgatgtcgga
 361 ttatgcgaga agctagcat ctgccgcagg gccgatgcg gatccgaga gactcgcca
 421 gatcggggac ttacaagcag taatggccgt aaaagtcctg gacagacacg tctctgctt
 481 acacacagac gtctcatgta gacagagagc gccagacacg gagacgccaa cattctgctt
 541 tgtacacgca cccacgtcgc tataccacca agacgtcgct atataccaag acgtctatgc
 601 ggttgggttc gacacacc cgttcatgta ggcgattaaa gcggtgcct acccctcata
 661 ctcgacaaac tgggcagatg agcaggtact gaaggctaag caatagtagg acggtatcata
 721 agacctgacg gaggtagac gaggcaagtt gtctattatg agaggaaaa agctaaaacc
 781 gtgcgaccgt gtgctgttct cagtagggtc aacgctctac ccggaaagcc gcaagctact
 841 taagaagctg cacctgccat cggtgttcca tttaaagggc aaactcagct tcacatgccg
 901 ctgtgataca gtggtttcgt gtgagggcta cgtcgttaag agaataacga tgagccagg
 961 ccctttatgg aaaaccacag ggtatgcggt aaaccaccac gcagacggat tcctgatgtg
1021 caagactacc gacacggttg acggcgaaag aatgtcattc tcggtgtgca catacgtgcc
1081 ggcgaccatt tgtgatcaaa acacggtca gaagtcacgc cggaggatgc
1141 acagaagctg ttggtgggggc tgaaccaatg aatagtggtt aacggcagaa gtaagtgggc
1201 tacgaacacc atgaaaaatt atctgcttcc cgtggtcgcc caaccttca aaagaacact
1261 aaaggagtgc cggaagataca tggaagataca ggggtcagag cacacggtct acagagaggcc
1321 gacctgctgc tgtctatggg cattcaagaa gcaataacga agctttgtgg taccgagtct
1381 tgataccaga aggttgtcaa tcccttgag gactagcggc aaatggttgt taagcaaggt
1441 gtggtcgtcc ggttgtcaa ttcccttgag gactagcggc aaatggttgt taagcaaggt
1501 gccaaaaacc gacctgatcc catacagcca gaagcccgga gaagcccgga acgcagaaaa
1561 agaagcagag gaagaacgag aagcagaact gacctaccac gccctaccac ctctacaggc
```

FIG. 24 (continued)

```
1621 agcacaggaa gatgttcagg tcgaaatcga cgtggaacag cttgaggaca gagcgggcgc
1681 aggaataata gagactccga gaggagctat caaagttact gcccaaccaa cagaccacgt
1741 cgtgggagag tacctgtgta tctccccgca gaccgtacta cgtagccaga agctcagtct
1801 gattcacgct ttggcggagc aagtgaagac gtgcacgcac caggaggta
1861 tgcggtcgaa gcgtacgacg gccgagtcct agtgccctca ggctatgcaa tctcgcctga
1921 agacttccag agtctaagcg aaagcgcaac gatggtgtat aacgaaagag agttcgtaaa
1981 cagaaagcta caccatattg cgatcgacgg acccagccct aacaccgacg aagagtcgta
2041 tgagctggtg agggcagaga ggacagaaca cgagtacgtc tacgacgtgg atcagagaag
2101 atgctgtaag aaggaagaag ccgcaggact ggtactggtg ggcgacttgc ctgtcttgaa
2161 ctaccacgaa ttcgcatatg aagggctaaa aatccgccct gcctgcccat acaaaattgc
2221 agtcatagga gtcttcggag taccgggatc tggcaagtca gctattatca agaacctagt
2281 taccaggcag gaccgtggtg ctagcggtga gaaagaaaac tgccaagaaa tcaccaccga
2341 cgtgatgaga cagagaggtc tagagatatc tgcacgtacg gttgactcgc tgctcttgaa
2401 tggatgcaac agaccagtcg acgtgttgta cgtagacgag accagtcgga gccactctgg
2461 aacgctactt gctttgatcg cccttgtgag aaagttgtac gttttgcgt tttgtggtga
2521 cccgaagcag tgcggcttct tcaatatgat gcagatgaaa gtcaactata atcacaacat
2581 ctgcaccaca gtgtaccaca aaagtatctc acactgcctg tgaccgccat
2641 tgtagtcatcg ttgcattacg caggcgtgt cagggcgtgt aatgagtaca acaagccgat
2701 tgtagtggac actacaggct caacaaaacc tgaccctgtg ttccaaaaat taacgtgctt
2761 cagagggtgg gttaaacaac tgcaaattga ctatcgtgga gaccgtgtca tgacagcagc
2821 cgcatccgct gggttaacca gggttaccagt ttaatgaaag ttaatgaaa
2881 cccgctctat gcatcaacgt cagagcacgc ctaacgtact cggaaggtaa
2941 actggtatgg aagacactt cagatgaccg gtgataaaag acgctgcaga acccaccaca
3001 aggaaacttc aaagcaacta ttaaggagtg ggaggtggag catgcatcaa tttgttgggc
3061 catctgcagt caccaaaatg cccaggaca attccaaaaat ctaaatgata ggcagtggtc
3121 taagagcttg gtccctatcc tcgaaacagc ggggatactca cctgaagtag ccctgaatga
3181 tcagataatt caagccttca aagagacaa agcatactca agaccaacg ctattttcta aacgttggt
3241 aatatgtacg cgcatgtatg gggtggatct gggtggatct ctatttcta tgttcgaatt
3301 gtctgtgtat tacgcggata accactggga taataggcct ggaggaaaa tgttcgaatt
```

FIG. 24 (continued)

```
3361 taacccgag gcagcatcca ttctagaaag aaagtatcca ttcacaaaag ggaagtggaa
3421 catcaacaag cagatctgcg tgactaccag gaggatagaa gactttaacc ctaccaccaa
3481 catcataccg gccaacagga gactaccaca ctcattagtg gccgaacacc gcccagtaaa
3541 agggaaaga atggaatggc tggttaacaa gataaacggc caccacgtgc cctggtgtcg
3601 tggctataac cttgcactgc ctactaagag agtcacttgg gtagcgccgt taggtgtccg
3661 cggagcggac tacacataca acctagagtt gggtctgcca gcaacgcttg gtaggtatga
3721 cctagtggtc ataaacatcc acacaccttt tcgcatacac cattaccaac agtgcgtcga
3781 ccacgcaatg aaactgcaaa tgctcgggg tgactcattg agactgctca aaccggcggg
3841 ctctctattg atcagagcat atggttacgc agatagaacc agtgaacgag tcatctgcgt
3901 attggacgc aagtttagat cgtctagagc gttgaaacca ccatgtgtca ccagcaacac
3961 tgagatgttt ttcctattca gcaactttga caactttca aggaattca caactcatgt
4021 catgaacaat caactgaatg cagccttcgt aggacaggtc accgagcag gatgcacc
4081 gtcgtaccgg gtaaacgca tggacatcgc tggaacgtc gaagagtgcg tagtcaacgc
4141 cgctaaccct cgcgggttac cgggtggcgg tgtttgcaag gcagtataca aaaatggcc
4201 ggagtccttt aagaacagtg caaccacgct gggaaccgca aaaacagtta tgtgcgtac
4261 gtatccagta atccacgctg atcccctaat cttctctaat tattcggagt ctgaaggga
4321 ccggaattg gcagctgct atacctctcc cgcaaggaa gtaactaggc tgggagtaaa
4381 tagtgtagct ataccctcc tctccacagg tgtatactca ggaggaaag acaggtgac
4441 ccagtcactg aaccacctct ttacagcat ggactcgacg gatgcagacg tggtcattca
4501 ctgccgcgac aaagaatggg agaagaaaat atctgaggcc atacagacg ggaccaagt
4561 agagctgctg gatgagcaca tctccataga gttcgcgtgc acccctgacag
4621 cagcttggca ggcagacac tctgcgatat gtccgtgtgc acccctgacag
4681 agggacccgt tttcatcaga cacggaaggc gcactgtact gcactacta tgtggccaa
4741 gcaaacagag gccatgagc tatggcggag atacatactac acactacta tgtggccaa
4801 caggcagaaa tgcccgttga ctgcccctg atatgcgcctg ggaaagtaa ttgaatcgat
4861 cctttgcgt tacgctatga atgctgcaga cgtcaccgg cccccaaaa ctgtcccgtg
4921 aagcataatt gtgtttctt cgtttcccct atgattc aaaagtac accacgtcac
4981 agtcaatgc tctaaggtaa tgctatttga tgctgcaca ccaaacgtg gagtcaaag
5041 ggaataga tcttcccagg agtctgcaca ggaggcgagt acaatcacgt cactgacgca
```

FIG. 24 (continued)

```
5101  tagtcaattc gacctaagcg ttgatggcga gatactgccc gtccgtcag  acctggatgc
5161  tgacgcccca gccctagaac cagcactaga cgacggggcg acacacgc  tgccatccac
5221  aacggaaaac ctgcgggccg tgtctgattg ggtaatgagc accgtacctg tcgcgccgcc
5281  cagaagaagg cgaggagaa  acctgactgt gacatgtgac gagagagaag ggaatataac
5341  accatggct  agcgtccgat tctttagggc agagctgtgt ccggtcgtac aagaaacagc
5401  ggagacgcgt gacacagcaa tgtctcttca ggcaccaccg agtaccgcca cggaaccgaa
5461  tcatccgccg atctccttcg gagcatcaag cgagacgttc cccattacat ctgggactt
5521  caacgaagga gaaatcgaaa gcttgtcttc tgagctacta actttcgag  acttcttacc
5581  aggagagtg  gatgacttga cagacagca  gtgggtatat atttctcgtcg gacaccggtc caggtcattt
5641  gttaagacta gacagggcag gtgggtatat attctcgtcg gacaccggtc caggtcattt
5701  acaacagaaa tcagtacgcc agtcagtgct gccgtgaac  acccgtgagg aagtccacga
5761  ggagaagtgt tacccaccta agctggatga agcaaaggag caactattac ttaagaaact
5821  ccaggagagt gcatccatgg ccaacagaag caggtatcag ccgtcaaac  cgccattcca
5881  gaaagcagca atcatccaga gactaacata aggctgccct gctgtaccgt gctgtaccgt
5941  cccaaagtc  cctacttccc tccaatcccg agcaggatgc aatgagttct ctccgatcaa
6001  cgtccgattg tccaatcccg agtccgcagt ggcagccatgc gatgcatatc tagctagaac
6061  ctatccaact gtctcatcat accaaattac cgacattcaat ccgtcaaaac tcaggagcta
6121  ggacggtcg  gagagttgcc tggaccgagc catcagaagc cgtgtaccgt cccattcca
6181  cccgaaacag cacgcttacc acgcgcagc  cacacagaaga aactgcaacg tcacacagat
6241  gaacacacta cagaatgtac tggcagcagc acctcaacgtg gagtgtttca aaaaattcgc
6301  gagggaatta cccactttgg actcagcagt attcaacgtg gagtgtttca aaaaattcgc
6361  atgcaaccaa gaatactggg aagaatttgc tgccaaaagc caactgagaa
6421  tttagcaacc tatgttacta aactaaaagg gcaagcctat tcgcaaaaac
6481  ccataatcta ctgccactac aggaagtacc aatggatagg ttcacagtag atatgaaaag
6541  ggacgtaaag gtgacttcctg gtacaaagca tacagaggaa agacctaagg tgcaggttat
6601  acaggcggct gaaccctttgg cgacagcata cctatgtggg attcacagag agctggttag
6661  gaggctgaac gccgtcctcc tacccaatgt acatacacta tttgacatgt ctgccgagga
6721  tttcgatgcc atcatagccg cacactttaa gccaggagac actgttttgg aaacggacat
6781  agcctcctt  gataagagcc actgcgctt  actgcgctt  actgcttga actgcttaga
```

FIG. 24 (continued)

```
6841 ggattaggg gtggatcact cccctgctgga cttgatagag gctgctttcg gagagattc
6901 cagctgtcac ctaccgacag gtacgcgctt caagttcggc gccatgatga aatcaggtat
6961 gttcctaaga ctgttcgtca acacattgtt aaacatcacc atcgccagcc gagtgctgga
7021 agatcgtctg acaaaatccg cgtgcgcggc cttcatcggc gacgacaaca taatacatgg
7081 agtcgtctcc gatgaattga tggcagccag atgtgccact tggatgaaca tggaagtgaa
7141 gatcatagat gcagttgtat cccttacttt tgtggagggt ttatactgca
7201 cgatactgtg acaggaacag cttgcagagt ggcagaccg ctaaaaaggc cgctggctga
7261 gggcaaaccg ctagcggcag gtgacgaaca agatgaagat agaagacgag cgctatactc
7321 cgagtgatc agatggcaac gaacagggct aattgatgag ctggagaaag cggtacagtc
7381 taggtacgaa gtgcaggta tatcagttgt ggtaatgtcc atggccacct ttgcaagctc
7441 cagatccaaa ttcgagaagc tcagagacc cgtcataact ttgtacgcg gtcctaaata
7501 ggtacgcact acagctacct attttgcaga aagtatctaa acactaatca gcctcgaccc
7561 gctacaatgg agttcatccc aaccaaact ttttacaata ggaggtacca gcctcgacct
7621 tggactccgc gccctactat ccaagtcatc aggccctca cgcgcgcgc gaggcaagct
7681 gggcaacttg cccagtcagt ctcagcagtt aataaactga caatgcgcgc caatgccacaa
7741 cagaaagccac gcaggaatcg gaagaatcaa aagcaacta aaaaacaaca ggcgccacaa
7801 aacaacacaa atcaaaagaa gcagccacct aaaagaaac cggctcaaaa gaaaaagaag
7861 ccggggcgca gagagaggat gtgcatgaaa atcgaaaatg attgtattt ctgggtcaag
7921 cacgaaggta aggtaacagg ttacgcgtgc ctggtggggg acaaagtaat gaaaccagca
7981 cacgtaaagg ggaccatcga taacgcggac ctggcgtgc cttggccttaa gcggtcatct
8041 aagtatgacc ttgaatgcgc gcagataccc gtgcacagga agtccgacgc ttcgaagttc
8101 acccatgaga aaccggaggg gtactacacg gagcagtaca gtcgcagga
8161 ggccgttca ccatccctac aggtgctggt ggccatagtc aaaaggag acagcggcac acccgatcttc
8221 gacaacaagg gacgcgtggt gacctgaccg gaataaagac ttaggaggag ctaatgaagg agccctgtaca
8281 gcctctcgg tggttcgccat ccagttatg tgcctgttgg attgtcacta aaatcaccc gttcccctgc
8341 gaagagtgga gtcttgccat acgcacgcc gaaaagtatg ctaatgaagg cgaggggcc
8401 tccagcccc cttgaggaca acctgggtac tatcagctac tacaagcatc ctaacactg
8461 cttgaggaca acgtcatgag cagcaccac gacaacttca cggaggaaac
8521 tctcccaccc gccagcgacg cagcaccttca atgtctataa agccacaaga
```

FIG. 24 (continued)

```
 8581  ccatacttag ctcactgtcc cgactgtgga gaaggcact  cgtgccatag tccgtagca
 8641  ctagaacgca tcagaaatga agcgacagac gggacgcgtga aaatccaggt ctccttgcaa
 8701  atcggaataa agacggatga cagccacgat tggaccaagc tgcgttatat ggacaaccac
 8761  atgccagcag acgcagagag ggcggggcta tttgtaagaa catcagcacc gtgtacgatt
 8821  actggacaa  tggacactt  catcctggcc cgatgtccaa aaggggaaac tctgacggtg
 8881  ggattcactg acagtaggaa gattagtcac tcatgtacgc acccattca  gctaccttgc
 8941  cctgtgatag gtcgggaaaa attccattcc cgaccgcagc acgtaaaaga catgccccca
 9001  agcacgtacg tgcagagcac cgccgcaact acggagaga  tagaggtaca cacagtcaat
 9061  gacaccctg  atcgcacatt aatgtcacaa cagtccggca acgtaaagat aacaactaca
 9121  ggccagacgg tgcggtacaa gtgtaattgc atgaaggact ccgaaaagga
 9181  gacaaagtga ttaataactg caaggtttgat ccgcgtcac  aacttgggga ccgaaaagga
 9241  aagtggcagt ataactcccc tctggtcccg cgtaatgctg aactgcctaa agcaaggaac
 9301  aaattcaca  tccgtttcc  gctgcaaat  gtaacatgcc gggtgcctaa ccaccccaaca
 9361  cccacgtga  cgtacgggaa aaaccaagtc atcatgctac tgtatcctga gtgtccttt  cctgcttagc
 9421  ctccctgtcct accggaatat gggagaagaa ccaaaatatc aagaagagtg gatgcagcgg gatatacctg
 9481  aagaggaaag tcgtgcact  cgtgccgact gaaggctcg  aggtcacgtg aagaggctgc agccctgatt
 9541  gagcgtata  agtggttgca gcagttattg  acaaacggta cagcccatgg gggcaaccac ttttttagcc
 9601  gagataattc  tgtattatta  tgagcgtgct acccatatga ctgtagtagt ccaccgcat  gatccgaac
 9661  gccacgttca tactcctgtc  gatggtggt  atggcagcgg ggatgcat   tgtgtcagtg catggattg
 9721  cgcagatgct gcatcagga  tgaactgaca ccaggagcta  ccgtcccttt  gtgtgcacga catcacgtgc
 9781  ctaatatgct gcaacctttt gtttggcta  gccacatacg aagaggctgc gatatacctg agagtgcaag
 9841  tggaacgagc agcaaacttt  gtttggcta  caagccctta ttccgtggc  agccctgatt atttatgttgg
 9901  gttctatgca actgtctgag actcttacca tgtctgtgta aaacgttggc ttttttagcc
 9961  gtaatgagcg tcggtgccca cactgtcagt gcttgagag  acgtaacagt gctacgtgc  gatccgaac
10021  acggtgggag taccgtata  gactcttgag tcgtcatccc aatagaactt catggtattg
10081  gagtacaaa  tcacacgtta catgtcagt  cactttcagt gtccgtac   gtgaagtgct agagtgcaag
10141  gagtacaaa  ccgtcatcc  gtctcatccc gtcttcaccg gcgtacagc  agagtgcaag
10201  gacaaaacc  tacctgacta cagctgacta gtcttcaccg gcgtctaccg gcgtctaccg atttatgttgg
```

FIG. 24 (continued)

```
10261 ggcggcgcct actgcttctg cgacgctgaa aacacgcagt tgagcgaagc acacgtggag
10321 aagtccgaat catgcaaaac agaatttgca tcagcataca gggctcatac cgcatctgca
10381 tcagctaagc tccgcgtcct ttaccaagga aataacatca ctgtaactgc ctatgcaaac
10441 ggcgaccatg ccgtcacagt taaggacgcc aaattcattg tgggccaat gtcttcagcc
10501 tggacacctt tcgacaacaa aattgtggtg tacaaaggtg acgtctataa catggactac
10561 ccgcccttg gcgcaggaag accaggacaa tttggcgata tccaaagtcg cacacctgag
10621 agtaaagacg tctatgctaa tacacaactg gtactgcaga gaccggctgt gggtacggta
10681 cacgtgccat actctcaggc accatctggc tttaagtatt ggctaaaaga acgcggggcg
10741 tcgctgcagc acacaggcac atttggctgc caaatagcaa caaacccggt aagagcggtg
10801 aactgcgccg taggaacat gcccatctcc atcgacatac cggaagcggc cttcactagg
10861 gtcgtcgacg cgccctcttt aacggacatg tcgtgcgagg taccagcctg caagtgtgcg
10921 tcagactttg ggggtcgc cattataaa tatgcagcca gcaagaaagg caagggaat
10981 gtgcattcga tgactaacgc cgtcactatt cgggaagctg agatagaagt tgaaggacgt
11041 tctcagctgc aaatctcttt ctcgacggcc ttagccagcg ccgaattccg cgtacaagtc
11101 tgttctacac aagtacactg tgcagcgag tgccaccccc cgaaggacca catagtcaac
11161 tacccggcgt cacataccac cctcggggtc caggacatct ccgctacggc gatgtcatgg
11221 gtgcagagaa tcagggagg tgtgttgctg gttgttgctg ttgccgcact gattctaatc
11281 gtggtgctat gcgtgtcgtt cagcaggcac taacttgaca attaagtatg aagtatatg
11341 tgtcccctaa gagacacact gtacatagca aataaatcact agatgcttat gctacgcaac
11401 cccgaataag taacaaaata caaaatcact gagaacatt aaaaatatca aatacataaa
11461 taggtatacg tgtccctaa gagacacatt gtatgtaggt gatagtata gatcaaaggg
11521 ccgaataacc cctgaatagt cacataccac gaaaatcaat aaaaatcata aaatagaaaa
11581 accataaaca gaagtagttc aaaggctat accataattg gcaaacggaa gagatgtagg
11641 ttaataaaaa tcaaatgaat tcaaatgaat gcaaacggac actttgagaa cataccgaac
11701 tcctaaaagc agccgaactc ctaggagcac actttgagaa gtaggcatag tttaatattt
11761 ttctccgaac ccacaggagac gtattggac ttattttgtt taattaatcg agggaatta
11821 aaaaaaaaa aaaaaaaaa aaaaaaaaa aaaaaaaaa aatgtgcgcg aatgtgcgcg
11881 attcttgaag acgaaagggc caggtgcac tttcgggga aatgtgcgcg gaaccctat
11941 ttgtttattt ttctaaatac attcaaatat gtatccgctc atgagacaat aaccctgata
```

FIG. 24 (continued)

```
12001 aatgcttcaa taatattgaa aaaggaagag tatgagtatt caacattcc gtgtcgccct
12061 tattcccttt tttgcgcat tttgcctcc tgttttttgct cacccagaaa cgctggtgaa
12121 agtaaaagat gctgaagatc agtgggtgc acgagtgggt tacatcgaac tggatctcaa
12181 cagcggtaag atccttgaga gtttcgccc cgaagaacgt tttccaatga tgagcacttt
12241 taaagttctg ctatgtggcg cggtattatc ccgtgttgac gccgggcaag agcaactcgg
12301 tcgccgcata cactattctc agaatgactt ggttgagtac tcaccagtca cagaaaagca
12361 tcttacggat ggcatgacag taagagaatt atgcagtgct gccataacca tgagtgataa
12421 cactgcggcc aacttactc tgacaacgat cggaggaccg aaggagctaa ccgctttttt
12481 gcacaacatg gggatcatg taactcgcct tgatcgttgg gaaccggagc tgaatgaagc
12541 cataccaaac gacgagcgtg acaccacgat gcctgtagca atggcaacaa cgttgcgcaa
12601 actattaact ggcgaactac ttactctagc ttcccggcaa caattaatag actggatgga
12661 ggcggataaa gttgcaggac cacttctgcg cctcggccct ccggctggct ggtttattgc
12721 tgataaatct ggagccggtg agcgtgggtc tcgcggtatc attgcagcac tggggccaga
12781 tggtaagccc tcccgtatcg tagttatcta cacgacgggg agtcaggcaa ctatggatga
12841 acgaaataga cagatcgctg agataggtgc ctcactgatt aagcattggt aactgtcaga
12901 ccaagtttac tcatatatac tttagattga tttaaaactt catttttaat ttaaaaggat
12961 ctaggtgaag atcctttttg ataatctcat gaccaaaatc ccttaacgtg agttttcgtt
13021 ccactgagcg tcagaccccg tagaaaagat caaaggatct tcttgagatc ctttttttct
13081 gcgcgtaatc tgctgcttgc aaacaaaaaa accaccgcta ccagcggtgg tttgtttgcc
13141 ggatcaagag ctaccaactc tttttccgaa ggtaactggc ttcagcagag cgcagatacc
13201 aaatactgtc cttctagtgt agccgtagtt aggccaccac ttcaagaact ctgtagcacc
13261 gcctacatac ctcgctctgc taatcctgtt accagtggct gctgccagtg gcgataagtc
13321 gtgtcttacc gggttggact caagacgata gttaccggat aaggcgcagc ggtcgggctg
13381 aacggggggt tcgtgcacac agcccagctt ggagcgaacg acctacaccg aactgagata
13441 cctacagcgt gagcattgag aaagcgccac gcttcccgaa gggagaaagg cggacaggta
13501 tccggtaagc ggcagggtcg gaacaggaga gcgcacgagg gagcttccag gggaaaacgc
13561 ctggtatctt tatagtcctg tcgggtttcg ccacctctga cttgagcgtc gattttgtg
13621 atgctcgtca tatgtcttct taccggtcg ccacctctga cttgagcgtc gattttgtg
13621 atgctcgtca tgtcttct gcctatgagc aaacgccagc aacgcggcct ttttacggttcctggcct
13681 tattgtcgtt agaacgcggc tacaatttat acataaccttt atgtatcata cacaatcgat
13741 ttaggtgaca ctatag
```

FIG. 25

Seq ID NO: 33

```
   1 atggctgcgt gagacacacg tagcctacca gttcttact gctctactct gcttagcaag
  61 agacttgaga accatcatg gatcccgtgt acgtggacat agacgccgac agcgccttt
 121 taaggccct gcagcgtgcg taccccatgt ttgaggtgga accaaggcag gtcacaccga
 181 atgaccatgc caattctcgc atctagctat aaaactaata gagcaggaaa
 241 ttgatcccga ctcaaccatc ctggacatag gcagcgcgcc agcaggagg atgatgtcgg
 301 ataggaagta ccactgcgtt tgccctatgc gcagcgcaga agaccctgag agactcgcca
 361 actacgcgag aaaactagca tctgcgcag gaaagtctt ggacagaaac atctccgaaa
 421 aaattggaga tctacaagca gtaatggctg taccagacgc agaaacgccc acattctgct
 481 tgcacactga cgtctcatgt agacaaaagg cggacgtcgc tatataccag gatgtctacg
 541 ccgtgcatgc accaacatcg ctgtaccacc aggcgattaa aggagtccgt gtagcatact
 601 ggataggtt tgatacaacc cgttcatgt ataatgccat gcaggtgca taccctctgt
 661 actcgacaga ctgggcagat gagcaggtgc tgaaggcaaa gaacatagga ttatgttcaa
 721 cagactgac ggaagtaga cgagttaga cgagttaga tgtctatcat gagaggaaaa aagatgaagc
 781 catgtgacg cgtactgttc tcagtcgggt caacgcttta cccggagagc cgtaagcttc
 841 ttaagagttg gcacttact tcagtgttcc atctaaaagg aagctcagc ttcacgtgcc
 901 gctgtgatac agtggtttcg tgtgaaggct atgtcgttaa gagataacg attagcccgg
 961 gcctctacgg taaaaccaca gggtacgcag taacccacca tgcagacgga ttcctaatgt
1021 gcaaaacaac cgatacggta gatggcgaga gagtgtcatt ttcggtatgc acgtacgtac
1081 ccgcaaccat ttgtgatcaa atgacaggta ttcttgccac ggaggttaca ccgaggatg
1141 cacagaagct gctggtggga ctgaaccaga ggatagtggt caatggcaga acgcagagga
1201 acacgaacac aatgaagaat tacttgcttc ctgtagtgc aaaacttttt ggcatcagca
1261 caaggaaatg ccgaaagat atggaaagatg aaaactttt ggcatcaga gaaaggacac
1321 tgacatgctg ctgcctttgg gcgttcaaga agcagagac cgaatttga tacaagaggc
1381 ctgacactca gtcaattcag aaagtccag ccgaattga cagctttgtg gtaccaagtc
1441 tgtggtcatc tggactgtcg atcccgctac ggaccagaat caagtggctg ctaagcaaag
```

FIG. 25 (continued)

```
1501  tgccaaagac tgatttgatc ccttacagcg gtgacgccaa agaagcccgc gacgctgaaa
1561  aagaagcaga agaagaacga gaagcggagc gaaactcgcg taactcgcga ggcactacca
1621  cggcacagga cgacgtccag gtcgaaattg acgtggaaca gctcgaagac agagctgggg
1681  caggaataat tgaaactcca agaggagcta tcaaagtcac tgcccaacca acagaccacg
1741  tcgtgggaga gtacttggta ctttcccgc agaccgtgtt acgaagccag aagctcagcc
1801  tgatccacgc attgcgggaa caagtgaaga catgcacaca cagcggacgg gcaggaaggt
1861  acgcggtcga agcatatgac ggctgccctc ttgtgccctc agctatgca atatcacctg
1921  aagacttcca gagcctgagc gaaagtgcga cgatggtgta caacgaaagg gagttcgtaa
1981  ataggaaatt acaccatatc gcgttgcacg gaccagccct gaacactgac gaggagtcgt
2041  acgagctggt aaggcagaa aggacagagc atgagtacgt ctatgatgtg gaccaaagaa
2101  ggtgctgcaa gaaagaggag gcagcccggc tggtactggt cggcgacttg accaaccgc
2161  cctaccatga gttcgcatat gaagggctga gaatccgccc gcctgccca tacaagacg
2221  cagtaatagg ggtctttga gtgccaggat ccggcaaatc agcaatcatt aagaacctag
2281  ttaccaggca agaccagtg agaccagtg agaaagaaaa ctgccaagaa atctccaccg
2341  acgtgatgcg acagaggaac ctggagatat ctgcacgcac ggtcgactca ctgctcttga
2401  acggactact tgctctgata gcccttggtga gacgaggca agcttttgcg tgccattctg
2461  gcacgtact tgctctgata gcccttggtga gacgaggca agcttttgcg tgccattctg
2521  atccgaaaca gtgcggcttc ttcaatatga tgcagatgaa agttaactac aaccataaca
2581  tctgcaccca agtgtaccat ccaggcggtg tacactgcct gtgactgcca
2641  ttgtgtcctc gttcattac aaaagtattt ccaggcggtg tacactgcct gtgactgcca
2701  ttgtagtgga tactacaggc gaagcacaac tgcgcacaa aaatgagtac aacaagccaa
2761  tcagagggtg ggttaagcaa tcgacaaaac ccgaccccgg agaccttgtg ctaacatgtt
2821  ctgcatctca gggctaacc ctgcaaattg acactcgtgg acacgaggtc atgacagcag
2881  accccttta cgcatcaaca tctatgcgt caggcaaaaa tctatgccgt gttaatgaaa
2941  aactagtatg aagacactt tctgagacc catggataaa gacactgcag aacccgccga
```

FIG. 25 (continued)

```
3001 aaggaaattt taaagcaaca attaaggaat gggaagtgga acatgcttca ataatggcgg
3061 gtatctgtaa ccaccaagtg acctttgaca cgttccagaa taaagccaat gtctgctggg
3121 cgaagagctt agtcccatc ctagaaacag caggataaa attaaacgac aggcagtggt
3181 cccagataat ccaggctttt aaagaagaca gagcatactc accgagtg gccctgaatg
3241 agatatgcac gcgcatgtac gggtagacc tggacagcgg actgttctct aaaccactgg
3301 tgtccgtgca tcatgcggat aatcactggg acaacaggcc gggaggaag atgttcggat
3361 tcaacccga agcggcgtcc atactggaga ggaattacc gtttacaaaa gggaagtgga
3421 ataccaaca gcaaatctgt gtgactacta gaggattga agatttaac ccgaacacca
3481 acattatacc tgccaacagg agattaccgc attcattggt ggccgaacat cgcccgtaa
3541 aaggggagag gatggaatgg ttggtcaaca aaataaatgg ccaccatgtg ctcctggtca
3601 gcggctacaa cctcgttctg cccactaaga gagtcacctg ggtggcgccg ctggcattc
3661 ggggagctga ctacacatac aacctagagt taggcctacc agcaacgctc ggtagatatg
3721 acctagtgat tataaacatc ttcgcataca tcattaccaa cagtgcgtgg
3781 atcacgcaat gaagctgcag atgctcggag gagactccct gagactgctc aagccgggtg
3841 gttcattact gatcaggca tacgctacg cagacagaac aagcgaacga gtagtctgcg
3901 tattggacg caagtttcga tcatccagag cgttgaaacc ataacggcag gccgtgcgtc actagcaaca
3961 ccgagatgtt tttcttgttc agcaactttg ataacggcag aaggaacttt acgacgcacg
4021 taatgaacaa ccagtcgaat gctgcttttg tggtcaggc caccgagca gggtgcgcac
4081 cgtcgtaccg ggttaaacg atggacatcg caaagaacag tgaagagtgt gtagtcaacg
4141 ccgccaacc tcgtggcta atggcgcgatg gcgtctgtaa agcagtatac aaaaaaatggc
4201 cggcgtcctt caagaacagt gcaacacccag tgggaccgc aaagacagtc atgtgcggta
4261 catacccggt aatccatgca gtaggaccta atttctcaaa ttactctgag tccgaaggag
4321 accgggatt ggcagtgct taccgagaag tcgctaagga ggtgtactc ctaggagtaa
4381 acagcgtagc tataccgctc ctttccaccg gtgtgtactc gtgtgtactc ctaggagtaa
4441 ctcagtcact aaaccacctt tttacagcat tagactcaac tgatgcagat gtggttatct
```

FIG. 25 (continued)

```
4501 actgccgcga caaggagtgg gagaagaaaa tagctgaggc catacaaatg aggacccaag
4561 tggaattact agacgaacac atctctgtag actgcgatat catccgagtg caccctgaca
4621 gcagtttggc aggtagaaaa gggtacagca ctacagaagg ttcactgtac tcctacttgg
4681 aagggacacg gttccatcag acggcagtgg acatggcaga agtatacacc atgtggccaa
4741 agcagacgga ggctaatgaa caagtttgct tgtacgcatt ggggaaagt atagaatcaa
4801 tcaggcaaaa gtgccagtg gatgacgcag atgcatcgtc gccccaaaa acgtcccgt
4861 gcctctgccg ttatgccatg acaccggaac gagtcaccag gcttcgtatg aaccatgtca
4921 caagcataat agtatgctca tcattcccc ttccaaagta taaaatagaa ggagtgcaga
4981 aagtcaagtg ttctaaagtg atgctgttcg accataacgt gccatcacgc gttagtccaa
5041 gggaatataa atcgcctcag gagaccgcac aagaagtaag ttcgaccacg tcactgacgc
5101 acagccaatt cgaccttagc gttgacggtg aggaactgcc cgctccgtct gacttggaag
5161 ctgacgctcc gattccggaa ccaacaccag acgacagagc ggtacttact ttgcctccca
5221 cgattgataa ttttcgct gtgtcagact gggtaatgaa acgagcagcg gtcgcaccac
5281 ccagaagaag acgtgggaaa aacttgaatg tcacctgcga cgagagagaa gggaacgtac
5341 ttcccatggc tagcgttcgg ttcttcagag cggatctgca ctccatcgta caggaaacgg
5401 cagagatacg gtctgtccgt gcgtccctcc aggcgccct gagtgtcgct acagaaccga
5461 atcaactgcc gatctcattt ggagcaccaa acgagactt cccataacg ttcggggatt
5521 ttgatgaagg ggagattgaa agcttgtcct ctgagttcct gaccttgtgg gacttctgc
5581 cgggcgaagt ggatgaccg acagacagcg actggtccac gtgttcagac acggacgacg
5641 aattatgact acgtgggaca gttgggtaca acagacaccggc tattctcatc tgacaccggc ccggccacc
5701 tgcaacagag gtctgtccgt cagacagtac tgccggtaaa tacccttggag gaagttcagg
5761 aggagaaatg ttaccacct aagttggatg aagtgaaaga gcagttgtta cttaagaaac
5821 tccaggaaag tgcgtccatg gctaacagaa gcaggtacca atcccgcaaa gtagagaaca
5881 tgaaagcaac aatatgact aggctgaagg gtggttgcaa actttattta atgtcggaga
5941 cccgaaagt tcctacctac cgaactacat atccggcacc agtgtactca cccccaatca
```

FIG. 25 (continued)

```
6001 atatccgact gtcaacccc gagtctgctg tggcagcgtg caatgagttc ctagcaagga
6061 actatccgac agttgcgtcg taccaaatca ccgatgagta cgatgcatac ctagacatgg
6121 tggacgggtc ggaaagttgc cttgaccggc cgacgttcaa cccatcaaag cttagaagtt
6181 atccaaaaca gcactcctac catgcaccca caatcagaag tgccgtacct tcccgttcc
6241 agaacacgct gcagaacgta ctggctgctg ctggtcgtg aaattgcaac gtcacacaga
6301 tgagagaact gcctactttg gattcagcgg tatttaatgt tgagtgcttt aaaaaatttg
6361 cgtgcaatca agaatactgg aaggaatttg ccgccagccc tattaggata acgactgaga
6421 acttgacaca ttatgtcaca aaactaaaag agcagcactg tttgccaaga
6481 cacataacct gctaccactg caggaggtgc gtttactgta gacaggtgaa
6541 gggacgtgaa ggtgactccg gggacgaagc acactgagga aagacctaaa gtgcaggtca
6601 tacaggcagc cgaacctttg gcaacagcat atctgtgtgg gatccacaga gagttggtca
6661 gaaggctgaa tgcagtcctt ctacctaatg tacacacgct gtttgacatg tctgccgagg
6721 actttgacgc cattattgcc gcgcacttca agccgtattg gaaaccgata
6781 tagcctcctt tgacagagc caagcgact cattggcgct cactgtctta atgttgctag
6841 aggatttggg ggtggatcat acttgataga ggctgccttc gggagatct
6901 ccagtgcca cctaccgacg ggcacccgtt taaagttcgg cgccatgatg aagtctggta
6961 tgttcctaac cctgttcgtc aaacactcac cttcatcgc catagccagc cgagtgctgg
7021 aggaccgctt gacaaggtct gcgtgcgcgg ccttcatcgg gtttgacatg ataatacatg
7081 gggttgtctc tgacgaactg atggcagcaa gtgtgctac atggatgaac atggaagtga
7141 agatcataga tgcgaggacg atgcgagag ccctgtactt ctgcggaggg tttatactgt
7201 atgacacagt agcagcacg gcccagcaa tggcgagacc gctaaagcgg ctgttcaagc
7261 tgggcaaacc gctgcagcg ggagatgaac cagaagacga cagaagacgt gcactggctg
7321 acgaagtggt tagatacgga cgaacaggaa taactgatga gctagacact gcggtacact
7381 ccaggtatga agtgcagggc acgatctgtc tggtaatgtc tatggccaagt tttgcaagct
7441 ctagatctaa ctttgagaag ctcagagggac ctcagagga ccgtcgtaac cctgtacggt ggtcctaaat
```

FIG. 25 (continued)

```
7501 aggtacgcac tacagctacc tatttcgtca gaaaccaatc gcagctactt gcatacctac
7561 cagctacaat ggagttcatc ccgacgcaaa attcaagtaa cttttctataa cagaaggtac caacccgac
7621 cctggcccc acgccctaca attcaagtaa ttagacctag accacgtcca cagaggcagg
7681 ctgggcaact cgcccagctg atctccgcag tcaacaaatt gaccatgcgc gcggtacctc
7741 aacagaagcc tcgcagaaat cggaaaaaca agaagcaaag gcagaagaag caggcgccgc
7801 aaaacgaccc aaagcaaaag cacaaaacca cacaaaagaa gccggtcaa aagaagaaga
7861 aaccaggccg tagggagaga atgtgcatga aaattgaaaa tgattgcatc ttcgaagtca
7921 agcatgaagg caaagtgatg ggctacgcat gctggtgggg ggataaagta atgaaaccag
7981 cacatgtgaa gggaactatc gacaatgccg atctggctaa actggccttt aagcggtcgt
8041 ctaaatacga tcttgaatgt gcacagatac cgtgcacat gaagtctgat gcctcgaagt
8101 ttaccccga gaaacccgag gggtactata actggcatca cggagcagtg cagtattcag
8161 gaggccggtt cactatcccg acgggtgcag gcaagccggc agacagcggc agaccgatct
8221 tcgacaacaa aggacgggtg gtggccatcg tcctaggagg ggccaacgaa ggtgccgca
8281 cggccctctc cgtggtgacg tggaacaaag acatcgtcac aaaaattacc cctgagggag
8341 ccgaagagtg gagcctcgcc ctcccggtct tgtgccgtgt ggcaaacact acattcccct
8401 gctctcagcg gcttgcaca cctgctgct acgaaaagga accgaaaagc accttgcgca
8461 tgcttgagga caacgtgatg agaccggat actaccagct actaaaaagca tcgctgactt
8521 gctctcccca ccgccaaaga cgcagtacta aggacaattt taatgtctat aaagccacaa
8581 gaccatatct agctcattgt cctgactgcg gagaagggca ttcgtgccac agccctatcg
8641 cattgagcg catcagaaat gaagcaaacgt gaaaatccag gaaaatcag gtctctttgc
8701 agatcgggat aaagacagat gacaagccg attggaccag gctgcgctat atggatagcc
8761 atacgccagc ggacgcggag cgagccggat tgcttgtaag gacttcagca ccgtgcacga
8821 tcacccggac catgggacac tttattctcg cccgatgccc gaaggagag acgctgacag
8881 tgggatttac ggacagcaga aagatcagcc acacccgttc acacatgcac catcatgaac
8941 cacctgtgat aggtaggag aggttccact ctcgaccaca acatggtaaa gagttacctt
```

FIG. 25 (continued)

```
 9001 gcagcacgta cgtgcagagc accgctgcca ctgctgagga cgtgcagagc gatagaggtg catatgcccc
 9061 cagatactcc tgaccgcacg ctgatgacgc agcagtctgg caacgtgaag atcacagtta
 9121 atgggcagac ggtgcggtac aagtcaact gcgtggctc aaacgaggga ctgacaacca
 9181 cagacaaagt gatcaataac tgcaaaattg atcagtgcca tgctgcagtc actaatcaca
 9241 agaattggca atacaactcc cctttagtcc cgcgcaacgc tgaactcggg gaccgtaaag
 9301 gaaagatcca catcccattc ccattggcaa acgtgacttg cagagtgcca aaagcaagaa
 9361 acctacagt aacttacgga aaaaaccaag tcaccatgct gctgtatcct gaccatccga
 9421 cactcttgtc ttacgtaac atgggacagg aaccaaaatta ccacgaggag tgggtgacac
 9481 acaagaagga ggttaccttg accgtgccta ctgagggtct ggagtcact tggggcaaca
 9541 acgaaccata caagtactgt ccgcagatgt ctacgaacgg tactgctcat ggtcaccac
 9601 atgagataat cttgtactat tatgagctgt acccactat gactgtagtc attgtgtcgg
 9661 tggcctcgtt cgtgttctg tcgatggtgg gcacagcagt gggaatgtgt gtgtgcgcac
 9721 ggcgcagatg cattacacca tatgaattaa cacccaggagc cactgttccc ttcctgctca
 9781 gcctgctatg ctgcgtcaga acgaccaagg cggccacata ttacgaggct gcgcatatc
 9841 tatggaacga acagcagccc ctgttctggt tgcaggctct tatccgctct gccgccttga
 9901 tcgtcctgtg caactgtctg aaactcttgc catgctttgc taagaccctg gcttttttag
 9961 ccgtaatgag catcggtgcc cacactgtga gcgcgtaaca acacgtaaca gtgatcccga
10021 acacggtggg agtaccgtat aagactcttg tcaacagacc gggttacagc cccatggtgt
10081 tggagatgga gctacaatca gtcacctgg aaccaacact gtcacttgac tacatcacgt
10141 gcgagtacaa aactgtcatc cctccccgt gtcacttgac gtcacttgac gcagagtgca
10201 aggacaagag cctaccagac tacagtgca aggtctttac tggagtctac ccattatgt
10261 ggggcggcgc ctactgcttt tgcgacgcg aaaatacgca attgagcgag gcacatgtag
10321 agaaatctga atcttgcaa acagagtttg catcggccta gaaacaacat accgcatcgg
10381 cgtcggcgaa gctccgcgtc ctttaccaag gaaacaacat taccgtagct gcctacgcta
10441 acggtgacca tgccgtcaca gtaaaggacg ccaagtttgt cgtgggccca atgtcctccg
```

FIG. 25 (continued)

```
10501  cctgacacc  tttgacaac  aaaatcgtgg  tgtacaaagg  cgacgtctac  aacatggact
10561  accacctt   tggcgcagga  agaccaggac  aatttggtga  cattcaaagt  cgtacaccgg
10621  aaagtaaaga cgtttatgcc  aacactcagt  tggtactaca  gaggccagca  gcaggcacgg
10681  tacatgtacc atactctcag  gcaccatctg  gcttcaagta  ttggctgaag  gaacgaggag
10741  catcgctaca gcacacggca  ccgttcggtt  gccagattgc  gacaaaccg   gtaagagctg
10801  taaattgcgc tgtgggaac   ataccattt   ccatcgacat  acggatgcg   gcctttacta
10861  gggttgtcga tgcacccctct gtaacggaca  tgtcatgcga  agtaccagcc  tgcactcact
10921  cctccgactt tggggcgtc   gccatcatca  aatacacagc  tagcaagaaa  ggtaaatgtg
10981  cagtacattc gatgaccaac  gccgttacca  ttcgagaagc  cgacgagttt  gtagagggga
11041  actcccagct gcaaatatcc  ttctcaacag  cccctggcaag cgccgagttt  cgcgtgcaag
11101  tgtgctccac acaagtacac  tgcgcagccg  catgccaccc  tccaaaggac  cacatagtca
11161  attacccagc atcacacacc  acccttggg   tccagatat   atccacaacg  gcaatgtctt
11221  gggtgcagaa gattacggga  ggagtaggat  taattgttgc  tgttgctgcc  ttaattttaa
11281  ttgtggtgct atgcgtgtcg  tttagcaggc  actaaaccga  tgataaggca  cgaaataact
11341  aaatagcaaa agtagaaagt  acataaccag  gtatatgtgc  ccctaagag   gcacaatata
11401  tatagctaag cactattaga  tcaaagggct  atacaacccc  tgaatagtaa  caaaacacaa
11461  aaaccaataa aaatcataaa  aagaaaaatc  tcataaacag  gtataagtgt  ccctaagtaa
11521  acacattgta tgtaggtagt  aagtatagat  caaagggcta  tattaaccc   tgaatagtaa
11581  caaacacaca aaacaacaaa  aactacaaaa  tagaaaatct  ataaacaaaa  gtagttcaaa
11641  gggctacaat acccctgaat  agtaacaatg  cataaaatgt  atcacacaaa  aagtgtgtac
11701  ccaaaagagg tacagtaaga  tacagtaaga  atcagtgaat  acttgagac   gagacgtagg
11761  tatttaagct tcctaaaagc  agccgaactc  agtaacaatg  gtaggcatag  cataccgaac
11821  tcttccacta ttctccgaac  ccacagggac  gtaggagatg  ttatttgtt   tttaatattt
11881  caaaaaaaaa aaaaaaaaa   aaaaaaaaa   aaaaaaaaa   agcggccgct  taattaatcg
11941  agggaatta  attcttgaag  acgaaagggc  caggtggcac  tttcgggga   aatgtgcgcg
```

FIG. 25 (continued)

```
12001  gaaccctat  ttgttattt  ttctaaatac  attcaaatat  gtatccgctc  atgagacaat
12061  aaccctgata  aatgcttcaa  taatattgaa  aaaggaagag  tatgagtatt  caacattcc
12121  gtgtcgccct  tattccctt   tttgccttcc  tttgccttgct tgttttgct   cacccagaaa
12181  cgctggtgaa  agtaaaagat  gctgaagatc  agttgggtgc  acgagtggt   tacatcgaac
12241  tggatctcaa  cagcggtaag  atccttgaga  gttttcgccc  cgaagaacgt  tttccaatga
12301  tgagcacttt  taaagttctg  ctatgtggcg  cggtattatc  cgtgttgac   gccgggcaag
12361  agcaactcgg  tcgccgcata  cactattctc  agaatgactt  ggttgagtac  tcaccagtca
12421  cagaaaagca  tcttacggat  gcatgacag   agaatgaatt  atgcagtgct  gccataacca
12481  tgagtgataa  cactgcggcc  aacttactc   tgacaacgat  cggaggaccg  aaggagctaa
12541  ccgctttt   gcacaacatg  gggatcatg   taactcgcct  tgatcgttgg  gaaccggagc
12601  tgaatgaagc  catacccaac  actattctagc ggcgaactgc ttactctagc  atggcaacaa
12661  cgttgcgcaa  actattaact  ggcgaactac  ttactctagc  ttcccggcaa  caattaatag
12721  actggatgga  ggcggataaa  gttgcaggac  cacttctgcg  ctcggccctt  ccggctggct
12781  ggtttatttgc tgataaatct  ggagccggtg  agcgtgggtc  tcgcggtatc  attgcagcac
12841  tggggccaga  tggtaagccc  tcccgtatcg  tagttatcta  cacgacggg   agtcaggcaa
12901  ctatggatga  acgaaataga  cagatcgctg  agataggtgc  ctcactgatt  aagcattggt
12961  aactgtcaga  ccaagtttac  tcatatatac  tttagattga  tttaaaactt  cattttaat
13021  ttaaaaggat  ctaggtgaag  atcctttttg  ataatctcat  gaccaaaatc  ccttaacgtg
13081  agttttcgtt  ccactgagcg  tcagacccg   tagaaaagat  caaaggatct  cttgagatc
13141  ctttttctcc  gcgtaaactc  tgcgcttgc   aaacaaaaaa  accaccgcta  ccagcggtgg
13201  tttgtttgcc  ggatcaagag  ctaccaactc  tttttccgaa  ggtaactggc  ttcagcagag
13261  cgcagatacc  aaatactgtc  cttctagtgt  agccgtagtt  aggccaccac  ttcaagaact
13321  ctgtagcacc  gcctacatac  ctcgctctgc  taatcctgtt  accagtggct  gctgccagtg
13381  gcgataagtc  gtgtcttacc  gggttggact  caagacgata  gttaccggat  aaggcgcagc
13441  ggtcgggctg  aacggggggt  tcgtgcacac  agcccagctt  ggagcgaacg  acctacaccg
```

FIG. 25 (continued)

```
13501 aactgagata cctacagcgt gagcattgag aaagcgccac gcttcccgaa gggagaaagg
13561 cggacaggta tccggtaagc ggcagggtcg gaacaggaga gcgcacgagg gagcttccag
13621 ggggaaacgc ctggtatctt tatagtcctg tcgggtttcg ccacctctga cttgagcgtc
13681 gatttttgtg atgctcgtca gggggcgga gcctatggaa aaacgccagc aacgcgagct
13741 cgtatggaca tattgtcgtt agaacgcggc tacaattaat acataacctt atgtatcata
13801 cacaatcgat ttaggtgaca ctatag
```

CHIKUNGUNYA VIRUS (CHIKV) VIRUS-LIKE PARTICLES (VLPS) COMPRISING THE C, E1, AND E2 STRUCTURAL PROTEINS

REFERENCE TO RELATED APPLICATIONS

This application is a divisional of U.S. patent application Ser. No. 17/850,706, filed Jun. 27, 2022, which is a divisional of U.S. patent application Ser. No. 16/520,113, filed Jul. 23, 2019, now U.S. Pat. No. 11,369,674, which is a divisional of U.S. patent application Ser. No. 15/145,483, filed May 3, 2016, now U.S. Pat. No. 10,369,208; which is a divisional of U.S. patent application Ser. No. 13/131,287, filed Sep. 19, 2011, now U.S. Pat. No. 9,353,353; which is the U.S. National Stage of International Patent Application No. PCT/US2009/006294, filed Nov. 24, 2009, which was published in English under PCT Article 21(2); which in turn claims the benefit of U.S. Provisional Application Nos. 61/118,206 and 61/201,118, filed on Nov. 26, 2008 and Dec. 5, 2008, respectively, the entire contents of each of which are incorporated herein by reference.

STATEMENT OF RIGHTS TO INVENTIONS MADE UNDER FEDERALLY SPONSORED RESEARCH

Research supporting this application was carried out by the United States of America as represented by the Secretary, Department of Health and Human Services. This research was supported by the Intramural Research Program, Vaccine Research Center, NIAID of the National Institute of Health. The Government has certain rights in this invention.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an .xml file in the form of the file name "4239-104859-31_Sequence.xml' (221,184 bytes), which was created on Apr. 18, 2024, and which is incorporated by reference herein.

BACKGROUND OF THE INVENTION

Chikungunya virus (CHIKV), a mosquito-borne alphavirus in the family Togaviridae, was first isolated in Tanzania in 1952. Infection by this virus causes human disease that is characterized by rash, high fever and, its hallmark feature, severe arthritis that can persist for years. Chikungunya virus (CHIKV) has infected millions of people in Africa, Europe, and Asia since its re-emergence in Kenya in 2004. The evolution and spread of the virus into new geographic areas, and the disease severity present a serious public health in the absence of a vaccines or anti-viral therapies. Therefore, the development of anti-viral therapies for CHIKV and vaccine development remains a high priority. Phylogenetic analysis of CHIKV showed that there are three genotypes: Asian, East/Central/South African and West African. The Asian and East/Central/South African genotypes are most similar, whereas the West African strains are more divergent. Therapeutic and/or prophylactic methods for treating or preventing Chikungunya viral disease are urgently required.

SUMMARY OF THE INVENTION

As described below, the present invention features compositions and methods for the prevention or treatment of one or more strains of Chikungunya virus, as well as other alphavirus-mediated diseases.

In one aspect, the invention provides a virus-like particle (VLP) containing one or more 35 (e.g., one, two, three, four, five) Chikungunya virus structural polypeptides. In one embodiment, the structural polypeptides are any one or more of capsid and envelope proteins E3, E2, 6K and E1.

In another aspect, the invention provides an isolated polynucleotide encoding a virus-like particle of the previous aspect or any other VLP delineated herein. In one embodiment, the polynucleotide encodes a Chikungunya virus polyprotein containing C-E3-E2-6K-E1.

In a related aspect, the invention provides an expression vector containing a polynucleotide encoding one or more Chikungunya virus structural polypeptides.

In another aspect, the invention provides a prokaryotic or eukaryotic cell (e.g., mammalian, human, insect) containing the expression vector of any previous aspect or any other expression vector delineated herein. In one embodiment, the cell is in vitro.

In another aspect, the invention provides an immunogenic composition containing an effective amount of a virus-like particle of any previous aspect or any other VLP delineated herein.

In a related aspect, the invention provides an immunogenic composition containing an effective amount of a VLP containing a Chikungunya structural polyprotein containing C-E3-E2-6K-E1 and an adjuvant.

In another aspect, the invention provides an immunogenic composition containing an effective amount of an expression vector of any previous aspect or otherwise delineated herein (e.g., a DNA vaccine).

In another aspect, the invention provides a vaccine containing an effective amount of one or more Chikungunya virus structural polypeptides that is any one or more of capsid (C) and envelope proteins E1, E2, E3 and 6K.

In another aspect, the invention provides a vaccine containing an effective amount of a virus-like particle of any previous aspect or containing a polyprotein containing C-E3-E2-6K-E1.

In another aspect, the invention provides a vaccine containing a polynucleotide encoding a Chikungunya structural polyprotein or fragment thereof. In one embodiment, the Chikungunya structural polyprotein is encoded by an expression vector of any previous aspect. In one embodiment, the expression vector comprises a CMV/R promoter. In another embodiment, the vaccine is a DNA vaccine.

In another aspect, the invention provides a method of inducing an immune response against Chikungunya in a subject (e.g. human), the method involving administering to the subject an effective amount of an immunogenic composition of any previous aspect or any other immunogenic composition delineated herein. In one embodiment, the immunogenic composition contains one or more Chikungunya virus structural polypeptides that is any one or more of capsid (C) and envelope proteins E1, E2, E3 and 6K. In another embodiment, the immunogenic composition comprises a polyprotein containing C-E3-E2-6K-E1. In another embodiment, the method induces neutralizing antibodies in a subject.

In another aspect, the invention provides a method for treating or preventing a Chikungunya infection in a subject, the method involving administering to the subject an effective amount of a vaccine of any previous aspect or an immunogenic composition of any previous aspect. In one embodiment, wherein the vaccine or immunogenic composition is administered in one or more doses.

In another aspect, the invention provides a method for producing a virus-like particle, the method involves expressing in a cell one or more Chikungunya structural protein capable of self-assembly to form a virus-like particle. In one embodiment, the method further involves isolating the virus-like particle.

In another aspect, the invention provides a virus-like particle (VLP) containing one or more alphavirus structural polypeptides (e.g., capsid or envelope polypeptide). In one embodiment, the alphavirus is any one or more of Chikungunya virus, Sindbis virus, Eastern equine encephalitis (EEE) virus, Western equine encephalitis (WEE) virus, and Venezuelan equine encephalitis (VEE) virus.

In another aspect, the invention provides an isolated polynucleotide encoding a virus-like particle of the previous aspect or otherwise delineated herein.

In another aspect, the invention provides an expression vector containing a polynucleotide encoding one or more alphavirus structural polypeptides wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides an immunogenic composition containing an effective amount of a virus-like particle of any previous aspect or otherwise delineated herein.

In another aspect, the invention provides a vaccine containing an effective amount of one or more alphavirus structural polypeptides or a polynucleotide encoding one or more alphavirus structural proteins, wherein the alphavirus is selected from the group consisting of Chikungunya virus, Sindbis virus, Eastern equine encephalitis (EEE) virus, Western equine encephalitis (WEE) virus, and Venezuelan equine encephalitis (VEE) virus.

In another aspect, the invention provides a method of inducing an immune response against an alphavirus in a subject, the method involving administering to the subject an effective amount of an immunogenic composition of a previous aspect. In one embodiment, the immunogenic composition contains one or more alphavirus structural polypeptides (e.g. envelope or capsid).

In another aspect, the invention provides a method for treating or preventing an alphavirus infection in a subject, the method involving administering to the subject an effective amount of a vaccine or an immunogenic composition of any previous aspect.

In another aspect, the invention provides a kit containing a VLP of any previous aspect, and instructions for use.

In another aspect, the invention provides a kit containing an immunogenic composition of any previous aspect, and instructions for use in a subject. In one embodiment, the immunogenic composition is provided in a first container and a second immunogenic composition is provided in a second container, and instructions for use in a prime boost immunization. In another embodiment, the immunogenic composition in the second container contains a VLP, viral polypeptide, or viral polynucleotide.

In another aspect, the invention provides a method for identifying inhibitors of Chikungunya virus entry into a eukaryotic cell, the method involving contacting a cell that expresses a Chikungunya virus receptor with a Chikungunya polypeptide selected from the group consisting of C, E3, E2, 6K, and E1 and a candidate compound, and assaying for viral entry, wherein a candidate compound that reduces viral entry in the cell relative to a control cell is identified as an inhibitor of Chikungunya virus entry. In one embodiment, the candidate inhibitor is an antibody, or fragment thereof or small molecule.

In another aspect, the invention provides a method for identifying inhibitors of Chikungunya viral entry involving contacting a cell that expresses a Chikungunya virus receptor with a candidate inhibitor and a pseudotyped virus containing a reporter gene; and measuring expression of the reporter gene in the cell, wherein a compound that reduces expression of the reporter gene relative to a control cell is identified as inhibiting viral entry. In one embodiment, the pseudotyped virus (e.g., lentivirus) contains one or more Chikungunya virus envelope proteins (e.g., E3, E2, 6K and E1). In one embodiment, the candidate inhibitor is an antibody, or fragment thereof or small molecule.

In another aspect, the invention provides a virus-like particle (VLP) containing one or more Chikungunya virus structural polypeptides for use in treating or preventing a Chikungunya infection.

In another aspect, the invention provides a method for treating or preventing a Chikungunya infection, the method involving administering a virus-like particle (VLP) containing one or more Chikungunya virus structural polypeptides prior to, subsequent to, concurrent with, or in any other sequence with the administration of one or more of another immunogenic composition, antiviral, or antibiotic agent.

In another aspect, the invention provides methods for treating or preventing a Chikungunya infection by administering neutralizing antibodies (e.g., mammalian, human) generated against a VLP of the invention to a subject (e.g., human).

In various embodiments of the above aspects or any other aspect of the invention delineated herein, the VLP contains one or more (1, 2, 3, 4) envelop proteins E3, E2, 6K and E1. In other embodiments, the VLP contains a polyprotein containing C-E3-E2-6K-E1 or a fragment thereof. In other embodiments of the above aspects or any other aspect of the invention delineated herein, a polynucleotide encodes one or more structural polypeptides that is any one or more of a alphavirus or Chikungunya virus capsid (C) and envelope proteins E3, E2, 6K and E1. In other embodiments, the polynucleotide encodes envelop proteins E3, E2, 6K and E1. In other embodiments, the polynucleotide encodes a Chikungunya virus polyprotein containing C-E3-E2-6K-E1. In still other embodiments, the expression vector is capable of expression in a prokaryotic or eukaryotic cell (e.g., mammal, human). In other embodiments, the structural polyprotein is derived from Chikungunya strain 37997 or LR2006. In other embodiments, the vector comprises the CMV/R promoter. In other embodiments, the expression vector is C-E37997 or C-E$_{OPY-1}$. In other embodiments, the VLP induces an immune response (e.g., a protective immune response) in a subject. In other embodiments, the immune response treats or prevents a Chikungunya infection in a subject. In other embodiments of the above aspects, the VLP induces antibodies against homologous or heterologous strains of Chikungunya. In embodiments of the above aspects, the adjuvant is an immunostimulating agent (e.g., Ribi, aluminum salts, muramyl peptides, bacterial cell wall components, saponin adjuvants).

In other embodiments of the above aspects, the vaccine or immunogenic composition is administered in one or more priming immunizations and one or more boosting immunizations. In still another embodiment, the priming immunizations are administered at one, two, three, four, five, six, seven or eight week intervals. In still another embodiment, the boosting immunizations are administered two weeks, one month, two months or three months after the priming immunization. In other embodiments of the above aspects or any other aspect of the invention delineated herein, the immunization protects the subject against viremia or the inflammatory consequences of infection. In other embodiments, the method protects a subject from lethality. In other embodiments, the method induces neutralizing antibodies in the subject.

The invention provides immunogenic compositions featuring virus-like particles comprising Chikungunya polypeptides for the prevention or treatment of Chikungunya viral disease. Compositions and articles defined by the invention were isolated or otherwise manufactured in connection with the examples provided below. Other features and advantages of the invention will be apparent from the detailed description, and from the claims.

BRIEF DESCRIPTION OF THE DRAWINGS

FIG. 1A is a schematic representation of the CHIKV genome and CHIKV E expression vector used for incorporation of CHIKV E from strains 37997 and LR2006 OPY-1 into pseudotyped lentiviral vectors. The CHIKV genome consists of nonstructural polyproteins NS1, NS2, NS3 and NS4 and structural polyproteins capsid (C) and envelope (E: E3, E2, 6K and E1) (top). The polypeptide E genes from strains 37997 and LR2006 OPY-1 were inserted into an expression vector (bottom). FIG. 1B includes two graphs. The graph on the left shows the infectivity of the indicated pseudotyped lentiviral vectors in several CHIKV-permissive cell lines, including 293A human renal epithelial, HeLa cervical epithelial, Vero renal epithelial, A549 squamous epithelial and baby hamster kidney (BHK) cells. The pseudotyped vectors were standardized by HIV-1 Gag p24 (left) or the indicated concentration of p24 and used to infect 293A cells (right). After incubation with pseudotyped vectors for 24 hours, cells were lysed and luciferase activity was measured. The experiment was performed in triplicate. FIG. 1C includes two graphs that show the pH-dependent entry of CHIKV pseudotyped lentiviral vectors. Pseudotyped lentiviral vectors were incubated in the presence of the indicated amounts of ammonium chloride (left) and chloroquine (right). The experiment was performed in triplicate. Data are presented as the percentage of activity at the indicated dose relative to activity with no treatment. FIG. 1D is a graph showing neutralization measured with pseudotyped lentiviral vectors in sera from mice injected with CHIKV (strain S-27). Sera were incubated at the indicated dilutions with VSV-G, CHIKV strain 37997 or LR2006 OPY-1 E-pseudotyped lentiviral vectors and the mixture infected to 293A cells. Luciferase activity was analyzed 24 hours after infection. The experiment was performed in triplicate. No inhibition was observed with control non-immune antisera.

FIG. 2A provides a schematic representation of CHIKV C-E or E expression vectors used for DNA vaccine and VLP production. The CHIKV structural polyproteins capsid plus envelope (C-E) or E alone from strains 37997 and LR2006 OPY-1 were inserted into an expression vector. 293T cells were transfected with each of the indicated plasmids. Expression was measured 48 h after transfection by Western blotting as described previously (29) with antisera reactive with CHIKV. FIG. 2B includes a graph, Western blot, and electron micrograph. VLPs were purified from the supernatants of 293F cells transfected with C-E expression vector (C-E$_{37997}$) (left). The supernatants were harvested 72 hours after transfection followed by OptiPrep™ density gradient centrifugation. Each fraction was characterized for its buoyant density (left upper panel) and protein content (left lower panel) by Western blot analysis with antisera to CHIKV. The fractionated VLPs were observed by transmission electron microscopy with magnification 20,000× (left, bar 100 nm) (right). FIG. 2C provides a comparison of cryo-EM reconstructions of CHIKV VLP with Sindbis virus showing that CHIKV VLP is structurally similar to alphaviruses. Shaded-surface representation of the 3D density map of CHIKV VLP (left upper panel) and Sindbis virus (right upper panel) viewed along an icosahedral 2-fold axis. The white triangle marks the boundary of an icosahedral asymmetric unit. The numbers show the positions of the icosahedral 2-, 3-, and 5-fold axes limiting an asymmetric unit. The central cross-section through the cryo-EM maps of CHIKV VLP (left lower panel) and Sindbis virus (right lower panel). The orientations of the icosahedral (2-, 3-, and 5-fold) axes as well as the quasi-threefold (q3) axis are shown with white lines. Maps are calculated to 18 Å resolution.

FIG. 3C shows results from monkeys immunized with VLP$_{37997}$ or PBS (control) at 0, 4, and 24 weeks. A neutralizing assay was performed with CHIKV strain 37997 (left panel) or LR2006 OPY-1 (right panel) E pseudotyped lentiviral vectors in sera collected from immunized monkeys at 10 days after each immunization. The symbols show the average of the six monkeys and bars show the standard error of the mean. FIG. 3D shows the neutralizing activity against CHIKV LR2006 OPY-1 in immunized monkeys' sera after the 2nd and 3rd immunizations was confirmed by a standard plaque reduction neutralization test (PRNT). The symbols show the average of the six monkeys and bars show the standard error of the mean.

FIGS. 4A-4D are graphs showing protection against CHIKV LR2006 OPY-1 challenge in monkeys immunized with VLPs and in a CHIKV mouse model after passive transfer of purified IgG. FIG. 4A quantitates results obtained in monkeys injected with PBS (Control) or immunized with VLP$_{37997}$. Monkeys were challenged with $10^{10}$ PFU of the CHIKV strain LR2006 OPY-1 15 weeks after the final boost. The peak viremia at 24 hours after challenge was measured by plaque assay. The serum dilutions started from 1:200 (limit of detection=1000 PFU/ml). Error bars represent the standard error of the mean. FIG. 4B is a graph showing the percentage of monocytes in the monkeys' white blood cells. Monocyte percentage was measured using a hematology analyzer before and 7 days after challenge with CHIKV. Error bars represent the standard error of the mean. A non-parametric two t-test was used for statistical analysis (Control vs. VLPs at 7 days, P=0.0036; Control at 0 days vs. 7 days, P=0.0015; VLPs at 0 days vs. 7 days, P>0.5). FIG. 4C shows the number of viral RNA copies present following passive transfer of purified IgG from a monkey immunized with VLPs (Immune) or a control monkey (Control IgG) into mice (2 mg of total IgG per mouse, n=5 per group). Recipient mice were challenged 24 hours after IgG transfer with a lethal LR2006 OPY-1 challenge (30 PFU) by intradermal injection. The viremia in the mice after challenge was measured by quantitative RT-PCR (limit of detection=40 RNA copies/ml). Error bars represent the standard error of the mean. FIG. 4D shows a survival curve of mice passively transferred with control IgG or CHIKV immunized IgG against lethal LR2006 OPY-1 challenge.

FIG. 7A shows the sequence of the insert (SEQ ID NO:1). FIG. 7B shows the sequence of the entire plasmid sequence (SEQ ID NO: 2).

FIG. 8B shows the sequence of the insert (SEQ ID NO:3). FIG. 8C shows the entire plasmid sequence (SEQ ID NO: 4).

FIG. 9B shows the entire plasmid sequence (SEQ ID NO: 5).

Figure 10B:
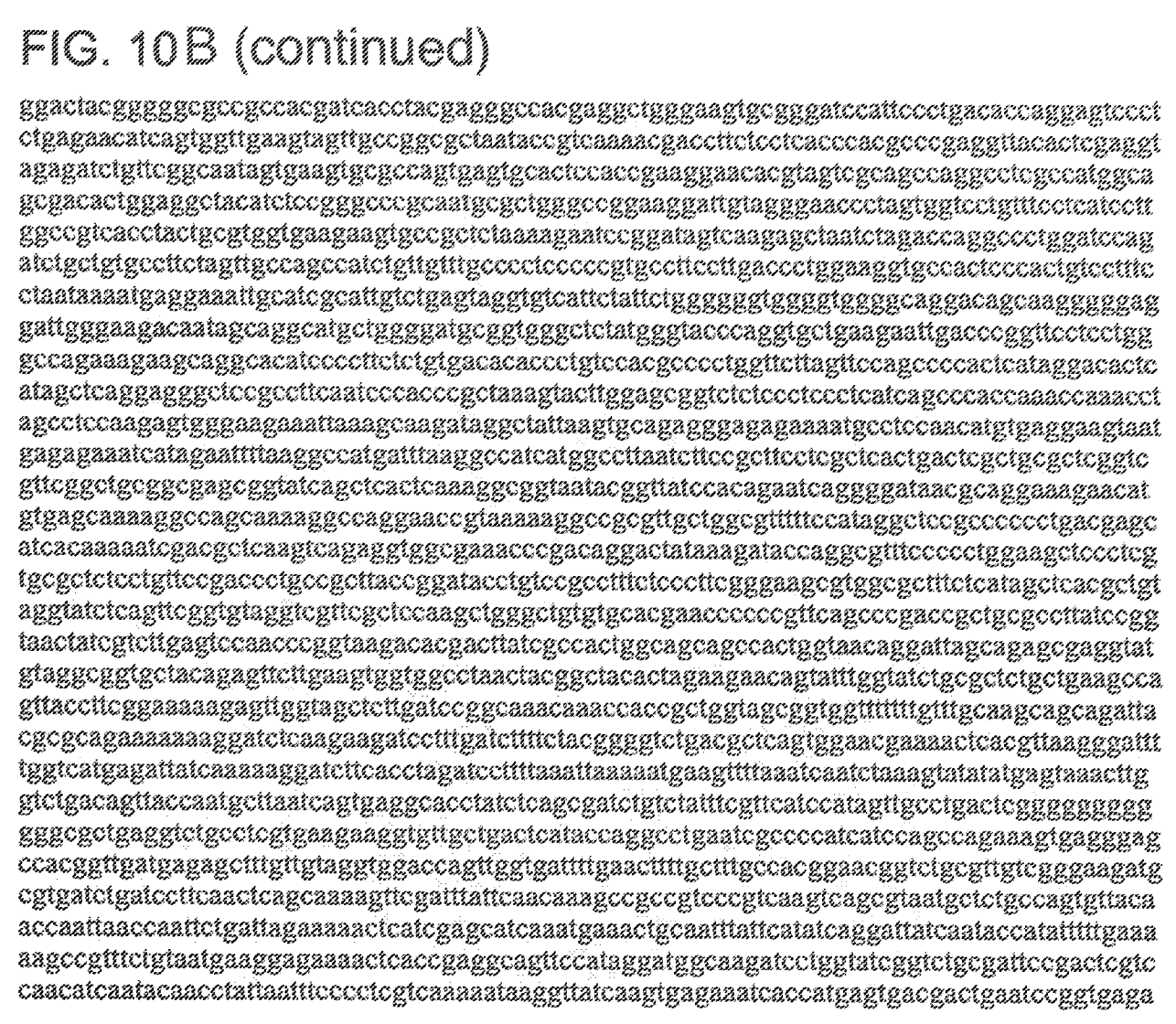

FIG. 10B shows the entire plasmid sequence (SEQ ID NO: 6).

FIGS. 11A and 11B. FIG. 11A shows the CMV/R-Getah virus VLP plasmid. FIG. 11B shows the entire plasmid sequence (SEQ ID NO: 7).

FIG. 12A shows the CMV/R-Venezuelan equine encephalitis virus VLP plasmid.

FIG. 12B shows the entire plasmid sequence (SEQ ID NO: 8).

Figure 13B:
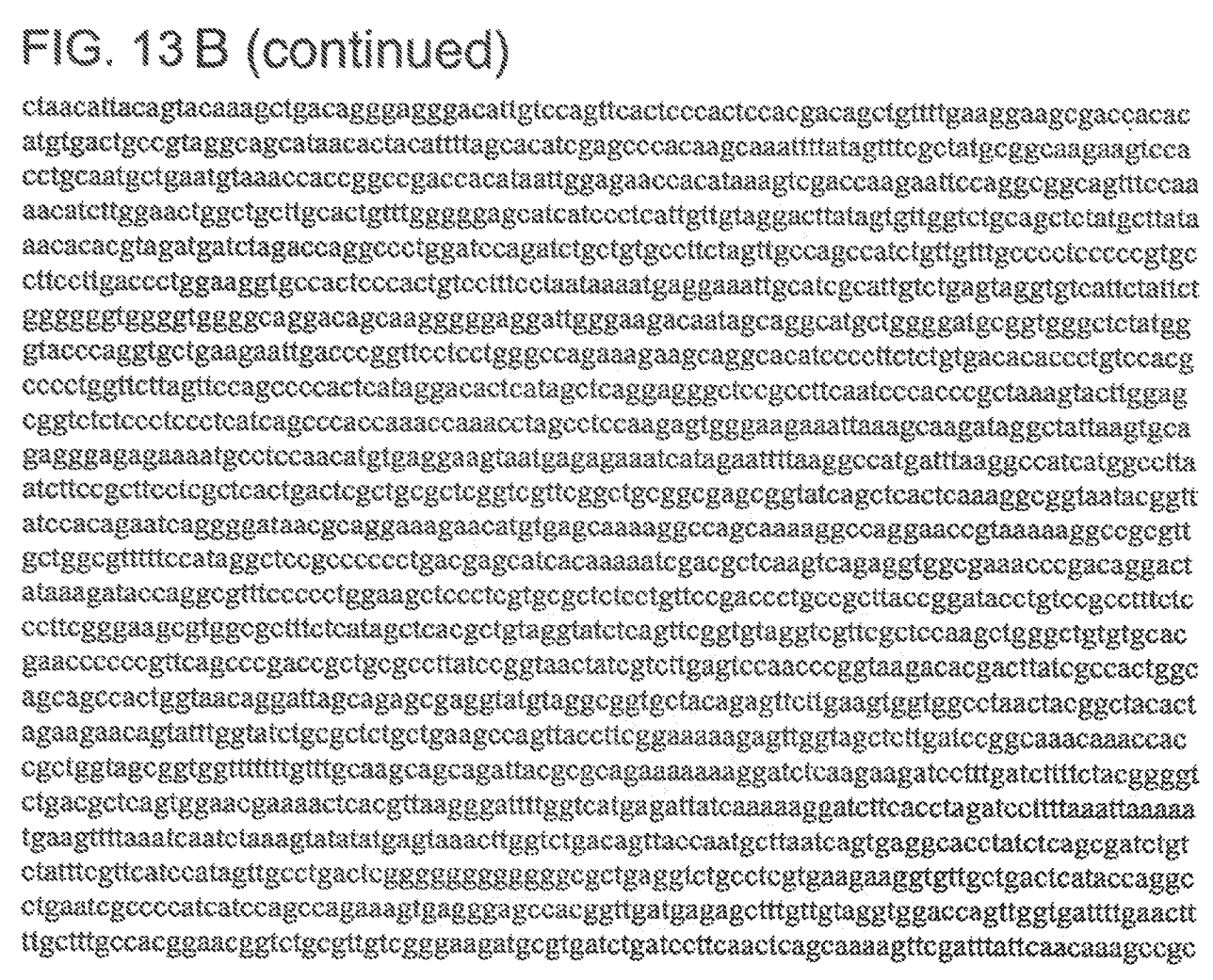

FIG. 13B shows the entire plasmid sequence (SEQ ID NO: 9).

Figure 14B:
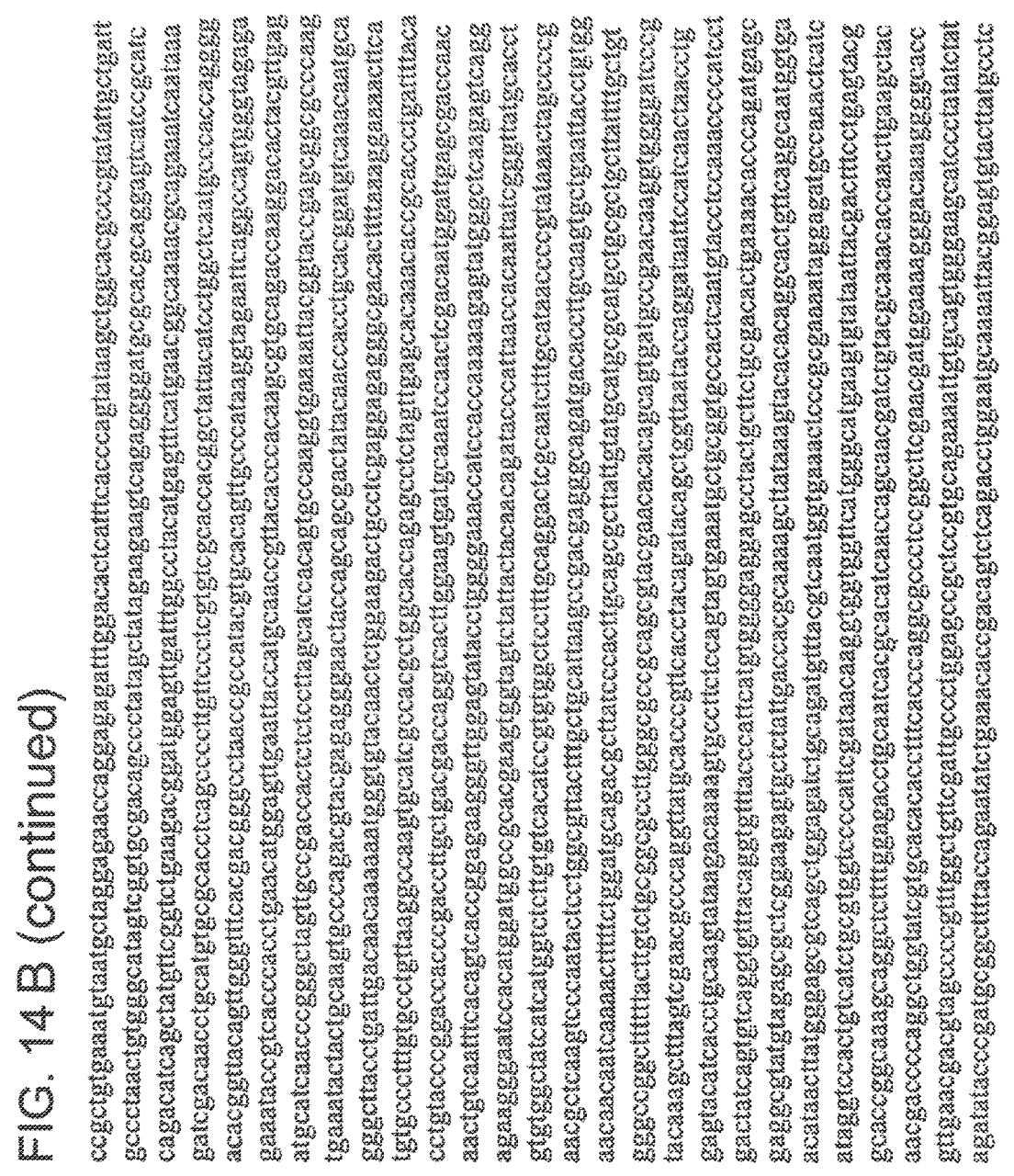
Figure 14B:
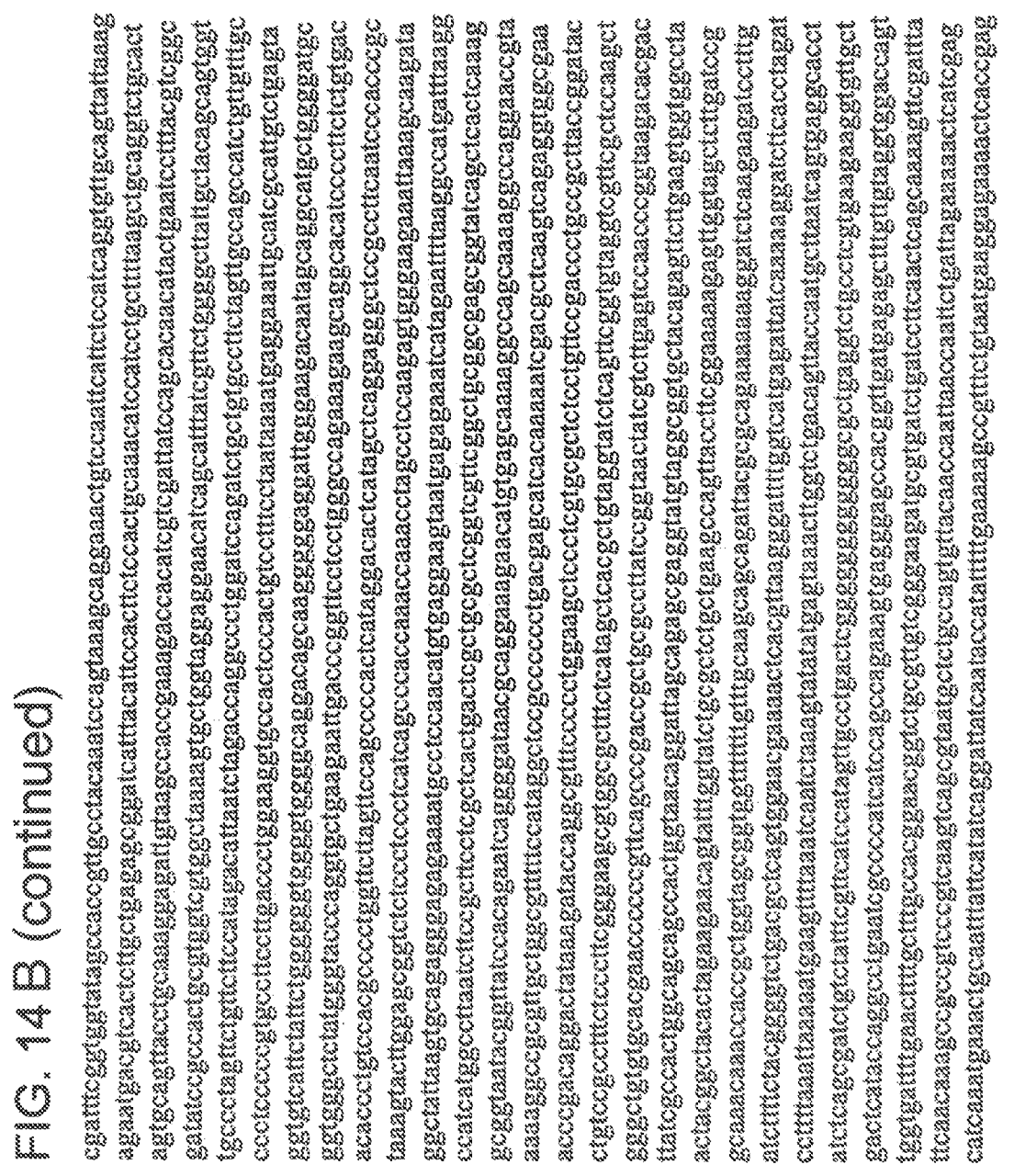

FIG. 14A shows the CMV/R-Eastern equine encephalitis virus VLP plasmid.

FIG. 14B shows the entire plasmid sequence (SEQ ID NO: 10).

FIG. 15B shows the entire plasmid sequence (SEQ ID NO: 11).

Figure 16B:
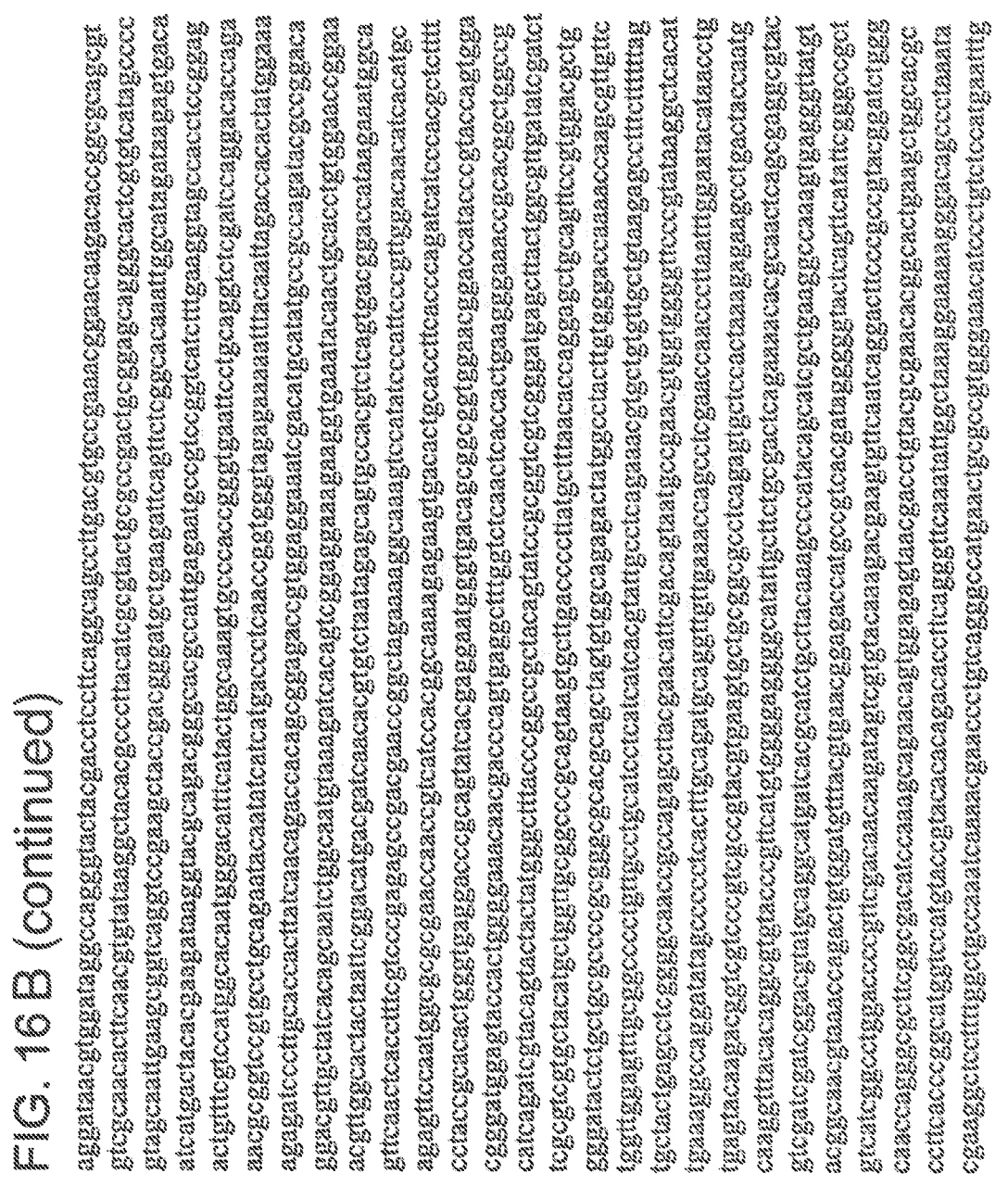
Figure 16B:
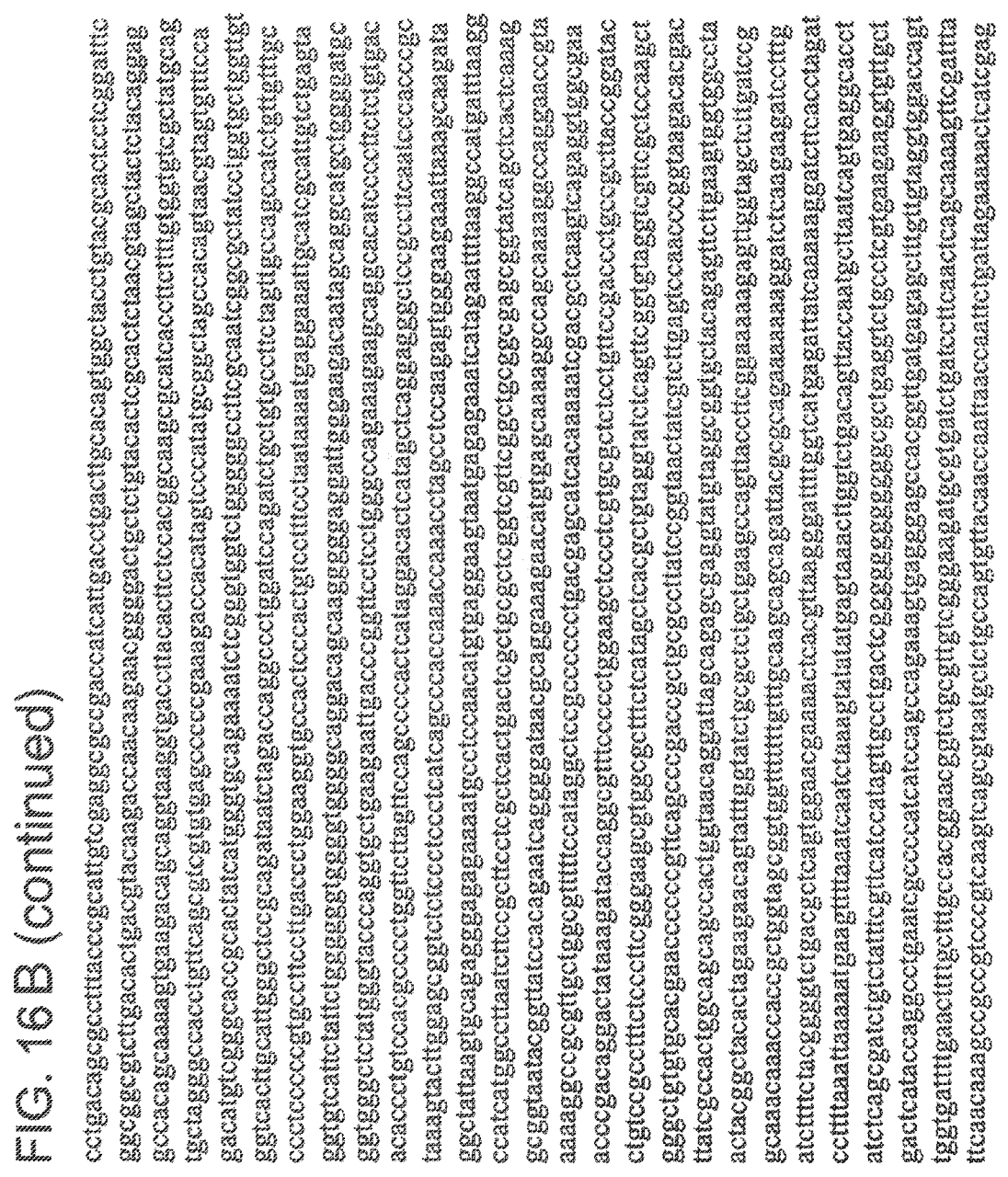

FIG. 16B shows the entire plasmid sequence (SEQ ID NO: 12).

Figure 17B:
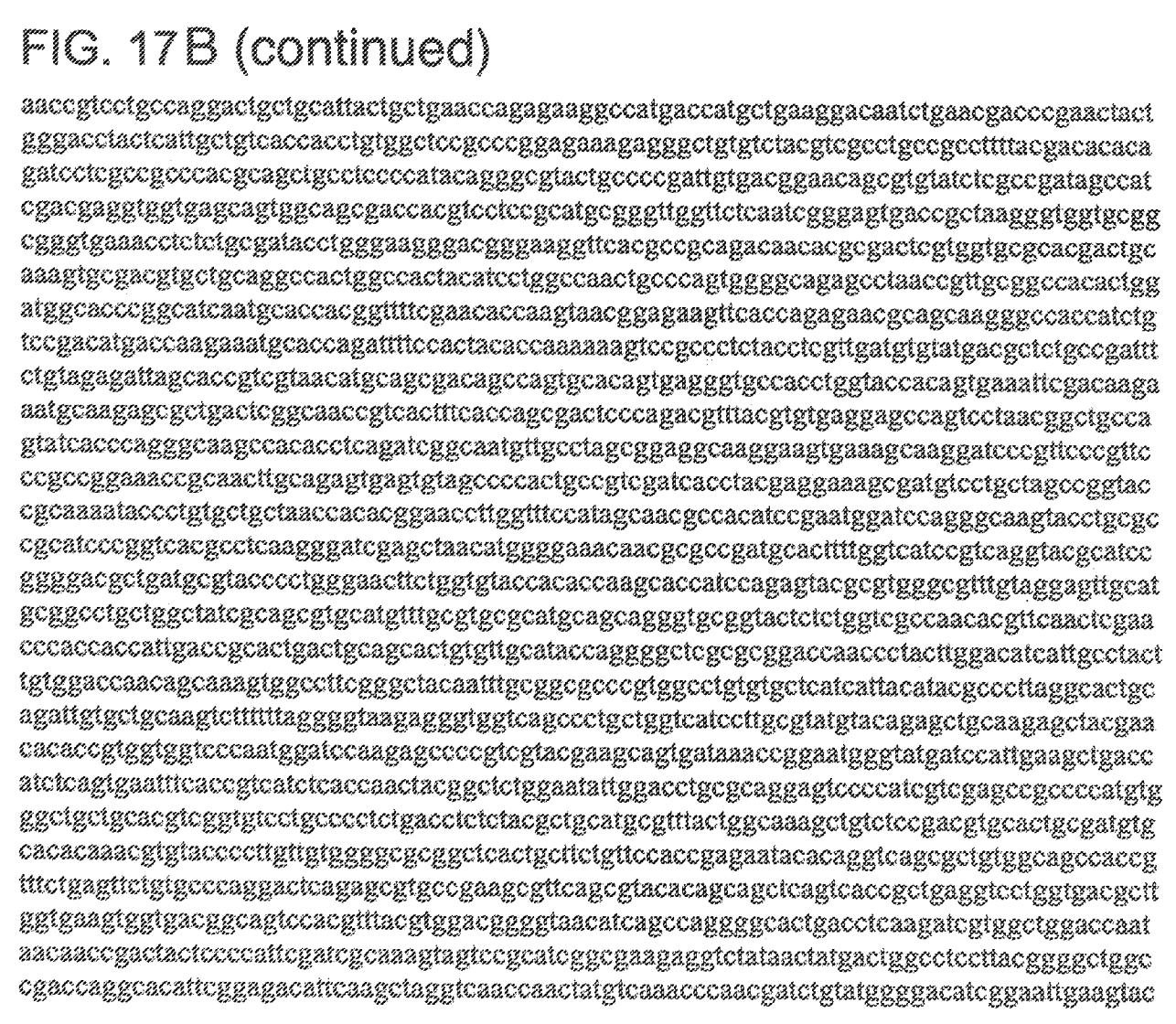
Figure 17B:
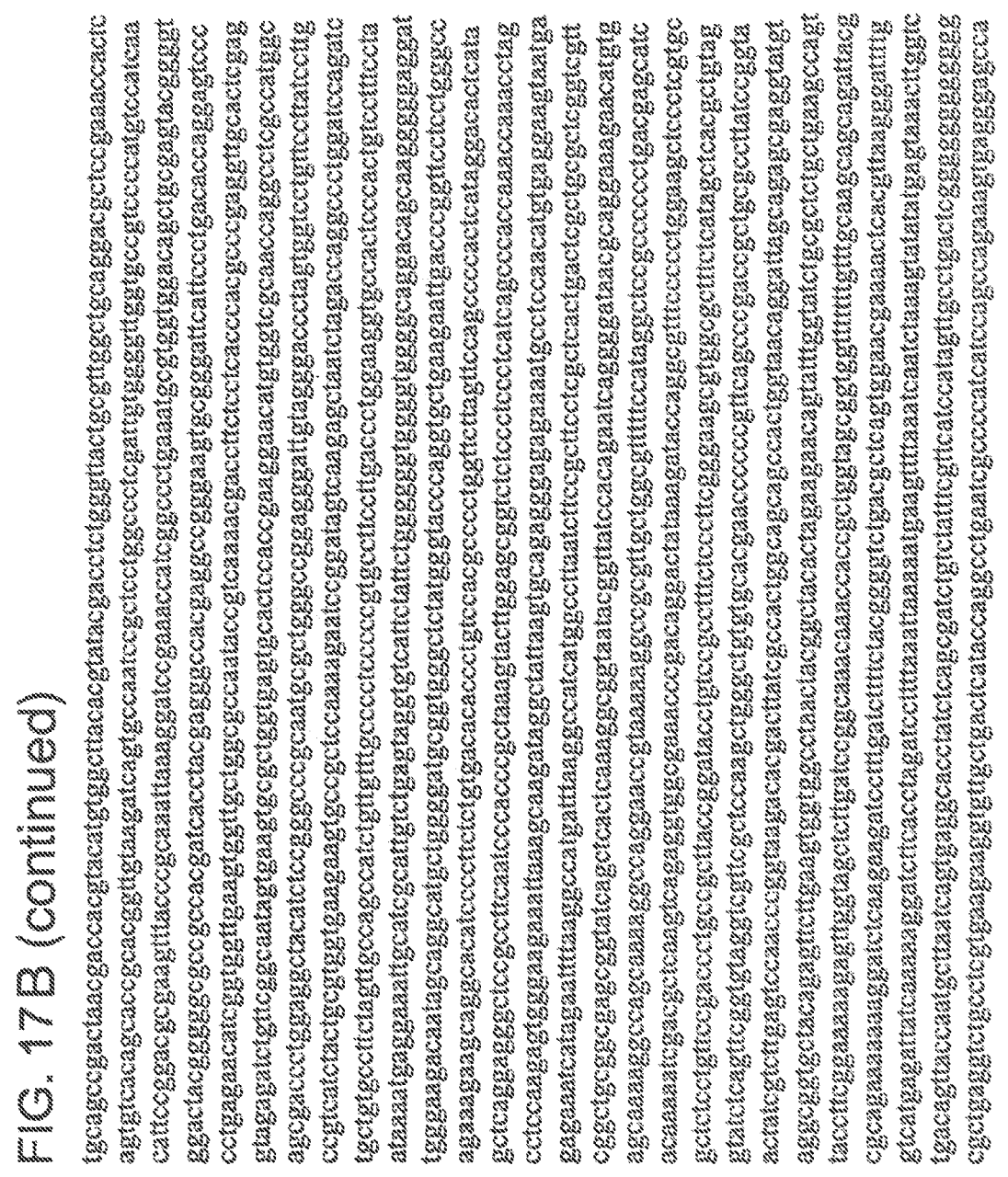

FIG. 17B shows the entire plasmid sequence (SEQ ID NO: 13).

Figure 18B:
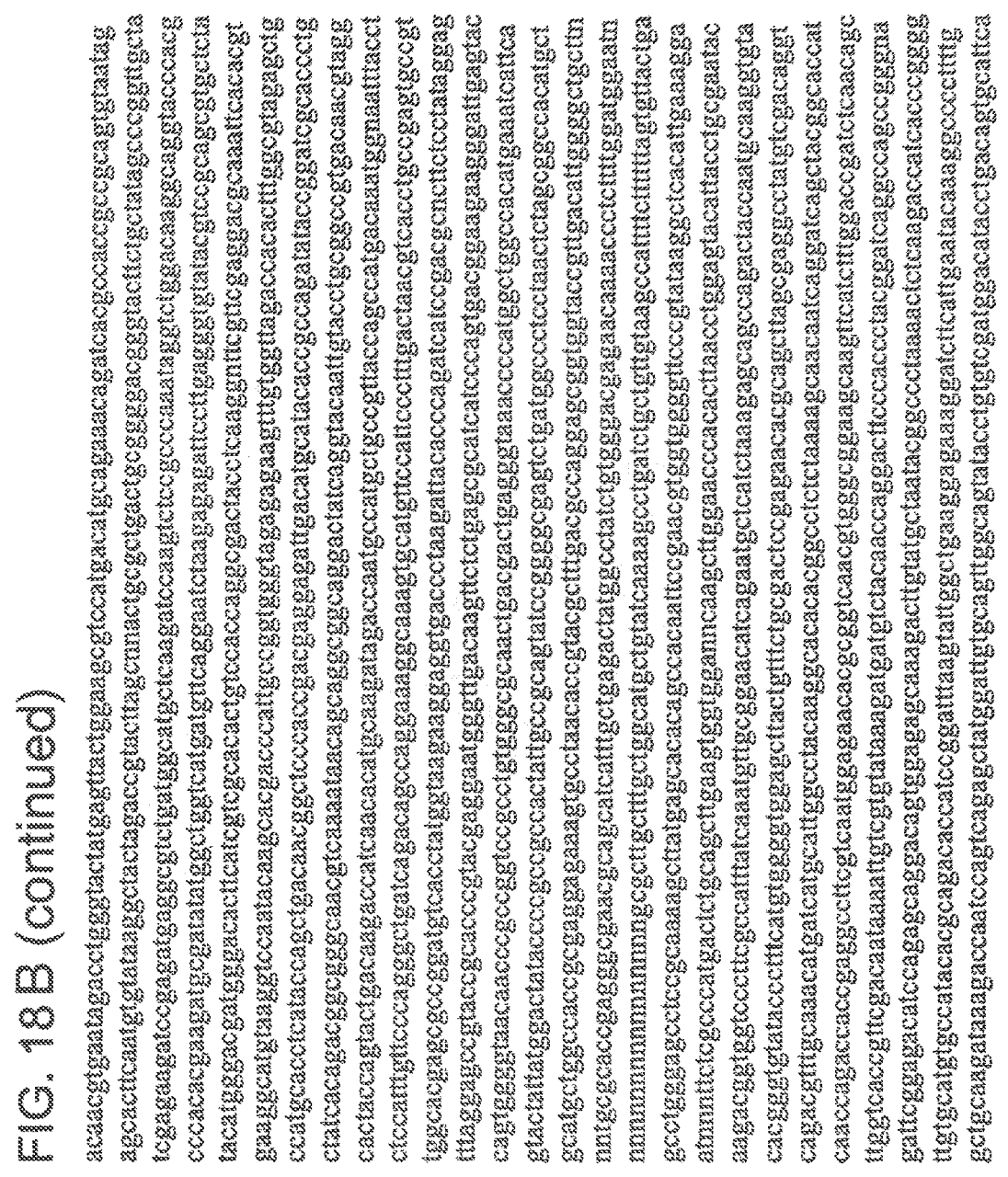

FIG. 18B shows the entire plasmid sequence (SEQ ID NO: 14).

Figure 19A:
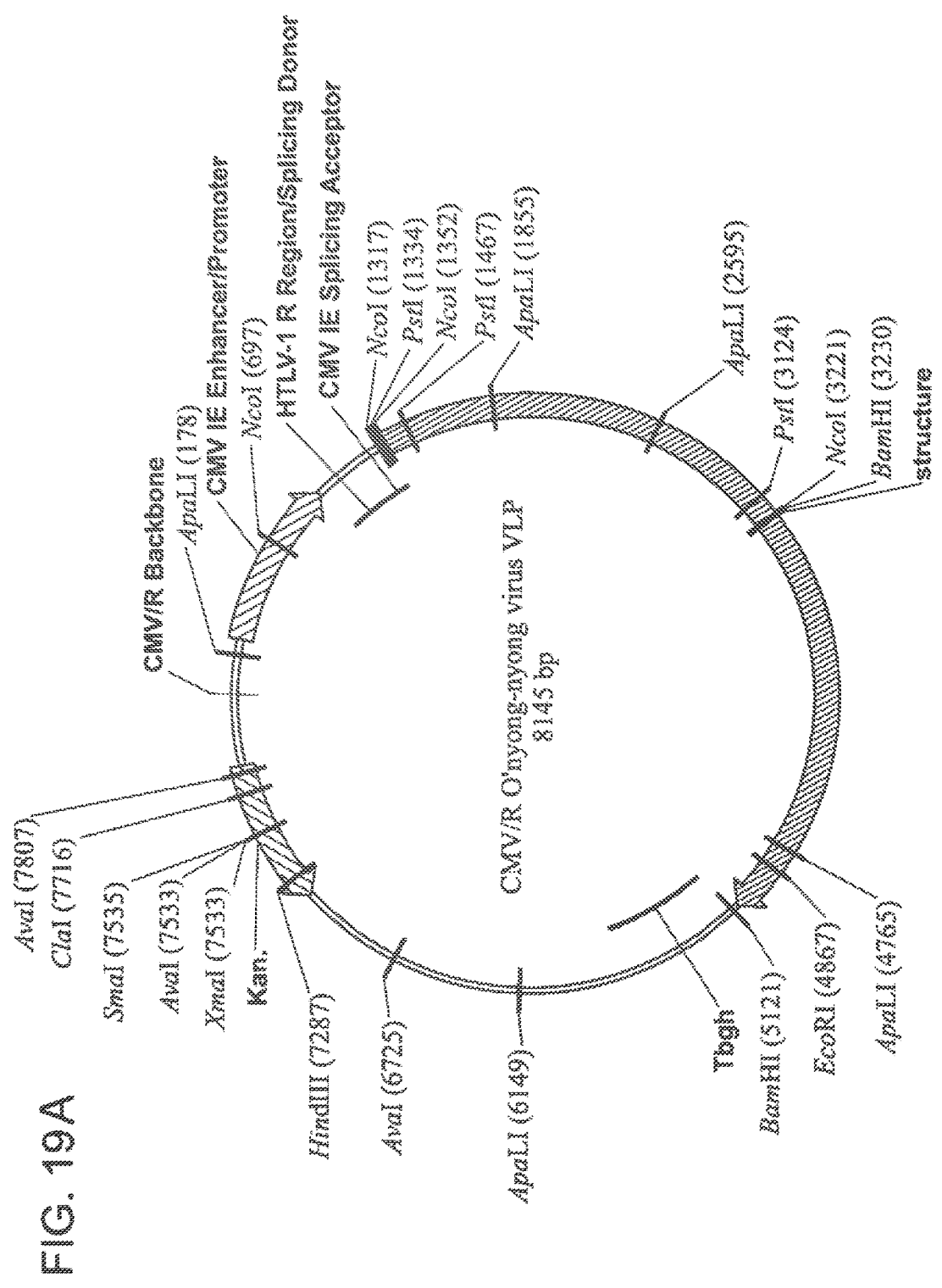
Figure 19B:
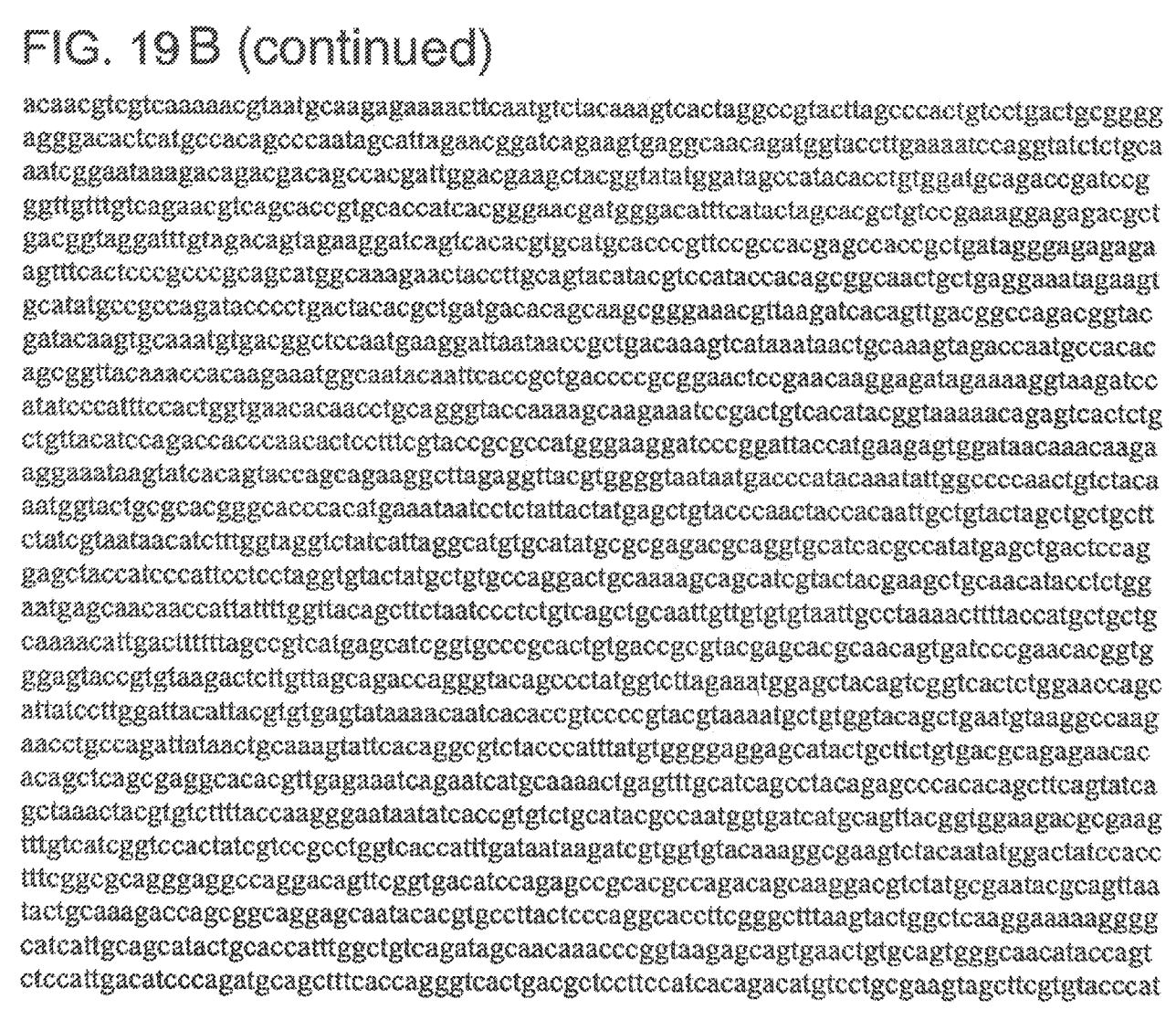

FIG. 19A shows the CMV/R-O'nyong-nyong virus VLP plasmid. FIG. 19B shows the entire plasmid sequence (SEQ ID NO: 15).

Figure 20A:
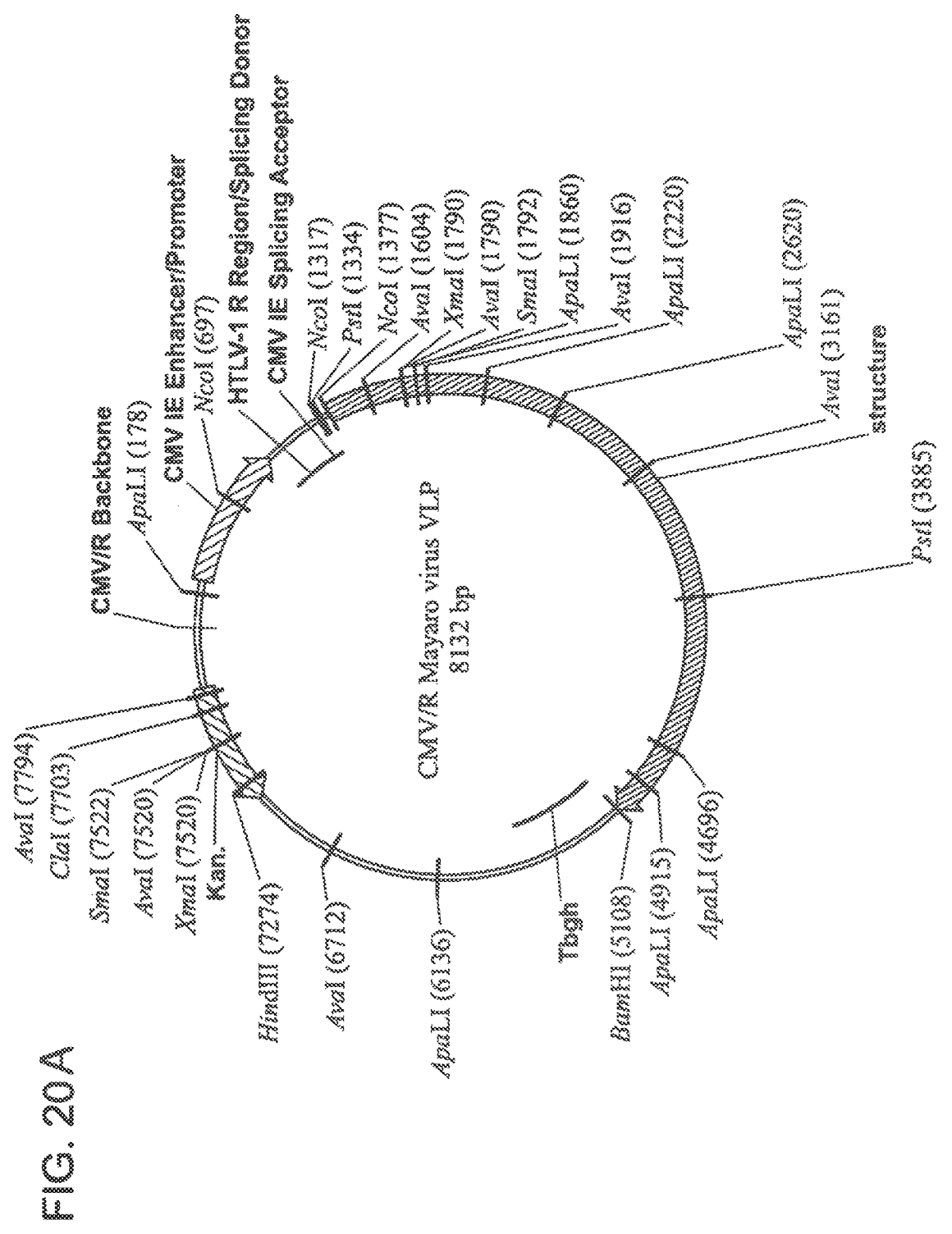
Figure 20B:
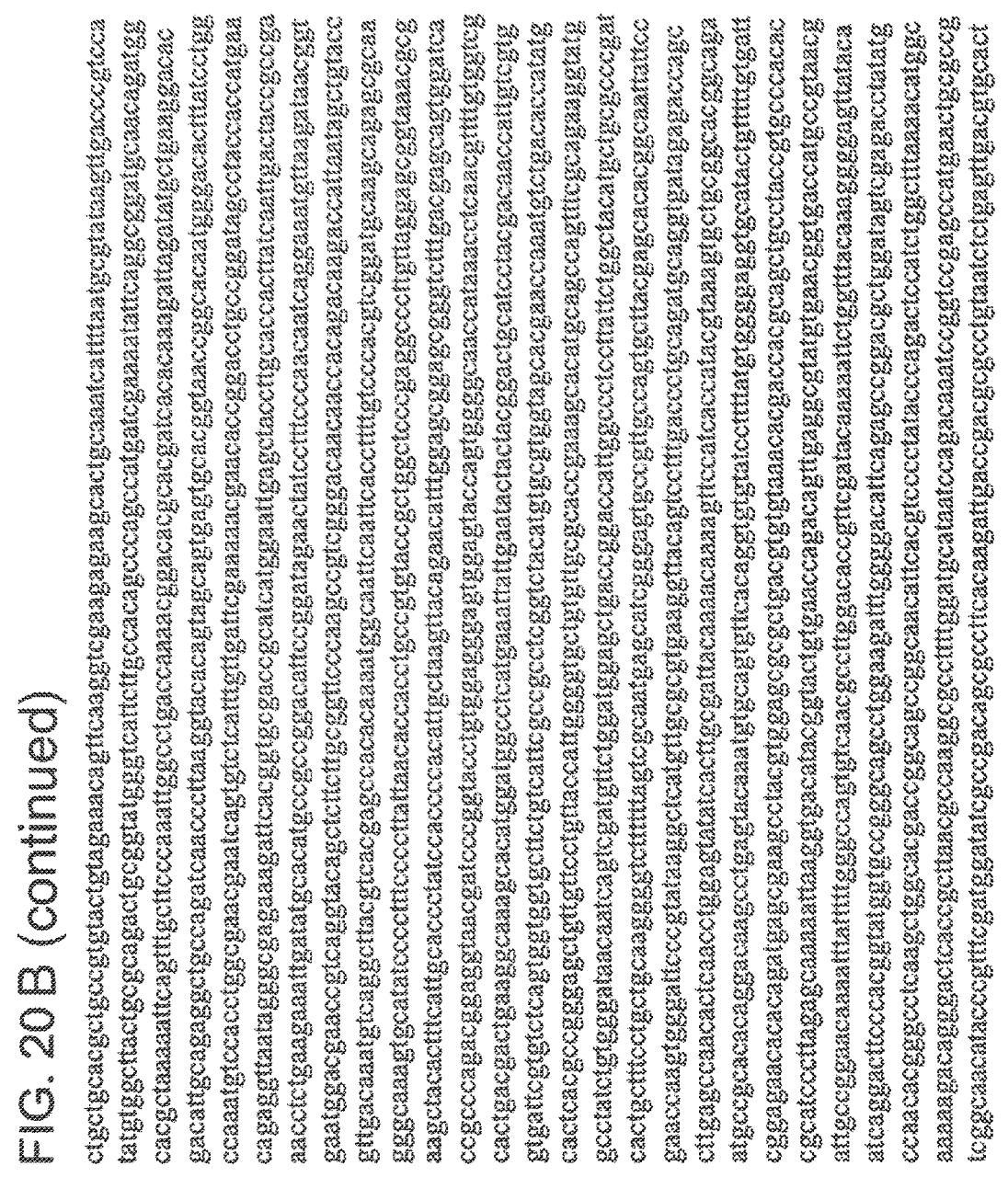

FIG. 20A shows the CMV/R-Mayaro virus VLP plasmid. FIG. 20B shows the entire plasmid sequence (SEQ ID NO: 16).

Figure 21A:
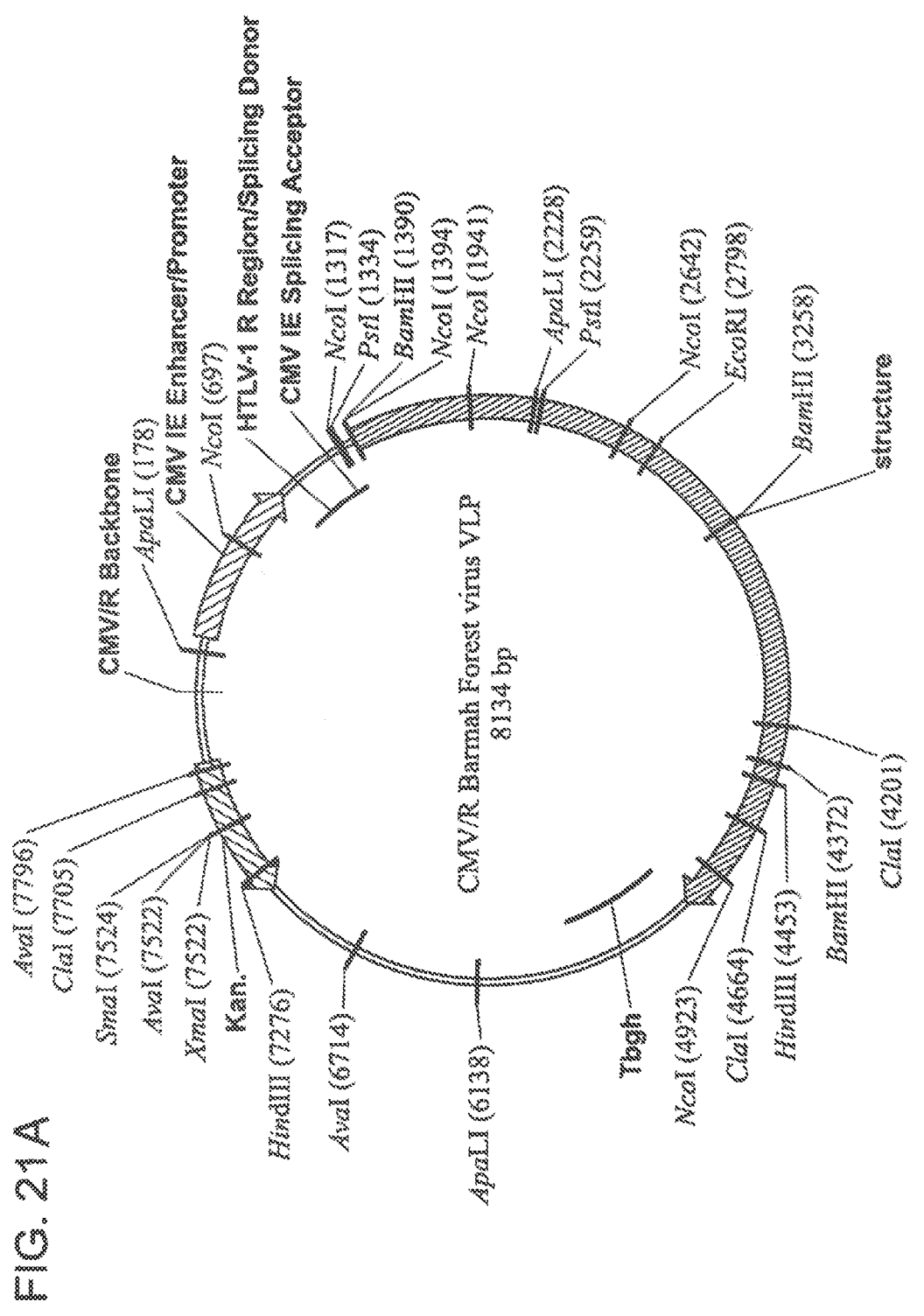
Figure 21B:
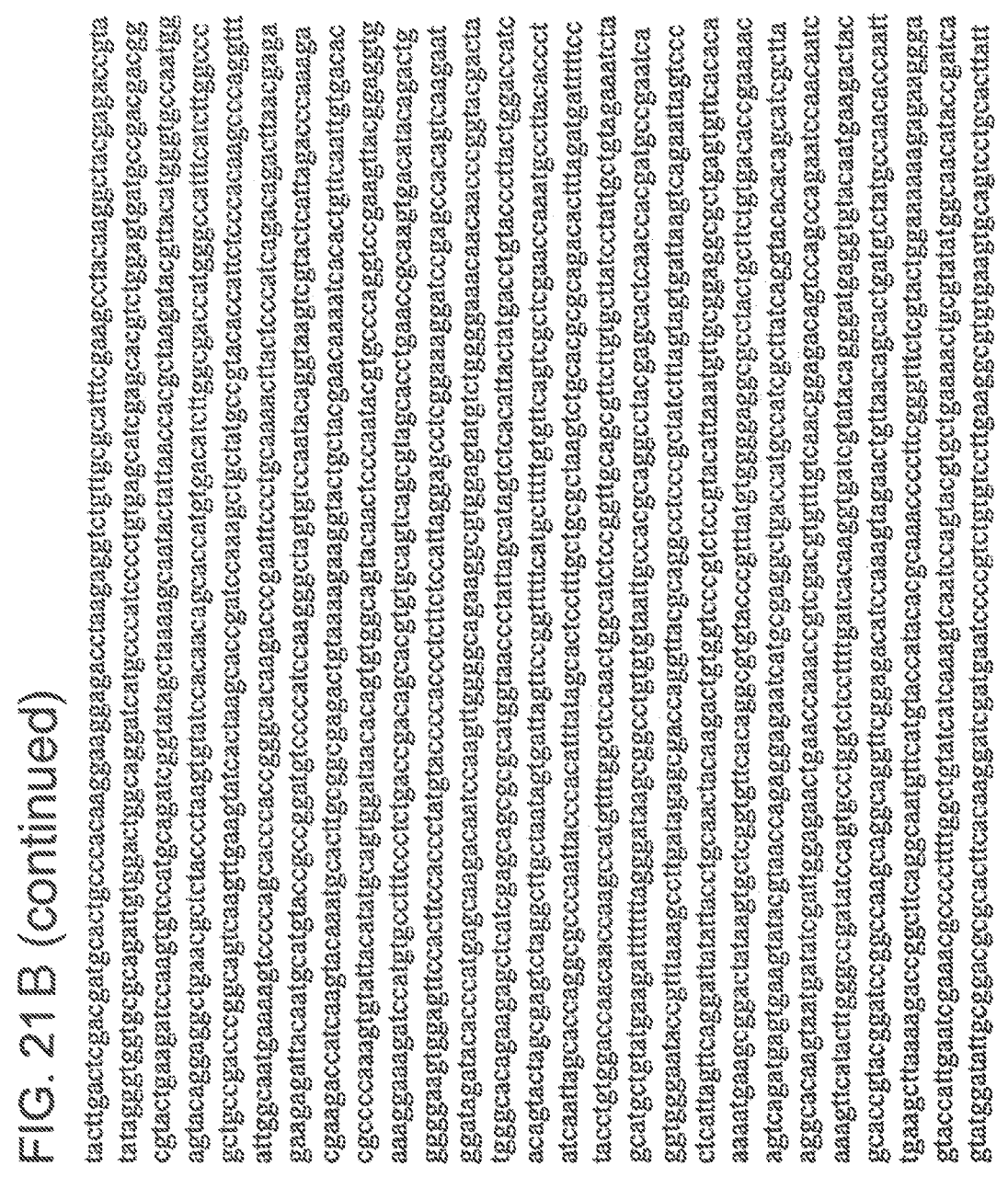

FIG. 21A shows the CMV/R-Barmah Forest virus VLP plasmid. FIG. 21B shows the entire plasmid sequence (SEQ ID NO: 17).

Figure 22B:
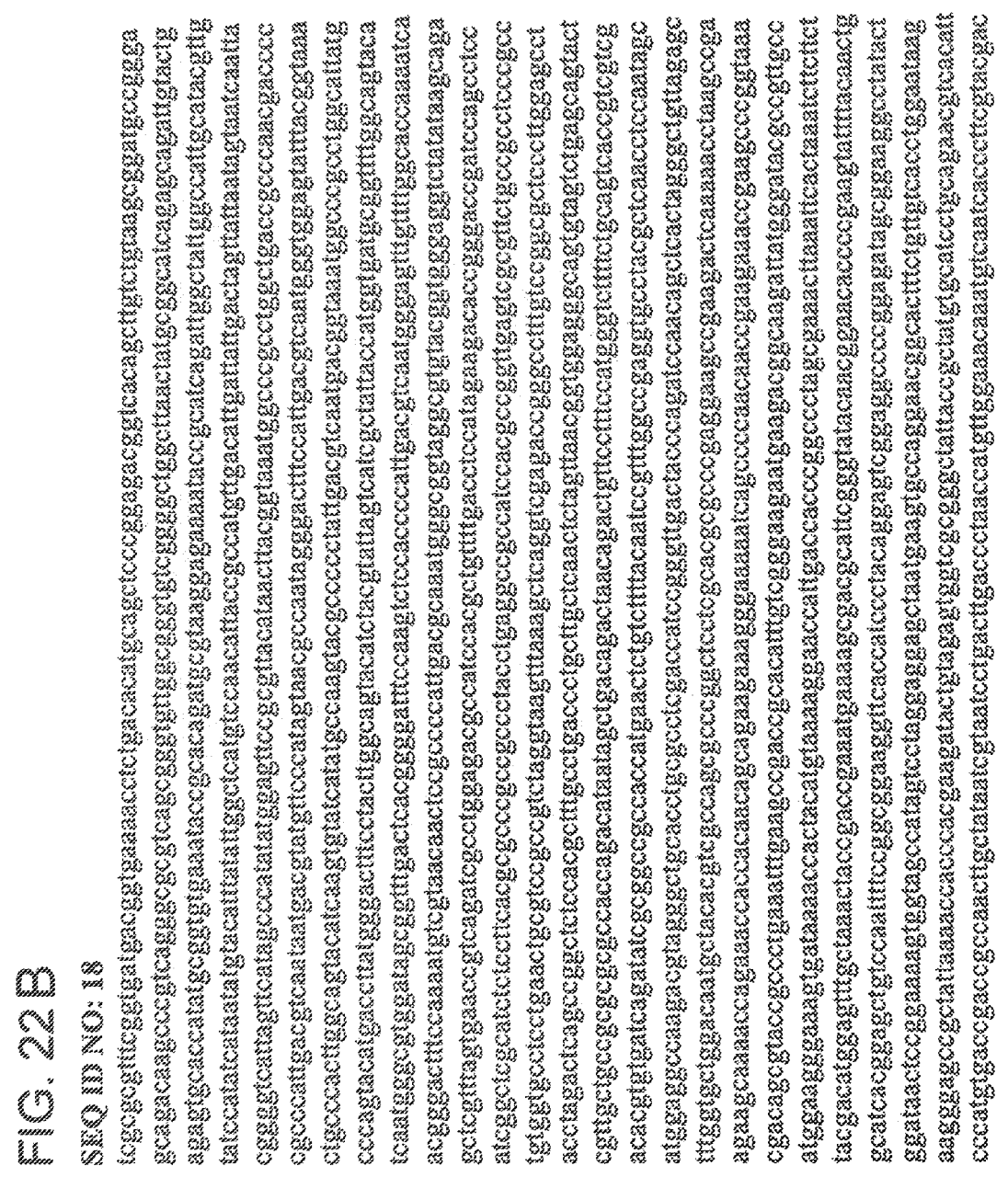

FIG. 22B shows the entire plasmid sequence (SEQ ID NO: 18).

FIG. 24 shows the sequence of Genbank Accession No. EU224268, which is a Cloning vector pCHIKV-LR ic, complete sequence. See, Tsetsarkin. K., Higgs, S., McGee, C. E., DeLamballerie, X., Charrel, R. N. and Vanlandingham, D. L. Infectious clones of Chikungunya virus (La Reunion isolate) for vector competence studies, Vector Borne Zoonotic Dis. 6 (4), 325-337 (2006).

FIG. 25 shows the sequence of Genbank Accession No. EU224270, which is the complete sequence of the Cloning vector pCHIK-37997ic.

DETAILED DESCRIPTION OF THE INVENTION

Figure 1A:
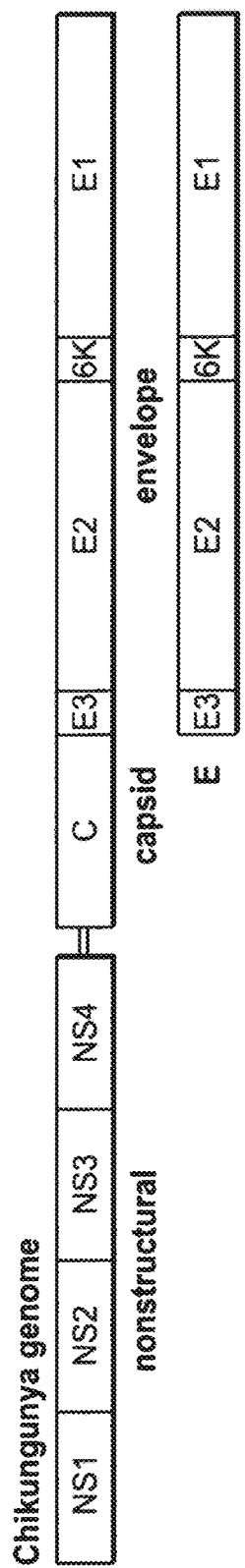
FIGS. 1A-1D show the characterization of CHIKV E pseudotyped lentiviral vectors.

Chikungunya virus (CHIKV) has infected millions of people in Africa, Europe, and Asia since its re-emergence in Kenya in 2004. The evolution and spread of the virus into new geographic areas, and the severity of the disease, present a serious public health threat in the absence of a vaccines or anti-viral therapies. The invention provides compositions and methods for inducing protective immunity. The invention is based, at least in part, on the discovery that a recombinant virus-like particle (VLP) vaccine protects against CHIKV infection in non-human primates. VLPs were generated by expression of viral structural proteins. These had similar buoyant density and morphology to replication-competent virus. Immunization with VLPs elicited neutralizing antibodies against homologous and heterologous envelope. Monkeys immunized with VLPs produced high titer cross-reactive neutralizing antibodies that protected against high dose challenge with emerging epidemic CHIKV. Furthermore, passive transfer of these antibodies from immune monkeys protected against lethal CHIKV challenge in immunodeficient mice, demonstrating that protection is mediated by the humoral immune response. Immunization with the VLP vaccine is a strategy that would prevent the infection and spread of CHIKV and related pathogenic viruses in humans.

Accordingly, the invention provides immunogenic compositions containing one or more alphavirus (e.g., Chikungunya virus) structural polypeptides. In particular, the immunogenic composition (e.g., vaccine) contains envelope or capsid polypeptides sufficient to form a virus-like particle.

The invention further provides nucleic acid molecules encoding alphavirus (Chikungunya) structural polypeptides, expression vectors comprising these coding sequences, and methods of using these nucleic acid molecules for the preparation of virus-like particles. In other embodiments, the invention provides DNA vaccines that provide for the expression of one or more viral polypeptides in the cell of a subject.

Definitions

By "alphavirus structural protein" is meant a polypeptide or fragment thereof having at least about 40% amino acid sequence identity to a naturally occurring viral capsid or envelope protein and having immunogenic activity in a mammal. In one embodiment, the alphavirus structural protein has at least about 85%, 90%, 95% or greater amino acid sequence identity with a Chikunguna virus structural protein or immunogenic fragment thereof. In one embodiment, the protein Exemplary alphaviruses include, but are not limited to, Western, Eastern, and Venezuelan equine encephalitis viruses, o'nyong-nyong virus, Ross River virus and Sindbis virus.

By "Chikungunya virus structural protein" is meant a polypeptide or fragment thereof having at least about 85% amino acid sequence identity to a naturally occurring Chikungunya virus capsid or envelope protein. In other embodiments, the amino acid sequence identity is at least about 90%, 95%, or more.

By "agent" is meant any small molecule chemical compound, antibody, nucleic acid molecule, or polypeptide, or fragments thereof.

As used herein, the term "adjuvant" is meant to refer to a compound that, when used in combination with a specific immunogen in a formulation, will augment, alter or modify the resultant immune response. In certain embodiments, the adjuvant is used in combination with a VLP. In other embodiments, the adjuvant is used in combination with a DNA vaccine. Modification of the immune response includes intensification or broadening the specificity of either or both antibody and cellular immune responses. Modification of the immune response can also mean decreasing or suppressing certain antigen-specific immune responses. In one embodiment, the adjuvant is Ribi adjuvant.

As used herein "alphavirus" is meant to refer to RNA-containing viruses that belong to the group IV Togaviridae family of viruses. Exemplary alphaviruses include but are not limited to Western, Eastern, and Venezuelan equine encephalitis viruses, o'nyong-nyong virus, Ross River virus and Sindbis virus.

As used herein "inducing immunity" is meant to refer to any immune response generated against an antigen. In one embodiment, immunity is mediated by antibodies against an infectious agent, which is exhibited by a vertebrate (e.g., a human), that prevents or ameliorates an infection or reduces at least one symptom thereof. VLPs or DNA vaccines of the invention can stimulate the production of antibodies that, for example, neutralize infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates an infection, for example CHIKV infection, or reduces at least one symptom thereof.

By "ameliorate" is meant decrease, suppress, attenuate, diminish, arrest, or stabilize the development or progression of a disease or a symptom thereof.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include viral infections including but not limited to Western, Eastern, and Venezuelan equine encephalitis viruses, o'nyong-nyong virus, Ross River virus and Sindbis virus.

By "effective amount" is meant the amount of an agent required to ameliorate the symptoms of a disease relative to an untreated patient. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or prevent a diseases delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid molecule (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (Sec, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "structural polyprotein" is meant a composite amino acid molecule comprising at least two separable polypeptides that contribute to a viral capsid or envelope. In one embodiment, the polypeptides are susceptible to cleavage with a viral enzyme (e.g., capsid autoproteinase and signalases).

An exemplary structural polyprotein sequence is provided at Genbank Accession No. ABX40006.1, which is reproduced below.

(SEQ ID NO: 24)
VINNCKVDQCHAAVTNHKKWQYNSPLVPRNAELGDRKGKIHIPFPLANVT

CRVPKARNPTVTYGKNQVIMLLYPDHPTLLSYRNMGEEPNYQEEWVMHKK

EVVLTVPTEGLEVTWGNNEPYKYWPQLSTNGTAHGHPHEIILYYYELYPT

MTVVVVSVATFILLSMVGMAAGMCMCARRRCITPYELTPGATVPFLLSLI

CCIRTAKAATYQEAAIYLWNEQQPLFWLQALIPLAALIVLCNCLRLLPCC

CKTLAFLAVMSVGAHTVSAYEHVTVIPNTVGVPYKTLVNRPGYSPMVLEM

ELLSVTLEPTLSLDYITCEYKTVIPSPYVKCCGTAECKDKNLPDYSCKVF

TGVYPEMWGGAYCFCDAENTQLSEAHVEKSESCKTEFASAYRAHTASASA

KLRVLYQGNNITVTAYANGDHAVTVKDAKFIVGPMSSAWTPFDNKIVVYK

GDVYNMDYPPFGAGRPGQFGDIQSRTPESKDVYANTQLVLQRPAVGTVHV

PYSQAPSGFKYWLKERGASLQHTAPFGCQIATNPVRAVNCAVGNMPISID

IPEAAFTRVVDAPSLTDMSCEVPACTHSSDFGGVAIIKYAASKKGKCAVH

SMTNAVTIREAEIEVEGNSQLQISFSTALASAEFRVQVCSTQVHCAAECH

PPKDHIVNYPASHTTLGVQDISATAMSWVQKITGGVGLVVAVAALILIVV

LCVSFSRH

An exemplary expression vector encoding the structural polyprotein shown above is provided at Genbank Accession No. EU224268 (FIG. 24).

A second exemplary structural polyprotein sequence is provided at Genbank Accession No. ABX40011.1, which is reproduced below:

(SEQ ID NO: 25)
VINNCKIDQCHAAVTNHKNWQYNSPLVPRNAELGDRKGKIHIPFPLANVT

CRVPKARNPTVTYGKNQVTMLLYPDHPTLLSYRNMGQEPNYHEEWVTHKK

EVTLTVPTEGLEVTWGNNEPYKYWPQMSTNGTAHGHPHEIILYYYELYPT

MTVVIVSVASFVLLSMVGTAVGMCVCARRRCITPYELTPGATVPFLLSLL

CCVRTTKAATYYEAAAYLWNEQQPLFWLQALIPLAALIVLCNCLKLLPCC

CKTLAFLAVMSIGAHTVSAYEHVTVIPNTVGVPYKTLVNRPGYSPMVLEM

ELQSVTLEPTLSLDYITCEYKTVIPSPYVKCCGTAECKDKSLPDYSCKVF

TGVYPFMWGGAYCFCDAENTQLSEAHVEKSESCKTEFASAYRAHTASASA

KLRVLYQGNNITVAAYANGDHAVTVKDAKFVVGPMSSAWTPFDNKIVVYK

GDVYNMDYPPFGAGRPGQFGDIQSRTPESKDVYANTQLVLQRPAAGTVHV

PYSQAPSGFKYWLKERGASLQHTAPFGCQIATNPVRAVNCAVGNIPISID

IPDAAFTRVVDAPSVTDMSCEVPACTHSSDFGGVAIIKYTASKKGKCAVH

SMTNAVTIREADVEVEGNSQLQISESTALASAEFRVQVCSTQVHCAAACH

PPKDHIVNYPASHTTLGVQDISTTAMSWVQKITGGVGLIVAVAALILIVV

LCVSFSRH

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the term "vaccine" refers to a formulation which contains VLPs or DNAs, or other gene-based vaccine vectors, of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs or DNA vaccines. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses. In certain embodiments, a vaccine can also be a protein. For example, recombinant proteins have been produced by genetically engineering cells to produce one or more foreign genes, which in turn produce proteins that serve as the immunogen.

As used herein, the term "virus-like particle" (VLP) refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Immunogenic Compositions

The invention provides compositions and methods for inducing an immunological response in a subject, particularly a human, which involves inoculating the subject with a VLP comprising one or more alphavirus or CHIKV polypeptides, or fragments thereof, in a suitable carrier for the purpose of inducing or enhancing an immune response. In one embodiment, an immune response protects the subject from a CHIKV infection, or inflammatory consequences thereof (e.g., arthritis). The administration of this immunological composition may be used either therapeutically in subjects already experiencing a CHIKV infection, or may be used prophylactically to prevent a CHIKV infection.

In certain embodiments, CHIKV candidate vaccines were developed by comparing the immunogenicity of gene products derived from two disparate strains, the 37997 strain from West Africa and the latest outbreak strain, OPY-1, of the East/Central/South African genotype, to develop CHIKV candidate vaccines. These strains share ~95% amino acid sequence similarity but have distinct biological differences, particularly related to their host range.

VLPs of the invention are useful for preparing vaccines and immunogenic compositions. One important feature of VLPs is the ability to express surface proteins so that the immune system of a vertebrate induces an immune response against said protein. However, not all proteins can be expressed on the surface of VLPs. There may be many reasons why certain proteins are not expressed, or be poorly expressed, on the surface of VLPs. One reason is that said protein is not directed to the membrane of a host cell or that said protein does not have a transmembrane domain.

The preparation of immunogenic compositions and vaccines is known to one skilled in the art. The vaccine includes a VLP comprising one or more CHIKV polypeptides, or fragments thereof. The invention also provides expression vectors encoding one or more CHIKV polypeptides or fragments thereof or variants thereof. Such an immunogenic composition is delivered in vivo in order to induce or enhance an immunological response in a subject, such as a humoral response.

For example, a VLP comprising one or more CHIKV polypeptides, or fragments or variants thereof are delivered in vivo in order to induce an immune response.

Typically vaccines are prepared in an injectable form, either as a liquid solution or as a suspension. Solid forms suitable for injection may also be prepared as emulsions, or with the polypeptides encapsulated in liposomes. Vaccine antigens are usually combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The VLP comprising one or more CHIKV polypeptides, or fragments or variants thereof may be administered in combination with an adjuvant (e.g., Ribi). Adjuvants are immunostimulating agents that enhance vaccine effectiveness. If desired, the VLP comprising one or more CHIKV polypeptides or fragments or variants thereof are administered in combination with an adjuvant that enhances the effectiveness of the immune response generated against the antigen of interest. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions, i.e. the VLP comprising one or more CHIKV polypeptides, pharmaceutically acceptable carrier and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The immunogenic compositions are typically administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

Immunogenic compositions are administered in a manner compatible with the dose formulation. The immunogenic composition comprises an immunologically effective amount of the VLP and other previously mentioned components. By an immunologically effective amount is meant a single dose, or a composition administered in a multiple dose schedule, that is effective for the treatment or prevention of an infection. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgement of the practitioner, but typically range between 5 µg to 250 µg of antigen per dose.

The invention provides a VLP for use in treating or preventing an alphavirus infection (e.g., Chikungunya infection).

Polypeptide Expression

In general, VLPs comprising one or more CHIKV polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, COS cells). Such cells are available from a wide range of sources (e.g., the American Type Culture Collection, Rockland, Md.; also, sec, e.g., Ausubel et al., supra). Non limiting examples of insect cells are, *Spodoptera frugiperda* (Sf) cells, e.g. Sf9, Sf21, *Trichoplusia ni* cells, e.g. High Five cells, and *Drosophila* S2 cells. Examples of fungi (including yeast) host cells are *S. cerevisiae*, *Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarrowia lipolytica*. Examples of mammalian cells are COS cells, baby hamster kidney cells, mouse L cells, LNCaP cells, Chinese hamster ovary (CHO) cells, human embryonic kidney (HEK) cells, African green monkey cells, CVI cells, HeLa cells, MDCK cells, Vero and Hep-2 cells. *Xenopus laevis* oocytes, or other cells of amphibian origin, may also be used. Prokaryotic host cells include bacterial cells, for example, *E. coli, B. subtilis*, and mycobacteria.

Methods of cloning said proteins are known in the art. For example, the gene encoding a specific CHIKV or any alphavirus protein can be isolated by RT-PCR from polyadenylated mRNA extracted from cells which had been infected with said virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

The invention further provides nucleotides that encode proteins, including chimeric molecules, cloned into an expression vector that can be expressed in a cell that provides for the formation of VLPs. An "expression vector" is a vector, such as a plasmid, that is capable of promoting expression, as well as replication of a nucleic acid incorporated therein. Typically, the nucleic acid molecule to be expressed is "operably linked" to a promoter and/or enhancer, and is subject to transcription regulatory control by the promoter and/or enhancer.

In one embodiment, the VLP comprises one or more alphavirus envelope proteins, and in particular CHIKV virus envelope proteins. In another embodiment, the one or more envelope proteins are any one or more of E3, E2, 6K and E1. In another embodiment, the VLP further comprises a CHIKV virus capsid protein. In related embodiments, the Chikungunya virus capsid protein is used. In still another embodiment, the VLPs are comprised of capsid, E3, E2, 6K and E1. In another embodiment, the expression vector is a mammalian expression vector or baculovirus vector.

The method of transformation or transfection and the choice of expression vehicle will depend on the host system selected. Transformation and transfection methods are described, e.g., in Ausubel et al. (supra); expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

Constructs and/or vectors provided herein comprise CHIKV polynucleotides that encode structural polypeptides, including envelope proteins or capsid proteins or portions thereof as described herein. The vector may be, for example, a phage, plasmid, viral, or retroviral vector. The constructs and/or vectors that comprise the nucleotides should be operatively linked to an appropriate promoter, such as the CMV promoter, phage lambda PL promoter, the *E. coli* lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

Recombinant constructs can be prepared and used to transfect, infect, or transform and can express viral proteins, including those described herein, into eukaryotic cells and/or prokaryotic cells. Thus, the invention provides for host cells which comprise a vector (or vectors) that contain nucleic acids which code for CHIKV structural genes, including capsid, E3, E2, 6K, and E1 or portions thereof, and/or any chimeric molecule described above, and permit the expression of CHIKV structural genes, including capsid E3, E2, 6K, and E1, or portions thereof, and/or any chimeric molecule described above in said host cell under conditions which allow the formation of VLPs.

In one embodiment, said vector is a recombinant baculovirus. In another embodiment, said recombinant baculovirus is transfected into an insect cell. In a preferred embodiment, said cell is an insect cell. In another embodiment, said insect cell is a SD cell.

In another embodiment, said vector and/or host cell comprise nucleotides that encode CHIKV genes, including capsid, E3, E2, 6K, and E1, or portions thereof as described herein. In another embodiment, said vector and/or host cell consists essentially of CHIKV capsid E3, E2, 6K, and E1, or portions thereof as described herein. In a further embodiment, said vector and/or host cell consists of CHIKV protein comprising capsid, E3, E2, 6K, and E1, or portions thereof, as described herein. These vector and/or host cell contain CHIKV core E3, E2, 6K, and E1, or portions thereof, as described herein, and may contain additional cellular constituents such as cellular proteins, baculovirus proteins, lipids, carbohydrates etc.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, a recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once a recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments or analogs (described herein).

CHIKV Polypeptides and Analogs

The invention provides VLPs comprising one or more CHIKV polypeptides. Also included in the invention are VLPs comprising one or more CHIKV polypeptides or fragments thereof that are modified in ways that enhance or do not inhibit their ability to modulate an immune response. In one embodiment, the invention provides methods for optimizing a CHIKV amino acid sequence or nucleic acid sequence by producing an alteration. Such alterations may include certain mutations, deletions, insertions, or post-translational modifications. The invention further includes analogs of any naturally-occurring polypeptide of the invention. Analogs can differ from the naturally-occurring the polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 10, 13, 15 amino acid residues, preferably at least 25 amino acid residues, and more preferably more than 35 amino acid residues.

Alterations of a alphavirus or CHIKV polypeptide include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

In one embodiment, the invention provides polypeptide variants that differ from a reference polypeptide. The term "variant" refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software. Desirably, variants show substantial biological activity. In one embodiment, a protein variant forms a VLP and elicits an antibody response when administered to a subject.

Natural variants can occur due to mutations in the proteins. These mutations may lead to antigenic variability within individual groups of infectious agents, for example CHIKV. Thus, a person infected with a particular strain develops antibody against that virus, as newer virus strains appear, the antibodies against the older strains no longer recognize the newer virus and reinfection can occur. The invention encompasses all antigenic and genetic variability of proteins from infectious agents for making VLPs.

Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., .beta. or .gamma. amino acids.

In addition to full-length polypeptides, the invention also includes fragments of any one of the polypeptides of the invention. As used herein, the term "a fragment" means at least 5, 10, 13, or 15. In other embodiments a fragment is at least 20 contiguous amino acids, at least 30 contiguous amino acids, or at least 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein analogs having a chemical structure designed to mimic CHIKV VLPs or one or more CHIKV polypeptides functional activity can be administered according to methods of the invention. CHIKV analogs may exceed the physiological activity of native CHIKV. Methods of analog design are well known in the art, and synthesis of analogs can be carried out according to such methods by modifying the chemical structures such that the resultant analogs exhibit the immunomodulatory activity of a native CHIKV polypeptide. These chemical modifications include, but are not limited to, substituting alternative R groups and varying the degree of saturation at specific carbon atoms of the native CHIKV molecule. Preferably, the analogs are relatively resistant to in vivo degradation, resulting in a more prolonged therapeutic effect upon administration. Assays for measuring functional activity include, but are not limited to, those described in the Examples below.

CHIKV Polynucleotides

In general, the invention includes any nucleic acid sequence encoding a VLP comprising one or more CHIKV polypeptides or a fragment thereof, where the fragment induces an immune response. An isolated nucleic acid molecule is can be manipulated by recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. In certain exemplary embodiments, the vector comprises Chikungunya$_{37997}$ or Chikungunya$_{OPY-1}$ nucleic acid segments, or fragments thereof. The vector may further comprise a CMV/R promoter. The vector may also comprise the capsid protein, or a fragment thereof.

In other exemplary embodiments, the vector comprises an envelope protein selected from the group consisting of E3, E2, 6K, and E1. In certain examples, the vaccine may comprise capsid, E3, E2, 6K and E1. In other examples, the vaccine may comprise E3, E2, 6K and E1.

According to certain preferred embodiments of the invention, C-Env$_{37997}$ is set forth as SEQ ID NO:1; Env$_{37997}$ is set forth as SEQ ID NO:19; C-Env$_{OPY-1}$ is set forth as SEQ ID NO:3; Env$_{OPY-1}$ is set forth as SEQ ID NO: 20.

Shown below is the nucleotide sequence corresponding to the capsid (SEQ ID NO: 21) and E3, E2, 6K and E1 (SEQ ID NO: 19) of the CMV/R-CHIKV C-E3-E2-6K-E1 plasmid (Strain 37997). The CMV/R expression vector is described, for example, in U.S. Pat. No. 7,094,598, which is incorporated herein in its entirety.

E3-E2-6K-E1

SEQ ID NO: 19
atgagcctcgccctcccggtcttgtgcctgttggcaaacactacattcc cctgctctcagccgccttgcacaccctgctgctacgaaaaggaaccgga aagcaccttgcgcatgcttgaggacaacgtgatgagaccoggatactac cagctactaaaagcatcgctgacttgctctccccaccgccaaagacgca gtactaaggacaattttaatgtctataaagccacaagaccatatctagc tcattgtcctgactgcggagaagggcattcgtgccacagccctatcgca ttggagcgcatcagaaatgaagcaacggacggaacgctgaaaatccagg tctctttgcagatcgggataaagacagatgacagccacgattggaccaa gctgcgctatatggatagccatacgccagcggacgcggagcgagccgga ttgcttgtaaggacttcagcaccgtgcacgatcacgggaccatgggac actttattctcgcccgatgcccgaaaggagagacgctgacagtgggatt tacggacagcagaaagatcagccacacatgcacacacccgttccatcat gaaccacctgtgataggtagggagaggttccactctcgaccacaacatg gtaaagagttaccttgcagcacgtacgtgcagagcaccgctgccactgc tgaggagatagaggtgcatatgccccagatactcctgaccgcacgctg atgacgcagcagtctggcaacgtgaagatcacagttaatgggcagacgg tgcggtacaagtgcaactgcggtggctcaaacgagggactgacaaccac agacaaagtgatcaataactgcaaaattgatcagtgccatgctgcagtc actaatcacaagaattggcaatacaactcccctttagtcccgcgcaacg ctgaactcggggaccgtaaaggaaagatccacatcccattcccattggc -continued

```
aaacgtgacttgcagagtgccaaaagcaagaaaccctacagtaacttac
ggaaaaaaccaagtcaccatgctgctgtatcctgaccatccgacactct
tgtcttaccgtaacatgggacaggaaccaaattaccacgaggagtgggt
gacacacaagaaggaggttaccttgaccgtgcctactgagggtctggag
gtcacttggggcaacaacgaaccatacaagtactggccgcagatgtcta
cgaacggtactgctcatggtcacccacatgagataatcttgtactatta
tgagctgtaccccactatgactgtagtcattgtgtcggtggcctcgttc
gtgcttctgtcgatggtgggcacagcagtgggaatgtgtgtgtgcgcac
ggcgcagatgcattacaccatatgaattaacaccaggagccactgttcc
cttcctgctcagcctgctatgctgcgtcagaacgaccaaggcggccaca
tattacgaggctgcggcatatctatggaacgaacagcagcccctgttct
ggttgcaggctcttatcccgctggccgccttgatcgtcctgtgcaactg
tctgaaactcttgccatgctgctgtaagaccctggcttttttagccgta
atgagcatcggtgcccacactgtgagcgcgtacgaacacgtaacagtga
tcccgaacacggtgggagtaccgtataagactcttgtcaacagaccggg
ttacagccccatggtgttggagatggagctacaatcagtcaccttggaa
ccaacactgtcacttgactacatcacgtgcgagtacaaaactgtcatcc
cctccccgtacgtgaagtgctgtggtacagcagagtgcaaggacaagag
cctaccagactacagctgcaaggtctttactggagtctacccatttatg
tggggcggcgcctactgcttttgcgacgccgaaaatacgcaattgagcg
aggcacatgtagagaaatctgaatcttgcaaaacagagtttgcatcggc
ctacagagcccacaccgcatcggcgtcggcgaagctccgcgtcctttac
caaggaaacaacattaccgtagctgcctacgctaacggtgaccatgccg
tcacagtaaaggacgccaagtttgtcgtgggcccaatgtcctccgcctg
gacaccttttgacaacaaaatcgtggtgtacaaaggcgacgtctacaac
atggactacccacctttggcgcaggaagaccaggacaatttggtgaca
ttcaaagtcgtacaccggaaagtaaagacgtttatgccaacactcagtt
ggtactacagaggccagcagcaggcacggtacatgtaccatactctcag
gcaccatctggcttcaagtattggctgaaggaacgaggagcatcgctac
agcacacggcaccgttcggttgccagattgcgacaaacccggtaagagc
tgtaaattgcgctgtggggaacataccaatttccatcgacataccggat
gcggcctttactagggttgtcgatgcaccctctgtaacggacatgtcat
gcgaagtaccagcctgcactcactcctccgactttggggcgtcgccat
catcaaatacacagctagcaagaaaggtaaatgtgcagtacattcgatg
accaacgccgttaccattcgagaagccgacgtagaagtagagggaact
cccagctgcaaatatccttctcaacagccctggcaagcgccgagtttcg
cgtgcaagtgtgctccacacaagtacactgcgcagccgcatgccaccct
ccaaaggaccacatagtcaattcccagcatcacacaccaccccttgggg
tccaggatatatccacaacggcaatgtcttgggtgcagaagattacggg
```

```
aggagtaggattaattgttgctgttgctgccttaattttaattgtggtg
ctatgcgtgtcgtttagcaggcac
```

Core

SEQ ID NO: 21
```
Atggagttcatcccgacgcaaactttctataacagaaggtaccaacccc
gaccctgggccccacgccctacaattcaagtaattagacctagaccacg
tccacagaggcaggctgggcaactcgcccagctgatctccgcagtcaac
aaattgaccatgcgcgcggtacctcaacagaagcctcgcagaaatcgga
aaaacaagaagcaaggcagaagaagcaggcgccgcaaaacgacccaaa
gcaaagaagcaaccaccacaaaagaagccggctcaaaagaagaagaaa
ccaggccgtagggagagaatgtgcatgaaaattgaaaatgattgcatct
tcgaagtcaagcatgaaggcaaagtgatgggctacgcatgcctggtggg
ggataaagtaatgaaaccagcacatgtgaagggaactatcgacaatgcc
gatctggctaaactggcctttaagcggtcgtctaaatacgatcttgaat
gtgcacagataccggtgcacatgaagtctgatgcctcgaagtttaccca
cgagaaacccgaggggtactataactggcatcacggagcagtgcagtat
tcaggaggccggttcactatcccgacgggtgcaggcaagccgggagaca
gcggcagaccgatcttcgacaacaaaggacgggtggtggccatcgtcct
aggaggggccaacgaaggtgcccgcacggccctctccgtggtgacgtgg
aacaaagacatcgtcacaaaaattacccctgagggagccgaagagtgg
```

Shown below is the nucleotide sequence corresponding to the capsid (SEQ ID NO: 22) and E3, E2, 6K and E1 (SEQ ID NO: 20) of the CMV/R-CHIKV C-E3-E2-6K-E1 plasmid (Strain OPY-1).

E3-E2-6K-E1

SEQ ID NO: 20
```
Atgagtcttgccatcccagttatgtgcctgttggcaaacaccacgttcc
cctgctcccagccccttgcacgcctgctgctacgaaaaggaaccgga
ggaaacccctacgcatgcttgaggacaacgtcatgagacctgggtactat
cagctgctacaagcatccttaacatgttctccccaccgccagcgacgca
gcaccaaggacaacttcaatgtctataaagccacaagaccatacttagc
tcactgtcccgactgtggagaagggcactcgtgccatagtcccgtagca
ctagaacgcatcagaaatgaagcgacagacgggacgctgaaaatccagg
tctccttgcaaatcggaataaagacggatgacagccacgattggaccaa
gctgcgttatatggacaaccacatgccagcagacgcagagagggcgggg
ctatttgtaagaacatcagcaccgtgtacgattactggaacaatgggac
acttcatcctggcccgatgtccaaaaggggaaactctgacggtgggatt
cactgacagtaggaagattagtcactcatgtacgcacccatttcaccac
gaccctcctgtgataggtcgggaaaaattccattcccgaccgcagcacg
gtaaagagctaccttcagcacgtacgtgcagagcaccgccgcaactac
cgaggagatagaggtacacatgccccagacacccctgatcgcacatta
atgtcacaacagtccggcaacgtaaagatcacagtcaatggccagacgg
tgcggtacaagtgtaattgcggtggctcaaatgaaggactaacaactac
```

-continued agacaaagtgattaataactgcaaggttgatcaatgtcatgccgcggtc accaatcacaaaaagtggcagtataactccctctggtcccgcgtaatg ctgaacttggggaccgaaaaggaaaaattcacatcccgtttccgctggc aaatgtaacatgcagggtgcctaaagcaaggaacccaccgtgacgtac gggaaaaaccaagtcatcatgctactgtatcctgaccacccaacactcc tgtcctaccggaatatgggagaagaaccaaactatcaagaagagtgggt gatgcataagaaggaagtcgtgctaaccgtgccgactgaagggctcgag gtcacgtggggcaacaacgagccgtataagtattggccgcagttatcta caaacggtacagcccatggccacccgcatgagataattctgtattatta tgagctgtaccccactatgactgtagtagttgtgtcagtggccacgttc atactcctgtcgatggtgggtatggcagcgggatgtgcatgtgtgcac gacgcagatgcatcacaccgtatgaactgacaccaggagctaccgtccc tttcctgcttagcctaatatgctgcatcagaacagctaaagcggccaca taccaagaggctgcgatatacctgtggaacgagcagcaaccttttgtttt ggctacaagcccttattccgctggcagccctgattgttctatgcaactg tctgagactcttaccatgctgctgtaaaacgttggcttttttagccgta atgagcgtcggtgcccacactgtgagcgcgtacgaacacgtaacagtga tcccgaacacggtgggagtaccgtataagactctagtcaatagacctgg ctacagcccatggtattggagatggaactactgtcagtcactttggag ccaacactatcgcttgattacatcacgtgcgagtacaaaaccgtcatcc cgtctccgtacgtgaagtgctgcggtacagcagagtgcaaggacaaaaa cctacctgactacagctgtaaggtcttcaccggcgtctacccatttatg tggggcggcgcctactgcttctgcgacgctgaaaacacgcagttgagcg aagcacacgtggagaagtccgaatcatgcaaaacagaatttgcatcagc atacagggctcataccgcatctgcatcagctaagctccgcgtccttac caaggaaataacatcactgtaactgcctatgcaaacggcgaccatgccg tcacagttaaggacgccaaattcattgtggggccaatgtcttcagcctg gacacctttcgacaacaaaattgtggtgtacaaaggtgacgtctataac atggactacccgcccttgggcaggaagaccaggacaatttggcgata tccaaagtcgcacacctgagagtaaagacgtctatgctaatacacaact ggtactgcagagaccggctgtgggtacggtacacgtgccatactctcag gcaccatctggctttaagtattggctaaaagaacgcggggcgtcgctgc agcacacagcaccatttggctgccaaatagcaacaaaccggtaagagc ggtgaactgcgccgtagggaacatgcccatctccatcgacataccggaa gcggccttcactagggtcgtcgacgcgccctctttaacggacatgtcgt gcgaggtaccagcctgcacccattcctcagactttgggggcgtcgccat tattaaatatgcagccagcaagaaaggcaagtgtgcggtgcattcgatg actaacgccgtcactattcgggaagctgagatagaagttgaagggaatt ctcagctgcaaatctcttctcgacggccttagccagcgccgaattccg cgtacaagtctgttctacacaagtacactgtgcagccgagtgccacccc -continued ccgaaggaccacatagtcaactacccggcgtcacataccaccctcgggg tccaggacatctccgctacggcgatgtcatgggtgcagaagatcacggg aggtgtgggactggttgttgctgttgccgcactgattctaatcgtggtg ctatgcgtgtcgttcagcaggcac Core

SEQ ID NO: 22 atggagttcatcccaacccaaacttttttacaataggaggtaccagcctc gaccctggactccgcgccctactatccaagtcatcaggcccagaccgcg ccctcagaggcaagctgggcaacttgcccagctgatctcagcagttaat aaactgacaatgcgcgcggtaccacaacagaagccacgcaggaatcgga agaataagaagcaaaagcaaaaacaacaggcgccacaaaacaacacaaa tcaaaagaagcagccacctaaaaagaaaccggctcaaaagaaaaagaag ccgggccgcagagagaggatgtgcatgaaaatcgaaaatgattgtattt tcgaagtcaagcacgaaggtaaggtaacaggttacgcgtgcctggtggg ggacaaagtaatgaaaccagcacacgtaaaggggaccatcgataacgcg gacctggccaaactggcctttaagcggtcatctaagtatgaccttgaat gcgcgcagatacccgtgcacatgaagtccgacgcttcgaagttcaccca tgagaaaccggaggggtactacaactggcaccacggagcagtacagtac tcaggaggccggttcaccatccctacaggtgctggcaaaccaggggaca gcggcagaccgatcttcgacaacaagggacgcgtggtggccatagtctt aggaggagctaatgaaggagcccgtacagccctctcggtggtgacctgg aataaagacattgtcactaaaatcaccccgaggggggccgaagagtgg In a particular embodiment, a nucleic acid molecule set forth as SEQ ID NO: 1, 19, 3 or 20 includes a nucleotide sequence encoding a polypeptide having at least about 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, or more identity (e.g., when compared to the overall length of the amino acid sequence) to a polypeptide encoding an envelope protein selected from capsid, E3, E2, 6K and E1 or E3, E2, 6K and E1.

In some embodiments of the invention proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host See U.S. patent publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. A person with skill in the art understands that various subcloning methods are available and are possible.

An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, as the term is used herein, because it is readily manipulatable by standard techniques known to those of ordinary skill in the art.

CHIKV VLP Production

The invention also provides constructs and methods for producing a VLP comprising CHIKV polypeptides, or fragments thereof, as well as compositions and methods that increase the efficiency of VLP production. For example, the addition of leader sequences to the CHIKV capsid, E3, E2, 6K, and E1 or portions thereof, that can improve the efficiency of protein transporting within the cell. In another example, a heterologous signal sequence can be fused to the CHIKV capsid, E3, E2, 6K, and E1 or portions thereof. In one embodiment, the signal sequence can be derived from the gene of an insect cell. Another method to increase efficiency of VLP production is to codon optimize the nucleotides that encode CHIKV capsid, E3, E2, 6K, and E1 or portions thereof, for a specific cell type.

Methods of cloning said proteins are known in the art. For example, the gene encoding a specific CHIKV or any alphavirus protein can be isolated by RT-PCR from polyadenylated mRNA extracted from cells which had been infected with said virus. The resulting gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the VLP comprises one or more alphavirus envelope proteins, and in particular CHIKV virus envelope proteins. In another embodiment, the one or more envelope proteins are selected from the group consisting of E3, E2, 6K and E1. In another embodiment, the VLP comprises a CHIKV virus capsid protein. In related embodiments, the Chikungunya virus capsid protein is used. In another embodiment, the VLPs are comprised of E3, E2, 6K and E1. In still another embodiment, the VLPs are comprised of capsid, E3, E2, 6K and E1. In another embodiment, the expression vector is a baculovirus vector.

The invention also provides methods of producing a VLP comprising CHIKV polypeptides, or fragments thereof. In one example, the method involves expressing in a cell a polynucleotide encoding a CHIKV polypeptide and culturing said cell, thereby producing VLPs. In one embodiment, a cell (e.g., human cell) is infected with a DNA vaccine, where the DNA vaccine is a DNA vector, comprising a nucleic acid segment encoding an alphavirus capsid protein or one or more alphavirus envelope proteins, or fragments thereof to produce an alphavirus VLP. In particular, the alphavirus is CHIKV.

Depending on the expression system and host cell selected, the VLPs are produced by growing host cells transformed by an expression vector under conditions whereby the recombinant proteins are expressed and VLPs are formed. In one embodiment, the invention comprises a method of producing a VLP, that involves transfecting vectors encoding at least one alphavirus protein into a suitable host cell and expressing said alphavirus protein under conditions that allow VLP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells that produce VLPs of the invention include, but are not limited to, batch, batch-fed, continuous and perfusion cell culture techniques. In one embodiment, a cell comprising a CHIKV or alphavirus polynucleotide is grown in a bioreactor or fermentation chamber where cells propagate and express protein (e.g. recombinant proteins) for purification and isolation. Typically, cell culture is performed under sterile, controlled temperature and atmospheric conditions. A bioreactor is a chamber used to culture cells in which environmental conditions such as temperature, atmosphere, agitation and/or pH can be monitored. In one embodiment, the bioreactor is a stainless steel chamber. In another embodiment, said bioreactor is a pre-sterilized plastic bag (e.g. Cellbag®, Wave Biotech, Bridgewater, N.J.). In other embodiment, said pre-sterilized plastic bags are about 50 L to 1000 L bags.

The VLPs are isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. A person of skill in the art appreciates that there are additional methods that can be used to make and purify VLPs. Accordingly, the invention is not limited to the methods described herein.

In general, production of VLPs of the invention is accomplished by seeding a mammalian cell (e.g., human embryonic kidney (293T) cells) or Sf9 cells (non-infected) into shaker flasks, allowing the cells to expand and scaling up as the cells grow and multiply (for example from a 125-ml flask to a 50 L Wave bag). The medium used to grow the cells is formulated for the appropriate cell line (preferably serum free media, e.g. insect medium ExCell-420, JRH). Next, the cells are transfected or infected with an appropriate vector (e.g., mammalian expression vector or for SF (cells recombinant baculovirus at the most efficient multiplicity of infection (e.g. from about 1 to about 3 plaque forming units per cell). The polynucleotides, or portions thereof, are expressed in the cells where they self assemble into VLPs and are secreted from the cells approximately 24 to 72 hours post infection. Usually, transfection or infection is most efficient when the cells are in mid-log phase of growth ($4$-$8.\times10^6$ cells/ml) and are at least about 90% viable.

VLPs of the invention are harvested approximately 48 to 120 hours post infection, when the levels of VLPs in the cell culture medium are near the maximum but before extensive cell lysis. The cell density and viability at the time of harvest can be about $0.5\times10^6$ cells/ml to about $1.5\times10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation.

The removal of cell and cellular debris from the cell culture medium containing VLPs of the invention can be accomplished by tangential flow filtration (TFF) with a single use, pre-sterilized hollow fiber 0.5 or 1.00 μm filter cartridge or a similar device.

Next, VLPs in the clarified culture medium are concentrated by ultrafiltration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltered VLPs can be furthered purified on a 20% to 60% discontinuous sucrose gradient in pH 7.2 PBS buffer with 0.5 M NaCl by centrifugation at 6,500×g for 18 hours at about 4 C to about 10 C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or .beta.-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25 C to about 27 C. The baculovirus can also be inactivated by incubating the sample containing the VLPs at 0.05% BPL at 4 C for 3 days, then at 37 C for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

In certain embodiments, a DNA vaccine or VLP comprises agents, such as nucleic acid molecules, siRNA, microRNA, chemotherapeutic agents, imaging agents, and/or other agents that need to be delivered to a patient.

Accordingly, the present invention provides methods of treating viral diseases and/or disorders or symptoms thereof which comprise administering a therapeutically effective amount of a pharmaceutical composition comprising a VLP or DNA of the formulae herein to a subject (e.g., a mammal such as a human). Thus, one embodiment is a method of treating a subject suffering from or susceptible to a viral infection, viral disease or disorder or symptom thereof. The method includes the step of administering to the mammal a therapeutic or prophylactic amount of an amount of a compound herein sufficient to treat the disease or disorder or symptom thereof, under conditions such that the disease or disorder is prevented or treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the agents herein, such as a VLP or DNA of a formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agents herein may be also used in the treatment of any other disorders in which an alphavirus may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with an alphavirus, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Compositions and Administration

The invention features pharmaceutical compositions that comprise VLPs of an alphavirus as described herein. The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a VLP of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

In particular embodiments, the invention encompasses an antigenic formulation comprising VLPs which comprises at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the pharmaceutical composition comprises VLPs of Chikungunya virus, and a pharmaceutically acceptable carrier. In other certain preferred embodiments, the pharmaceutical composition comprises VLPs of Chikungunya virus, an adjuvant, and a pharmaceutically acceptable carrier.

In one embodiment, the VLPs are comprised of Chikungunya virus envelope proteins, for example, the envelope proteins can be selected from the group consisting of E3, E2, 6K and E1. In another embodiment, the pharmaceutical composition further comprises a Chikungunya virus capsid protein. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

The invention also encompasses a vaccine formulation comprising VLPs that comprise at least one viral protein, for example one alphavirus protein. The alphavirus may be selected from the group consisting of, but not limited to, Chikungunya virus, Sindbis virus, Eastern equine encephalitis (EEE) virus, Western equine encephalitis (WEE) virus, and Venezuelan equine encephalitis (VEE) virus.

In certain preferred embodiments, the vaccine composition comprises VLPs of Chikungunya virus, and a pharmaceutically acceptable carrier. In other certain preferred embodiments, the vaccine composition comprises VLPs of Chikungunya virus, an adjuvant, and a pharmaceutically acceptable carrier. In one embodiment, the vaccine composition comprises VLPs of Chikungunya virus envelope proteins, for example, the envelope proteins can be selected from the group consisting of E3, E2, 6K and E1. In another embodiment, the vaccine composition further comprises a Chikungunya virus capsid protein and a pharmaceutically acceptable carrier or excipient. The Chikungunya virus capsid protein is, in certain examples, a capsid protein. In certain examples, the VLPs are comprised of E3, E2, 6K and E1. In other examples, the VLPs are comprised of capsid, E3, E2, 6K and E1.

Pharmaceutically acceptable carriers include but are not limited to saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

In certain embodiments, the VLP composition is supplied in liquid form, for example in a sealed container indicating the quantity and concentration of the VLP composition. Preferably, the liquid form of the VLP composition is supplied in a hermetically sealed container at least about 50 μg/ml, more preferably at least about 100 μg/ml, at least about 200 μg/ml, at least 500 μg/ml, or at least 1 mg/ml.

Generally, VLPs or DNA vaccines of the invention are administered in an effective amount or quantity (as described herein) sufficient to stimulate an immune response against one or more strains of a virus a described here, for example an alphavirus, e.g. CHIKV. Preferably, administration of the VLP of the invention elicits immunity against a virus, for example an alphavirus, in particular example CHIKV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract or small particle aerosol (less than 10 microns) or spray into the lower respiratory tract. While any of the above routes of delivery results in an immune response, intranasal administration confers the added benefit of eliciting mucosal immunity at the site of entry of many viruses, including alphaviruses, for example CHIKV.

Thus, the invention also comprises a method of formulating a vaccine or antigenic composition that induces immunity to an infection or at least one symptom thereof to a mammal, comprising adding to said formulation an effective dose of VLPs, e.g. CHIKV VLP. In one embodiment, the infection is an alphavirus infection, for example, but not limited to, Chikungunya virus, Sindbis virus, Eastern equine encephalitis (EEE) virus, Western equine encephalitis (WEE) virus, and Venezuelan equine encephalitis (VEE) virus.

In certain cases, stimulation of immunity with a single dose is preferred, however additional dosages can be also be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections. Similarly, adults who are particularly susceptible to repeated or serious infections, such as, for example, health care workers, day care workers, family members of young children, the elderly, and individuals with compromised cardiopulmonary function or immune systems may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Prime Boost

The present methods also include a variety of prime-boost regimens. In these methods, one or more priming immunizations is followed by one or more boosting immunizations. The actual immunogenic composition can be the same or different for each immunization and the type of immunogenic composition (e.g., containing protein or expression vector), the route, and formulation of the immunogens can also be varied.

For example, in one embodiment, the prime comprises administering a DNA or gene-based vaccine as described herein and the boost comprises administering a VLP as described herein. In another embodiment, the prime comprises administering a VLP as described herein and the boost comprises administering a DNA or other gene-based vaccine as described herein.

One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

Methods of administering a composition comprising VLPs and/or DNA vaccines (vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition comprising VLPs of the invention may induce an antibody or other immune response that is substantially higher than other routes of administration. In another embodiment, intranasal or other mucosal routes of administration of a composition comprising VLPs of the invention may induce an antibody or other immune response that will induce cross protection against other strains of the virus. Administration can be intramuscular, subdermal, intraperitoneal. In one preferred embodiment, the administration is intramuscular.

In yet another embodiment, the vaccine and/or antigenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or antigenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, said VLPs of the invention can be administered as part of a combination therapy. For example, VLPs of the invention can be formulated with other immunogenic compositions, antivirals and/or antibiotics. A VLP may be administered concurrently, subsequent to, or sequentially with another immunogenic composition, antiviral, antibiotic, or any other agent that prevents or treats an alphavirus (e.g., Chikungunya infection).

The dosage of the pharmaceutical formulation can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. Said dosages can be determined from animal studies. A non-limiting list of animals used to study the efficacy of vaccines include the guinea pig, hamster, ferrets, chinchilla, mouse and cotton rat, and non-human primates. Most animals are not natural hosts to infectious agents but can still serve in studies of various aspects of the disease. For example, any of the above animals can be dosed with a vaccine candidate, e.g. VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611). Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients (2nd Edition)," herein incorporated by reference in its entirety for all purposes, is envisioned within the scope of this invention.

Exemplary adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween-80 emulsion also is contemplated. MF-59, Novasomes®, MHC antigens may also be used.

The VLPs of the invention can also be formulated with "immune stimulators." These are the body's own chemical messengers (cytokines) to increase the immune system's response. Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immunostimulatory molecules can be administered in the same formulation as the VLPs, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Delivery

The VLPs of the invention are useful for preparing compositions that stimulate an immune response. Such compositions are useful for the treatment or prevention or a viral infection (e.g., a CHIKV or other alphavirus infection). Both mucosal and cellular immunity may contribute to immunity to infectious agents and disease. In one embodiment, the invention encompasses a method of inducing immunity to a viral infection, for example Chikungunya virus infection in a subject, by administering to the subject a Chikungunya virus VLP or a DNA vaccine.

The invention also provides a method to induce immunity to viral infection or at least one symptom thereof in a subject, comprising administering at least one effective dose of a VLP or DNA vaccine as described herein, for example a VLP comprising one or more viral proteins, for example one or more CHIKV virus envelope proteins or a DNA vaccine comprising a nucleic acid segment encoding an alphavirus capsid protein or one or more alphavirus envelope proteins, or fragments thereof. In certain cases, the VLP further comprises a virus capsid protein. In another embodiment, the method comprises inducing immunity to a viral infection, e.g. CHIKV infection or at least one symptom thereof by administering said formulation in multiple doses.

VLPs of the invention can induce substantial immunity in a vertebrate (e.g. a human) when administered to said vertebrate. The substantial immunity results from an immune response against VLPs of the invention that protects or ameliorates infection or at least reduces a symptom of infection in said vertebrate. In some instances, if the said vertebrate is infected, said infection will be asymptomatic. The response may be not a fully protective response. In this case, if said vertebrate is infected with an infectious agent, the vertebrate will experience reduced symptoms or a shorter duration of symptoms compared to a non-immunized vertebrate.

In one embodiment, the invention comprises a method of inducing substantial immunity to alphavirus infection or at least one symptom thereof in a subject, comprising administering at least one effective dose of a VLP and/or a DNA vaccine comprising a nucleic acid segment encoding an alphavirus capsid protein or one or more alphavirus envelope proteins, or fragments thereof. In particular embodiments, the infection is CHIKV and the VLP comprises one or more CHIKV envelope protein as described herein. In another embodiment, the invention comprises a method of vaccinating a mammal against an alphavirus comprising administering to said mammal a protection-inducing amount of VLPs or DNA vaccines comprising at least one alphavirus protein. In one embodiment, said method comprises administering DNA vaccines comprising capsid, E3, E2, 6K and E1. In another embodiment, said method comprises administering DNA vaccines comprising E3, E2, 6K and E1. In another embodiment, said method comprises administering DNA vaccines comprising C-$Env_{37997}$ as set forth as SEQ ID NO:1. In another embodiment, said method comprises administering DNA vaccines comprising $Env_{37997}$ as set forth as SEQ ID NO: 19. In another embodiment, said method comprises administering DNA vaccines comprising C-$Env_{OPY-1}$ as set forth as SEQ ID NO:3. In another embodiment, said method comprises administering DNA vaccines comprising $Env_{OPY-1}$ as set forth as SEQ ID NO:20. In one embodiment, said method comprises administering VLPs comprising capsid, E3, E2, 6K and E1. In another embodiment, said method comprises administering VLPs comprising E3, E2, 6K and E1. In one embodiment, said method comprises administering VLPs comprised of Chikungunya virus envelope proteins.

In another embodiment, the invention comprises a method of inducing a protective cellular response to a viral infection or at least one symptom thereof in a subject, comprising administering at least one effective dose of a DNA vaccine or a VLP.

As mentioned above, the VLPs of the invention prevent or reduce at least one symptom of an infection in a subject. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of viral infection or additional symptoms, a reduced severity of viral symptoms or a suitable assays (e.g. antibody titer and/or T-cell activation assay). The objective assessment comprises both animal and human assessments.

The invention also provides assays to identify inhibitors of viral entry comprising, in at least one embodiment, genetically modified target cells expressing at least one Chikungunya viral receptor, together with any co-receptors which might be required for infection or entry. These cells are genetically modified in the sense that they express a reporter gene, such as an affinity tag, a fluorogenic protein or an enzyme able to convert substrates into fluorogenic, chromogenic or luminometric products. Coupling this type of reporter signal to an inhibition of viral infection is accomplished by arranging the expression of the reporter gene to be strongly decreased (downregulated) upon infection with the virus of interest. In principle, this can be ensured by any suitable means, but especially preferred are:

The reporter gene product itself is fused to a cellular protein which, upon infection with the virus of interest is itself downregulated. For example, the reporter gene product can be fused to the corresponding viral receptor, which in many cases is downregulated upon infection.

Thus in one aspect a compound library may be screened for the ability to inhibit the infection of cells with Chikungunya virus (CHIKV). An appropriate indicator cell line is generated that stably expresses a reporter gene. In one example, these cells are seeded in microtiter plates and incubated with CHIKV particles in presence of different compounds, e.g., antibodies, in each well. Upon infection, the fusion protein is downregulated due to the expression of the viral genes. Consequently, only cells that have not been infected with CHIKV will express the reporter gene. Thus, wells that exhibit a positive reporter signal contain compounds that inhibit infection. Variations and modifications of these assays will be apparent from the relevant sections of the description which explain individual parts of the assay in more detail. Specifically, in one embodiment, the reporter gene can be expressed when infection occurs rather than the reporter gene being downregulated upon infection. In further embodiments, the viral particles are pseudotyped viral particles comprising one or more envelope protein and, optionally, the capsid protein from CHIKV.

In another embodiment, the invention provides methods for identifying inhibitors of viral entry using a reporter gene system as exemplified herein. Briefly, the invention provides recombinant lentiviral vectors expressing a reporter gene. Cells are incubated and co-transfected with an expression vector, e.g., $Env_{37997}$, $Env_{OPY-1}$, and a reporter plasmid using a standard techniques.

Cells are plated into one day prior to infection. CHIKV Env-pseudotyped lentiviral vectors encoding the reporter gene are first titrated by serial dilution. Similar amounts of pseudotyped vectors are then incubated with the candidate inhibitors prior to adding the virus. Cells are then lysed using cell lysis buffer and the reporter gene activity is measured. Inhibitors of viral entry are identified based on the expression of the reporter gene.

Kits

The invention also provides for a pharmaceutical pack or kit comprising one or more containers filled with one or more of the ingredients of the vaccine formulations of the invention. In a preferred embodiment, the kit comprises two containers, one containing VLPs and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the VLP formulation be packaged in a hermetically sealed container such as an ampoule or sachette indicating the quantity of composition. In one embodiment, the VLP composition is supplied as a liquid, in another embodiment, as a dry sterilized lyophilized powder or water free concentrate in a hermetically sealed container and can be reconstituted, e.g., with water or saline to the appropriate concentration for administration to a subject.

The invention also features a kit comprising a VLP as described herein. The invention also features kits comprising a DNA vaccine as described herein and instructions for use.

The invention also features a kit comprising a VLP in a first container and a DNA vaccine in a second container, and instructions for use in a prime boost immunization.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1B:
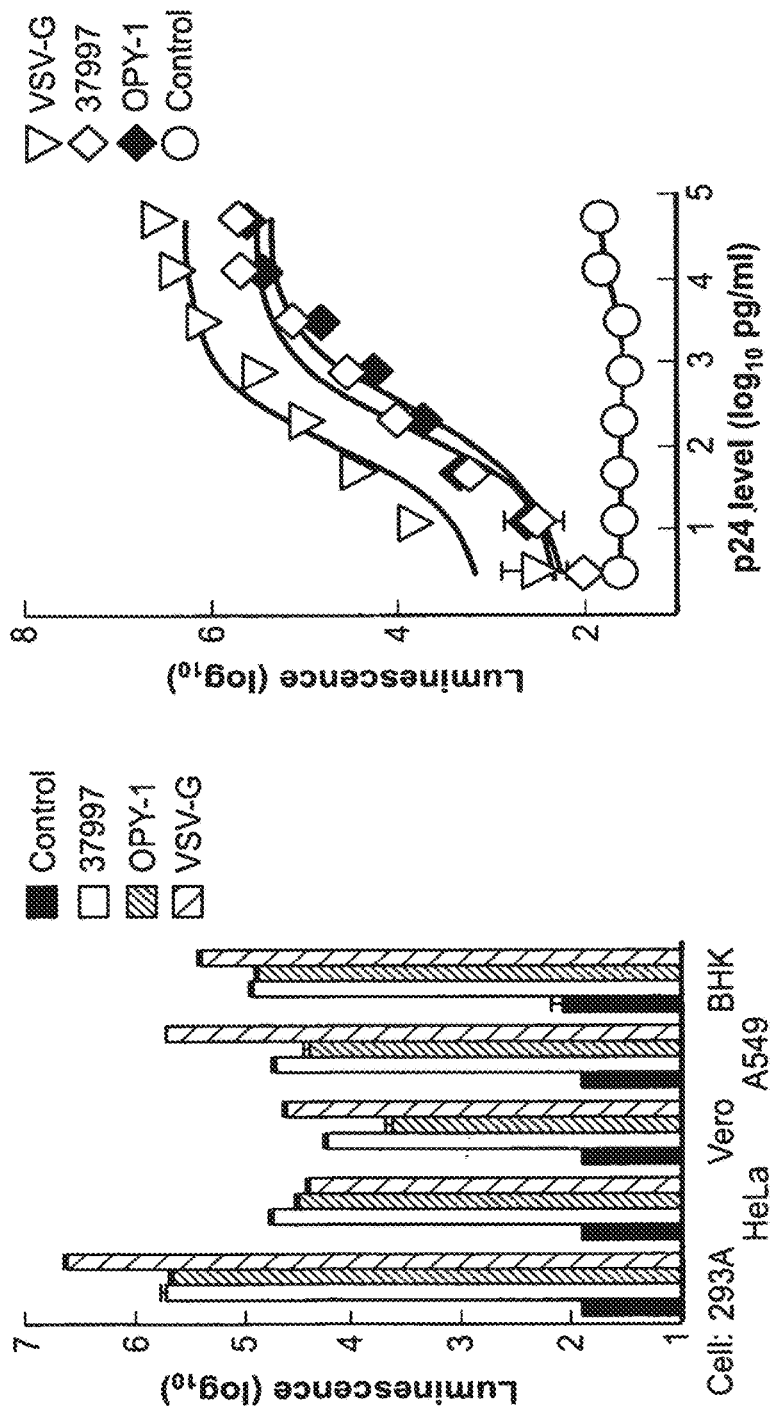
Figure 5:
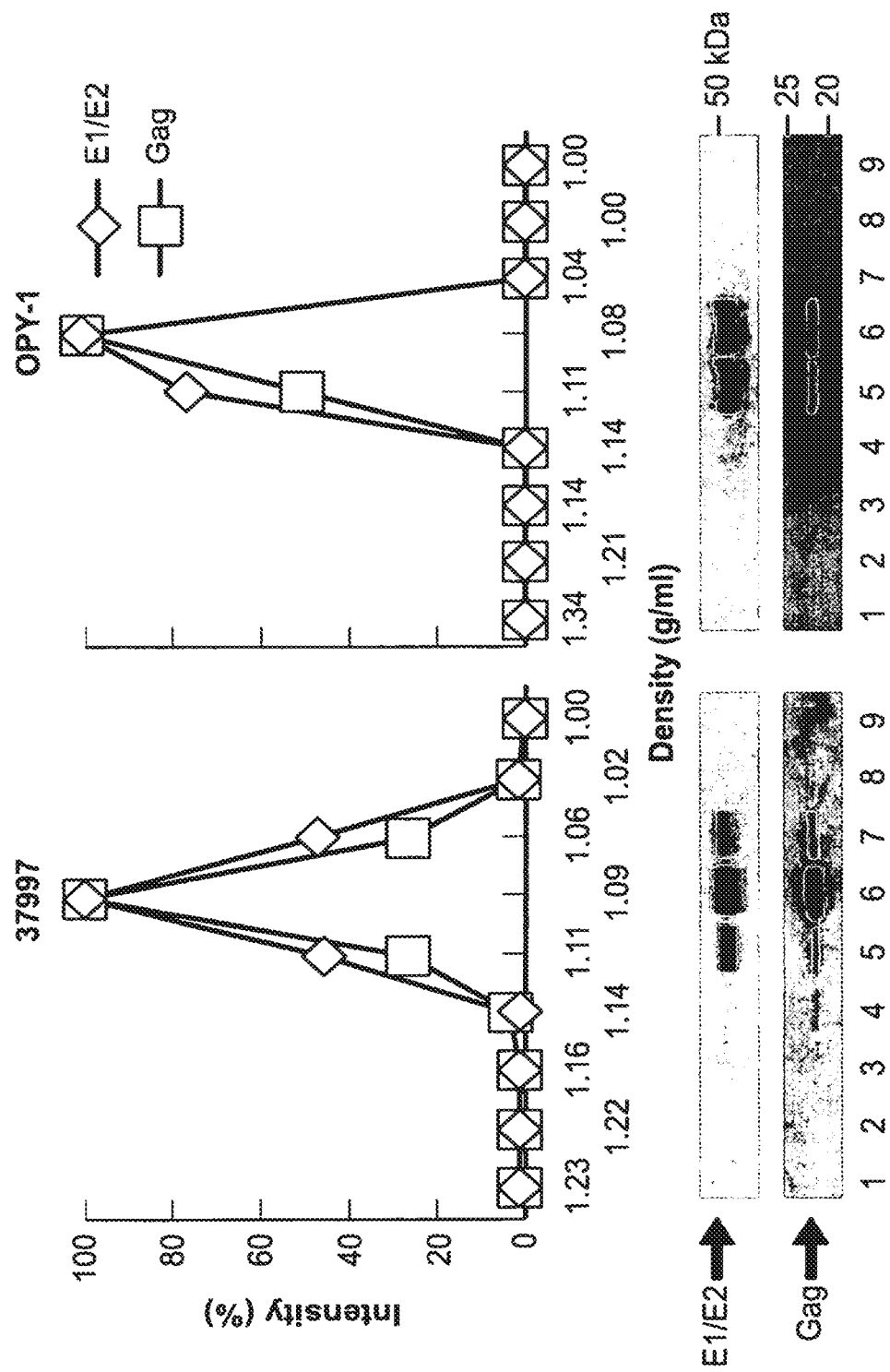
FIG. 5 shows the characterization of CHIKV E pseudotyped lentiviral vectors by buoyant density sedimentation and Western blot analysis. Plasmids encoding the indicated CHIKV Env strains were cotransfected with lentiviral expression vectors into 293T cells. Forty-eight hours after transfection, supernatants were harvested and run on sedimentation gradients as described previously. Quantification of gradient fractions is shown with the indicated strains, showing colocalization of Env with the Gag fraction of the expected buoyant density for lentiviral particles (1.08-1.1 g/ml) (upper panel). Western blot analysis of gradient fractions for CHIKV E1/E2 and Gag are shown (lower panel).
Figure 6:
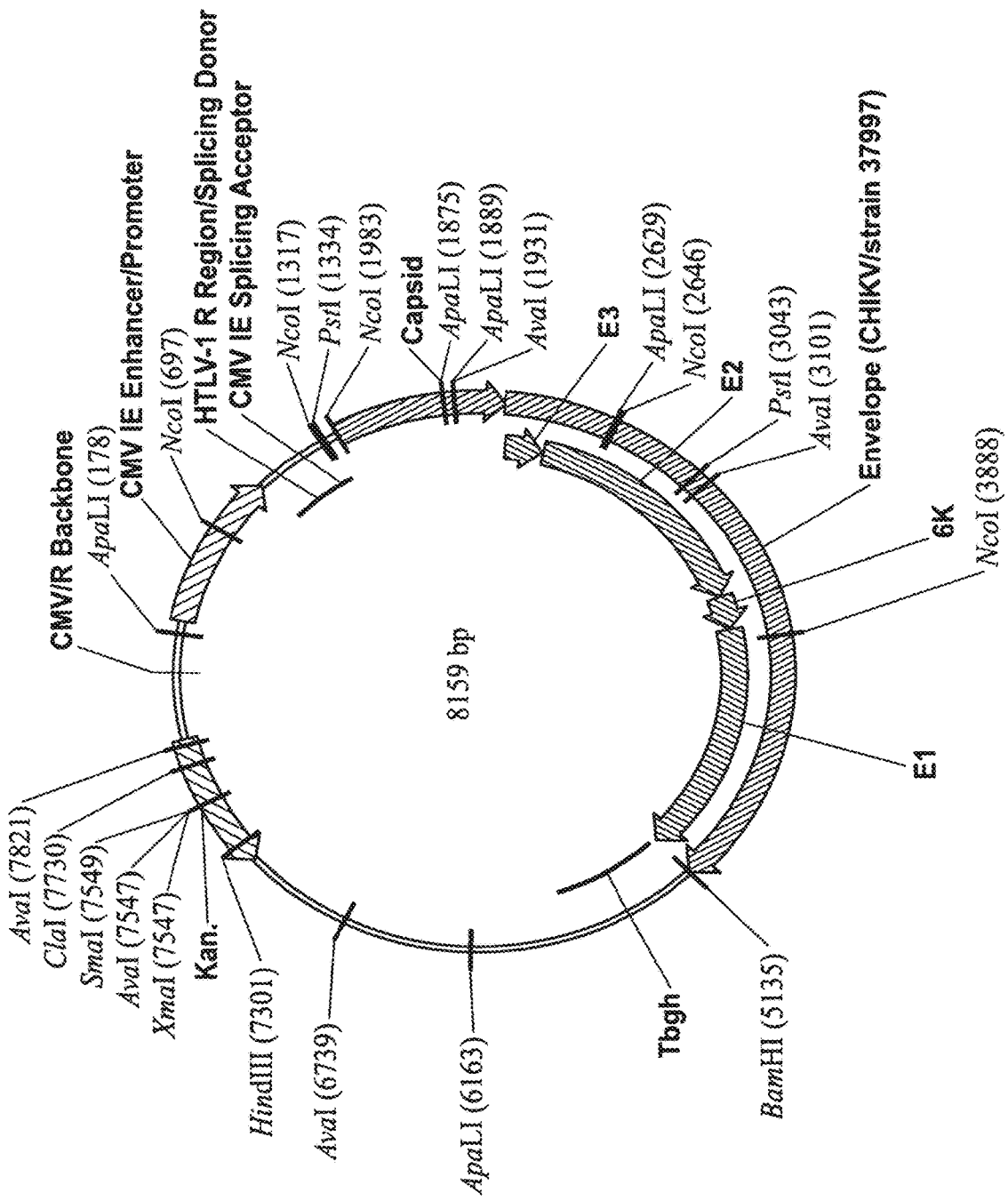
FIG. 6 shows the CMV/R-CHIKV C-E3-E2-6K-E1 plasmid (Strain 37997).
Figure 8A:
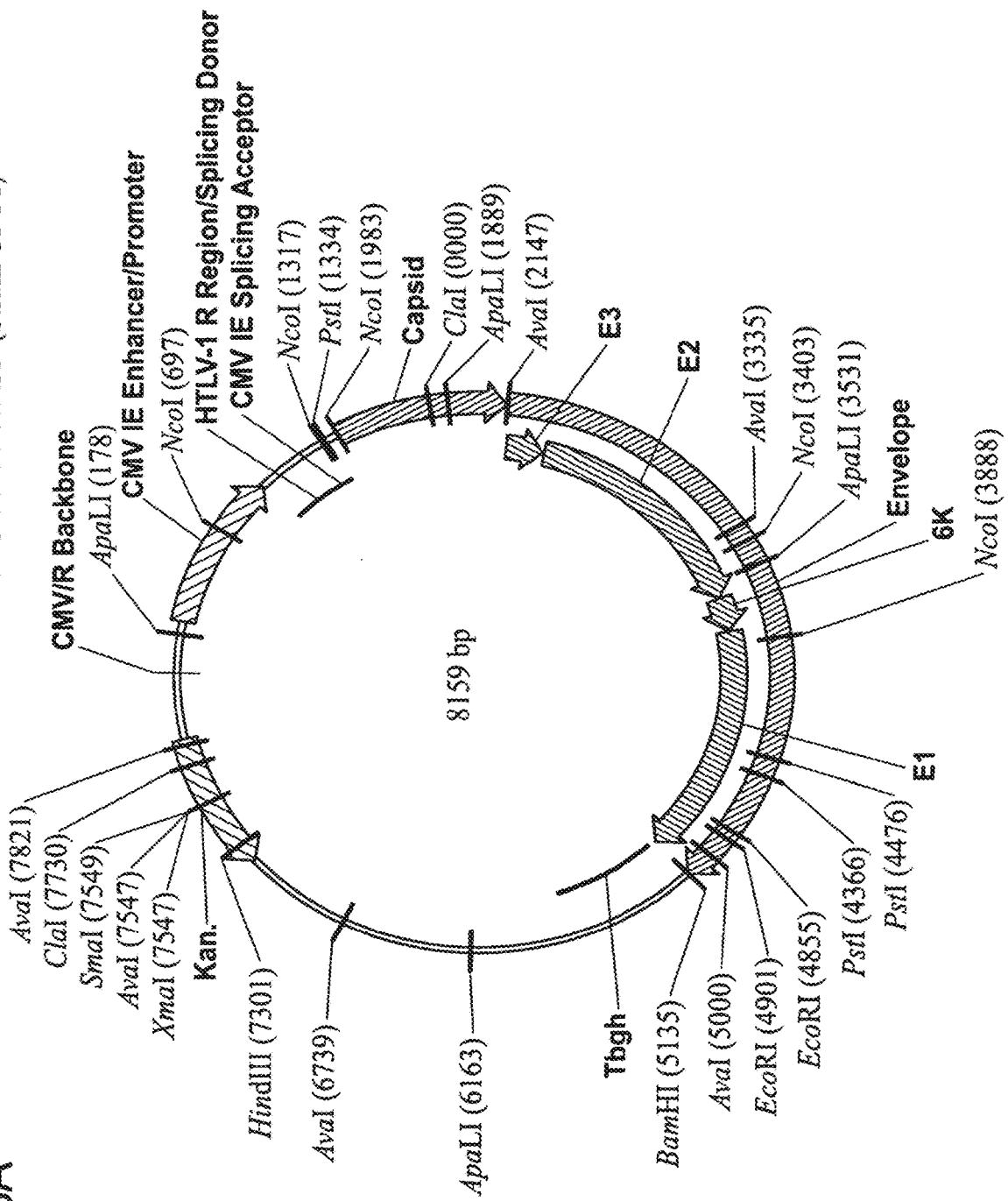
FIG. 8A shows the CMV/R-CHIKV C-E3-E2-6K-E1 plasmid (Strain OPY1).
Figure 9A:
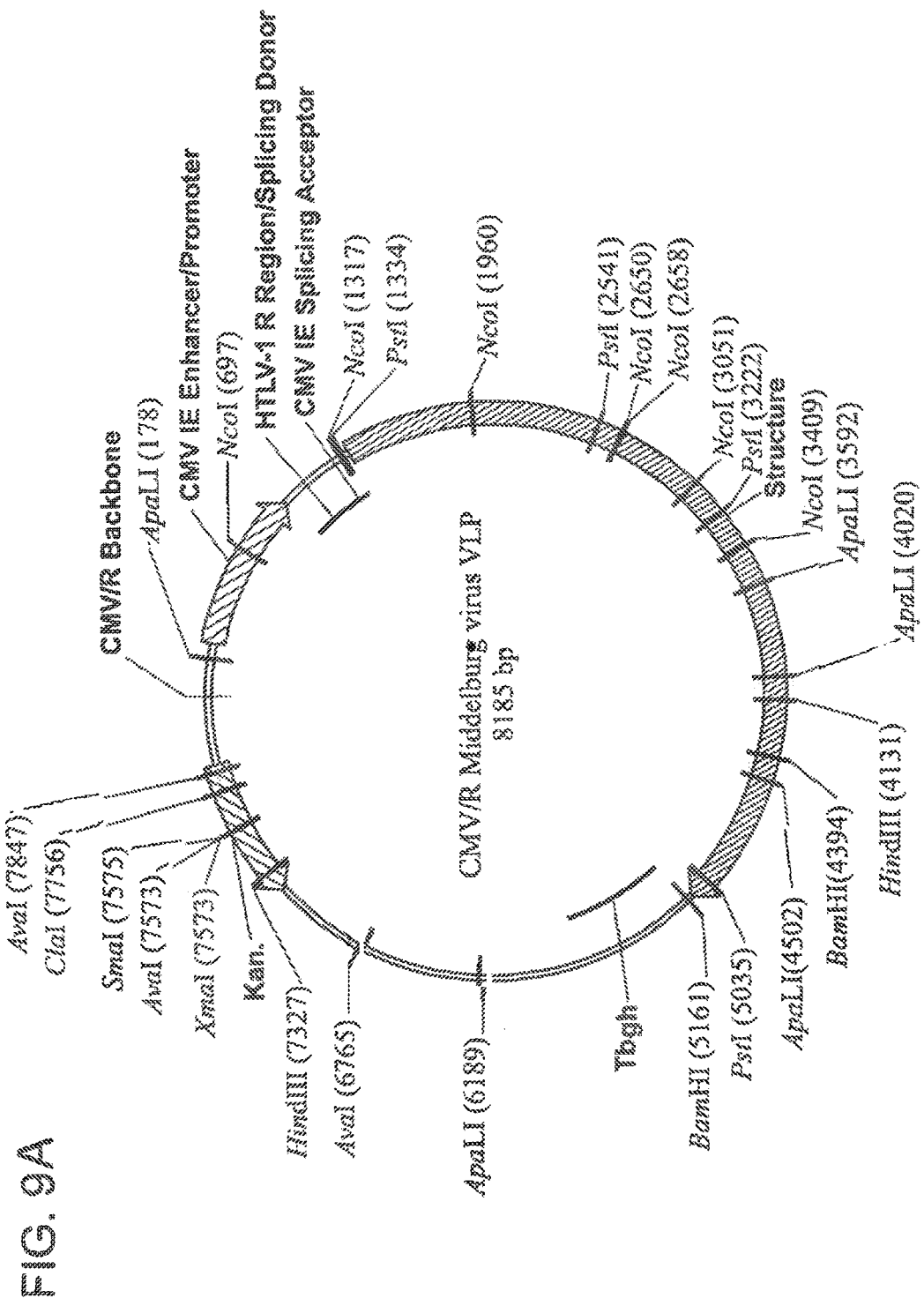
FIG. 9A shows the CMV/R-Middleburg virus VLP plasmid.
Figure 10A:
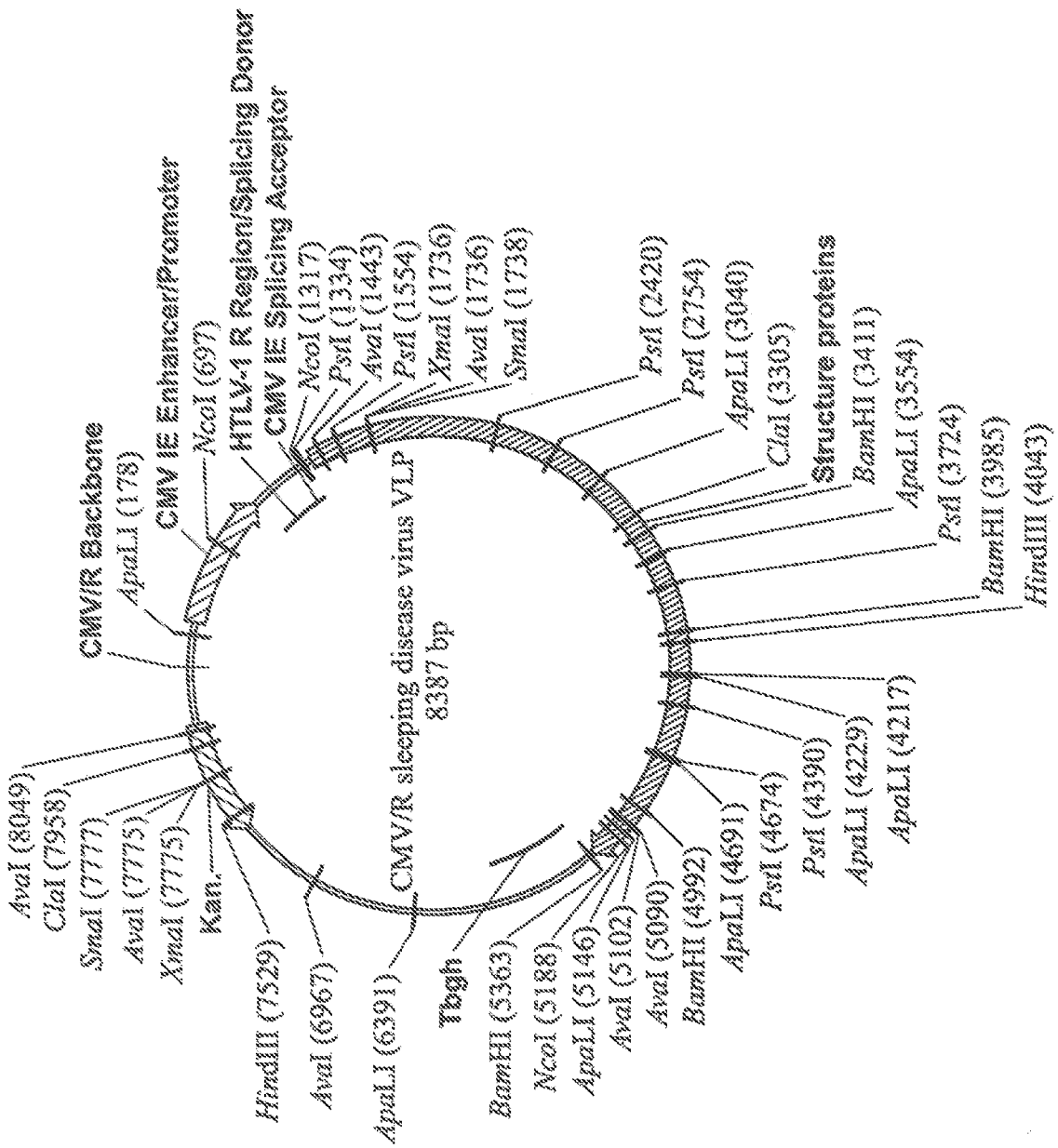
FIG. 10A shows the CMV/R-Sleeping disease virus VLP plasmid.
Figure 11A:
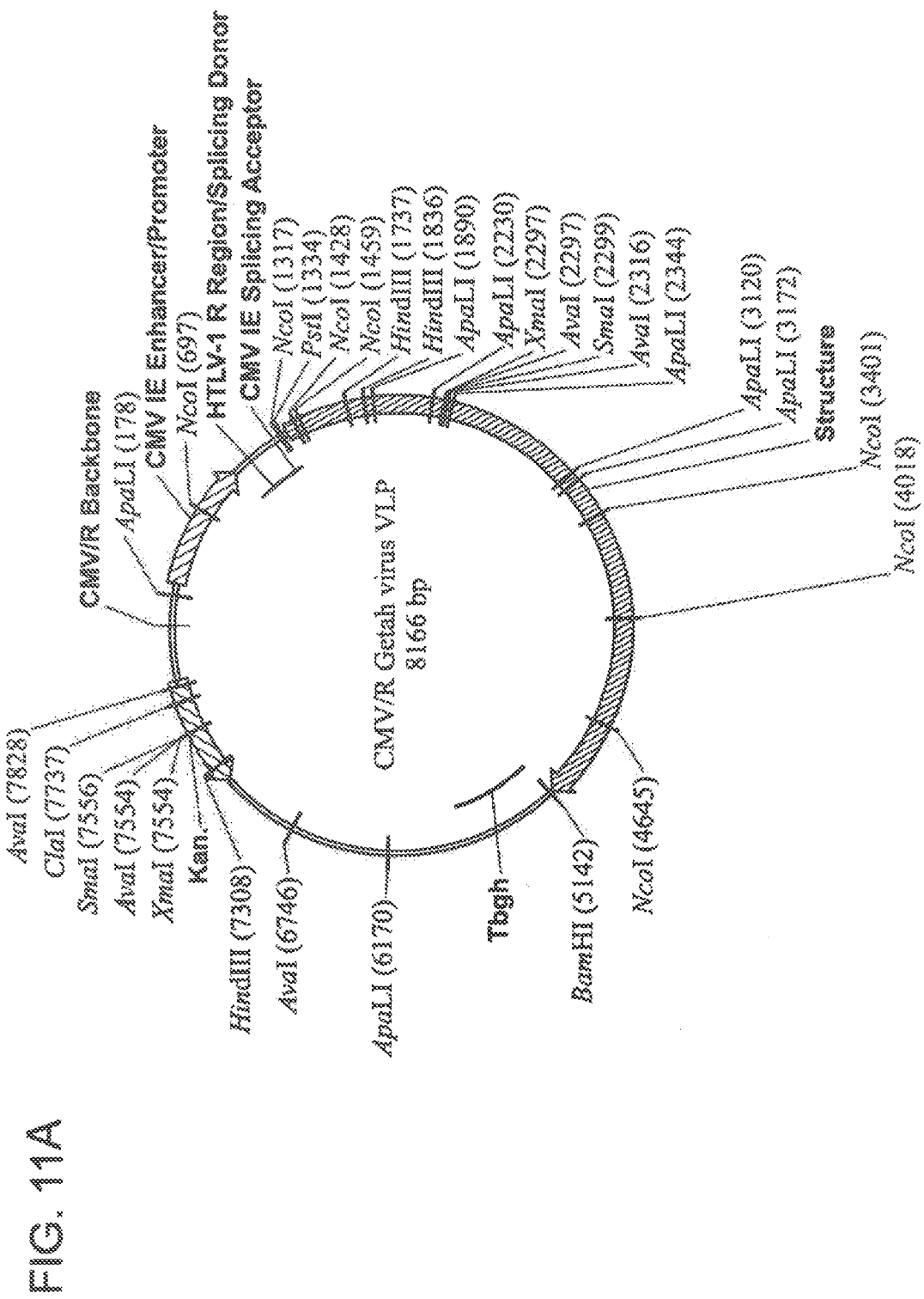
Figure 13A:
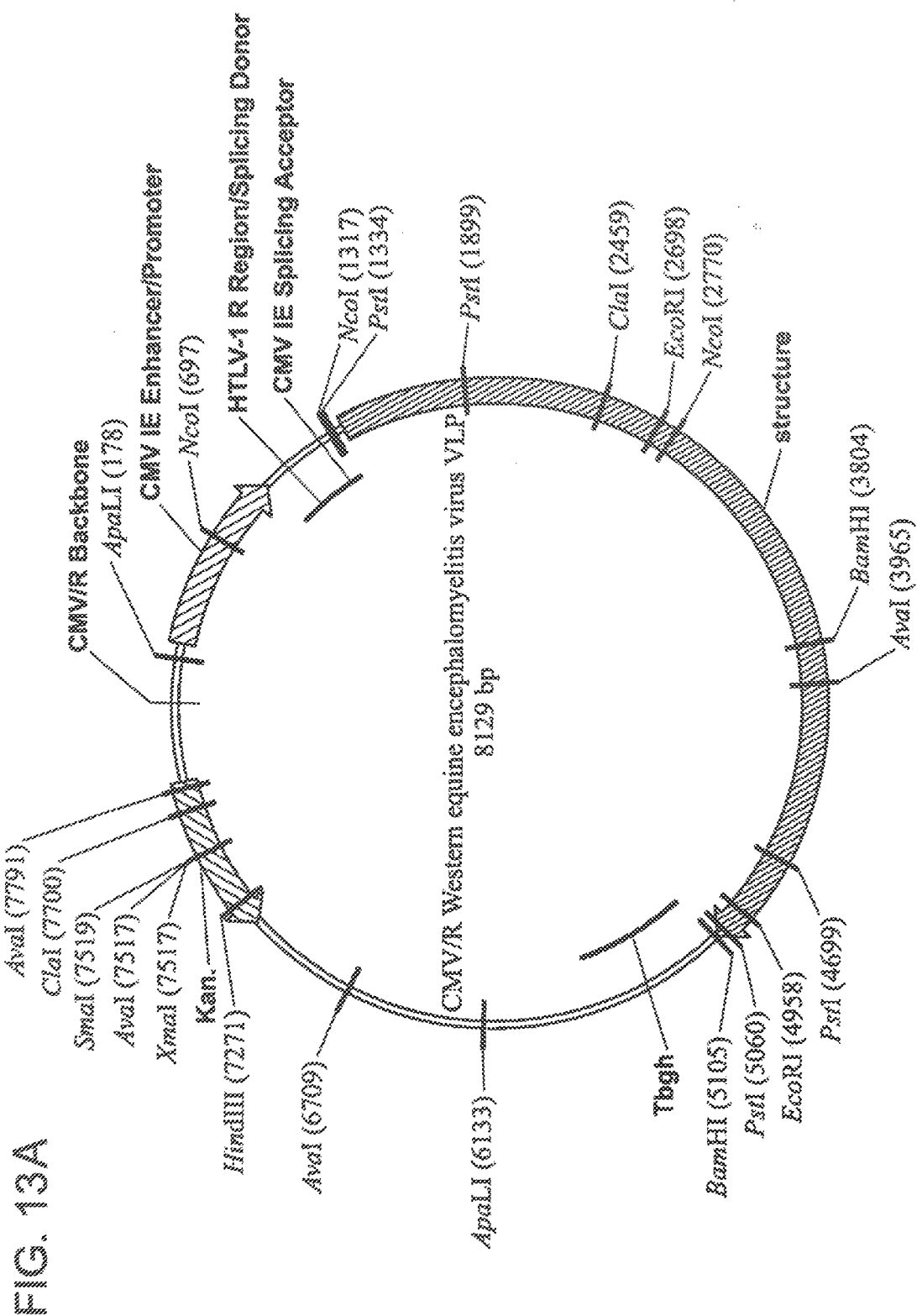
FIG. 13A shows the CMV/R-Western equine encephalitis virus VLP plasmid.
Figure 15A:
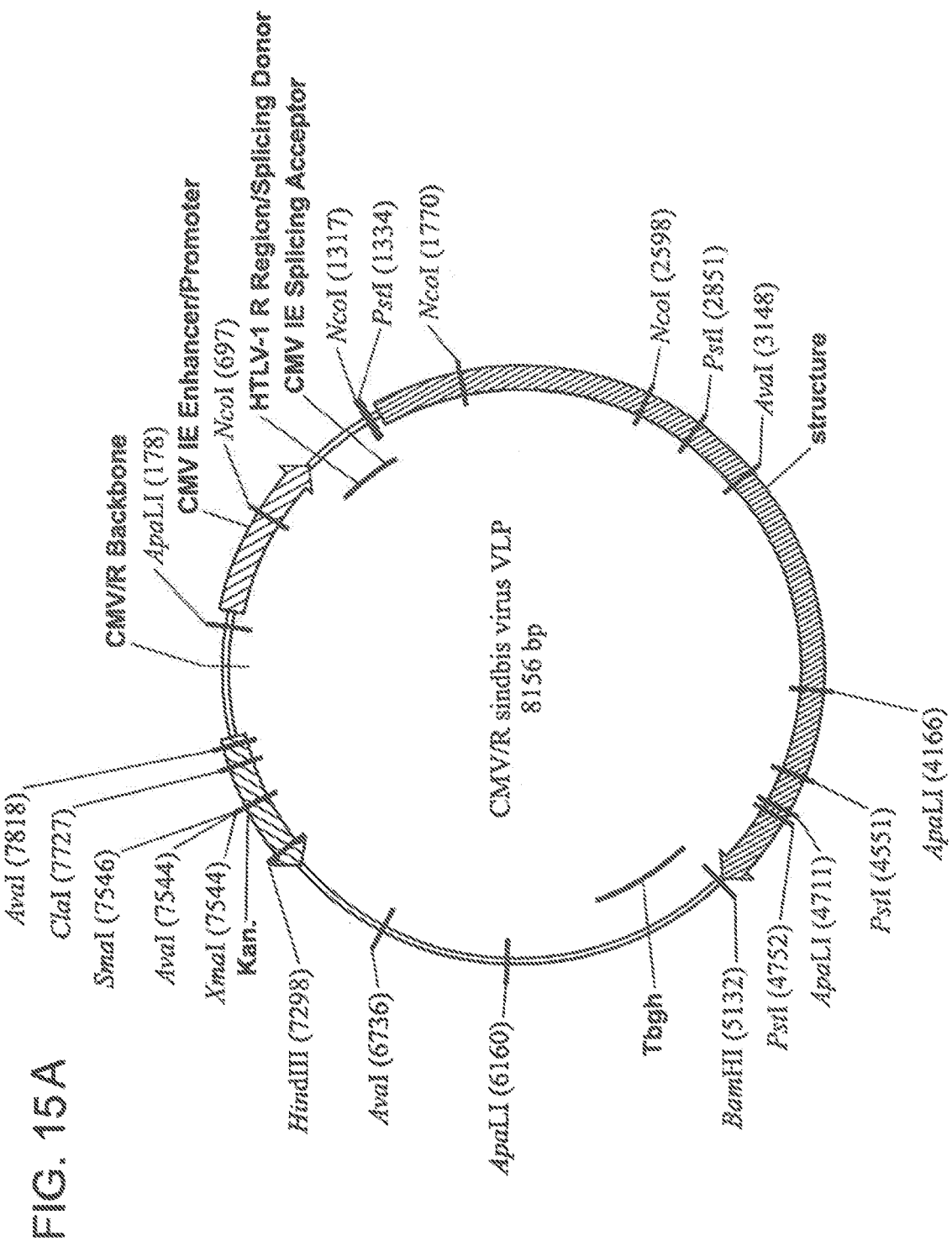
FIG. 15A shows the CMV/R-Sindbis virus VLP plasmid.
Figure 16A:
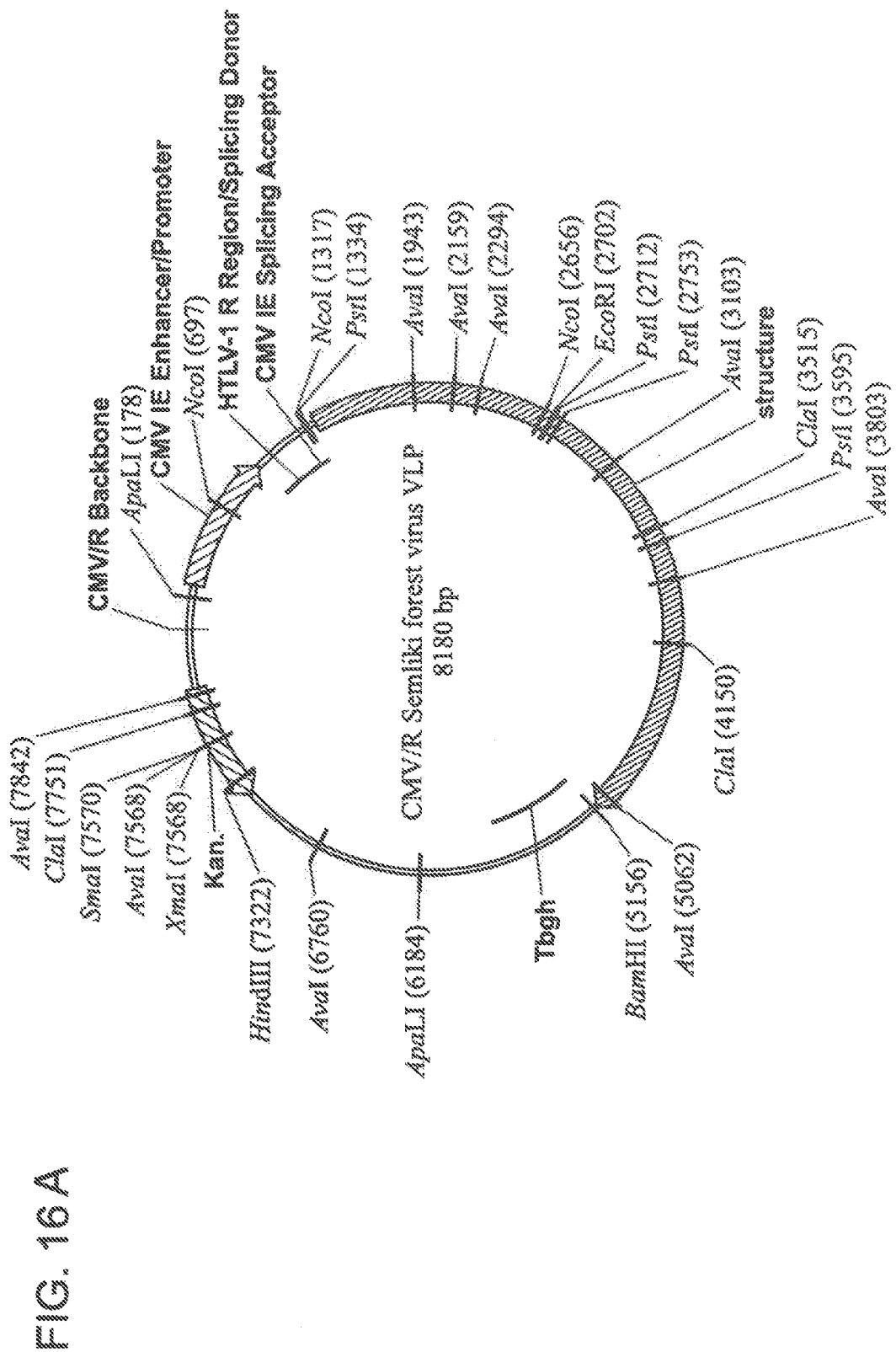
FIG. 16A shows the CMV/R-Semliki forest virus VLP plasmid.
Figure 17A:
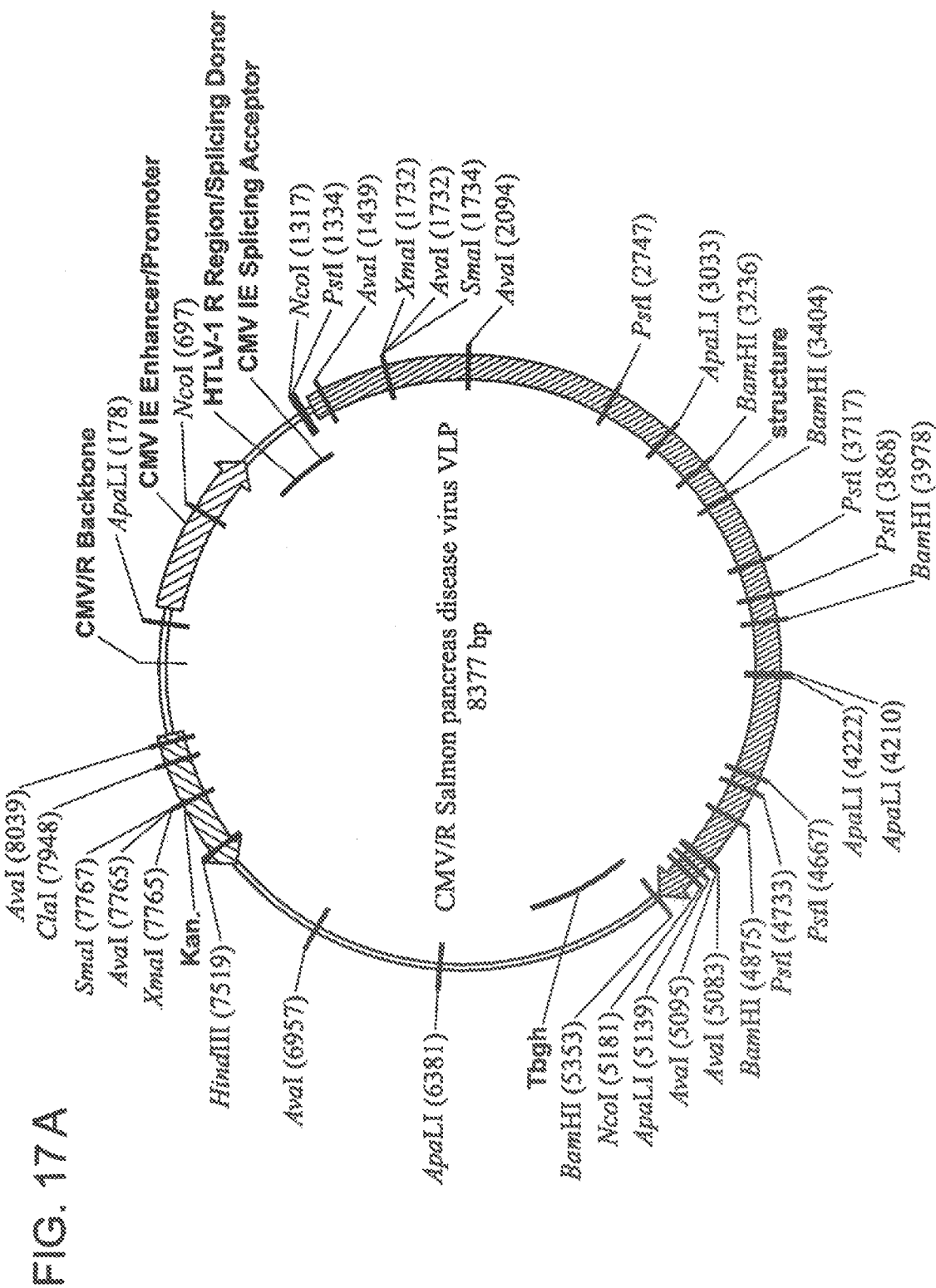
FIG. 17A shows the CMV/R-Salmon pancreas disease virus VLP plasmid.
Figure 18A:
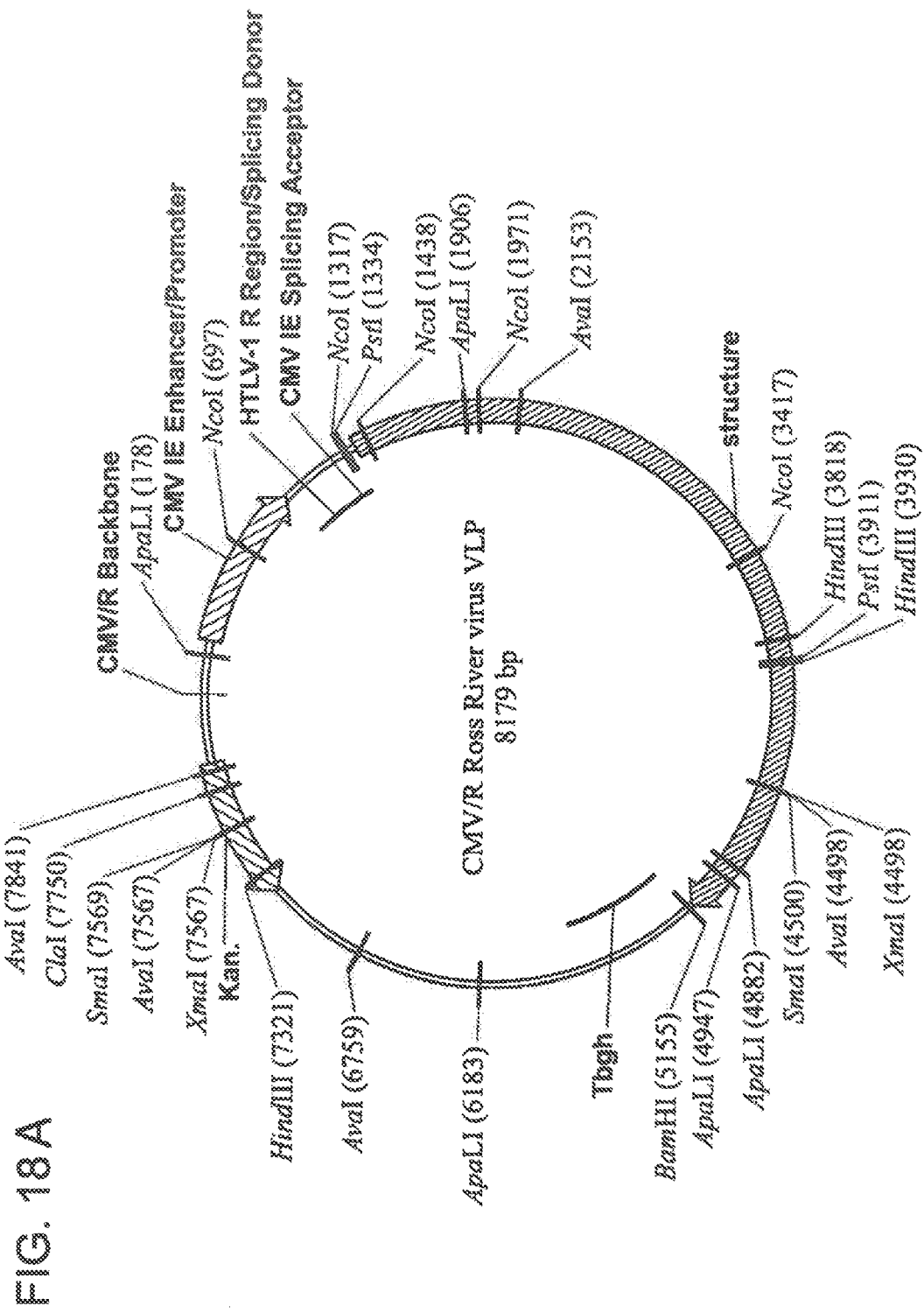
FIG. 18A shows the CMV/R-Ross River virus VLP plasmid.
Figure 22A:
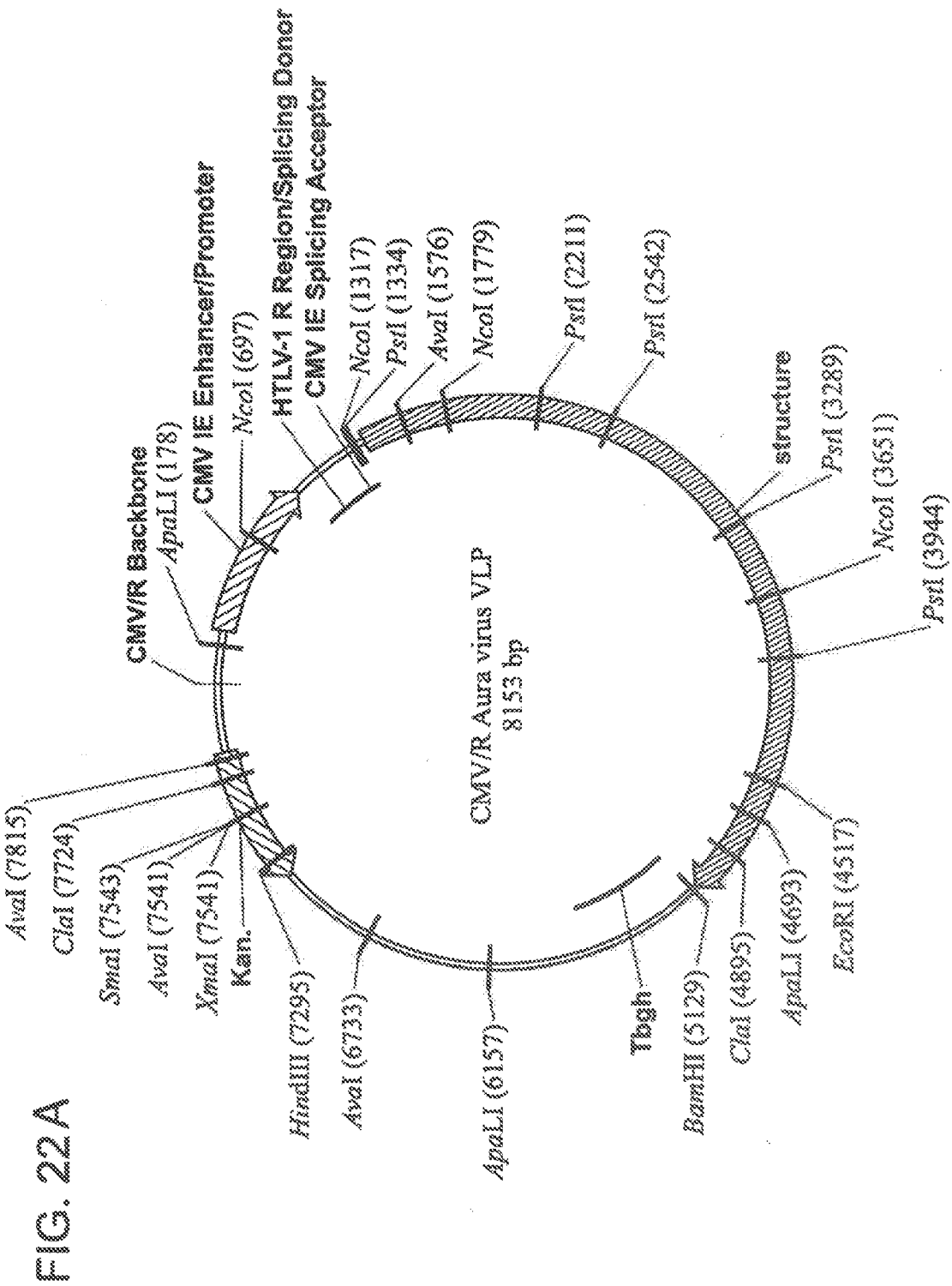
FIG. 22A shows the CMV/R-Aura virus VLP plasmid.
Figure 23A:
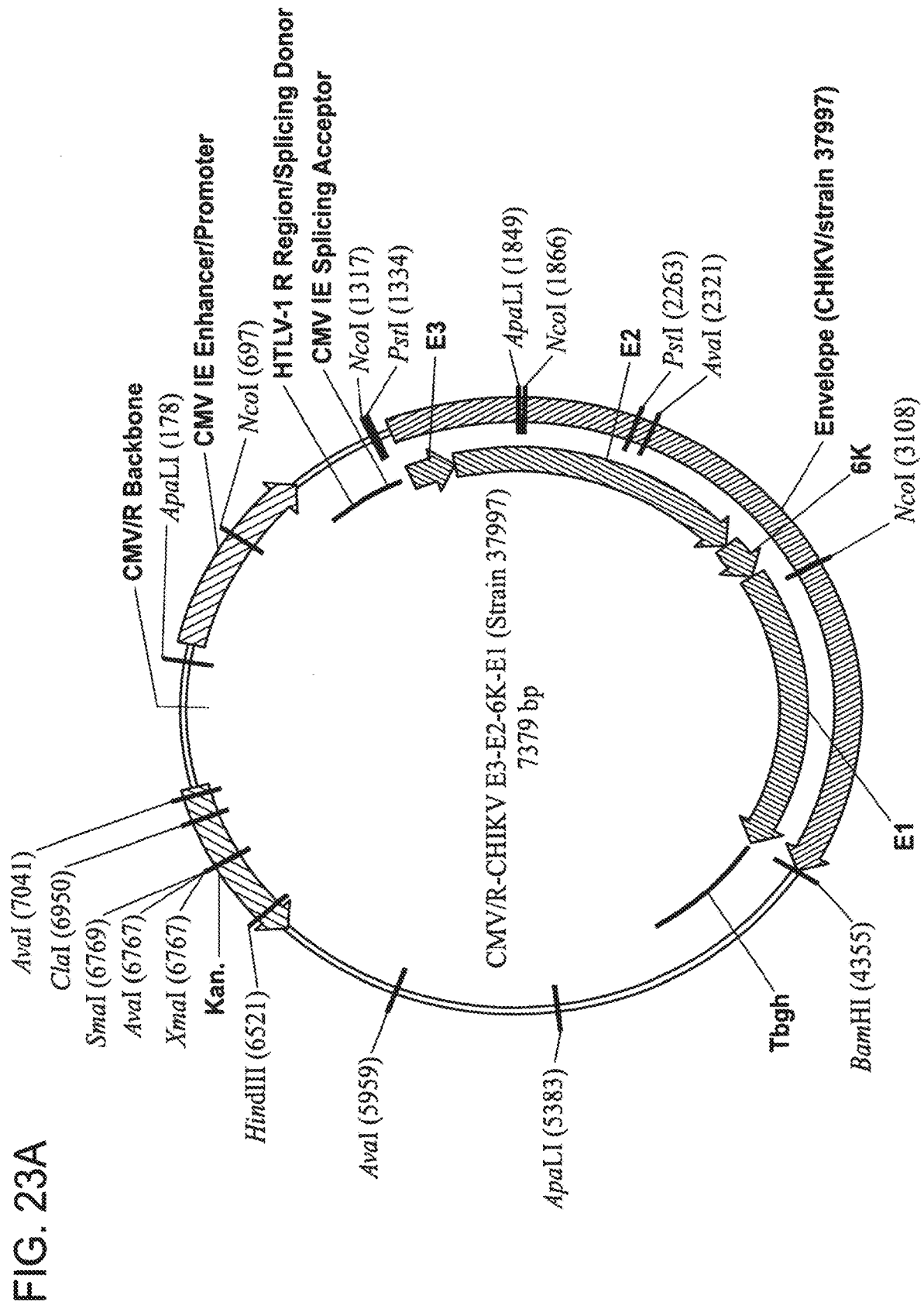
FIG. 23A shows the CMV/R-CHIKV E3-E2-6K-E1 plasmid (Strain 37997) and the sequence of the insert without the capsid (C) (SEQ ID NO:19).
Figure 23B:
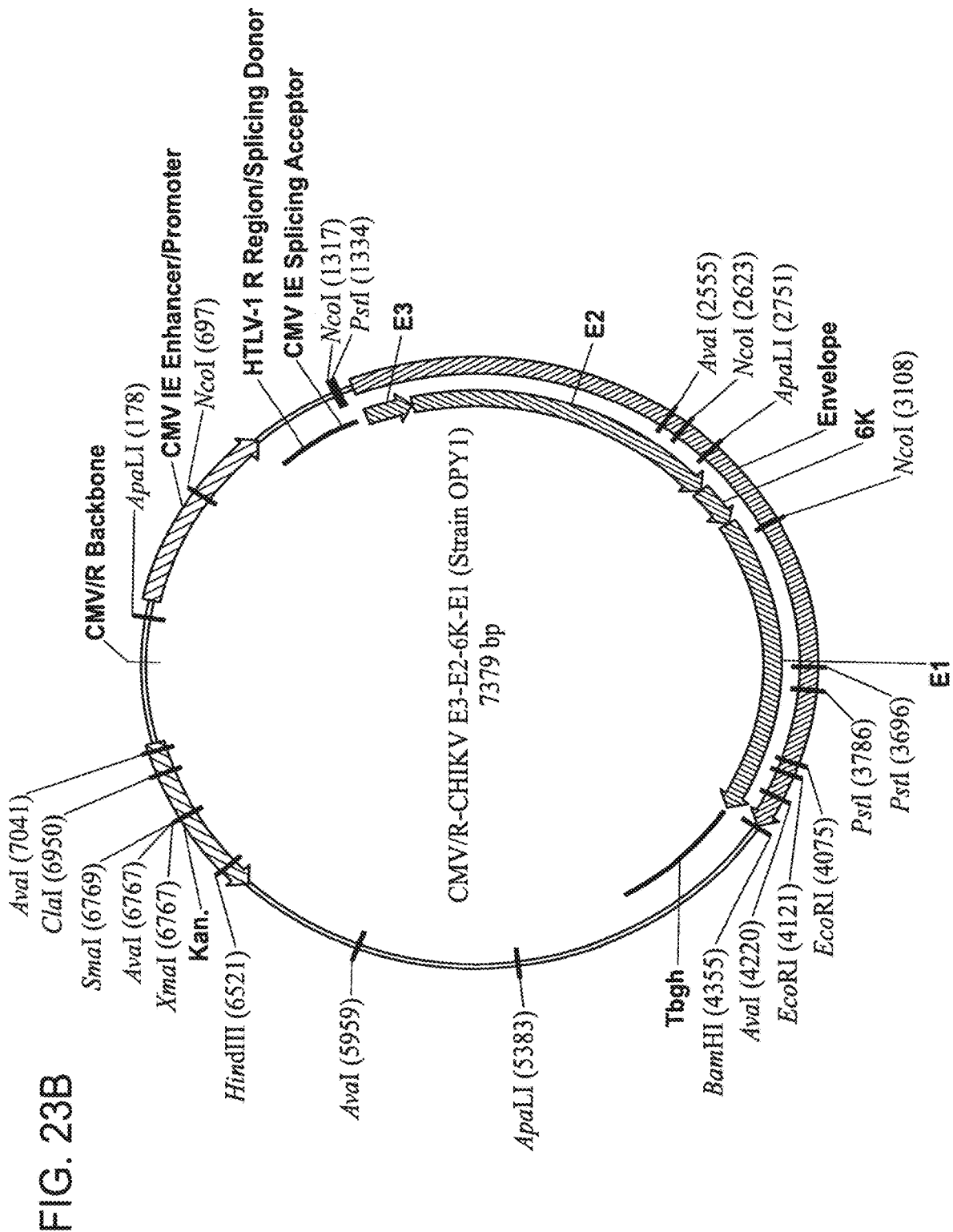
FIG. 23B shows the CMV/R-CHIKV E3-E2-6K-E1 plasmid (Strain OPY1) and the sequence of the insert without the capsid (C) (SEQ ID NO: 20).

Example 1: Lentiviral Vectors Pseudotyped with CHIKV Envelope Mediated Entry Through the Same Mechanism as Wild Type Virus To examine the mechanism and specificity of CHIKV cell entry, lentiviral vector reporters were pseudotyped with glycoproteins from different CHIKV strains that mediate entry into permissive cells. The CHIKV spike on the virion surface is formed by three E1-E2 heterodimers, where E1 glycoproteins mediate fusion and E2 glycoproteins interact with the host receptor. CHIKV E genes expressing the native polypeptide, E3-E2-6K-E1 polyprotein, for the 37997 and for LR2006 OPY-1 strains were inserted into an expression vector ($E_{37997}$ and $E_{OPY-1}$) (FIG. 1A, FIGS. 6, 7A, 7B, and 8A-8C). The incorporation of the two CHIKV Es into the pseudotyped lentiviral vectors was verified by buoyant density gradient sedimentation of the virus. Both CHIKV E and HIV-1 Gag had the same buoyant density as lentivirus particles (FIG. 5). The 37997 and LR2006 OPY-1 CHIKV pseudotyped lentiviral vectors infected several permissive cell lines (Sourisseau et al., *PLoS. Pathog.* 3, e89 (2007)) as measured by luciferase reporter activity, while a control devoid of CHIKV envelope proteins did not infect these cell lines (FIG. 1B, left), and infectivity was dose-dependent (FIG. 1B, right).

Figure 1C:
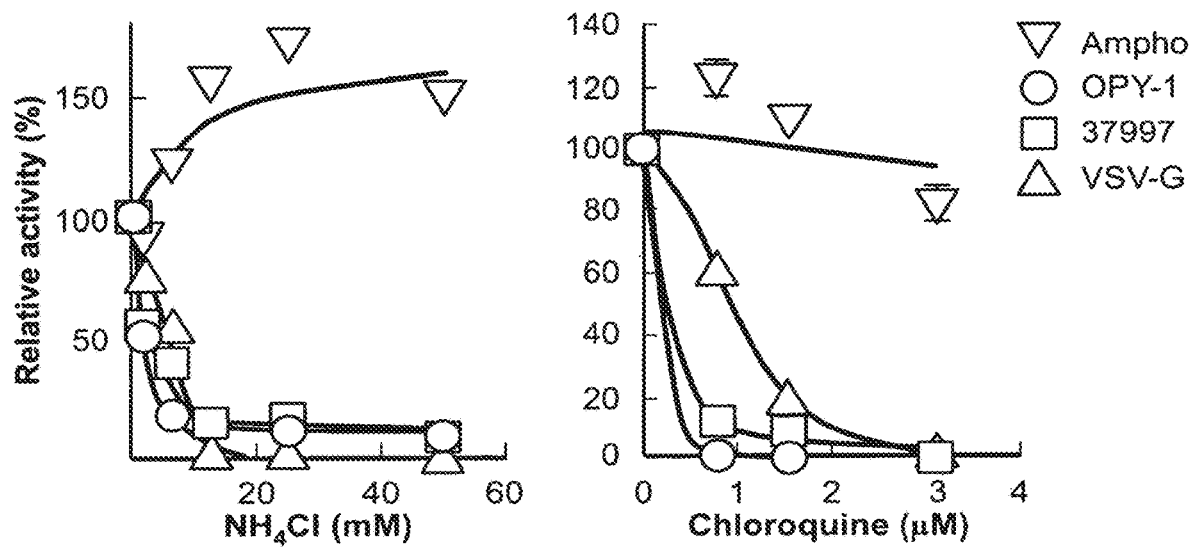
Figure 1D:
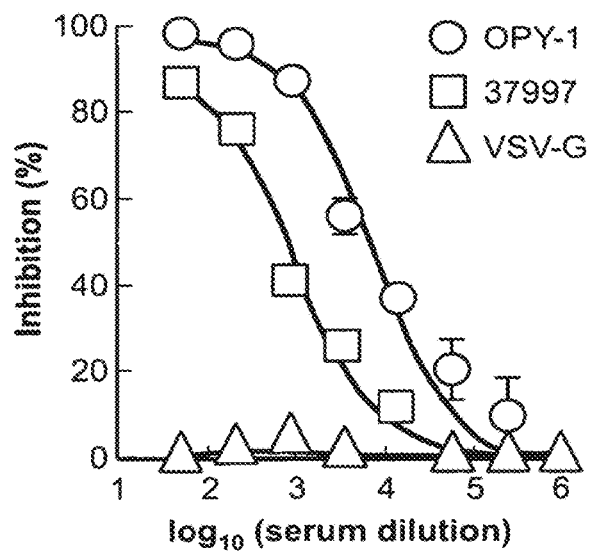

To determine whether entry occurred through the same mechanism as native virus, the pH and endosome dependence of entry was analyzed as described previously (Yang et al., *J. Virol.* 78, 5642 (2004)). CHIKV infects cells through a process of pH-dependent cell fusion. Thus, addition of ammonium chloride or chloroquine, which prevents acidification of the endosome, caused a dose-dependent reduction in CHIKV pseudotyped vector entry (FIG. 1C). Similar inhibition of entry was observed with VSV-G, known to enter in this fashion, but not with amphotropic murine leukemia virus (MuLV) glycoprotein 70, which enters in a pH-independent fashion. These findings demonstrated that lentiviral vectors pseudotyped with CHIKV envelope mediated entry through the same mechanism as wild type virus. Sera from mice injected with a CHIKV strain were next examined. Incubation of immune sera with the CHIKV pseudotyped lentiviral vector but not VSV-G pseudotyped vector inhibited entry (FIG. 1D). The specificity and potency of neutralizing antibodies could therefore be quantified without exposure to infectious virus.

Example 2: VLPs have Morphology of Wild Type Virus

Figure 2A:
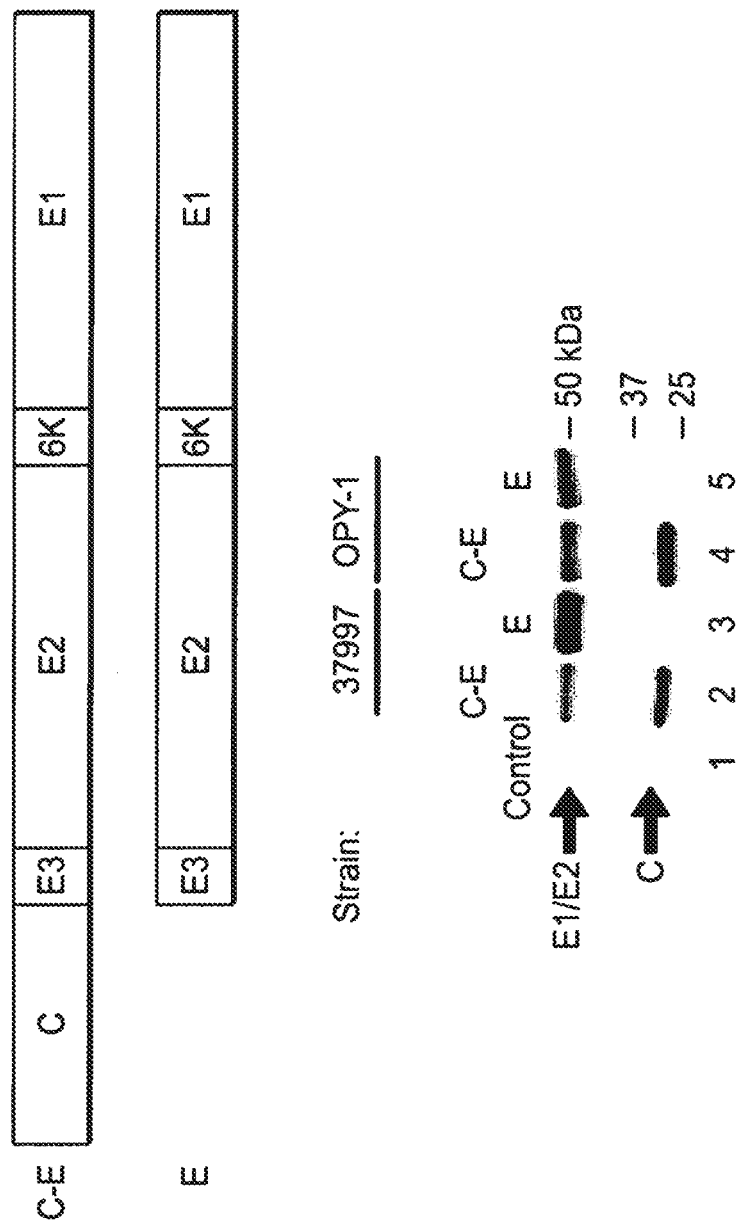
FIGS. 2A-2C show the schematic representation of plasmid expression vectors and characterization of CHIKV VLPs.
Figure 2B:
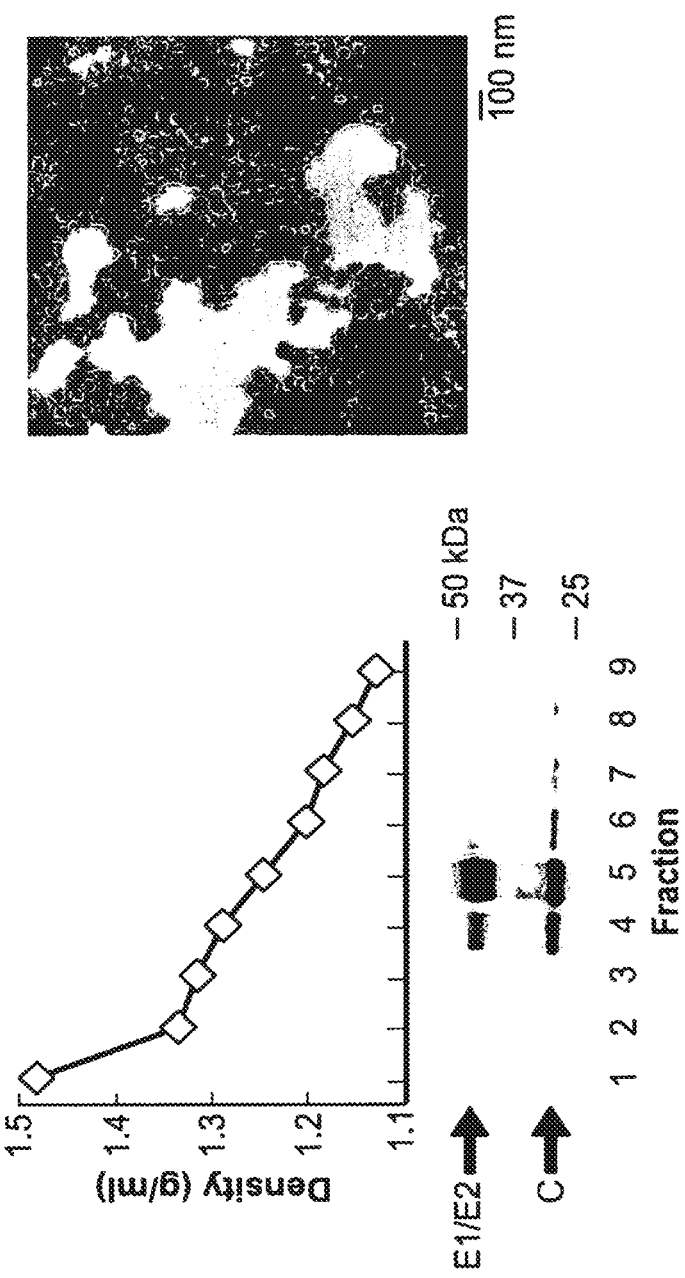

CHIKV encodes 4 nonstructural proteins, NS1, NS2, NS3 and NS4, which are involved in virus replication, and 5 structural proteins, which consist of capsid (C) and envelope proteins (E; E1, E2, E3 and 6K) that are synthesized as polyproteins and are cleaved by capsid autoproteinase and signalases (Strauss, *Microbiol. Rev.* 58, 491 (1994)). Eukaryotic expression vectors encoding C-E3-E2-6K-E1 from strains 37997 and LR2006 OPY-1 (C-$E_{37997}$ and C-$E_{OPY-1}$) were analyzed for their ability to give rise to VLP. The plasmids C-$E_{37997}$ or C-$E_{OPY-1}$ or the expression vectors described above, $E_{37997}$ or $E_{OPY-1}$ (FIG. 2A, upper panel), were transfected into human embryonic kidney (293T) cells, and expression was confirmed by Western blotting (FIG. 2A, lower panel). C and E1/E2 proteins were detected in the supernatant after transfection of the C-$E_{37997}$ or C-$E_{OPY-1}$ vector, suggesting that CHIKV VLPs had been generated. VLPs were purified by buoyant density gradient sedimentation. The yield of VLPs from strain 37997 was 10-20 mg/L, approximately 100 times higher than that from strain LR2006 OPY-1; strain 37997 was therefore chosen for further VLP characterization and development. Fractionation of clarified supernatant showed peak incorporation of E1/E2 at a density of 1.2 g/ml (FIG. 2B, left), comparable to the density of wild type CHIKV. Examination of the purified fraction from strain 37997 by electron microscopy revealed VLPs with the same morphologie appearance as wild type virus (FIG. 2B, right).

Figure 2C:
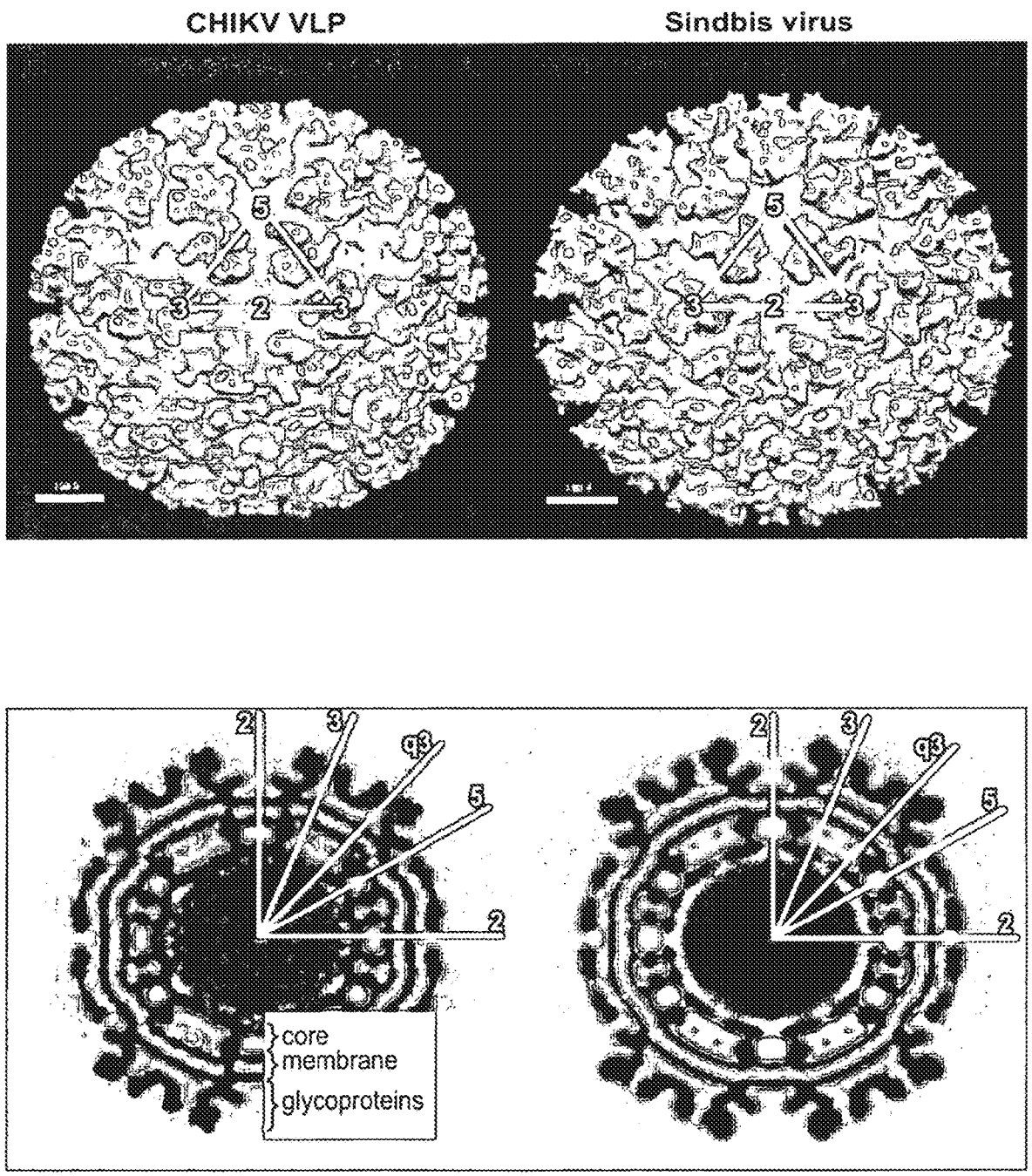

Cryoelectron microscopy and three dimensional image reconstruction assuming icosahedral symmetry showed that the VLPs had an external diameter of 65 nm and a core diameter of 40 nm (FIG. 2C, left). The potent immunogenic E1/E2 glycoproteins are organized into 240 heterodimers, assembled into 80 glycoprotein spikes arranged with T=4 quasi symmetry on the surface of the VLPs (FIG. 2C, left), closely similar to the structure of Sindbis virus (FIG. 2C, right). In addition, the organization of the nucleocapsid core is also remarkably similar to that of other alphaviruses.

Figure 3A:
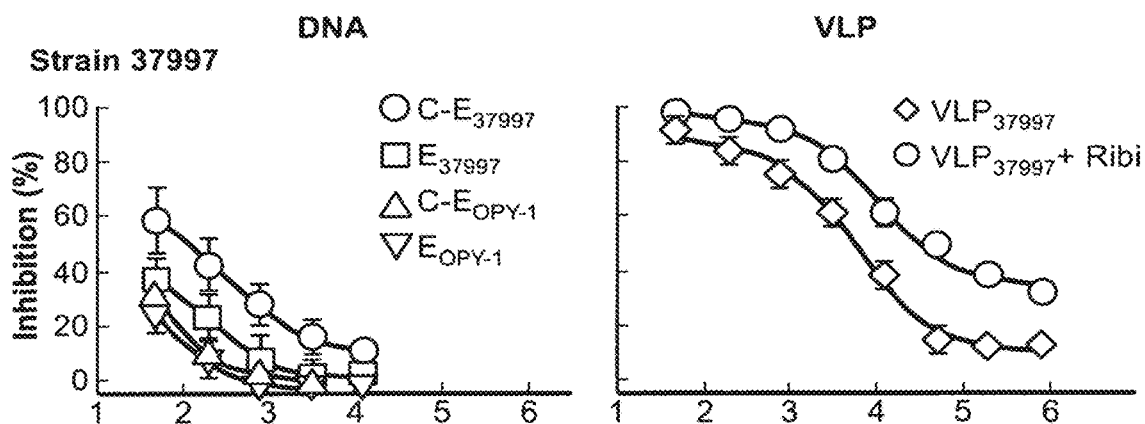
FIGS. 3A-3D are graphs showing the neutralization of CHIKV strains 37997 and LR2006 OPY-1 after DNA or VLP vaccination in mice and monkeys. Sera from immunized mice 10 days after the final immunization were tested with CHIKV strain 37997 (FIG. 3A) or LR2006 OPY-1 (FIG. 3B) E pseudotyped lentiviral vectors. Mice were immunized with the indicated DNA or VLP$_{37997}$. Each C-E or E (strain 37997 and LR2006 OPY-1, respectively) plasmid was injected at 0, 3 and 6 weeks. VLP$_{37997}$ with or without Ribi adjuvant was injected at 2 and 6 weeks. The experiment was performed in triplicate. The symbols show the average of the five mice and bars show the standard error of the mean. The curve fit was calculated by Prism software.
Figure 3B:
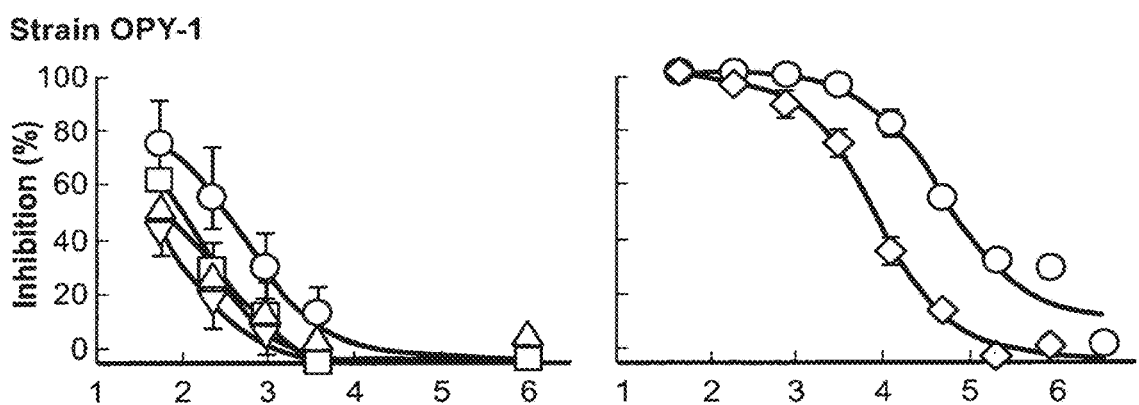

Example 3: VLPs Induced a More Potent Neutralizing Antibody Response to CHIKV than DNA Vaccines The immunogenicity of DNA and VLP vaccines was determined in mice immunized with DNA vaccines encoding C-E or E (strains 37997 and LR2006 OPY-1) or VLPs from strain 37997 ($VLP_{37997}$) in the presence or absence of Ribi adjuvant. Mice injected with VLPs with adjuvant generated the highest titer neutralizing responses against both the homologous strain 37997 (FIG. 3A, right panel; IC50, 1:10, 703) and the heterologous strain LR2006 OPY-1 (FIG. 3B, right panel; IC50, 1:54, 600). While immunization with the plasmids encoding C-E and E from both strains elicited neutralizing responses, these responses were 100-fold lower than the VLP-immunized mice (FIG. 3A, B; left panel). These results indicate that VLPs elicited a more potent neutralizing antibody response than DNA vaccines.

Figure 3C:
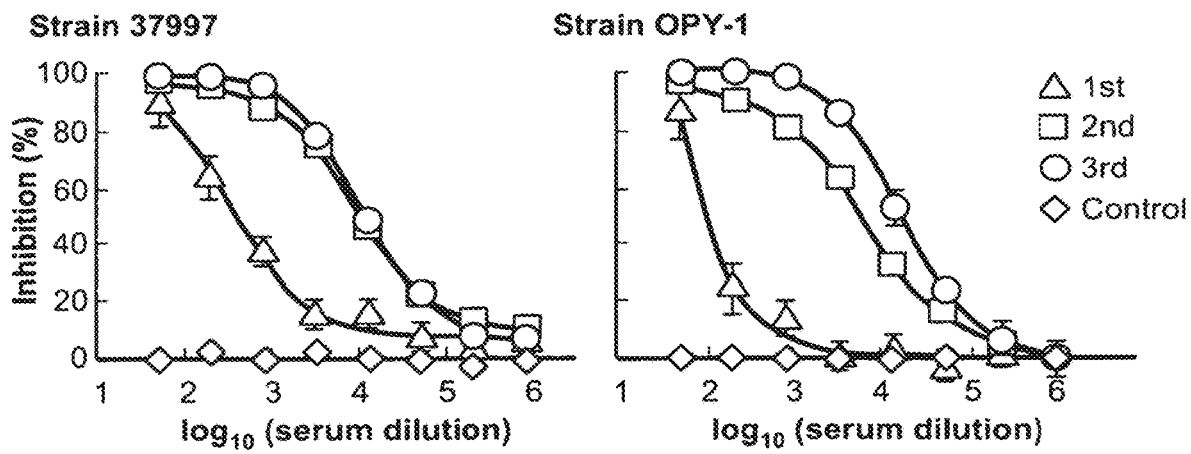
Figure 3D:
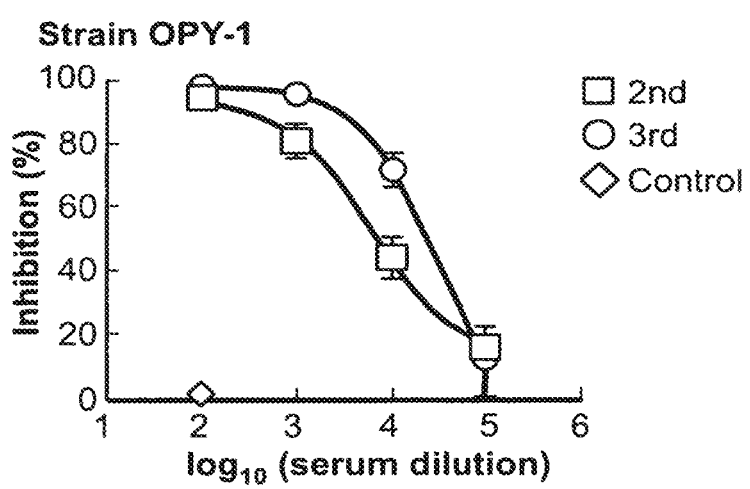

To characterize VLP-induced immune responses in a model with strong predictive value for humans, rhesus macaques were immunized with VLPs. Monkeys were injected with $VLP_{37997}$ or PBS alone as a control. Sera from immunized and control monkeys were tested against CHIKV strain 37997 and LR2006 OPY-1 pseudotyped lentiviral vectors. All non-human primates (NHP) immunized with VLPs developed substantial neutralizing activity to both homologous and heterologous strains after primary immunization that increased after boosting (FIG. 3C; left panel: strain 37997, right panel: strain LR2006 OPY-1). To confirm that these antibodies neutralized infectious virus, a plaque reduction neutralization test (PRNT) was performed against the CHIKV LR2006 OPY-1. The antisera from the immunized monkeys elicited neutralizing antibody responses against LR2006 OPY-1 at titers that exceeded 1:40,000 (FIG. 3D). These data suggested that neutralizing antibodies using pseudotyped lentiviral vectors correlated with the PRNT assay, and that all immunized monkeys generated potent neutralizing antibody responses against CHIKV.

Figures 4A, 4B:
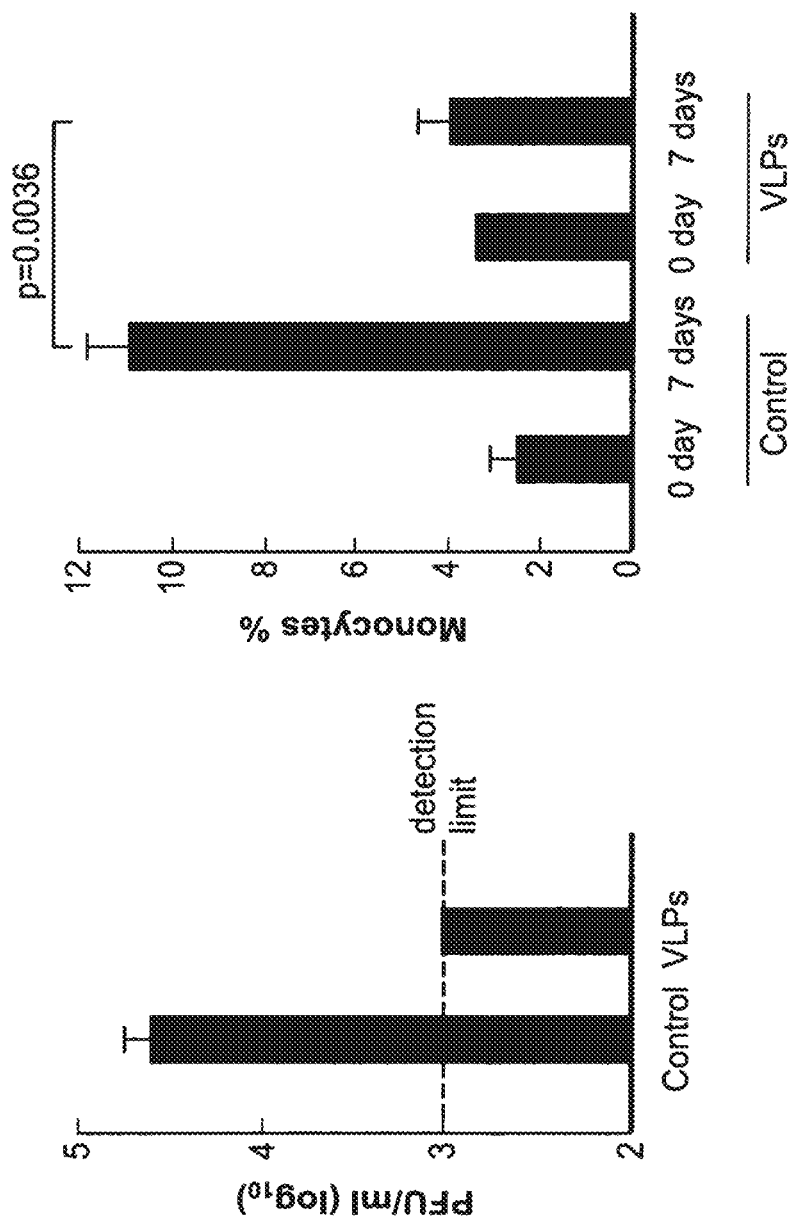

Example 4: Primate VLP Immunization Protected Against Viremia and Inflammatory Consequences of CHIKV Infection The ability of the VLP vaccine to protect against infection was determined by intravenous challenge of monkeys immunized with VLPs or controls using a high titer LR2006 OPY-1 virus stock 15 weeks after the final immunization. Similar to humans, infection in the NHP resulted in non-lethal viremia and a pro-inflammatory response as measured by an increase in monocyte counts. The control monkeys showed viremia beginning at 6 hours and lasting until 72 hours after challenge, while all of the immunized monkeys controlled the challenge virus completely (FIG. 4A). Similarly, the monocyte counts in control monkeys increased markedly relative to vaccinated monkeys by 4 days after challenge (FIG. 4B, Control vs. VLPs; p=0.0036). These data indicated that immunization protected against viremia as well as the inflammatory consequences of infection. To define the mechanism of protection in these animals, the question of whether immune IgG could protect against lethal challenge was examined using an adoptive transfer model.

Example 5: Humoral Immune Responses Induced by CHIKV VLPs Conferred Protection Against CHIKV Infection Previous studies have shown that immunodeficient mice with defective type-I IFN signaling developed severe infection, displaying symptoms and tissue tropism analogous to humans, and providing a model to evaluate immune mechanisms of protection. Purified total IgG from immune or control monkeys was passively transferred into these mice. The recipient mice were challenged intradermally 24 hours after IgG transfer with a lethal dose of LR2006 OPY-1. Recipients of purified CHIKV immune IgG demonstrated no detectable viremia after infection and were completely protected from lethality (FIGS. 4C, D). In contrast, all mice that received purified IgG from control monkeys showed severe infection and viremia, and all died. These results indicate that humoral immune responses induced by CHIKV VLPs conferred protection against CHIKV infection.

As reported herein, VLPs and plasmid DNA vaccines against CHIKV were evaluated for their ability to elicit cross-strain neutralizing antibodies. Immunization with VLPs showed cross-strain reactivity and 100-fold higher titers than DNA vaccines, and monkeys showed protection against CHIKV infection at a dose higher than that likely to be encountered in the field. Moreover, passively transferred antibody from monkeys immunized with VLPs protected against a lethal challenge in a relevant murine model, which suggests that the humoral response is important for protection against CHIKV. The current outbreaks of CHIKV fever have occurred largely in Southern Asia and underscore the need for a human vaccine. These infections represent the spread of a virus first recognized in Kenya in 2004 before dissemination to several islands in the Indian Ocean in 2005-2006. The Reunion Island outbreak alone infected 244,000 people with an overall seroprevalence of 35%. The virus then spread to other continents, and by 2008 was reported in 37 countries with an estimated 1.4-6.5 million cases in India, Africa, Europe and Southeast Asia.

In 2009 the number of cases has continued to increase, in part because the current epidemic strain of CHIKV has adapted to a new vector, the Asian tiger mosquito, Ae. albopictus, which can survive in more temperate climates, including Europe and the United States. CHIKV continues to cause substantial morbidity and has resulted in significant economic losses. While there were no reports of mortality in previous chikungunya epidemics, more than 260 deaths during the latest outbreak were directly attributed to the virus. To date, there has been limited success in developing a safe and effective CHIKV vaccine. A live CHIKV vaccine candidate caused transient arthralgia in volunteers. Other efforts, which include a live attenuated vaccine, a formalin-killed vaccine, a Venezuelan equine encephalitis/CHIKV chimeric live attenuated vaccine and a consensus-based DNA vaccine (Muthumani et al., Vaccine 26, 5128 (2008)) have not yet proven to be both safe and effective. Although CHIKV strains vary widely, individual strains are antigenically related, so a vaccine that works against heterologous strains may be achieved (Harrison et al., Am. J Trop. Med. Hyg. 16, 786 (1967)). The safety and efficacy of VLP vaccines in general make them promising candidates for further study.

VLPs are known to be highly immunogenic and elicit higher titer neutralizing antibody responses than subunit vaccines based on individual proteins. Such VLPs authentically present viral spikes and other surface components in a repetitive array that effectively elicits recognition by B-cells to stimulate antibody secretion. This recognition leads to B cell signaling and MHC class II up-regulation that facilitates the generation of high titer specific antibodies. VLPs from other viruses, including hepatitis B virus (HBV) and human papillomavirus (HPV), elicit high titer neutralizing antibody responses that contribute to protective immunity in humans.

The vaccines described herein represent the first use of recombinant VLPs to prevent infection by alphaviruses. The spread of mosquito species worldwide has been aided by changes in trade, travel or global climate and may potentially cause other alphavirus outbreaks. This approach to vaccine development may prove useful for other alphaviruses of increasing concern, including Western, Eastern, and Venezuelan equine encephalitis viruses, o'nyong-nyong virus and Ross River virus.

The results reported herein were obtained using the following methods and materials.

Vector Construction

Plasmids encoding the structural polyproteins C, E1, E2, E3 and 6K (strains 37997 and LR2006 OPY-1, GenBank EU224270) (FIG. 25) and EU224268 (FIG. 24), respectively) were synthesized as previously described (Yang et al., Science 317, 825 (2007)) (GeneArt, Regensburg, Germany). Plasmids encoding the polyproteins E3, E2, 6K, and E1 were amplified by PCR using the sense primer 5' GCTCTAGACACCAT-GAGCCTCGCCCTCCCGGTCTTG 3' (SEQ ID NO:26) and antisense primer 5' TGGATCCTCATT-AGTGCCTGCTAAACGACA 3' (37997) (SEQ ID NO:27) and the sense primer 5' GCTCTAGACACCATGAGTCTTGC-CATCCCAGTTATG 3' (SEQ ID NO:28) and antisense primer 5' TGGATCCTCATTAGTGCCTGCTGAACGACA 3' (LR2006 OPY-1) (SEQ ID NO:29). XbaI and BamHI sites were inserted for cloning. Each fragment was digested with XbaI/BamHI and inserted into a eukaryotic expression vector under the control of a cytomegalovirus enhancer/promoter, CMV/R (Yang et al., Science 317, 825 (2007)) (C-$E_{37997}$, $E_{37997}$ and $E_{OPY-1}$). To confirm expression of CHIKV C and E proteins, 293T cells were transfected using a FuGENE™ 6 Transfection Reagent kit (Roche Diagnostics GmbH, Germany) with 3 µg of the plasmid DNAs, following the manufacturer's recommendations.

Cell Culture 293T and 293A (human embryonic kidney cells), Vero (African green monkey kidney epithelial cells), HeLa (human cervical adenocarcinoma), A549 (human lung carcinoma) and BHK (baby hamster kidney cells) were cultured in Dulbecco's modified Eagle's medium (DMEM; GIBCO BRL) containing 10% heat-inactivated fetal bovine serum (FBS) (GIBCO BRL).

Production of Pseudotyped Lentiviral Vectors

Lentiviral vectors expressing glycoproteins from different CHIKV strains were created. The recombinant lentiviral vectors expressing a luciferase reporter gene were produced as previously described (Naldini et al., Proc. Natl. Acad. Sci. USA 93, 11382 (1996), Yang et al., Science 317, 825 (2007)). Briefly, 293T cells were co-transfected with 500 ng CHIKV E plasmid from either strain ($E_{37997}$ or $E_{OPY-1}$), 7 µg of a transducing vector encoding a luciferase reporter gene (pHR'CMV-luciferase plasmid), and 7 µg of a packaging plasmid expressing human immunodeficiency virus-1 (HIV-1) structural proteins (pCMVΔR8.2). 2 µg of vesicular stomatitis virus glycoprotein (VSV-G), 2 µg of pNGVL-4070A amphotropic MuLV gp70 expression vector or 500 ng of empty vector served as positive and negative controls for these pseudotyped reporters respectively. After a calcium phosphate transfection (Invitrogen, Carlsbad, Calif.) overnight, the culture media was replenished with fresh media. 48 hours later, supernatants were harvested, filtered through a 0.45 µm syringe filter, stored in aliquots, and frozen at −80° C. The viruses were standardized by the amount of HIV-1 Gag p24. CHIKV pseudotyped lentiviral vectors harvested 72 h after transfection were normalized according to HIV-1 Gag p24 levels before infection, as previously described (Yang et al., Science 317, 825 (2007)).

Neutralization of CHIKV E Pseudotyped Lentiviral Vectors by Mouse and Monkey Antisera The neutralization assay was performed as described previously (Yang et al., Science 317, 825 (2007)). A total of $10^4$ 293 A cells were plated into each well of a 96-well dish one day prior to infection. CHIKV E-pseudotyped lentiviral vectors encoding luciferase were first titrated by serial dilution. Similar amounts of pseudotyped lentiviral vectors (with p24 levels of approximately 50 ng/ml) were then incubated with the indicated dilutions of mouse antisera for 60 minutes at room temperature prior to adding the virus: sera solution to 293A cells ($10^4$ cells/well in a 96-well dish, 50 µl/well, in triplicate). Sera from non-immune mice or monkeys were used as a negative control. After a 24 hour incubation, cells were lysed using cell lysis buffer (Cell Signal) and the luciferase activity was measured using Microbeta® JET (PerkinElmer, Turku, Finland) following incubation with "Luciferase assay reagent" (Promega, Madison, Wis.), according to the manufacturer's protocol. Inhibition values were calculated as follows: inhibition (%)=[1−(luciferase activity (cps) in pseudotyped lentiviral vector infected cells incubated with the indicated dilutions of mouse antisera)/(luciferase activity (cps) in pseudotyped lentiviral vector infected cells incubated with the same dilutions of non-immune mouse serum)]×100. The $IC_{50}$ was calculated with Prism software (version 5).

Electron Microscopy

The morphology of the VLPs was examined by the Image Analysis Laboratory at the National Cancer Institute. VLPs were purified by OptiPrep™ density centrifugation and were then fixed in 4% formaldehyde in PBS. Negative-stain electron microscopy for viral diagnosis has been described previously (Palmer and Martin, Electron Microscopy in Viral Diagnosis (CRC Press, Boca Raton, Fla., 1988)). Briefly, 1.0 µl of the sample was placed onto a carbon-coated Formvar-filmed copper grid (Tousimis Research Corp., Rockville, Md.) and VLPs allowed to attach. The VLPs were negatively stained by addition of 2 µl of 1% PTA solution (phosphotungstic acid, pH 7.0) (Fisher Scientific Co., Fairlawn, N.J.). The grid was then examined by electron microscope (Hitachi H7000, Tokyo, Japan) operated at 75 kV. Digital images were taken by a CCD camera (AMT, Danvers, Mass.).

Cryo-Electron Microscopy and Image Analysis

Chikungunya VLPs were flash-frozen on holey grids in liquid ethane. Images were recorded at 47K magnification with a CM300 FEG microscope with electron dose levels of approximately 20 $e^{i}/Å^2$. All micrographs were digitized at 6.35 µm pixel$^{i1}$ using a Nikon scanner. Individual particle images were boxed using the program e2boxer in the EMAN2 package (Tang et al., J Struct. Biol. 157, 38 (2007)). CTF parameters were determined and phases were flipped using the CTFIT program from the EMAN package (Ludtke et al., J Struct. Biol. 128, 82 (1999)). An initial model was constructed in EMAN using assigned 2-, 3-, and 5-fold views and was refined in EMAN assuming icosahedral symmetry. The number of particles incorporated into the final reconstruction was 1489, giving a final resolution of 18 Å based on a 0.5 Fourier shell correlation threshold.

Buoyant Density Gradient Sedimentation Analysis and Purification of VLPs

Buoyant density gradient analysis and purification of VLPs was performed as described previously (Akahata et al., J. Virol. 79, 626 (2005)). Briefly, a 293-derived suspension cell line, 293F (2.5×10$^8$ cells) (Invitrogen) was transfected with 293fectin transfection reagent (Invitrogen) and 125 µg of C-$E_{37997}$ plasmid following the manufacturer's recommendations. The supernatants were harvested 72 h after transfection and filtered through a 0.45 µm pore size filter, then layered onto a 60% OptiPrep™ (Iodixanol) medium (Invitrogen) and centrifuged at 50,000×g for 1.5 h with a Surespin 630 rotor (Sorvall). The supernatants were removed to leave 4 ml above the virus band and mixed to a 20% final concentration of OptiPrep™. A density gradient was formed by centrifugation at 360,000×g for 3.5 hr with an NVT100 rotor (Beckman). 500 µl of each fraction was collected, weighed, and the densities of the fractions were plotted. 20 µl of each fraction was separated on a 4%-15% SDS-PAGE gel, transferred onto an Immobilon-P membrane, and blotted with sera from mice injected with the CHIKV strain S-27 (ATCC, VR-1241AF) and goat anti-mouse immunoglobulins linked to horseradish peroxidase (Santa Cruz Biotechnology).

Immunizations and Challenge of Mouse and Monkeys

Nineteen µg of VLPs (equivalent to approximately 10 µg of E1/E2) in 60 µl normal saline were mixed with 60 µl of Ribi solution (Sigma Adjuvant system, Sigma-Aldrich) per mouse following the manufacturer's recommendations. Female 6- to 8-week-old BALB/c mice were injected in the right and left quadriceps muscles with VLPs in normal saline or Ribi in 120 µl total volume, two times at weeks 2 and 6. For DNA vaccination groups, the mice were injected in the right and left quadriceps muscles with a total of 15 µg of purified plasmid C-$E_{37997}$, $E_{37997}$, C-$E_{OPY-1}$ or $E_{OPY-1}$ suspended in 100 µl of normal saline three times at weeks 0, 3 and 6. Five mice/group were injected. 10 days after the last injection, sera and spleen were collected.

In the monkey experiments, rhesus macaques (Macaca mulatta) weighing 3-4 kg were injected intramuscularly in the anterior quadriceps with either twenty µg of VLPs in 1 ml PBS (VLP group) or 1 ml PBS alone (control group) at weeks 0, 4 and 24. Six monkeys/group were injected. Blood was collected to measure antibody titers on days −14, 0, 10, 28, 38, 56, 70, 161 and 178. The monkeys (n=3 per group, randomly selected from each group) were challenged with $10^{10}$ PFU of CHIKV (strain LR2006 OPY-1) by intravenous injection. Blood was collected to measure viremia at 0, 6, 24, 48, 72, 96, 120 and 168 hours. The monkeys were sacrificed at 168 h after challenge. The whole blood cells were measured using a hematology analyzer (IDEXX Laboratories, Inc., Westbrook, Me.). Bleeds were EDTA-anticoagulated using 20-22 gauge needles and either syringes or vacuum tubes. The maximum blood volume removed did not exceed 20% (12 ml/kg) per month, with no more than 15% (9 ml/kg) removed during any single draw.

All animal experiments were reviewed and approved by the Animal Care and Use Committee, Vaccine Research Center (YRC), National Institute of Allergy and Infectious Diseases and performed in accordance with all relevant federal and National Institutes of Health guidelines and regulations.

Virus Preparation

CHIKV (strain LR2006 OPY-1) was prepared and the virus titers were determined as previously described (Tsetsarkin et al., PLoS. Pathog. 3, e201 (2007) and Pastorino et al., J Virol. Methods 124, 65 (2005)). Briefly, viral RNA transcribed from plasmid CHIK-LR is was transfected into BHK-21 cells by electroporation. The supernatants from the transfected cells were aliquotted and the stock virus was titrated and tissue culture infectious dose 50% ($TCID_{50}$) endpoint titers were determined using Vero cells. To produce virus for vertebrate challenge, C6/36 (*Aedes albopictus*) cells grown to confluence in T150 flasks were infected with stock virus at a multiplicity of infection of 0.03. Supernatants were harvested at 48 hrs post-infection, aliquotted and titrated to determine $TCID_{50}$ endpoint titers on Vero cells.

Plaque Assay

Serum samples were tested for CHIKV neutralizing antibody by a standard plaque reduction neutralization test (PRNT). Briefly, monkey sera were heat inactivated at 56° C. for 30 minutes and diluted in virus diluent (PBS/5% BSA). Diluted serum samples were mixed with an equal volume of 40 PFU CHIKV (strain LR2006 OPY-1) and incubated for 1 hr at 37° C. Six-well plates of confluent Vero cells were inoculated with 200 μl of the serum-virus mixtures in duplicate and incubated at 37° C. for 1 hr. Plates were overlaid with 3 ml of medium containing 0.9% agarose (Lonza Rockland, Rockland, Me.) and incubated at 37° C. in a 5% $CO_2$ incubator for 2 days. A second overlay medium containing neutral red and 1% agarose was then added and the plates were incubated overnight before plaques were visualized and counted. The viremia in the monkeys after challenge was measured by plaque assay. Six-well plates of confluent Vero cells were inoculated with 200 μl of the serum-PBS mixtures in duplicate. The serum dilutions were 1:200, 1:400, 1:800, 1:1000, 1:10,000 and 1:100,000, since at lower dilutions toxicities were observed in the cells (detection limit 1:200 dilution=1000 PFU/ml).

Passive Transfer of Immunoglobulin and Challenge in $IFN\alpha/\beta R^{-/-}$ Mice $IFN\alpha/\beta R^{-/-}$ mice were kindly given by Robert Seder and Daniel D. Pinschewer. IgG was purified from the serum in monkeys immunized with CHIKV VLPs or injected with PBS (control) using a HiTrap™ Protein G HP column (GE Healthcare) following the manufacturer's recommendations. IgG was further purified using a Melon Gel IgG Purification Kit (Pierce) following the manufacturer's recommendations. Purified IgG was dialyzed 3 times against PBS. 2 mg of purified IgG (from approximately 200 μl of serum) was administered intravenously into each recipient $IFN\alpha/\beta R^{-/-}$ mouse by tail vein injection 24 h before challenge. The mice were challenged with 30 PFU of CHIKV (strain LR2006 OPY-1) by intradermal injection.

Detection of CHIKV RNA by Quantitative RT-PCR

For RNA isolation, serum samples were spun down at 10,000×g for 1 hr, liquid poured off and 1 ml of RNA-STAT 60 (Isotex Diagnostics, Friendswood, Tex.) added. Samples were then incubated at RT for 5 min and resuspended in 250 μl of chloroform by vortexing. The samples were spun down at 10,000×g for 1 hr, the aqueous top-layer removed, 0.5 ml isopropanol and 10 μl tRNA (10 μg/ml) added and precipitated overnight at −20° C. Samples were spun down for 1 hr, washed with cold 75% ethanol and spun again for another hour. RNA was resuspended in 30 μl RNAse-free water. For RT-PCR, 10% RNA was added to TaqMan reagents (Applied Biosystems, Foster City, Calif.) along with primers and probe (listed below) and amplified in a 7700 Sequence Detection System (Applied Biosystems). Briefly, the sample was reverse-transcribed at 48° C. for 30 min., held at 95° C. for 10 min, then run for 40 cycles of 95° C. for 30 s and 60° C. for 1 min. The signal was compared to a standard curve of known concentrations of plasmid containing the LR2006 OPY-1 sequence starting at $10^7$ down to 1 copy/mL and multiplied by 10, giving a detection range from 40-$10^8$ copies/mL. All samples were performed in triplicate. The primers and probe were designed to bind to a highly conserved region on the E1 structural protein gene. Primer sequences: CHIK-F 5' AAGCTCCGCGTCCTTTACCAAG 3' (SEQ ID NO:30) and CHIK-R 5' CCAAAT-TGTCCTGGTCTTCCT3' (SEQ ID NO:31). Probe sequence: CHICK-P FAM-CCAATGTCTTCAGCCTGGACACCTTT-TAMRA (SEQ ID NO:32) as described previously (Huang et al., *J. Virol.* 78, 12557 (2004); Pastorino et al., J Virol. Methods 124, 65 (2005)).

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The invention claimed is:

1. A kit comprising a virus-like particle (VLP) comprising CHIKV strain 37997 structural proteins, wherein the CHIKV strain 37997 structural proteins comprise at least CHIKV capsid (C) protein, CHIKV E2 protein, and CHIKV E1 protein, and wherein the VLP does not carry genetic information encoding the VLP proteins.

2. The kit of claim 1, wherein the one or more structural proteins are selected from CHKV capsid (C) protein, CHKV E3 protein, CHKV E2 protein, CHKV 6K protein and CHKV E1 protein.

3. The kit of claim 1, wherein the VLP comprises CHIKV envelope proteins E3, E2, 6K and E1.

4. The kit of claim 1, wherein the VLP comprises CHIKV envelope proteins E1 and E2, and CHIKV capsid protein.

5. The kit of claim 1, wherein the VLP comprises a polyprotein comprising C-E3-E2-6K-E1.

* * * * *

SEQUENCE LISTING

```
Sequence total quantity: 33
SEQ ID NO: 1            moltype = DNA  length = 3747
FEATURE                 Location/Qualifiers
misc_feature            1..3747
                        note = Description of Artificial Sequence: Synthetic
                        polynucleotide
source                  1..3747
                        mol_type = other DNA
                        organism = synthetic construct
SEQUENCE: 1
atggagttca tcccgacgca aactttctat aacagaaggt accaacccccg accctgggcc   60
ccacgcccta caattcaagt aattagacct agaccacgtc cacagaggca ggctgggcaa  120
ctcgcccagc tgatctccgc agtcaacaaa ttgaccatgc gcgcggtacc tcaacagaag  180
cctcgcagaa atcggaaaaa caagaagcaa aggcagaaga agcaggcgcc gcaaaacgac  240
ccaaagcaaa agaagcaacc accacaaaag aagccggctc aaaagaagaa gaaaccaggc  300
cgtagggaga gaatgtgcat gaaaattgaa aatgattgca tcttcgaagt caagcatgaa  360
ggcaaagtga tgggctacgc atgcctggtg ggggataaag taatgaaacc agcacatgtg  420
```

```
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtgccat cgtcctagga ggggccaagc aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagaccggg atactaccag ctactaaaag catcgctgac ttgctctcag    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggg   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacaccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tcaaacgagg gactgacaac cacagacaaa   1620
gtgatcaata actgcaaaat tgatcagtgc catgctgcag tcactaatca aagaattgg   1680
caatacaact ccccctttag cccgcgcaac gctgaactcg gggaccgtaa aggaaagatc   1740
cacatcccat tcccattggc aaacgtgact tgcagagtgc caaaagcaag aaaccctaca   1800
gtaacttacg gaaaaaacca agtcaccatg ctgctgtatc ctgaccatcc gacactcttg   1860
tcttaccgta acatgggaca ggaaccaaat taccacgagg agtgggtgac acacaagaag   1920
gaggttacct tgaccgtgcc tactgagggt ctggaggtca cttggggcaa caacgaacca   1980
tacaagtact ggccgcagat gtctacgaac ggtactgctc atggtcaccc acatgagata   2040
atcttgtact attatgagct gtaccccact atgactgtag tcattgtgtc ggtggcctcg   2100
ttcgtgcttc tgtcgatggt gggcacagca gtgggaatgt gtgtgtgcgc acggcgcaga   2160
tgcattacac catatgaatt aacaccagga gccactgttc ccttcctgct cagcctgcta   2220
tgctgcgtca gaacgaccaa ggcgccaca tattcgagg ctgcggcata tctatggaac   2280
gaacagcagc ccctgttctg gttgcaggct cttatcccgc tggccgcctt gatcgtcctg   2340
tgcaactgtc tgaaactctt gccatgctgc tgtaagaccc tggcttttt agccgtaatg   2400
agcatcggtg cccacactgt gagcgcgtac gaacacgtaa cagtgatccc gaacacggtg   2460
ggagtaccgt ataagactct tgtcaacaga ccgggttaca gcccatggt gttggagtg   2520
gagctacaat cagtcacctt ggaaccaaca ctgtcacttg actacatcac gtgcgagtac   2580
aaaactgtca tcccctcccc gtacgtgaag tgctgtggta cagcagagtg caaggacaag   2640
agcctaccag actacagctg caaggtcttt actggagtct acccatttat gtggggcggc   2700
gcctactgct tttgcgacgc cgaaaatacg caattggcag aggcacatgt agagaaatct   2760
gaatcttgca aaacagagtt tgcatcggcc tacagagccc acaccgcatc ggcgtcggcg   2820
aagctccgcg tcctttacca aggaacaac attaccgtag ctgcctacgc taacggtgac   2880
catgccgtca cagtaaagga cgccaagttt gtcgtgggcc caatgtcctc cgcctggaca   2940
ccttttgaca acaaaatcgt ggtgtacaaa ggcgacgtct acaacatgga ctacccacct   3000
tttggcgcag gaagaccagg acaatttggt gacattcaaa gtcgtacacc ggaaagtaaa   3060
gacgtttatg ccaacactca gttggtacta cagaggccag cagcaggcac ggtacatgta   3120
ccatactctc aggcaccatc tggcttcaag tattggctga aggaacgagg agcatcgcta   3180
cagcacacgg caccgttcgg ttgccagatt gcgacaaacc cggtaagagc tgtaaattgc   3240
gctgtgggga acataccaat ttccatcgac ataccggatg cggcctttac tagggttgtc   3300
gatgcaccct ctgtaacgga catgtcatgc gaagtaccag cctgcactca ctcctccgac   3360
tttgggggcg tcgccatcat caaatacaca gctagcaaga aaggtaaatg tgcagtacat   3420
tcgatgacca acgccgttac cattcgagaa gccgacgtag aagtagaggg gaactcccag   3480
ctgcaaatat ccttctcaac agccctggca agcgccgagt ttcgcgtgca agtgtgctcc   3540
acacaagtac actgcgcagc cgcatgccac cctccaaagg accacatagt caattaccca   3600
gcatcacaca ccacccttgg ggtccaggat atatccacaa cggcaatgtc ttgggtgcag   3660
aagattacgg gaggagtagg attaattgtt gctgttgctg ccttaatttt aattgtggtg   3720
ctatgcgtgt cgtttagcag gcactaa                                       3747
```

```
SEQ ID NO: 2           moltype = DNA   length = 8159
FEATURE                Location/Qualifiers
misc_feature           1..8159
                       note = Description of Artificial Sequence: Synthetic
                       polynucleotide
source                 1..8159
                       mol_type = other DNA
                       organism = synthetic construct
SEQUENCE: 2
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
```

```
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgga ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgctctagac   1380
accatggagt tcatcccgac gcaaactttc tataacagaa ggtaccaacc ccgaccctgg   1440
gccccacgcc ctacaattca agtaattaga cctagaccac gtccacgagg gcaggctggg   1500
caactcgccc agctgatctc cgcagtcaac aaattgacca tgcgcgcggt acctcaacag   1560
aagcctcgca gaaatcggaa aaacaagaag caaaggcaga agaagcaggc gccgcaaaac   1620
gacccaaagc aaaagaagca accaccacaa aagaagccgg ctcaaaagaa gaagaaacca   1680
ggccgtaggg agagaatgtg catgaaaatt gaaaatgatt gcatcttcga agtcaagcat   1740
gaaggcaaag tgatgggcta cgcatgcctg gtggggata aagtaatgaa accagcacat   1800
gtgaagggaa ctatcgacaa tgccgatctg gctaaactgg cctttaagcg gtcgtctaaa   1860
tacgatcttg aatgtgcaca gataccggtg cacatgaagt ctgatgcctc gaagtttacc   1920
cacgagaaac ccgaggggta ctataactgg catcacggag cagtgcagta tcaggaggc    1980
cggttcacta tcccgacggg tgcaggcaag ccggagaca gcggcagacc gatcttgac     2040
aacaaaggac gggtggtggc catcgtccta ggaggggccg acgaaggtgc ccgcacgacg    2100
ctctccgtgg tgacgtggaa caagacatc gtcacaaaaa ttaccctga gggagccgaa     2160
gagtggagcc tcgccctccc ggtcttgtgc ctgttggcaa acactacatt ccctgctct    2220
cagccgcctt gcacaccctg ctgctacgaa aggaaccgg aaagcacctt gcgcatgctt    2280
gaggacaacg tgatgagacc cggatactac cagctactaa aagcatcgct gacttgctct   2340
ccccaccgcc aaagacgcag tactaaggac aattttaatg tctataaagc cacaagacca   2400
tatctagctc attgtcctga ctgcggagaa gggcattcgt gccacagccc tatcgcattg   2460
gagcgcatca gaaatgaagc aacgacgga acgctgaaaa tccaggtctc tttgcagatc    2520
gggataaaga cagatgacag ccacgattgg accaagctgc gctatatgga tagccatacg   2580
ccagcggacg cggagcgagc cggattgctt gtaaggactt cagcaccgtg cacgatcacc   2640
gggaccatgg gacactttat tctcgcccga tgcccgaaag gagagacgct gacagtggga   2700
tttacggaca gcagaaagat cagccacaca tgcacacacc cgttccatca tgaaccacct   2760
gtgataggta gggagaggtt ccactctcga ccacaacatg gtaaagagtt accttgcgac   2820
acgtacgtgc agagcaccgc tgccactgct gaggagtag aggtgcatat gcccccagat    2880
actcctgacc gcacgctgat gacgcagcag tctggcaacg tgaagatcac agttaatggg   2940
cagacggtgc ggtacaagtg caactgcggt ggctcaaacg agggactgac aaccacagac   3000
aaagtgatca ataactgcaa aattgatcag tgccatgctg cagtcactaa tcacaagaat   3060
tggcaataca actcccttt agtcccgcgc aacgctgaac tcgggaccg taaaggaaag    3120
atccacatcc cattcccatt ggcaaacgtg acttgcagag tgccaaaagc aagaaaccct   3180
acagtaactt acgaaaaaa ccaagtcacc atgctgctgt atcctgacca tccgacactc    3240
ttgtcttacc gtaacatggg acaggaacca aattaccacg aggagtgggt gacacacaag   3300
aaggaggtta ccttgaccgt gcctactgga gtctgaagg tcacttgggg caacaacgaa    3360
ccatacaagt actggcccgca gatgtctacg aacggtactc tcatggtca cccacatgag   3420
ataatcttgt actattatga gctgtacccc actatgactg tagtcattgt gtcggtggcc   3480
tcgttcgtgc ttctgtcgat ggtgggcaca gcagtggaa tgtgtgtgtg cgcacggcgc    3540
agatgcatta caccatatga attaacacca ggagccatga ttccctttcc gctcagcctg   3600
ctatgctgcg tcagaacgac caaggcggcc acatattacg aggctgcggc atatctatgg   3660
aacgaacagc agccctgtt ctggttcag gctcttatcc cgctggccgc cttgatcgtc    3720
ctgtgcaact gtctgaaact cttgccatgc tgctgtaaga ccctgccttt tttagccgta   3780
atgagcgtgg tgccacac tgtgagcgcg tacgaacacg taacagtgat cccgaacacg    3840
gtgggagtac cgtataagac tcttgtcaac agaccgggtt acagcccat ggtgttggag    3900
atggagctac aatcagtcac cttggaacca acactgtcac ttgactacat cacgtgcgag   3960
tacaaaactg tcatcccctc cccgtacgtg aagtgctgtg gtacagcaga gtgcaaggac   4020
aagagcctac cagactacag ctgcaaggtc tttactggag tctacccatt tatgtgggc    4080
ggcgcctact gcttttgcga cgccgaaat acgcaattga gcgaggcaca tgtagagaaa   4140
tctgaatctt gcaaaacaga gtttgcatcg gcctacagag cccacaccgc atcggcgtcg   4200
gcgaagctcc gcgtccttta ccaaggaaac aacattaccg tagctgccta cgctaacggt   4260
gaccatgccg tcacagtaaa ggacgccaag tttgtcgtgg gccaatgtc ctccgactgg   4320
acacctttg acaacaaaat cgtggtgtac aaaggcgacg tctacaacat ggactaccca   4380
ccttttggcg caggaagacc aggacaattt ggtgacattc aaagtcgtac accgaaagt    4440
aaagacgttt atgccaacac tcagttggta ctacagaggc cagcagcagg cacggtacat   4500
gtaccatact ctcaggcacc atctggcttc aagtattggc tgaaggaacg aggagcatcg   4560
ctacagcaca cggcaccgtt cggttgccag attgcgacaa acccggtaag agctgtaaat   4620
tgcgctgtgg gaacatacc aatttccatc gacataccgg atgcggcctt tactagggtt   4680
gtcgatgcac cctctgtaac ggacatgtca tgcgaagtac cagcctgcac tcactcctcc   4740
gactttgggg gcgtcgccat catcaaatac acagctagca agaaaggtaa atgtgcagta   4800
cattcgatga ccaacgccgt taccattcga gaagccgacg tagaagtaga ggggaactcc   4860
cagctgcaaa tatccttctc aacagcccctg gcaagtgcaga gtttcgcgt gcaagtgtgc   4920
tccacacaag tacactgcgc agccgcatgc caccctccaa aggaccacat agtcaattac   4980
ccagcatcac acaccaccct tggggtccag gatatatcca aacggcaat gtcttgggtg   5040
cagaagatta cgggaggagt aggattaatt gttgctgttg ctgccttaat tttaattgtg   5100
gtgctatgcg tgtcgtttag caggcactaa tgaggatcca gatctgctgt gccttctagt   5160
tgccagccat ctgttgtttg ccctccccc gtgccttcct tgaccctgga aggtgccact   5220
cccactgtcc tttcctaata aaatgaggaa attgcatcgc attgtctgag taggtgtcat   5280
tctattctgg ggggtggggt ggggcaggac agcaaggggg aggattggga agacaatagc   5340
aggcatgctg gggatgcggt gggctctatg gtacccaggg tgctgaagaa ttgacccggt   5400
tcctcctggg ccagaaagaa gcaggcacat ccccttctct gtgacacacc ctgtccacgc   5460
ccctggttct tagttccagc cccactcata ggacactcat agctcaggag ggctccgcct   5520
```

```
tcaatcccac cgctaaagt acttggagcg gtctctccct ccctcatcag cccaccaaac  5580
caaacctagc ctccaagagt gggaagaaat taaagcaaga taggctatta agtgcagagg  5640
gagagaaaat gcctccaaca tgtgaggaag taatgagaga aatcatagaa ttttaaggcc  5700
atgatttaag gccatcatgg ccttaatctt ccgcttcctc gctcactgac tcgctgcgct  5760
cggtcgttcg gctgcggcga gcggtatcag ctcactcaaa ggcggtaata cggttatcca  5820
cagaatcagg ggataacgca ggaaagaaca tgtgagcaaa aggccagcaa aaggccagga  5880
accgtaaaaa ggccgcgttg ctggcgtttt tccataggct ccgcccccct gacgagcatc  5940
acaaaaatcg acgctcaagt cagaggtggc gaaacccgac aggactataa agataccagg  6000
cgtttccccc tggaagctcc ctcgtgcgct ctcctgttcc gaccctgccg cttaccggat  6060
acctgtccgc ctttctccct tcgggaagcg tggcgctttc tcatagctca cgctgtaggt  6120
atctcagttc ggtgtaggtc gttcgctcca agctgggctg tgtgcacgaa ccccccgttc  6180
agcccgaccg ctgcgcctta tccggtaact atcgtcttga gtccaacccg gtaagacacg  6240
acttatcgcc actggcagca gccactggta acaggattag cagagcgagg tatgtaggcg  6300
gtgctacaga gttcttgaag tggtggccta actacggcta cactagaaga acagtatttg  6360
gtatctgcgc tctgctgaag ccagttacct tcggaaaaag agttggtagc tcttgatccg  6420
gcaaacaaac caccgctggt agcggtggtt tttttgtttg caagcagcag attacgcgca  6480
gaaaaaaagg atctcaagaa gatcctttga tcttttctac ggggtctgac gctcagtgga  6540
acgaaaactc acgttaaggg attttggtca tgagattatc aaaaaggatc ttcacctaga  6600
tccttttaaa ttaaaaatga agttttaaat caatctaaag tatatatgag taaacttggt  6660
ctgacagtta ccaatgctta atcagtgagg cacctatctc agcgatctgt ctatttcgtt  6720
catccatagt tgcctgactc ccccgggggg ggcgctgagg tctgcctcgt gaagaaggtg  6780
ttgctgactc ataccaggcc tgaatcgccc catcatccag ccagaaagtg agggagccac  6840
ggttgatgag agctttgttg taggtggacc agttggtgat tttgaacttt tgctttgcca  6900
cggaacggtc tgcgttgtcg ggaagatgcg tgatctgatc cttcaactca gcaaaagttc  6960
gatttattca acaaagccgc cgtcccgtca agtcagcgta atgctctgcc agtgttacaa  7020
ccaattaacc aattctgatt agaaaaactc atcgagcatc aaatgaaact gcaatttatt  7080
catatcagga ttatcaatac catatttttg aaaaagccgt ttctgtaatg aaggagaaaa  7140
ctcaccgagg cagttccata ggatggcaag atcctggtat cggtctgcga ttccgactcg  7200
tccaacatca atacaaccta ttaatttccc ctcgtcaaaa ataaggttat caagtgagaa  7260
atcaccatga gtgacgactg aatccggtga gaatggcaaa agcttatgca tttctttcca  7320
gacttgttca acaggccagc cattacgctc gtcatcaaaa tcactcgcat caaccaaacc  7380
gttattcatt cgtgattgcg cctgagcgag acgaaatacg cgatcgctgt taaaaggaca  7440
attacaaaca ggaatcgaat gcaaccggcg caggaacact gccagcgcat caacaatatt  7500
ttcacctgaa tcaggatatt cttctaatac ctggaatgct gttttcccgg ggatcgcagt  7560
ggtgagtaac catgcatcat caggagtacg gataaaatgc ttgatggtcg gaagaggcat  7620
aaattccgtc agccagttta gtctgaccat ctcatctgta acatcattgg caacgctacc  7680
tttgccatgt ttcagaaaca actctggcgc atcgggcttc ccatacaatc gatagattgt  7740
cgcacctgat tgcccgacat tatcgcgagc ccatttatac ccatataaat cagcatccat  7800
gttggaattt aatcgcggcc tcgagcaaga cgtttcccgt tgaatatggc tcataacacc  7860
ccttgtatta ctgtttatgt aagcagacag ttttattgtt catgatgata tatttttatc  7920
ttgtgcaatg taacatcaga gattttgaga cacaacgtgg ctttcccccc cccccattta  7980
tgaagcatt tatcagggtt attgtctcat gagcggatac atatttgaat gtatttagaa  8040
aaataaacaa atagggggttc gcgcacatt tccccgaaaa gtgccacctg acgtctaaga  8100
aaccattatt atcatgacat taacctataaa aataggcgt atcacgaggc cctttcgtc   8159

SEQ ID NO: 3           moltype = DNA  length = 3744
FEATURE                Location/Qualifiers
misc_feature           1..3744
                       note = Description of Artificial Sequence: Synthetic
                       polynucleotide
source                 1..3744
                       mol_type = other DNA
                       organism = synthetic construct
SEQUENCE: 3
atggagttca tcccaaccca aactttttac aataggaggt accagcctcg accctggact    60
ccgcgcccta ctatccaagt catcaggccc agaccgcgcc ctcagaggca agctgggcaa   120
cttgcccagc tgatctcagc agttaataaa ctgacaatgc gcgcggtacc acaacagaag   180
ccacgcagga atcggaagaa taagaagcaa agcaaaaac aacaggcgcc acaaaacaac    240
acaaatcaaa agaagcagcc acctaaaaag aaaccggctc aaaagaaaaa gaagccgggc   300
cgcagagaga ggatgtgcat gaaaatcgaa aatgattgta ttttcgaagt caagcacgaa   360
ggtaaggtaa caggttacgc gtgcctggtg ggggacaaag taatgaaacc agcacacgta   420
aaggggacca tcgataacgc ggacctgcc aaactggcct ttaagcggtc atctaagtat    480
gaccttgaat gcgcgcagat acccgtgcac atgaagtccg acgcttcgaa gttcacccat   540
gagaaaccgg agggggtacta caactggcac cacggagcag tacgtactc aggaggccgg   600
ttcaccatcc ctacaggtgc tggcaaacca gggacagcg gcagaccgat cttcgacaac   660
aagggacgcg tggtggccat agtcttagga ggagctaatg aaggagcccg tacagccctc   720
tcggtggtga cctggaataa agacattgtc actaaaatca ccccgaggg ggccgaagag   780
tggagtcttg ccatcccagt tatgtgcctt tggcaaaca ccacgttccc ctgctccag    840
ccccctgca cgccctgctg ctacgaaaag gaaccggagg aaaccctcag catgcttgag   900
gacaacgtca tgagacctgg gtactatcag ctgctacaag catccttaac atgttctccc   960
caccgccagc gacgcagcac caaggacaac ttcaatgtct ataaagccac aagaccatac  1020
ttagctcact gtcccgactg tggagaaggg cactcgtgcc atagtcccgt agcactgaaa  1080
cgcatcagaa atgaagcgac agacgggacg ctgaaaatcc aggtctcctt gcaaatcgga  1140
ataaagacgg atgacagcca cgattggacc aagctgcgtt atatggacaa ccatatgcca  1200
gcagacgcag agagggcggg gctatttgta agaacatcag caccgtgtac gattactgga  1260
acaatgggac acttcatcct ggcccgatgt ccaaaagggg aaactctgac ggtgggattc  1320
actgacagta ggaagattag tcactcatgt acgcacccat tcaccacga ccctcctgtg  1380
ataggtcggg aaaaattcca ttcccgaccg cagcacggta aagagctacc ttgcagcacg  1440
tacgtgcaga gcaccgccgc aactaccgag gagatagagg tacacatgcc cccagacacc  1500
```

-continued

```
cctgatcgca cattaatgtc acaacagtcc ggcaacgtaa agatcacagt caatggccag   1560
acggtgcggt acaagtgtaa ttgcggtggc tcaaatgaag gactaacaac tacagacaaa   1620
gtgattaata actgcaaggt tgatcaatgt catgccgcgg tcaccaatca caaaaagtgg   1680
cagtataact cccctctggt cccgcgtaat gctgaacttg ggaccgaaaa aggaaaaatt   1740
cacatcccgt ttccgctggc aaatgtaaca tgcagggtgc ctaaagcaag gaaccccacc   1800
gtgacgtacg ggaaaaacca agtcatcatg ctactgtatc ctgaccaccc aacactcctg   1860
tcctaccgga atatgggaga agaaccaaac tatcaagaag agtgggtgat gcataagaag   1920
gaagtcgtgc taaccgtgcc gactgaaggg ctcgaggtca cgtggggcaa caacgagccg   1980
tataagtatt ggccgcagtt atctacaaac ggtacagccc atggccaccc gcatagata    2040
attctgtatt attatgagct gtacccact atgactgtag tagttgtgtc agtggccacg    2100
ttcatactcc tgtcgatggt gggtatggca gcggggatgt gcatgtgtgc acgacgcaga   2160
tgcatcacac cgtatgaact gacaccagga gctaccgtcc ctttcctgct agcctaata    2220
tgctgcatca gaacagctaa agcggccaca taccaagagg ctgcgatata cctgtggaac   2280
gagcagcaac cttttgttttg gctacaagcc cttattccgc tggcagccct gattgttcta   2340
tgcaactgtc tgagactctt accatgctgc tgtaaaacgt tggcttttttt agccgtaatg   2400
agcgtcggtg cccacactgt gagcgcgtac gaacacgtaa cagtgatccc gaacacggtg   2460
ggagtaccgt ataagactct agtcaataga cctggctaca gccccatggt attggagatg   2520
gaactactgt cagtcacttt ggagccaaca ctatcgcttg attacatcac gtgcgagtac   2580
aaaaccgtca tcccgtctcc gtacgtgaag tgctgcggta cagcagagtg caaggacaaa   2640
aacctacctg actacagctg taaggtcttc accggcgtct acccatttat gtggggcggc   2700
gcctactgct tctgcgacgc tgaaaacacg cagttgagcg aagcacacgt ggagaagtcc   2760
gaatcatgca aaacagaatt tgcatcagca tacagggctc ataccgcatc tgcatcagct   2820
aagctccgcg tcctttacca aggaaataac atcactgtaa ctgcctatgc aaacggcgac   2880
catgccgtca cagttaagga cgccaaattc attgtggggc caatgtcttc agcctggaca   2940
cctttcgaca acaaaattgt ggtgtacaaa ggtgacgtct ataacatgga ctacccgccc   3000
tttggcgcag gaagaccagg acaatttggc gatatccaaa gtcgcacacc tgagagtaaa   3060
gacgtctatg ctaatacaca actggtactg cagagaccgg ctgtgggtac ggtacacgtg   3120
ccatactctc aggcaccatc tggctttaag tattggctaa aagaacgcgg ggcgtcgctg   3180
cagcacacag caccatttgg ctgccaaata gcaacaaacc cggtaagagc ggtgaactgc   3240
gccgtaggga acatgcccat ctccatcgac ataccgaaga cggcctttcac tagggtcgtc   3300
gacgcgccct cttttaacgga catgtcgtgc gaggtaccag cctgcaccca ttcctcagac   3360
tttgggggcg tcgccattat taaatatgca gccagcaaga aaggcaagtg tgcggtgcat   3420
tcgatgacta acgccgtcac tattcgggaa gctgagatag aagttgaagg gaattctcag   3480
ctgcaaatct ctttctcgac ggccttagcc agcgccgaat tccgcgtaca agtctgttct   3540
acacaagtac actgtgcagc cgagtgccac ccccgaagg accacatgt caactacccg    3600
gcgtcacata ccaccctcgg ggtccaggac atctccgcta cggcgatgtc atgggtgcag   3660
aagatcacgg gaggtgtggg actggttgtt gctgttgccg cactgattct aatcgtggtg   3720
ctatgcgtgt cgttcagcag gcac                                         3744
```

SEQ ID NO: 4          moltype = DNA   length = 8159
FEATURE               Location/Qualifiers
misc_feature         1..8159
                       note = Description of Artificial Sequence: Synthetic
                       polynucleotide
source                1..8159
                       mol_type = other DNA
                       organism = synthetic construct
SEQUENCE: 4

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcagattgc   240
ctattggcca ttgcatacgt tgtatccata tcataaatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagga ctttccattg acgtcaatgg gtggagtatt tacggtaaac     540
tgcccacttg gcagtacatc aagtgtatca tatgccaagt acgcccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctccctg gagcctacct agactcagcc ggctctccac gctttgcctg    1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgtctagac    1380
accatggagt tcatcccaac ccaaactttt acaatagga ggtaccagcc tcgaccctgg    1440
actccgcgcc ctactatcca agtcatcagg cccagaccgc gccctcagag caagctggg    1500
caacttgccc agctgatctc acagttaat aaactgctaa tgccgcggtt accaacaag    1560
aagcacgca ggaatcggaa gataagaag caaaagcaaa acaacaggc gccacaaaac     1620
aacacaaatc aaaagaagca gccacctaaa agaaaccgg ctcaaaagaa aaagaagccg    1680
ggccgcagag agaggatgtg catgaaaatc gaaatgatt gtattttcga agtcaagcac    1740
gaaggtaagg taacaggtta cgcgtgcctg gtggggaca aagtaatgaa accagcacac    1800
gtaaagggga ccatcgataa cgcggacctg gccaaactgg ccttaagcg gtcatctaag    1860
```

-continued

```
tatgaccttg aatgcgcgca gatacccgtg cacatgaagt ccgacgcttc gaagttcacc    1920
catgagaaac cggaggggta ctacaactgg caccacggag cagtacagta ctcaggaggc    1980
cggttcacca tccctacagg tgctggcaaa ccaggggaca gcggcagacc gatcttcgac    2040
aacaaggac gcgtggtggc catagtctta ggaggagcta atgaaggagc ccgtacagcc      2100
ctctcggtgg tgacctggaa taaagacatt gtcactaaaa tcaccccccga ggggccgaa    2160
gagtggagtc ttgccatccc agttatgtgc ctgttggcaa acaccacgtt ccctgctcc      2220
cagcccctt gcacgccctg ctgctacgaa aaggaaccgg aggaaccct acgcatgctt       2280
gaggacaacg tcatgagacc tgggtactat cagctgctac aagcatcctt aacatgttct    2340
ccccaccgcc agcgacgcag caccaaggac aacttcaatg tctataaagc cacaagacca    2400
tacttagctc actgtcccga ctgtgggaga gggcactcgt gccatagtcc cgtagcacta    2460
gaacgcatca gaaatgaagc gacagacggg acgctgaaaa tccaggtctc cttgcaaatc    2520
ggaataaaga cggatgacag ccacgattgg accaagctgc gttatatgga caaccacatg    2580
ccagcagacg cagagagggc ggggctattt gtaagaacat cagcaccgtg tacgattact    2640
ggaacaatgg gacacttcat cctggcccga tgtccaaaag gggaaactct gacggtggga    2700
ttcactgaca gtaggaagat tagtcactca tgtacgcacc catttcacca cgaccctcct    2760
gtgataggtc gggaaaaatt ccattcccga ccgcagcacg gtaaagagct accttgcagc    2820
acgtacgtgc agagcaccgc cgcaactacc gaggagatag aggtacacat gccccagac    2880
accctgatc gcacattaat gtcacaacag tccggcaacg taaagatcac agtcaatggc    2940
cagacggtgc ggtacaagtg taattgcggt ggctcaaatg aaggactaac aactacagac    3000
aaagtgatta taactgcaa ggttgatcaa tgtcatgccg cggtcaccaa tcacaaaaag     3060
tggcagtata actcccctct ggtcccgcgt aatgctgaac ttggggaccg aaaaggaaaa    3120
attcacatcc cgtttccgct ggcaaatgta acatgcaggg tgcctaaagc aaggaacccc    3180
accgtgacgt acgggaaaaa ccaagtcatc atgctactgt atcctgacca cccaacactc    3240
ctgtcctacc ggaatatggg agaagaacca aactatcaag aagagtgggt gatgcataag    3300
aaggaagtcg tgctaaccgt gccgactgaa gggctcgagg tcacgtgggg caacaacgag    3360
ccgtataagt attggccgca gttatctaca aacggtacag cccatgcca cccgcatgga    3420
ataattctgt attattatga gctgtacccc actatgactg tagtagttgt gtcagtggcc    3480
acgttcatac tcctgtcgat ggtgggtatg gcagcgggga tgtgcatgtg tgcacgacgc    3540
agatgcatca caccgtatga actgacacca ggagctaccg tccctttcct gcttagccta    3600
atatgctgca tcagaacagc taaagcggcc acataccaag aggctgcgat ataccttggg    3660
aacgagcagc aacctttgtt ttggctacaa gcccttattc cgctggcagc cctgattgtt    3720
ctatgcaact gtctgagact cttaccatgc tgctgtaaaa cgttggcttt tttagccgta    3780
atgagcgtcg tgcccacac tgtgagcgcg tacgaacacg taacagtgat cccgaacacg    3840
gtgggagtac cgtataagac tctagtcaat agacctggct acagcccat ggtattggag     3900
atggaactac tgtcagtcac ttttggagcca acactatcgc ttgattacat cacgtgcgag    3960
tacaaaaccg tcatcccgtc tccgtacgtg aagtgctgcg gtacagcaga gtgcaaggac    4020
aaaaacctac ctgactacag ctgtaaggtc ttcaccggcg tctacccatt tatgtggggc    4080
ggcgcctact gcttctgcga cgctgaaaac acgcagttga gcgaagcaca cgtggagaag    4140
tccgaatcat gcaaaacaga atttgcatca gcatacaggg ctcataccgc atctgcatca    4200
gctaagctcc gcgtcctta ccaaggaaat aacatcactg taactgccta tgcaaacggc     4260
gaccatgccg tcacagttaa ggacgccaaa ttcattgtgg ggccaatgtc ttcagctggg    4320
acacctttcg acaacaaat tgtggtgtac aaaggtgacg tctataacat ggactacccg    4380
cccttggcg caggaagacc aggacaattt ggcgatatcc aaagtcgcac acctgagagt    4440
aaagacgtct atgctaatac acaactggta ctgcagagac cggctgtggg tacggtacac    4500
gtgccatact ctcaggcacc atctggcttt aagtattggc taaagaacg cggggcgtcg    4560
ctgcagcaca cagcaccatt tggctgccaa atagcaacaa acccgtaag agcggtgaac    4620
tgcgccgtag ggaacatgcc catctccatc gacataccgg aagcggcctt cactagggtc    4680
gtcgacgcgc cctctttaac ggacatgtcg tgcgaggtac cagccgtcac ccattcctca    4740
gactttgggg gcgtcgccat tattaaatat gcagccagca agaaaggcaa gtgtgcggtg    4800
cattcgatga ctaacgccgt cactattcgg gaagctgaga tagaagttga agggaattct    4860
cagctgcaaa tctcttttct gacggcctta gccagcgccg aattccgcgt acaagtctgt    4920
tctacacaag tacactgtgc agccgagtgc caccccccga aggaccacat agtcaactac    4980
ccggcgtcac ataccaccct cggggtccag gacatctccg ctacggcgat gtcatgggtg    5040
cagaagatca cgggaggtgt gggactggtt gttgctgttg ccgcactgat tctaatcgtg    5100
gtgctatgcg tgtcgttcag caggcactaa tgaggatcca gatctgctgt gcctttctagt    5160
tgccagccat ctgttgtttg ccctccccc gtgccttcct tgaccctgga aggtgccact    5220
cccactgtcc tttcctaata aaatgaggaa attgcatcgc attgtctgag taggtgtcat    5280
tctattctgg ggggtggggt ggggcaggac agcaaggggg aggattggga agacaatagc    5340
aggcatgctg gggatgcggt gggctctatg ggtacccagg tgctgaagaa ttgacccggt    5400
tcctcctggg ccagaaagaa gcaggcacat cccccttctct gtgacacacc ctgtccacgc    5460
ccctggttct tagttccagc cccactcata ggacactcat agctcaggag gctccgcct    5520
tcaatcccac ccgctaaagt acttggagcg gtctctccct ccctcatcag cccaccaaac    5580
caaacctagc ctcaagagt gggaagaaat taaagcaaga taggctatta agtgcagagg    5640
gagaaaaat gcctccaaca tgtgagaaag taatgagaga aatcataga ttttaaggcc      5700
atgatttaag gccatcatgg ccttaatctt ccgcttcctc gctcactgac tcgctgcgct    5760
cggtcgttcg gctgcggcga gcggtatcag ctcactcaaa ggcggtaata cggttatcca    5820
cagaatcagg ggataacgca ggaaagaaca tgtgagcaaa aggccagcaa aaggccagga    5880
accgtaaaaa ggccgcgttg ctggcgtttt tccataggct ccgcccccct gacgagcatc    5940
acaaaaatcg acgctcaagt cagaggtggc gaaacccgac aggactataa agataccagg    6000
cgtttccccc tggaagctcc ctcgtgcgct ctcctgttcc gaccctgccg cttaccggat    6060
acctgtccgc ctttctccct tcgggaagcg tggcgctttc tcatagctca cgctgtaggt    6120
atctcagttc ggtgtaggtc gttcgctcca agctgggctg tgtgcacgaa ccccccgttc    6180
agcccgaccg ctgcgcctta tccggtaact atcgtcttga gtccaacccg gtaagacacg    6240
acttatcgcc actggcagca gccactggta acaggattag cagagcgagg tatgtaggcg    6300
gtgctacaga gttcttgaag tggtggccta actacggcta cactagaaga acagtatttg    6360
gtatctgcgc tctgctgaag ccagttacct tcggaaaaag agttggtagc tcttgatccg    6420
gcaaacaaac caccgctggt agcggtggtt tttttgtttg caagcagcag attacgcgca    6480
gaaaaaaagg atctcaagaa gatcctttga tcttttctac ggggtctgac gctcagtgga    6540
acgaaaactc acgttaaggg attttggtca tgagattatc aaaaaggatc ttcacctaga    6600
```

```
tccttttaaa ttaaaaatga agttttaaat caatctaaag tatatatgag taaacttggt    6660
ctgacagtta ccaatgctta atcagtgagg cacctatctc agcgatctgt ctatttcgtt    6720
catccatagt tgcctgactc gggggggggg ggcgctgagg tctgcctcgt gaagaaggtg    6780
ttgctgactc ataccaggcc tgaatcgccc catcatccag ccagaaagtg agggagccac    6840
ggttgatgag agctttgttg taggtggacc agttggtgat tttgaacttt tgctttgcca    6900
cggaacggtc tgcgttgtcg ggaagatgcg tgatctgatc cttcaactca gcaaaagttc    6960
gatttattca acaaagccgc cgtcccgtca agtcagcgta atgctctgcc agtgttacaa    7020
ccaattaacc aattctgatt agaaaaactc atcgagcatc aaatgaaact gcaatttatt    7080
catatcagga ttatcaatac catattttg aaaaagccgt ttctgtaatg aaggagaaaa    7140
ctcaccgagg cagttccata ggatggcaag atcctggtat cggtctgcga ttccgactcg    7200
tccaacatca atacaaccta ttaatttccc ctcgtcaaaa ataaggttat caagtgagaa    7260
atcaccatga gtgacgactg aatccggtga gaatggcaaa agcttatgca tttctttcca    7320
gacttgttca acaggccagc cattacgctc gtcatcaaaa tcactcgcat caaccaaacc    7380
gttattcatt cgtgattgcg cctgagcgag acgaaatacg cgatcgctgt taaaaggaca    7440
attacaaaca ggaatcgaat gcaaccggcg caggaacact gccagcgcat caacaatatt    7500
ttcacctgaa tcaggatatt cttctaatac ctggaatgct gttttcccgg ggatcgcagt    7560
ggtgagtaac catgcatcat caggagtacg gataaaatgc ttgatggtcg aagaggcat    7620
aaattccgtc agccagttta gtctgaccat ctcatctgta acatcattgg caacgctacc    7680
tttgccatgt ttcagaaaca actctggcgc atcgggcttc ccatacaatc gatagattgt    7740
cgcacctgat tgcccgacat tatcgcgagc ccatttatac ccatataaat cagcatccat    7800
gttggaattt aatcgcggcc tcgagcaaga cgtttcccgt tgaatatggc tcataacacc    7860
ccttgtatta ctgtttatgt aagcagacag tttttattgt tcatgatgata tatttttatc    7920
ttgtgcaatg taacatcaga gattttgaga cacaacgtgg ctttcccccc cccccatta    7980
ttgaagcatt tatcagggtt attgtctcat gagcggatac atatttgaat gtatttagaa    8040
aaataaacaa atagggggttc cgcgcacatt tccccgaaaa gtgccacctg acgtctaaga    8100
aaccattatt atcatgacat taacctataa aaataggcgt atcacgaggc cctttcgtc     8159
```

SEQ ID NO: 5          moltype = DNA   length = 8185
FEATURE               Location/Qualifiers
misc_feature          1..8185
                      note = Description of Artificial Sequence: Synthetic
                      polynucleotide
source                1..8185
                      mol_type = other DNA
                      organism = synthetic construct
SEQUENCE: 5

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcggggt tcggggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga cttttccatg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta cagactgtt cctttccatg   1320
ggtcttttct gcagtcaccg tcgtcgacac gtgtgatcaa tgaattacat acctacgcag   1380
acgttctacg gccgccgatg gctgcctcgc ccggcggccc ggccctgggt ggctccacca   1440
cccgtatact atccaccacc gccacccgtg cctgtcgacc cgcaagcgca gcaaatgcaa   1500
caacttattg ctgcggtcaa tacgctggct ataaggcaga atggcacccg aacacctgga   1560
caacaacgaa ggaaacgtca atcaaacaaa ccaaagagga aacagacacc cccgaagaaa   1620
cagaacccgg cgaaaacaaa gaacaagcag aaaccgcaac caccaagtcc taagaacgg   1680
aaacccggca agagagaaag gaaatgcatg aagatagaa atgattgcat attcgaggtc   1740
aagctcgaag gcaaggtcac tgggtacgcc tgcctggtag gagataaagt gatgaaacca   1800
gcacacgtga aaggagtcat agataaccct gaccttgcca agctagcttt taagaaatcg   1860
agcaagtatg accttgagtg tgcgcaaatt ccggtccaca tggtcaga tgcctgcag    1920
ttcacccacg agaaaccaga aggacactac aactggcaca atggtgcagt acaatacctg   1980
aacggaagat ttaccatccc gacaggtgct gggaagccag gggacagcgg taggcctatc   2040
tttgacaaca agggtcgcgt agtggccatt gtgctggggg agccaacga gggagcgagg   2100
acggctctat cggttgtcac ctggaacaaa gacatggtta cgcgcatcac cccagaagga   2160
actgaggagt ggactgccct ggtgacaact gcttgcatcc tgagcaatct gactttcgat   2220
tgcagctgc caccatgtgc gccttgctgc tatgaaaaag acgcagaggg caccctgagg   2280
atgcggagg acaacgtcga taaccccgga tactacgatc tcctggctgc atcaacgcat   2340
tgtgacgccc cgcagcggcg tcgccgcagg gggctaactg aggactacga ggcttataaa   2400
ctcactaagc cgtacatagc ctattgctct gactgcggga cggacagtt ttgctacagc   2460
ccgatagcta ttgagagagt cagggccgag catcgggacg gaatgctcaa gatacagatc   2520
tctgcgcaaa taggcctgca ggtggacgga gctcatcgct ggacgaaaat cagatacatg   2580
```

```
aaagggcacg acgtggagga cacagacagg aactcactgg aggtgttcac caccggagag   2640
tgtacggtcc atggcaccat ggggcatttc atcgtagcta catgccccga aggtgactcc   2700
ttgacagtgg cgttcgttga caaacataag gtcaggcacg cttgcaggat agcatacaag   2760
catcgtgtcc ccgtattggg cagagagcac tttacggtac ggccacatca tggagtagaa   2820
ttgccatgca ccacgtacgc catgagaaca tcagtcacta ccgaagaaat agaaatgcac   2880
gtggcgcatg acgtgcccga caacacctttt ctatccaaga ccggaaataa agtgaagata   2940
acgccaaaag gaaagtctat tcgctacaac tgcacgtgtg ggtctaagga gagcggtgtc   3000
acaaagcaag caaagaatt tgacaactgc gaagtttcgc agtgccacac catggtgacc   3060
gcccacgata agtggcagtt taactctcct tatgtcccta gggcaggctc aggcaagaaa   3120
ggaaagatcc acgtacccctt tccactgagc aactctacgt gcagagttcc gttggcgcct   3180
ttaccgaaca ccatcccggc aaagaatgga atcacactgc agttgcatcc ggtcgccccg   3240
acgctactta cctaccgcac cctcggagag aaaccagaac accacacaga atggatatca   3300
gaaagttgcg aacgtacact ccccgtacct gaggaggggt tggagtacac atggggcaat   3360
cacgccctg tgagactgtg ggcacaactg acgactaagg gttcagccca tgggatgccg   3420
cacgaaatct tctcatatta ctatggattg taccctgcca cgacggttgc agtgtgcgtg   3480
gggctagcgt gtgtgatctt gctggctctg tccgcgtcct gctgcctgtg cgtgtcagcg   3540
agaaataagt gcttgacccc gtacgcgttg acgccaggag ccgtggtgcc gtgcactttg   3600
agcttattgt gctgcgcccc cagagccaag gccgcaactg ttgcggagac agcggcatat   3660
ctatgggacg agaaccagac ggtgttctgg atgcaattcg caatcccgt agcatgcttt   3720
atgatagtga catattgcct gcgccacttg atgctgtgct gtaggaccgc ttctttttta   3780
gtggcagtaa gcctgggaat gggggcgacc caggcgtatg agcatagtgt aacgctcccc   3840
aacgcggtcg gatttccgta cagagcccat gtagacagac caggggttctc tccattaacg   3900
ctccatatgg aggtagtctc cactagccta gagccgacgc tcgccctgga ttacgtcact   3960
tgcgagtaca aaacggtggt gccgtcgcct aagtcacct gttgcggcat gtcggagtgt   4020
gcacaccagc aaaaagcgga cttcaatgt aaagtctaca ccgccgtcta ccccttttg    4080
tgggcgggtg cctactgctt tgcaattcg gaaaacactc agctgagcga agcttatgtt   4140
gagcggagcg aggtgtgcaa acacgatcac gcagcggcgt atcgcgctca tacagccgca   4200
ttgaaggcta aaatcagagt gacctacggt tccacgaacg ggacggctga ggcgtttgtc   4260
aacgagaga gcaccgcacg aattggagac ctgaaaatga tcctaggtcc catatccacc   4320
gcgtggagcc cctttgaccc aaagatcgtc gtctacaagg acgaagtcta caatcaggat   4380
tatccaccgt acggatccgg gcaaccgggt agatttgggg acttacagag caggaccacc   4440
gagagtaacg atgtgtacgc caatactgca ctgaagctgg ctcgcccatc tgccggcacg   4500
gtgcacgttc catatcccca gacgccgtcc gggtttaagt attggctaaa agaaaaaggg   4560
gacgcattga accacaaggc tccttttcggc tgcatcatca agacgaaccc cgtaagggca   4620
gaaaattgtg cagtcggaaa cataccagtg tctctagaca ttccgacgc ggcttttaca    4680
cgcatagtcg acgcaccatc gctaaccggc ctgaagtgcg aggtggcgac ttgcacgcac   4740
tcatcggact ttgaggcac tttggtggtg gagtacaaga ccgacaaagt ggggacgtgc   4800
gccgtccact cagaatccaa cacggctgtt atgcaggaga cgagtctgtc cgtgacgatg   4860
gacggccgag gtacgttgca ttttcctccacc gcctcagcct caccgtcctt cgtactgaaa   4920
gtgtgcagta gcaaaaccac ttgcacagca aagtgcgtgc cgccaaagga ccacgtcgtc   4980
ccttttcctg ccaaccacaa caatgttgtg tcccggact tttccagtac tgcagtgtct    5040
tggctcaccc acactatggg cggagctact gtggtgattg ctattgggat caccatattc   5100
ttaatagtta cttgcatagc ttttagtagg cactaggcgg ccgctctaga ccaggccctg   5160
gatccagatc tgctgtgcct tctagttgcc agcacatctgt tgtttgcccc tccccgtgc    5220
cttccttgac cctggaaggt gccactccca ctgtccttttc ctaataaaat gaggaaattg   5280
catcgcattg tctgagtagg tgtcattcta ttctgggggg tggggtgggg caggacagca   5340
agggggagga ttgggaagac aatagcaggc atgctgggga tgcggtggga tctatgggta   5400
cccaggtgct gaagaattga cccggttcct cctgggccag aaagaagcag gcacatcccc   5460
ttctctgtga cacaccctgt ccacgcccct ggttcttagt tccagccca ctcataggac     5520
actcatagct caggagggct ccgccttcaa tcccacccgc taaagtactt ggagcggtct   5580
ctcccctccct catcagccca ccaaaaccaaa cctagcctcc aagagtggga agaaattaaa   5640
gcaagatagg ctattaagtg cagagggaga gaaaatgcct ccaacatgtg aggaagtaat   5700
gagagaaatc atagaatttt aaggccatga tttaaggcca tcatggcctt aatcttccgc   5760
ttcctcgctc actgactcgc tgcgctcggt cgttcggctg cggcgagcgg tatcagctca   5820
ctcaaaggcg gtaatacggt tatccacaga atcaggggat aacgcaggaa agaacatgtg   5880
agcaaaaggc cagcaaaagg ccaggaaccg taaaaaggcc gcgttgctgg cgttttttcca   5940
taggctccgc cccctgacg agcatcacaa aaatcgacgc tcaagtcaga ggtggcgaaa    6000
cccgacagga ctataaagat accaggcgtt tcccctgga agctccctcg tgcgctctcc    6060
tgttccgacc ctgccgctta ccggatacct gtccgccttt ctcccttcgg gaagcgtggc   6120
gctttctcat agctcacgct gtaggtatct cagttcggtg taggtcgttc gctccaagct   6180
gggctgtgtg cacgaacccc ccgttcagcc cgaccgctgc gccttatccg gtaactatcg   6240
tcttgagtcc aacccggtaa gacacgactt atcgccactg gcagcagcca ctggtaacag   6300
gattagcaga gcgaggtatg taggcggtgc tacagagttc ttgaagtggt ggcctaacta   6360
cggctacact agaagaacag tatttggtat ctgcgctctg ctgaagccag ttaccttcgg   6420
aaaaagagtt ggtagctctt gatccggcaa acaaaccacc gctggtagcg gtggtttttt   6480
tgtttgcaag cagcagatta cgcgcagaaa aaaaggatct caagaagatc ctttgatctt   6540
ttctacgggg tctgacgctc agtggaacga aaactcacgt taagggattt tggtcatgag   6600
attatcaaaa aggatcttca cctagatcct tttaaattaa aaatgaagtt ttaaatcaat   6660
ctaaagtata tatgagtaaa cttggtctga cagttaccaa tgcttaatca gtgaggcacc   6720
tatctcagcg atctgtctat ttcgttcatc catagttgcc tgactcgggg ggggggggcg   6780
ctgaggtctg cctcgtgaag aaggtgttgc tgactcatac caggcctgaa tcgccccatc   6840
atccagccaa aaagtgaggg agccacggtt gatgagagct ttgttgtagg tggaccagtt   6900
ggtgattttg aacttttgct ttgccacgga acggtctgcg ttgtcgggaa gatgcgtgat   6960
ctgatccttc aactcagcaa aagttcgatt tattcaacaa agccgccgtc ccgtcaagtc   7020
agcgtaatgc tctgccagtg ttacaaccaa ttaaccaatt ctgattagaa aaactcatcg   7080
agcatcaaat gaaactgcaa tttattcata tcaggattat caataccata ttttgaaaa    7140
agccgtttct gtaatgaagg agaaaactca ccgaggcagt tccataggat ggcaagatcc   7200
tggtatcggt ctgcgattcc gactcgtcca acatcaatac aacctattaa tttcccctcg   7260
tcaaaaataa ggttatcaag tgagaaatca ccatgagtga cgactgaatc cggtgagaat   7320
```

```
ggcaaaagct tatgcatttc tttccagact tgttcaacag gccagccatt acgctcgtca 7380
tcaaaatcac tcgcatcaac caaaccgtta ttcattcgtg attgcgcctg agcgagacga 7440
aatacgcgat cgctgttaaa aggacaatta caaacaggaa tcgaatgcaa ccggcgcagg 7500
aacactgcca gcgcatcaac aatattttca cctgaatcag gatattcttc taatacctgg 7560
aatgctgttt tcccggggat cgcagtggtg agtaaccatg catcatcagg agtacggata 7620
aaatgcttga tggtcggaag aggcataaat tccgtcagcc agtttagtct gaccatctca 7680
tctgtaacat cattggcaac gctacctttg ccatgtttca gaaacaactc tggcgcatcg 7740
ggcttcccat acaatcgata gattgtcgca cctgattgcc cgacattatc gcgagcccat 7800
ttatacccat ataaatcagc atccatgttg gaatttaatc gcggcctcga gcaagacgtt 7860
tcccgttgaa tatggctcat aacacccctt gtattactgt ttatgtaagc agacagtttt 7920
attgttcatg atgatatatt tttatcttgt gcaatgtaac atcagagatt ttgagacaca 7980
acgtggcttt cccccccccc ccattattga agcatttatc agggttattg tctcatgagc 8040
ggatacatat ttgaatgtat ttagaaaaat aaacaaatag gggttccgcg cacatttccc 8100
cgaaaagtgc cacctgacgt ctaagaaacc attattatca tgacattaac ctataaaaat 8160
aggcgtatca cgaggccctt tcgtc                                       8185

SEQ ID NO: 6            moltype = DNA  length = 8387
FEATURE                 Location/Qualifiers
misc_feature            1..8387
                        note = Description of Artificial Sequence: Synthetic
                        polynucleotide
source                  1..8387
                        mol_type = other DNA
                        organism = synthetic construct
SEQUENCE: 6
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcgggctgg cttaactatg cggcatcaga gcagattgta ctgagagtgc 180
accatatgcg gtgtgaaata ccgcacagat gcgtaaggag aaaataccgc atcagattgg 240
ctattggcca ttgcatacgt tgtatccata tcataatatg tacatttata ttggctcatg 300
tccaacatta ccgccatgtt gacattgatt attgactagt tattaatagt aatcaattac 360
ggggtcatta gttcatagcc catatatgga gttccgcgtt acataactta cggtaaatgg 420
cccgcctggc tgaccgccca acgacccccg cccattgacg tcaataatga cgtatgttcc 480
catagtaacg ccaataggga cttcccattg acgtcaatgg gtggagtatt tacggtaaac 540
tgcccacttg gcagtacatc aagtgtatca tatgccaagt acgccccta ttgacgtcaa 600
tgacggtaaa tggcccgcct ggcattatgc ccagtacatg accttatggg actttcctac 660
ttggcagtac atctacgtat tagtcatcgc tattaccatg gtgatgcggt tttggcagta 720
catcaatggg cgtggatagc ggtttgactc acggggattt ccaagtctcc accccattga 780
cgtcaatggg agtttgtttt ggcaccaaaa tcaacgggac tttccaaaat gtcgtaacaa 840
ctccgcccca ttgacgcaaa tgggcggtag gcgtgtacgg tgggaggtct atataagcag 900
agctcgttta gtgaaccgtc agatcgcctg gagacgccat ccacgctgtt ttgacctcca 960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctgt 1080
ggtgcctcct gaactgcgtc cgccgtctag gtaagtttaa agctcaggtc gagaccgggc 1140
ctttgtccgg cgctccctttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta acagactctt cctttccatg 1320
ggtcttttct gcagtcaccg tcgtcgacac gtgtgatcag atatcgcggc cgccaccatg 1380
tttcccatgc aattcaccaa ctcagcctat cgccagatgg agcccatgtt cgcaccggct 1440
tctcgaggac aagtacagcc gtatcggccg cgcacaaagc gccgcaagaa gccgcaagtc 1500
ggcaacgctg ctattgctgc cctcgcgaac cagatgacgg cgctccagct gcaggtggct 1560
ggacttgccg gccaggcaag ggtgaccgt cgtggaccga gacgtgttca gaaaaacaag 1620
cagaagaaga agaactcttc caacggagaa aaacccaagg agaagaagaa gaagcaaaaa 1680
caacaggaga agaaagggag cggcggtgaa aaagccaaga gccgcggaa ccggcccggg 1740
aaggagtgaa ggatctccgt aaagcgtgcc cgacagagca ccttccccgt gtaccatgac 1800
ggtgccatat ccggctatgc ggtgctgatt ggctccgcg tgtttaagcc agcgcacgtg 1860
aagggtaagt tcgaccaccc cgaactggcg gacatcaagt tccaggtcgc cgaggtcatg 1920
gacctcgaag cagccgcata ccctaagtgc atgcgagacc aggcggctga accagcaacc 1980
atgatggatg gagtgtacaa tgggagtac ggcaatattc aggagtggag gacaattttg 2040
tattcgatgc gagcggcaga ggcaagccgg ggtgacagtg gcaggccatt caccgacaac 2100
tcaggaaagg ttgtcggtat cgtcctcgga ggaggacccg atggtaggcg cacacgtctc 2160
tccgtgatag gtttcgacaa gaagctgaag gccagagaga tcgcctacag cgaggccatc 2220
ccttggacac gcgcaccagc tctcctgctg ctgcctatgg tcatcgcctg cacctacaac 2280
tccaataccat ttgattgctc caaaccgtcc tgccaggatt gttgcattac tgctgaacca 2340
aagaaggcca tgactatgct gaaggacaac ctgaatgacc gaactactg ggacctgctc 2400
attgccgtca ccacctgcag ttccgcccga aaaagaggg ctgtgtctac gtcgcctgtc 2460
gccgtttacg acacacaaat tctcgccgcc cacgcagctg cctccccgta tagggcgtac 2520
tgcccccgatt gtgacggaac tgcctgcatc tcgccgatag ctatcgacga ggtggtaagt 2580
agcggtagtg accacgtcct tcgcatccgg gtcggttctc aatcgggagt gaccgctaaa 2640
ggcggtgcgg cgggtgaaac ctctctgcga tacctgggaa gggacggtaa ggtttacgcc 2700
gcggacaaca cgcggctcgt ggtgcgcacc actgcaaagt gtgacgtgct gcaggccact 2760
ggccactaca ttctggccaa ctgcccagtg ggcagagtc tcactgttgc ggccacactg 2820
gacggtaccc ggcatcaatg caccacggtt ttcgaacatc aagtaacgga gaagttcaca 2880
agagaacgca caagggcca tcacctgtcc gatctgacca agaaatgcac caggttctca 2940
accaccccga gaagtccgc gctctatctc gttgatgtgt atgatgctct gccgacttct 3000
gtagagatca gcaccgtggt gacatgcaac gaaagacagt gcacagtgag ggtgccacc 3060
ggtaccacag tgaaattcga taagaggtgc aagaacgctg ccaaagagac cgtcacctc 3120
accagcgact cccagacgtt tacgtgcgag gagccggtcc taacgccgc cagcatcacc 3180
cagggcaagc cgcacctcag atcgtcaatg ttgcccagcg gaggcaaaga ggtgaaagcg 3240
```

```
aggattccat tcccgttccc gccagagact gcgacttgca gagtgagcat cgccccactg   3300
ccatcgatta cctatgagga aagcgatgtt ctgctggccg gcactgcgaa ataccccgtg   3360
ctgctaacta cacggaacct tggtttccat agcaacgcca catctgaatg gatccagggt   3420
aagtacctgc gccgcatccc ggtcacgccc aagggattg aactaatgtt gggaaacaac    3480
gcaccgctgc acttctggtc atctgtcagg tacgcatctg gagacgccga cgcgtacccc   3540
tgggaacttc tggtgcacca catcaagcac catccggagt acgcgtgggc gtttgtagga   3600
gttgcatgtg gcctgctggc cgttgcagca tgcatgttcg cgtgcgcatg caacagggtg   3660
cggtactctc tgctcgccaa cacgttcaac ccgaacccac caccattgac cgcactgact   3720
gcagcattgt gctgcatacc tggggctcgc gcggatcaac cctacctgga catcattgcg   3780
tacttgtgga ccaacagcaa agtggccttc gggctgcaat gcgcggcgcc cgtggcttgc   3840
atgctcatcg ttacatacgc ccttagacat tgcagattgt gctgcaattc tttttttaggg  3900
gtaagagggt ggtcggctct gctggtcatc cttgcgtatg tacagagctg caaggcgtac   3960
gaacacaccg tggtggtccc aatggatcca agagccccgt cgtacgaggc ggtgataaac   4020
cggaatgggt atgaccccct gaagcttacc atcgcagtga actttaccgt catctcacca   4080
actacggctc tggaatactg gacctgtgca ggagtccctg tcgtcgagcc gccccatgtg   4140
ggctgctgca cgtcagtgtc ctgccctcc gacctctcca cgctgcacgc gttcaccggc    4200
aaagccgtct ccgacgtgca ctgcgatgtg cacacgaacg tgtacccctt gttgtggggt   4260
gcggctcact gcttctgttc cactgaaaac acgcaggtcg gcgctgtggc cgccaccgtt   4320
tctgagttct gtgctcagga ctcagagcgc gccgaggcgt tcagcgttca cagcagctca   4380
gtcactgcag agattctggt gacgcttggt gaagtggtga cggcggtcca cgtttacgtg   4440
gacggggtaa catcagccag gggtaccgac ctcaagatcg tggctggccc aataacaact   4500
gactactccc cgtttgaccg caaagtagtc cgtatcggcg aagaggtcta taattacgac   4560
tggcctcctt acggggctgg tcgaccaggc acattcggag acattcaagc taggtcaacc   4620
aactatgtca aacccaatga tctgtacggg gacatcggaa ttgaagtact gcagccgact   4680
aatgaccacg tgcacgtggc ttacacgtat acgacctctg ggttgctgcg ttggttgcag   4740
gacgctccga aaccactcag tgtcacagca ccgcacggtt gtaagatcag tgctaaccga   4800
ctcctggccc tcgattgtgg ggttggtgcc gtcccgatgt ccatcaacat tccggacgtg   4860
aagttcaccc gcaaactaaa ggacccgaaa ccttcggccc tgaaatgcgt ggtgacagt    4920
tgcgagtacg gggtggacta cggggcgcc gccacgatca cctacgaggg ccacgaggct    4980
gggaagtgcg ggatccattc cctgacacca ggagtccctc tgagaacatc agtggttgaa   5040
gtagttgccg gcgctaatac cgtcaaaacg accttctcct cacccacgcc cgaggttaca   5100
ctcgaggtag agatctgttc ggcaatagtg aagtgcgcca gtgagtgcac tccaccgaag   5160
gaacacgtag tcgcagccag gcctcgccat ggcagcgaca ctggaggcta catctccggg   5220
cccgcaatgc gctgggccgg aaggattgta gggaacccta catgcagtca ttcctcatcc   5280
ttggccgtca cctactgcgt ggtgaagaag tgccgctcta aaagaatccg gatagtcaag   5340
agctaatcta gaccaggccc tggatccaga tctgctgtgc cttctagttg ccagccatct   5400
gttgtttgcc cctccccgt gccttccttg accctggaag gtgccactcc cactgtcctt    5460
tcctaataaa atgaggaaat tgcatcgcat tgtctgagta ggtgtcattc tattctgggg   5520
gctgtagctgg ggacag caaggggag gattgggaag acaatagcag gcatgctggg       5580
```



```
aggattccat tcccgttccc gccagagact gcgacttgca gagtgagcat cgccccactg   3300
ccatcgatta cctatgagga aagcgatgtt ctgctggccg gcactgcgaa ataccccgtg   3360
ctgctaacta cacggaacct tggtttccat agcaacgcca catctgaatg gatccagggt   3420
aagtacctgc gccgcatccc ggtcacgccc aagggattg  aactaatgtt gggaaacaac   3480
gcaccgctgc acttctggtc atctgtcagg tacgcatctg gagacgccga cgcgtacccc   3540
tgggaacttc tggtgcacca catcaagcac catccggagt acgcgtgggc gtttgtagga   3600
gttgcatgtg gcctgctggc cgttgcagca tgcatgttcg cgtgcgcatg caacagggtg   3660
cggtactctc tgctcgccaa cacgttcaac ccgaacccac caccattgac cgcactgact   3720
gcagcattgt gctgcatacc tggggctcgc gcggatcaac cctacctgga catcattgcg   3780
tacttgtgga ccaacagcaa agtggccttc gggctgcaat gcgcggcgcc cgtggcttgc   3840
atgctcatcg ttacatacgc ccttagacat tgcagattgt gctgcaattc tttttttaggg  3900
gtaagagggt ggtcggctct gctggtcatc cttgcgtatg tacagagctg caaggcgtac   3960
gaacacaccg tggtggtccc aatggatcca agagccccgt cgtacgaggc ggtgataaac   4020
cggaatgggt atgaccccct gaagcttacc atcgcagtga actttaccgt catctcacca   4080
actacggctc tggaatactg gacctgtgca ggagtccctg tcgtcgagcc gccccatgtg   4140
ggctgctgca cgtcagtgtc ctgccctcc  gacctctcca cgctgcacgc gttcaccggc   4200
aaagccgtct ccgacgtgca ctgcgatgtg cacacgaacg tgtacccctt gttgtggggt   4260
gcggctcact gcttctgttc cactgaaaac acgcaggtcg gcgctgtggc cgccaccgtt   4320
tctgagttct gtgctcagga ctcagagcgc gccgaggcgt tcagcgttca cagcagctca   4380
gtcactgcag agattctggt gacgcttggt gaagtggtga cggcggtcca cgtttacgtg   4440
gacggggtaa catcagccag gggtaccgac ctcaagatcg tggctggccc aataacaact   4500
gactactccc cgtttgaccg caaagtagtc cgtatcggcg aagaggtcta taattacgac   4560
tggcctcctt acggggctgg tcgaccaggc acattcggag acattcaagc taggtcaacc   4620
aactatgtca aacccaatga tctgtacggg gacatcggaa ttgaagtact gcagccgact   4680
aatgaccacg tgcacgtggc ttacacgtat acgacctctg ggttgctgcg ttggttgcag   4740
gacgctccga aaccactcag tgtcacagca ccgcacggtt gtaagatcag tgctaaccga   4800
ctcctggccc tcgattgtgg ggttggtgcc gtcccgatgt ccatcaacat tccggacgtg   4860
aagttcaccc gcaaactaaa ggacccgaaa ccttcggccc tgaaatgcgt ggtgacagt    4920
tgcgagtacg gggtggacta cggggcgcc  gccacgatca cctacgaggg ccacgaggct   4980
gggaagtgcg ggatccattc cctgacacca ggagtccctc tgagaacatc agtggttgaa   5040
gtagttgccg gcgctaatac cgtcaaaacg accttctcct cacccacgcc cgaggttaca   5100
ctcgaggtag agatctgttc ggcaatagtg aagtgcgcca gtgagtgcac tccaccgaag   5160
gaacacgtag tcgcagccag gcctcgccat ggcagcgaca ctggaggcta catctccggg   5220
cccgcaatgc gctgggccgg aaggattgta gggaacccta catgcagtca ttcctcatcc   5280
ttggccgtca cctactgcgt ggtgaagaag tgccgctcta aaagaatccg gatagtcaag   5340
agctaatcta gaccaggccc tggatccaga tctgctgtgc cttctagttg ccagccatct   5400
gttgtttgcc cctccccgt  gccttccttg accctggaag gtgccactcc cactgtcctt   5460
tcctaataaa atgaggaaat tgcatcgcat tgtctgagta ggtgtcattc tattctgggg   5520
ggtggggtgg ggcaggacag caaggggag  gattgggaag acaatagcag gcatgctggg   5580
gatgcggtgg gctctatggg tacccaggtg ctgaagaatt gacccggttc ctcctgggcc   5640
agaaagaagc aggcacatcc ccttctctgt gacacaccct gtccacgccc ctggttctta   5700
gttccagccc cactcatagg acactcatag ctcaggaggg ctccgccttc aatcccaccc   5760
gctaaagtac ttggagcggt ctctccctcc ctcatcagcc caccaaacca aacctagcct   5820
ccaagagtgg gaagaaatta aagcaagata ggctattaag tgcagaggga gagaaaatgc   5880
ctccaacatg tgaggaagta atgagagaaa tcatagaatt ttaaggccat gatttaaggc   5940
catcatggcc ttaatcttcc gcttcctcgc tcactgactc gctgcgctcg gtcgttcggc   6000
tgcggcgagc ggtatcagct cactcaaagg cggtaatacg gttatccaca gaatcagggg   6060
ataacgcagg aaagaacatg tgagcaaaag gccagcaaaa ggccaggaac cgtaaaaagg   6120
ccgcgttgct ggcgtttttc cataggctcc gcccccctga cgagcatcac aaaaatcgac   6180
gctcaagtca gaggtggcga aacccgacag gactataaag ataccaggcg tttccccctg   6240
gaagctcccct cgtgcgctct cctgttccga cctgcgctt taccggatac ctgtccgcct   6300
ttctcccttc gggaagcgtg gcgctttctc atagctcacg ctgtaggtat ctcagttcgg   6360
tgtaggtcgt tcgctccaag ctgggctgtg tgcacgaacc cccgttcag  cccgaccgct   6420
gcgccttatc cggtaactat cgtcttgagt ccaacccgt  aagacacgac ttatcgccac   6480
tggcagcagc cactggtaac aggattagca gagcgaggta tgtaggcggt gctacagagt   6540
tcttgaagtg gtggcctaac tacggctaca ctagaagaac agtatttggt atctgcgctc   6600
tgctgaagcc agttaccttc ggaaaaagag ttggtagctc ttgatccggc aaacaaacca   6660
ccgctggtag cggtggtttt tttgtttgca agcagcagat tacgcgcaga aaaaaaggat   6720
ctcaagaaga tcctttgatc ttttctacgg ggtctgacgc tcagtggaac gaaaactcac   6780
gttaagggat tttggtcatg agattatcaa aaggatctt  cacctagatc ctttttaaatt   6840
aaaaatgaag ttttaaatca atctaaagta tatatgagta aacttggtct gacagttacc   6900
aatgcttaat cagtgaggca cctatctcag cgatctgtct atttcgttca tccatagttg   6960
cctgactcgg gggggggggg cgctgaggtc tgcctcgtga agaaggtgtt gctgactcat   7020
accaggcctg aatcgcccca tcatccagcc agaaagtgag ggagccacgg ttgatgagag   7080
cttttgttgta ggtggaccag ttggtgattt tgaactttgt ctttgccacg gaacggtctg   7140
cgttgtcggg aagatgcgtg atctgatcct tcaactcagc aaaagttcga tttattcaac   7200
aaagccgccg tccgtcaag  tcagcgtaat gctctgccag tgttacaacc aattaaccaa   7260
ttctgattag aaaaactcat cgagcatcaa atgaaactgc aatttattca tatccaggatt  7320
atcaatacca tattttgaa  aaagccgttt ctgtaatgaa ggagaaaact caccgaggca   7380
gttccatagg atggcaagat cctggtatcg gtctgcgatt ccgactcgtc aacatcaat    7440
acaacctatt aatttcccct cgtcaaaaat aaggttatca agtgagaaat caccatgagt   7500
gacgactgaa tccggtgaga atggcaaaag cttatgcatt tctttccaga cttgttcaac   7560
aggccagcca ttacgctcgt catcaaaatc actcgcatca accaaaccgt tattcattcg   7620
tgattgcgcc tgagcgagac gaaatacgcg atcgctgtta aaaggacaat tacaaacagg   7680
aatcgaatgc aaccggcgca ggaacactgc cagcgcatca acaatatttt cacctgaatc   7740
aggatattct tctaatacct ggaatgctgt ttttccgggg atcgcagtgg tgagtaacca   7800
tgcatcatca ggagtacgga taaaatgctt gatggtcgga agaggcataa attccgtcag   7860
ccagtttagt ctgaccatct catctgtaac atcattggca acgctacctt tgccatgttt   7920
cagaaacaac tctggcgcat cgggcttccc atacaatcga tagattgtcg cacctgattg   7980
```

```
cccgacatta tcgcgagccc atttataccc atataaatca gcatccatgt tggaatttaa    8040
tcgcggcctc gagcaagacg tttcccgttg aatatggctc ataacacccc ttgtattact    8100
gtttatgtaa gcagacagtt ttattgttca tgatgatata tttttatctt gtgcaatgta    8160
acatcagaga ttttgagaca caacgtggct ttcccccccc ccccattatt gaagcattta    8220
tcagggttat tgtctcatga gcggatacat atttgaatgt atttagaaaa ataaacaaat    8280
aggggttccg cgcacatttc cccgaaaagt gccacctgac gtctaagaaa ccattattat    8340
catgacatta acctataaaa ataggcgtat cacgaggccc tttcgtc                  8387
```

| | |
|---|---|
| SEQ ID NO: 7 | moltype = DNA  length = 8166 |
| FEATURE | Location/Qualifiers |
| misc_feature | 1..8166 |
| | note = Description of Artificial Sequence: Synthetic polynucleotide |
| source | 1..8166 |
| | mol_type = other DNA |
| | organism = synthetic construct |

```
SEQUENCE: 7
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatgcg gtgtgaaata ccgcacagat gcgtaaggag aaaataccgc atcagattgg    240
ctattggcca ttgcatacgt tgtatccata tcataatagt tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca cgacccccgc ccattgacg tcaataatga cgtatgttcc     480
catagtaacg ccaataggga cttttccattg acgtcaatg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatgcg gtggatagc ggtttgactc acggggattt ccaagtctcc acccccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc    1020
cgccctacct gaggccgcca tccacgcgcc ttgagtcgta ttctgccgcc tccgtcctg    1080
ggtgcctcct gaactgcgtc cgccgtctag gtaagtttaa agctcaggtc gagaccgggc    1140
ctttgtccgg cgctccttg gagcctacct agactcagcc ggctccac gctttgcctg      1200
accctgcttg ctcaactcta gttaacgtg gagggcagtg tagtctgagc agtactcgtt    1260
gctgccgcgc gcgccaccag acataatagc tgacagacta acagactgtt ccttccatg    1320
ggtcttttct gcagtcaccg tcgtcgacac gtgtgatcac accatgaatt acattccaac    1380
tcaaaacctt tacggacgcc gttggcgacc acgcccggcg taccgtccat ggcgggtgcc    1440
gatgcagccg gccccaccca tggtgattcc tgagctgcaa actccgatcg tccaggccca    1500
acagatgcag cagctaatca gtgcagtttc tgccctgacg accaagcaaa atggcaaagc    1560
accgaagaag ccgaagaaaa agccgcaaaa agcgaaggct aagaaaaacg aacagcaaaa    1620
gaagaacgag aacaagaaac caccgcctaa gcagaagaat ccggctaaga agaagaaacc    1680
aggaaaaagg gaacgcatgt gcatgaagat agagaatgat tgcatcttcg aggtcaagct    1740
tgacgggtaag gtcacgggat acgcctgcct agtcgggat aaagtgatga gcccgcaca     1800
cgtcaaaggt gtgatcgaca accccgacct agcgaagctt acctacaaga aatcgagcaa    1860
gtatgacctg gagtgcgccc agataccagt gcacatgaag tcagatgctt caaagtacac    1920
ccatgaaaaa ccagaagggc actacaattg gcatcacggt gcagtgcagt acagcggtgg    1980
caggtcaca atcccgacag gcgcaggtaa accaggacgc agcggccggc cgatcttcga    2040
caacaaagga cgcgtggtgg ccattgtcct ggggagggcc aacgaaggag ccaggactgc    2100
cctatccgtc gtgacctgga ccaaagacat ggtcacacgg tacaccccag aaggaacaga    2160
agaatggtcc gccgccttga tgatgtgcgt cttagccaac gttacattcc catgctcaga    2220
gccgcgtgt gcaccctgtt gctatgaaaa acaaccagaa cagacactga ggatgttaga    2280
ggacaacgtg gaccgcccgg gctactacga cctgctcgag gccacgatga cgtgtaacaa    2340
tagtgcacgc caccgtcgca gtgtgacgaa acacttcaac gtctacaagg ccacgaaacc    2400
gtatctagcg tattgcgcgg actgcggaga cgggcagttc tgttacagcc cggtggctat    2460
agaaaaaatt agggatgagg cttccatgg catgataaaa atccaggtcg cagcgcaaat    2520
tggcatcaac aaggaggaa cacacgaaca caacaaaatc aggtacatcg ccgggcatga    2580
catgaaagag gcaaaccggg actctttaca agtgcatact tccggtgtgt gcgcatttcg    2640
aggcacgatg ggccacttca tcgtggccta ctgccctcca ggggacgaac taaaggtcca    2700
gttccaagat gcagaatcgc acacccaggc ctgcaaagtg cagtacaaac acgcaccggc    2760
cccagtaggc agagaaaaat tcaccgtcag gccccacttc ggtatcgaat tgccatgcac    2820
aacgtaccag ctgactaccg caccgacgga ggaagatc gacatgcata ccccaccgga    2880
tatcccgac ataacgttgc tgtcgcagca gtcaggtaat gtaaagatca cagcaggagg    2940
aaaaaccatc agatacaact gcacgtgtgg tagtggcaac gtgggcacca ccagtagcga    3000
caagactatc aattcgtgca aaatagcaca gtgccacgct gcggtgacta accacgataa    3060
gtggcagtac acctcctcgt ttgtccctag agcgaccag ttgtctcgca aggtaaagt     3120
gcacgtacct ttccctctga ccaactccac atgcagggtg cctgttcac gtgcaccagg    3180
tgtcacatac ggaaagagag aactgacagt gaaactgcac ccagatcatc ccacgctgtt    3240
gacgtaccgg agtctaggag cagatccgcg cccgtatgag gagtggatag accgatacgt    3300
cgaacggacc atacggtga ccgaagatgg gatcgagtac agatgggaa caacccacc     3360
cgtgcgcttg tgggcacagc tgacaactga aggcaaagcc catggtcgca cgcacgagat    3420
catactctat tactatgggc tatcccagc agccaccatc gccgccgtct cagccgcggg    3480
tctcgcagtc gtactatcgc tgctggcgt atgttacatg ttcgcactg cacgccgcaa    3540
gtgcctgacc ccatacgccc tgaccccggg agctgtcgtc ccggtaacac taggagtact    3600
atgctgcgca ccacgagcgc atgccgcgtc atttgcggaa tctatggcgt atctatggga    3660
tgagaatcaa accctgtttt ggctggagct tgcaacgccg ctcgctgcca taatcatact    3720
```

```
tgtatgctgc ctgaagaacc tgctttgctg ctgcaaaccg ctttcttttt tagtgctggt  3780
gagcctggga actcccgtcg taaaatctta cgaacacacc gcaacgatcc cgaatgtggt  3840
gggattcccg tataaggctc acattgagag aacggcttc tccccgatga ccctacagct  3900
tgaagtactt ggaaccagct tggaaccCac gctaaactta gagtacataa cctgtgaata  3960
caagacagtc gtgccatcac cttatatcaa gtgctgcggg acatcagaat gcagatccat  4020
ggagcgcccc gactatcaat gccaggtcta cacaggagtg tacccattta tgtggggcga  4080
cgcatactgc ttctgcgaca ctgagaacac ccagctgagt gaagcatacg ttgatagatc  4140
ggacgtatgc aagcacgacc atgccgccgc ctacaaggcg catactgcgg caatgaaagc  4200
caccatccga ataagctacg ggaacctcaa tcagacaaca acggcgttcg tcaacgggga  4260
gcacacagtg accgtcggag gcagcaggtt tacttttggt ccaatcctca ctgcctggac  4320
gcctttcgac aacaagatcg tcgtctacaa gaacgacgtc tacaaccagg acttcccacc  4380
ctacgggtca ggacaaccag ggaggtttgg agacatccag agcaggacgg tagagagcaa  4440
ggacctgtat gccaacaccg ccctcaagtt gtcaagacct tcgtccgtca ctgttcacgt  4500
gccttacaca cagacccctt ctggctttaa gtactggata aaagagagag gcacgtcgct  4560
gaatgacaag gctcccttg gatgcgtaat caagaccaac ccagtcagag cagaaaattg  4620
cgccgttggc aacatcccag tctccatgga catcccggac accgcgttta cgcgcgtgat  4680
tgatgcacct gccgtcacaa acctggagtg ccaagtgggc gtctgcacgc actcatcgga  4740
cttcggcggg atcgcgactc tgactttcaa aactgacaaa cccggaaaat gtgctgtcca  4800
ttctcattcg aacgtagcca ccatacagga ggcagctgtg gacatcaaaa cagatgccaa  4860
gataaccctg catttctcta cagcatcagc atccccggca ttcaaggtat ctgtgtgcag  4920
tgccaaaacg acatgcatgg cagcgtgtga gccgccgaag gaccacatcg tcccttatgg  4980
ggcgaggcat aacaaccaag ttttcctga catgtctggc acggcaatga catgggtgca  5040
gcgggtagcc ggcggactcg gcgggctaac actcgccgca gtgcagtac ttatactggt  5100
gacgtgtgtg actatgcgcc gctaatctag accaggccct ggatccagat ctgctgtgcc  5160
ttctagttgc cagccatctg ttgtttgccc ctcccccgtg ccttcttga ccctggaagg  5220
tgccactccc actgtccttt cctaataaaa tgaggaaatt catcgcatt gctctgagtag  5280
gtgtcattct attctggggg gtggggtggg gcaggacagc aagggggagg attgtcagaaga  5340
caatagcagg catgctgggg atgcggtggg ctctatgggt acccaggtgc tgaagaattg  5400
acccggttcc tcctgggcca gaaagaagca ggcacatccc cttctctgtg acacaccctg  5460
tccacgcccc tggttcttag ttccagcccc actcataga cactcatagc tcaggagggc  5520
tccgccttca atcccacccg ctaaagtact tggagcggtc tctccctccc tcatcagccc  5580
accaaaccaa acctagcctc caagagtggg aagaaattaa agcaagatag gctattaagt  5640
gcagaggag agaaaatgcc tccaacatgt gaggaagtaa tgagagaaat catagaattt  5700
taaggccatg atttaaggcc atcatggcct taatcttccg cttcctcgct cactgactcg  5760
ctgcgctcgg tcgttcggct gcggcgagcg gtatcagctc actcaaaggc ggtaatacgg  5820
ttatccacag aatcagggga taacgcagga agaacatgt gagcaaaagg ccagcaaaag  5880
gccaggaacc gtaaaaaggc cgcgttgctg gcgtttttcc ataggctccg cccccctgac  5940
gagcatcaca aaaatcgacg ctcaagtcag aggtggcgaa acccgacagg actataaaga  6000
taccggcgt ttccccctgg aagctccctc gtgcgctctc ctgttccgac cctgccgctt  6060
accggatacc tgtccgcctt tctcccttcg ggaagcgtgg cgctttctca tagctcacgc  6120
tgtaggtatc tcagttcggt gtaggtcgtt cgctccaagc tgggctgtgt gcacgaaccc  6180
cccgttcagc ccgaccgctg cgccttatcc ggtaactatc gtcttgagtc aacccggta  6240
agacacgact tatcgccact ggcagcagcc actggtaaca ggattagcag agcgaggtat  6300
gtaggcggtg ctacagagtt cttgaagtgg tggcctaact acggctacac tagaagaaca  6360
gtatttggta tctgcgctct gctgaagcca gttaccttcg gaaaaagagt tggtagctct  6420
tgatccggca aacaaaccac cgctggtagc ggtggttttt tgtttgcaa gcagcagatt  6480
acgcgcagaa aaaaaggatc tcaagaagat cctttgatct tttctacggg gtctgacgct  6540
cagtggaacg aaaactcacg ttaagggatt ttggtcatga gattatcaaa aaggatcttc  6600
acctagatcc ttttaaatta aaaatgaagt tttaaatcaa tctaaagtat atatgagtaa  6660
acttggtctg acagttacca atgcttaatc agtgaggcac ctatctcagc gatctgtcta  6720
tttcgttcat ccatagttgc ctgactcggg gggggggggg gcctgaggtct gcctcgtgaa  6780
gaaggtgttg ctgactcata ccaggcctga atcgccccat catccagcca gaaagtgagg  6840
gagccacggt tgatgagagc tttgttgtag tggaccagt tggtgatttt gaacttttgc  6900
tttgccacgg aacggtctgc gttgtcggga agatgcgtga tctgatcctt caactcagca  6960
aaagttcgat ttattcaaca aagccgccgt ccctgtcagt cagcgtaatg ctctgccagt  7020
gttacaacca attaaccaat tctgattaga aaaactcatc gagcatcaaa tgaaactgca  7080
atttattcat atcaggatta tcaataccat atttttgaaa aagccgtttc tgtaatgaag  7140
gagaaaactc accgaggcag ttccatagga tggcaagatc ctggtatcgg tctgcgattc  7200
cgactcgtcc aacatcaata caacctatta atttcccctc gtcaaaaata aggttatcaa  7260
gtgagaaatc accatgagtg acgactgaat ccggtgagaa tggcaaaagc ttatgcattt  7320
ctttccagac ttgttcaaca ggccagccat tacgctcgtc atcaaaatca ctcgcatcaa  7380
ccaaaccgtt attcattcgt gattgcgcct gagcgagacg aaatacgcga tcgctgttaa  7440
aaggacaatt acaaacagga atcgaatgca accggcgcag gaacactgcc agcgcatcaa  7500
caatattttc acctgaatca ggatattctt ctaatacctg gaatgctgtt ttcccggga  7560
tcgcagtggt gagtaaccat gcatcatcag gagtacggat aaaatgcttg atggtcgaa  7620
gaggcataaa ttccgtcagc cagtttagtc tgaccatctc atctgtaaca tcattggcaa  7680
cgctaccttt gccatgtttc agaaacaact ctggcgcatc gggcttccca tacaatcgat  7740
agattgtcgc acctgattgc ccgacattat cgcgagccca tttataccca tataaatcag  7800
catccatgtt ggaatttaat cgcggcctcg agcaagacgt ttcccgttga atatggctca  7860
taacacccct tgtattactg tttatgtaag cagacagttt tattgttcat gatgatatat  7920
ttttatcttg tgcaatgtaa catcagagat tttgagacac aacgtggctt tcccccccc  7980
cccattattg aagcatttat cagggttatt gtctcatgag cggatacata tttgaatgta  8040
tttagaaaaa taaacaaata ggggttccgc gcacatttcc ccgaaaagtg ccacctgacg  8100
tctaagaaac cattattatc atgacattaa cctataaaaa taggcgtatc acgaggccct  8160
ttcgtc                                                            8166

SEQ ID NO: 8             moltype = DNA   length = 8186
FEATURE                  Location/Qualifiers
misc_feature             1..8186
```

```
                note = Description of Artificial Sequence: Synthetic
                      polynucleotide
source          1..8186
                mol_type = other DNA
                organism = synthetic construct
SEQUENCE: 8
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgaccccg cccattgacg tcaataatga cgtatgttcc    480
catagtaacg ccaatagga cttcccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct ataagcag    900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgccaccatg  1380
ttcccgttcc aaccaatgta tccgatgcag ccaatgcct atcgtaaccc gttcgcggcc   1440
ccgcgcaggc cctggttccc cagaaccgac cctttctgg cgatgcaggt gcaggaatta   1500
acccgctcga tggctaacct gacgttcaag caacgccggg acgcgccacc tgaggggcca  1560
cctgctaaga aacctaagag ggaggccccg caaaagcaaa aaggggagg ccaagggaag   1620
aagaagaaca accaggggaa gaagaaggcc aagacggggc cgcctaatcc gaaggcacag  1680
agtggaaaca agaagaagcc caacaagaaa ccaggcaaga gacagcgcat ggtcatgaaa  1740
ttggaatctg acaagacatt cccaattatg ctggaaggga agattaacgg ctacgcttgc  1800
gtggtcggag ggaagttat caggccgatg cacgtggaag gcaagatcga caacgacgtt   1860
ctggccgcac ttaagacgaa gaaagcatcc aaatatgatc ttgagtatgc agatgtgcca  1920
cagaacatgc gggccgatac attcaagtac acccatgaga agcccaagg ctattacagc   1980
tggcatcatg gagcagtcca atatgaaaat gggcgtttca cggtgccaaa aggagttggg  2040
gccaaggag acagcggaag acccattctg gataatcagg gacgggtggt cgctattgtg   2100
ctgggagtg tgaatgaagg atctaggaca gcccttcag tcgtcatgtg gaacgagaag    2160
ggagtaactg tgaagtatac tccggagaac tgcgagcaat ggtcactagt gaccactgga  2220
tgcctgctcg ccaatgtgac gttcccatgt gccgaaccac caatttgcta cgacagaaaa  2280
ccagcagaga ctttgccat gctcagcgtt aacgttgaca cccgggcta cgatgagctg    2340
ctggaagcag ctgttaagtg ccccggaaga aaaaggagat ctaccgagga gctgtttaag  2400
gagtataagc taacgcgccc ttacatggcc agatgcata gatgtgccgt tgggagctgc  2460
catagtccaa tagcaattga ggcagtgaag agcgacgggc acgacgcta tgttagcttc   2520
cagacttcct cgcagtatgg cctggattcc tctggcaact aaagggaag gactatgcgg   2580
tatgatatgc acgggaccat tgaagagata ccactacatc aagtgtcact ccacacatct  2640
cgcccgtgtc acattgtgga tgggcatggt tattttctgc ttgctaggtg cccggcaggg  2700
gactccatca ccatggaatt taagaaaggt tcagtcacac actcctgctc agtgccgtat  2760
gaagtgaaat taatcctgt aggcagagaa ctctacactc atccaccaga acacggagca  2820
gagcaagcgt gccaagtcta cgcgcacgat gcacagaaca gaggagctta tgtcgagatg  2880
caccctccgg gctcagaagt ggacagcagt ttgatttcct tgagcggcag ttcagtcacc  2940
gtgacacctc ctgtcgggac tagcgccttg gtgaaatgca gtcggcgg cacaaagatc   3000
tccgaaacca tcaacaaggc aaaacagttc agccagtgca aagaagga gcagtgcaga   3060
gcatatcgac tgcagaatga caagtgggtg tataattctg acaaactgcc caaagcagcg  3120
ggagccaccc taaaaggaaa actacacgtc ccgttcttgc tggcagacgg caaatgcacc  3180
gtgcctctag caccggaacc tatgataacc ttcggtttcc gatcagtgtc actgaaactg  3240
cacccctaaga atcccacata tctgaccact cgccaacttg ctgatgagcc tcattacacg  3300
cacgagctca tatctgaacc agctgttagg aattttaccg tcactgaaaa ggggtgggag  3360
tttgtatggg gaaaccatcc gccgaaaagg ttttggcac aggaaacagc acccggaaat    3420
ccacatgggc tgccacatga ggtgataact cattattacc acagatgcta tgtccacc    3480
atcctgggtt tgtcaatttg cgccgccatt gtaaccgttt ccgttgcagc gtccacctgg  3540
ctgttttgca atccagagtt tcgtgccta actccttacc ggctaacacc taacgccagg   3600
atgccgcttt gcctggccgt gctttgctgc gcccgcactg cccgggccga gaccacctgg  3660
gagtccttgg atcacctatg gaacaataac caacagatgt tctggattca attgctgatc  3720
cctctggccg ccttgattgt agtgactcgc ctgctcaggt gcgtgtgctg tgtagtgcct  3780
tttttagtcg tggccggcgc cgcaggcgcc ggcgcctacg agcacgcgac cacgatgccg  3840
agccaagcgg gaatctcgta taacaccata gtcaacagag caggctacgc gccactccct  3900
atcagcataa caccaacaaa gatcaagctg ataccacacg tgaacttgga gtacgtcacc  3960
tgccactaca aaacaggaat ggattcacca gccatcaaat gctgcggatc tcaggaatgt  4020
actccaacta acaggcctga tgaacagtgc aaagttttca ccggggttta cccgttcatg  4080
tggggaggt catattgctt ttgcgacact gagaatactc aggtcagcaa ggcctacgta   4140
atgaaatctg acgactgcct tgcggatcat gctgaagcat acaaagcgca cacagcctca  4200
gtgcaggcgt tcctcaacat cacagtgggg gaacactcta ttgtgaccac cgtgtatgtg  4260
aatgagaaa ctcctgtgaa cttcaatggg gtcaaactaa ctgcaggtcc actttccaca  4320
gcttggacac cctttgacag aaaaatcgtg cagtatgccg gggagatcta taattacgat  4380
```

```
tttcctgagt atgqggcagg acaaccagga gcatttggag acatacaatc cagaacagtc  4440
tcaagctcag atctgtatgc caataccaac ctagtgctgc agagacccaa agcaggagcg  4500
atccatgtgc catacactca ggaccatcg ggttttgagc aatggaagaa agataaagct  4560
ccgtcattga aattcaccgc cccttcgga tgcgaaatat atacaaaccc cattcgcgcc  4620
gaaaattgtg ctgtagggtc aattccatta gcctttgaca ttcccgacgc cttgttcacc  4680
agggtgtcag aaacaccgac acttcagcg gccgaatgca ctcttaacga gtgcgtgtat  4740
tcatccgact ttggcgggat cgccacggtc aagtattcgg ccagcaagtc aggcaagtgc  4800
gcagtccatg tgccatcagg gactgctacc ctaaaagaag cagcagtcga gctaaccgag  4860
caagggtcgg cgaccattca tttctcgacc gcaaatatcc acccggagtt caggctccaa  4920
atatgcacat catatgtcac gtgcaaaggt gattgtcacc ccccgaaaga ccacattgtg  4980
acacacccc agtatcacgc ccaaacattt acagccgcgg tgtcaaaaac cgcgtggacg  5040
tggttaacat ccctgctggg aggatcggcc gtaattatta taattggctt agtgctggct  5100
actattgtgg ccatgtacgt gctgaccaac cagaaacata attgtatctag accaggccct  5160
ggatccagat ctgctgtgcc ttctagttgc cagccatctg ttgtttgccc ctccccgtg  5220
ccttccttga ccctgaaggg tgccactccc actgtccttt cctaataaaa tgaggaaatt  5280
gcatcgcatt gtctgagtag gtgtcattct attctggggg gtgggtggg caggacagc  5340
aaggggggagg attgggaaga caatagcagg catgctgggg atgcggtggg ctctatgggt  5400
acccaggtgc tgaagaattg acccaggttcc tcctgggca gaaagaagca ggcacatccc  5460
cttctctgtg acacaccctg tccacgcccc tggttcttag ttccagcccc actcatagga  5520
cactcatagc tcaggagggc tccgccttca atcccaccg ctaaagtact ggagcggtc  5580
tctccctccc tcatcagccc accaaaccaa acctagcctc caagagtggg aagaaaattaa  5640
agcaagatag gctattaagt gcagaaggag agaaaatgcc tccaacatgt gggaagtaa  5700
tgagagaaat catagaattt taaggccatg atttaaggcc atcatggcct taatcttccg  5760
cttcctcgct cactgactcg ctgcgctcgg tcgttcggct gcggcgagcg gtatcagctc  5820
actcaaaggc ggtaatacgg ttatccacag aatcagggga taacgcagga agaacatgt  5880
gagcaaaaagg ccagcaaaag gccaggaacc gtaaaaggc cgcgttgctg gcgttttcc  5940
ataggctccg cccccctgac gagcatcaca aaaatcgacg ctcaagtcag aggtggcgaa  6000
acccgacagg actataaaga taccaggcgt ttccccctgg aagctccctc gtgcgctctc  6060
ctgttccgac cctgccgctt accggatacc tgtccgcctt tctcccttcg ggaagcgtgg  6120
cgctttctca tagctcacgc tgtaggtatc tcagttcgtt gtaggtcgtt cgctccaagc  6180
tgggctgtgt gcacgaaccc cccgttcagc ccgaccgctg cgccttatcc ggtaactatc  6240
gtcttgagtc caacccggta agacacgact tatcgccact ggcagcagcc actggtaaca  6300
ggattagcag agcgaggtat gtaggcggtg ctacagagtt cttgaagtgg tggcctaact  6360
acggctacac tagaagaaca gtatttggta tctgcgctct gctgaagcca gttaccttcg  6420
gaaaaagagt tggtagctct tgatccggca acaaaccac cgctggtagc ggtggttttt  6480
ttgtttgcaa gcagcagatt acgcgcagaa aaaaaggatc tcaagaagat cctttgatct  6540
tttctacggg gtctgacgct cagtggaacg aaaactcacg ttaagggatt ttggtcatga  6600
gattatcaaa aaggatcttc acctagatcc ttttaaatta aaaatgaagt tttaaatcaa  6660
tctaaagtat atatgagtaa acttggtctg acagttacca atgcttaatc agtgaggcac  6720
ctatctcagc gatctgtcta tttcgttcat ccatagttgc ctgactcggg gggggggggc  6780
gctgaggtct gcctcgtgaa aaggtgttg ctgactcata ccaggcctga atcgccccat  6840
catccagcca gaaagtgagg gagccacggt tgatgagagc tttgttgtag gtggaccagt  6900
tggtgatttt gaactttgc tttgcacgg aacggtctgc gttgtcggga agatgcgtga  6960
tctgatcctt caactcagca aaagttcgat ttattcaaca aagccgccgt cccgtcaagt  7020
cagcgtaatg ctctgccagt gttacaacca attaaccaat tctgattaga aaaactcatc  7080
gagcatcaaa tgaaactgca atttattcat atcaggatta tcaataccat ttttttgaaa  7140
aagccgtttc tgtaatgaag gagaaaactc accgaggcag ttccatgga tggcaagatc  7200
ctggtatcgg tctgcgattc cgactcgtcc aacatcaata caacctatta atttcccctc  7260
gtcaaaaata aggttatcaa gtgagaaatc accatgagtg acgactgaat ccggtgagaa  7320
tggcaaaagc ttatgcattt cttttccagac ttgttcaaca ggccagccat tacgctcgtc  7380
atcaaaatca ctcgcatcaa ccaaaccgtt attcattcgt gattgcgcct gagcgagacg  7440
aaatacgcga tcgctgttaa aaggacaatt acaaacagga atcgaatgca accggcgcag  7500
gaacactgcc agcgcatcaa caatatttc acctgaatca ggatattctt ctaatacctg  7560
gaatgctgtt ttcccgggga tcgcagtggt gagtaaccat gcatcatcag gagtacggat  7620
aaaatgcttg atggtcggaa gaggcataaa ttccgtcagc cagtttagtc tgaccatctc  7680
atctgtaaca tcattggcaa cgctacctt gccatgtttc agaaacaact ctggcgcatc  7740
gggcttccca tacaatcgat agattgtcgc acctgattgc ccgacattat cgcgagccca  7800
tttatccca tataaatcag catccatgtt ggaatttaat cgcggcctcg agcaagacgt  7860
ttcccgttga atatggctca taacaccct tgtattactg tttatgtaag cagacagttt  7920
tattgttcat gatgatatat ttttatcttg tgcaatgtaa catcagagat tttgagacac  7980
aacgtggctt tccccccccc ccccattatttg aagcatttat cagggttatt gtctcatgag  8040
cggatacata tttgaatgta tttagaaaaa taaacaaata ggggttccgc gcacatttcc  8100
ccgaaagtg ccacctgacg tctaagaaac cattattatc atgacattaa cctataaaaa  8160
taggcgtatc acgaggccct tcgtc                                        8186
```

SEQ ID NO: 9         moltype = DNA  length = 8129
FEATURE               Location/Qualifiers
misc_feature       1..8129
                      note = Description of Artificial Sequence: Synthetic
                      polynucleotide
source                1..8129
                      mol_type = other DNA
                      organism = synthetic construct
SEQUENCE: 9

```
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcagattgg  240
ctattggcca ttgcatacgt tgtatccata tcataatatg tacatttata ttggctcatg  300
```

```
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggA ctttccattg acgtcaatgg gtggagtatt tacggtaaac   540
tgcccacttg gcagtacatc aagtgtatca tatgccaagt acgccccctA ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag cgtgtacggt gggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgccgg cgccaccatg  1380
tttccatacc ctcagctgaa cttttccacca gtttacccta caaatccgat ggcttaccga  1440
gatccaaacc ctcctaggcg ccgctggagg ccgtttcggc cccgctggc tgctcaaatc  1500
gaagatctta ggaggtcgat agtcaacttg actttcaaac aacgatcacc taatccgccg  1560
ccaggtccac cgccaaagaa gaagaagagt gctcctaagc caaaacctac tcagcctaaa  1620
aagaagaagc agcaagccaa gaggacgaaa cgcaagccta aaccagggaa acgacaacgt  1680
atgtgtatga agttggagtc ggacaagaca tttccgatca tgctgaacgg ccaagtgaat  1740
ggatatgcct gcgttgtcgg aggaaggctg atgaaaccac tccacgttga aggaaaaatt  1800
gataatgagc aattagcggc cgtgaaattg aagaaggcta gcatgtacga cttggagtac  1860
ggcgacgttc cccagaacat gaaatcagac acgctgcagt acaccagcga caaaccaccg  1920
ggcttctaca actggcacca cggcgcagtc cagtatgaga atgggagatt taccgtaccg  1980
agaggagtgg gcgggaaagg cgacagcgga agaccgatcc tggacaacag aggcagagtt  2040
gtggctattg ttctaggagg tgcaaatgag ggcacgcgta cggcgcttcc agtggtcact  2100
tggaaccaga aaggggtgac cattagggat accccccgaag gttctgaacc gtggtcacta  2160
gttacagcgc tatgcgtgct ttcgaatgtc acgttccat cgcacaaacc accgtgtgc  2220
tattcactga cgccagaacg aacactcgac gtgctcgaag agaacgtcga caatccaaat  2280
tacgacacgc tctggagaa cgtcttgaaa tgtccatcac gccggcccaa acgaagcatt  2340
accgatgact tcacactgac cagtccctac ctgggggttct gcccgtattg cagacactca  2400
acgccgtgtt tcagcccaat aaaaattgag aacgtgtggg acgaatctga tgatggatcg  2460
attagaatcc aggtctcggc acaattcggc tacaatcagg caggcactgc ggatgtcacc  2520
aaattccgtt acatgtcttt cgaccacgac catgacatca aggaagacag tatgcagaaa  2580
atagctatca gcacatctgg accctgccgt cgtcttgtcc acaaagggta cttcctgtta  2640
gctcaatgtc ctccaggtga cagtgtaacc gtcagtatca cgagcggagc atctgagaat  2700
tcatgcaccg tggagaaaaa gatcaggagg aagtttgtcg gtagagagga gtacttgttc  2760
ccacccgtcc atggaaagct ggtaaagtgc cacgtttacg atcacttgaa ggagacgtct  2820
gccgggtaca taacatgca caggccaggc ccacacgcgt ataagtccta tctggaggaa  2880
gcgtcaggcg aagtgtacat taaaccaccct tctggcaaga acgtcaccta cgaatgtaag  2940
tgtggcgact acagcacagg tatcgtgagc acgcgaacga agtgaacgg ctgcactaaa  3000
gcaaaacagt gcattgccta caagagcgac caaacgaaat gggtcttcaa ctcgccggat  3060
cttattaggc acacagacca ctcagtgcaa ggtaaattgc acattccatt ccgcttgaca  3120
ccgacagtct gcccggttcc gttagctcac acgcctacag tcacgaagtg gttcaaaggc  3180
atcaccctcc acctggactgc aatgcgacca acattgctga caacgagaaa attggggctg  3240
cgagcagacg caacagcaga atggattaca gggtctacat ccaggaattt ttctgtgggg  3300
cgagaagggc tggagtacgt atgggggtaac catgaaccag tcagagtctg ggcccaggag  3360
tcggcaccag gcgacccaca tggatggccg catgagatca tcatcccacta ttatcatcgg  3420
catccagtct acactgtcat tgtgctgtgt ggtgtcgctc ttgctatcct ggtaggcact  3480
gcatcatcag cagcttgcat cgccaaagca agaagagact gcctgacgcc atacgcgctt  3540
gcaccgaacg caacggtacc cacagcatta gcggttttgt gctgcattcg gccaaccaac  3600
gctgaaacat ttggagaaac tttgaaccat ctgtggttta acaaccaacc gtttctctgt  3660
gcacagttgt gcattcctct ggcagcgctt gttattctgt tccgctgctt ttcatgctgc  3720
atgccttttt tattggttgc aggcgtctgc ctggggaagg tagacgcctt cgaacatgcg  3780
accactgtgc caaatgttcc gggatcccg tataaggcgt tggtcgaacg cgcaggttac  3840
gcgccactta acctggagat caccggtcgtc tcatcggaat taacacctc aactaacaag  3900
gagtacgtga cctgcaaatt ccacacagtc attccttcac cacaagttaa atgctgcggg  3960
tccctcgagt gcaaggcatc ctcaaaggcg gattacacat gccgcgtttt tggcggtgtg  4020
tacccttca tgtggggagg cgcacaatgc ttctgtgaca gtgagaacac acaactgagt  4080
gaggcgtacg tcgagttcgc tccagactgc actatagatc acgcagtcgc actaaaagtt  4140
cacacagctg ctctgaaagt cggcctgcgt atagtatacg gcaacaccac cgcgcacctg  4200
gatacgtttg tcaatggcgt cacgccaggt tcctcacggg acctgaaggt catagcaggg  4260
ccgatatcag ccgcttttc acccttgac cataaggtcg tcatcagaaa ggggcttgtt  4320
tacaactacg acttccctga gtatggagct atgaaaccag gagcgttcgg cgatattcaa  4380
gcatcctcgc ttgatgctac agacatagta gcccgcactg acatacggct gctgaagcct  4440
tctgtcaaga acatccacgt cccctacacc caagcagtat cagggtatga atgtggaag  4500
aacaactcag gacgacccct gcaagaaaca gcaccatttg gatgtaaaat tgaagtggag  4560
cctctgcgag cgtctaactg tgcttacggg cacatcccta tctcgattga catccctgat  4620
gcagcttttg tgagatcatc agaatcacca acaattttag aagttagctg cacagtagca  4680
gactgcattt attctgcaga cttttggtgt tctctaacat tacagtacaa agctgacagg  4740
gagggacatt gtccagttca ctcccactcc acgacagctg ttttgaagga agcgaccaca  4800
catgtgactg ccgtaggcag cataacacta catttagca catcgagccc acaagcaaat  4860
tttatagttt cgctatgcgg caagaagtcc acctgcaatg ctgaatgtaa accaccggcc  4920
gaccacataa ttgagaacc acataaagtc gaccaagaat tccaggcggc agtttccaaa  4980
acatcttgga actggctgct tgcactgttt gggggagcat catccctcat tgttgtagga  5040
```

```
cttatagtgt tggtctgcag ctctatgctt ataaacacac gtagatgatc tagaccaggc   5100
cctggatcca gatctgctgt gccttctagt tgccagccat ctgttgtttg ccctccccc    5160
gtgccttcct tgaccctgga aggtgccact cccactgtcc tttcctaata aaatgaggaa   5220
attgcatcgc attgtctgag taggtgtcat tctattctgg ggggtggggt ggggcaggac   5280
agcaaggggg aggattggga agacaatagc aggcatgcgg gggatgcggt gggctctatg   5340
ggtacccagg tgctgaagaa ttgacccggt tcctcctggg ccagaaagaa gcaggcacat   5400
cccttctct gtgacacacc ctgtccacgc cctggttct tagttccagc cccactcata    5460
ggacactcat agctcaggag ggctccgcct tcaatcccac ccgctaaagt acttggagcg   5520
gtctctccct ccctcatcag cccaccaaac caaacctgc ctccaagagt gggaagaaat    5580
taaagcaaga taggctatta agtgcagagg gagagaaaat gcctccaaca tgtgaggaag   5640
taatgagaga aatcatagaa ttttaaggcc atgatttaag gccatcatgg ccttaatctt   5700
ccgcttcctc gctcactgac tcgctgcgct cggtcgttcg gctgcggcga gcggtatcag   5760
ctcactcaaa ggcggtaata cggttatcca cagaatcagg ggataacgca ggaaagaaca   5820
tgtgagcaaa aggccagcaa aaggccagga accgtaaaaa ggccgcgttg ctggcgtttt   5880
tccataggct ccgccccct gacgagcatc acaaaaatcg acgctcaagt cagaggtggc    5940
gaaacccgac aggactataa agataccagg cgtttccccc tggaagctcc ctcgtgcgct   6000
ctcctgttcc gaccctgccg cttaccggat acctgtccgc ctttctccct tcgggaagcg   6060
tggcgctttc tcatagctca cgctgtaggt atctcagttc ggtgtaggtc gttcgctcca   6120
agctgggctg tgtgcacgaa ccccccgttc agcccgaccg ctgcgcctta ccggtaact    6180
atcgtcttga gtccaacccg gtaagacacg acttatcgcc actggcagca gccactggta   6240
acaggattag cagagcgagg tatgtaggcg gtgctacaga gttcttgaag tggtggccta   6300
actacggcta cactagaaga acagtatttg gtatctgcgc tctgctgaag ccagttacct   6360
tcggaaaaag agttggtagc tcttgatccg gcaaacaaac caccgctggt agcggtggtt   6420
tttttgtttg caagcagcag attacgcgca gaaaaaaagg atctcaagaa gatcctttga   6480
tcttttctac ggggtctgac gctcagtgga acgaaaactc acgttaaggg attttggtca   6540
tgagattatc aaaaaggatc ttcacctaga tccttttaaa ttaaaaatga agttttaaat   6600
caatctaaag tatatatgag taaacttggt ctgacagtta ccaatgctta atcagtgagg   6660
cacctatctc agcgatctgt ctatttcgtt catccatagt tgcctgactc ccccgggggg   6720
ggcgctgagg tctgcctcgt gaagaaggtg ttgctgactc ataccaggcc tgaatcgccc   6780
catcatccag ccagaaagtg agggagccac ggttgatgag agctttgttg taggtggacc   6840
agttggtgat tttgaacttt tgctttgcca cggaacggtc tgcgttgtcg ggaagatgcg   6900
tgatctgatc cttcaactca gcaaaagttc gatttattca acaaagccgc cgtcccgtca   6960
agtcagcgta atgctctgcc agtgttacaa ccaattaacc aattctgatt agaaaaactc   7020
atcgagcatc aaatgaaact gcaatttatt catatcagga ttatcaatac catattttt   7080
aaaaagccgt ttctgtaatg aaggagaaaa ctcaccgagg cagttccata ggatggcaag   7140
atcctggtat cggtctgcga ttccgactcg tccaacatca atacaaccta ttaatttccc   7200
ctcgtcaaaa ataaggttat caagtgagaa atcaccatga gtgacgactg aatccggtga   7260
gaatggcaaa agcttatgca tttctttcca gacttgttca acaggccagc cattacgctc   7320
gtcatcaaaa tcactcgcat caaccaaacc gttattcatt cgtgattgcg cctgagcgag   7380
acgaaatacg cgatcgctgt taaaaggaca attacaaaca ggaatcgaat gcaaccggcg   7440
caggaacact gccagcgcat caacaatatt ttcacctgaa tcaggatatt cttctaatac   7500
ctggaatgct gttttccgg ggatcgcagt ggtgagtaac catgcatcat caggagtacg    7560
gataaaatgc ttgatggtcg gaagaggcat aaattccgtc agccagttta gtctgaccat   7620
ctcatctgta acatcattgg caacgctacc tttgccatgt ttcagaaaca actctggcgc   7680
atcgggcttc ccatacaatc gatagattgt cgcacctgat tgcccgacat tatcgcgagc   7740
ccatttatac ccatataaat cagcatccat gttgaatttt aatcgcggcc tcgagcaaga   7800
cgtttccgt tgaatatggc tcataacacc ccttgtatta ctgtttatgt aagcagacag    7860
ttttattgtt catgatgata tatttttatc ttgtgcaatg taacatcaga gattttgaga   7920
cacaacgtgg ctttcccccc cccccatta ttgaagcatt tatcagggtt attgtctcat    7980
gagcggatac atatttgaat gtatttagaa aaataaacaa ataggggttc cgcgcacatt   8040
tccccgaaaa gtgccacctg acgtctaaga aaccattatt atcatgacat taacctataa   8100
aaataggcgt atcacgaggc cctttcgtc                                    8129

SEQ ID NO: 10           moltype = DNA   length = 8144
FEATURE                 Location/Qualifiers
misc_feature            1..8144
                        note = Description of Artificial Sequence: Synthetic
                        polynucleotide
source                  1..8144
                        mol_type = other DNA
                        organism = synthetic construct
SEQUENCE: 10
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga cttccattg acgtcaatgg gtggagtatt tacggtaaac     540
tgcccacttg gcagtacatc aagtgtatca tatgccaagt acgccccta ttgacgtcaa    600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
```

```
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgccaccatg   1380
ttcccatacc ctacacttaa ctacccgcct atggcgccga ttaacccgat ggcttaccgg   1440
gatcctaatc cgcctaggcg caggtggcgg ccctttaggc caccacttgc agctcaaatt   1500
gaggacctga gacgttccat cgctaacctg actttgaaac aacgagcacc taaccctcca   1560
gcaggaccgc ccgccaaacg caagaagcct gcgccaagcc taagcctgcg caggaaaaag   1620
aagcgaccac caccacctgc caagaaacaa aaacgtaaac ctaaaccagg caaacgacag   1680
cgaatgtgta tgaagctaga gtcagataaa acgtttccaa tcatgttgaa cggacaggtg   1740
aatggttacg cgtgcgtcgt gggtggacga gtgttcaaac cgctgcacgt agaaggcaga   1800
atagacaatg agcaactggc cgccatcaag ctgaagaagg ccagcatata tgaccttgag   1860
tatggtgatg tgccacaatg catgaaatca gataccctcc agtacaccag tgacaagcct   1920
cctggctttt ataactggca ccatggagct gtacagtatg agaacaatag gttcaccgta   1980
ccacgggggg tcggtggaaa gggtgacagc gggagaccta ttcttgacaa caaaggtaga   2040
gtcgtcgcaa ttgtcctggg tggagtcaac gaaggatcca ggactggtgt ggacgctgct   2100
acatggaacc aaaaaggggt tacagtcaaa gatacaccag aggggtcaga gccatggtcg   2160
cttgccactg tcatgtgcgt cctggccaat atcacgtttc catgtgatca accaccctgc   2220
atgccatgct gttatgaaaa gaatccacac gaaacactca ccatgttgga acagaattac   2280
gacagccgag cctatgatca gctgctgaat gccgctgtga aatgtaatgc taggagaacc   2340
aggagagatt tggacactca tttcacccag tataagctgg cacgcccgta tattgctgat   2400
tgccctaact gtgggcatag tcggtgcgac agccctatat ctatagaaga agtcagaggg   2460
gatgcgcacg caggagtcat ccgcatccag acatcagcta tgttcggtct gaagacggat   2520
ggagttgatt tggcctacat gagtttcatg aacggcaaca gcagaaatct aataaagatc   2580
gacaacctgc atgtgcgcac ctcagcccct tgttccctcg tgtcgcacca cggctattac   2640
atcctggctc aatgcccacc aggggacacg gttacagttg ggtttcacga cgggcctaac   2700
cgccatacgt gcacagttgc ccataaggta gaattcaggc cagtgggtag agagaaatac   2760
cgtcacccac ctgaactgg agttgaatta ccatgcaacc gttcacccca caagcgtcga   2820
gaccaaggac actacgttga gatgcatcaa cccgggctag ttgccgacca ctctctcctt   2880
agcatccaca gtgccaaggt gaaaattacg gtaccgagcg cgcccaagt gaaatactac   2940
tgcaagtgcc cagacgtacg agagggaact accagcagcg actatacaac cacctgcacg   3000
gatgtcaaac aatgcagggc ttacctgatt gacaacaaaa aatgggtgta caactctgga   3060
agactgcctc gaggagaggg cgacacttttt aaaggaaac ttcatgtgcc ctttgtgcct   3120
gttaaggcca agtgcatcgc cacgctggca ccagagcctc tagttgagca caaacaccgc   3180
accctgattt tacacctgta cccggaccac ccgaccttgc tgacgaccag gtcacttgga   3240
agtgatgcaa atccaactcg acaatggatt gagcgaccaa caactgtcaa tttcacagtc   3300
accggagaag ggttggagta tacctgggga aaccatccac caaaaagagt atgggctcaa   3360
gagtcaggag aagggaatcc acatggatgg ccgcacgaag tggtagtcta ttactacaac   3420
agatacccat taaccacaat tatcgggtta tgcacctgtg tggctatcat catggtctct   3480
tgtgtcacat ccgtgtggct cctttgcagg actcgcaatc tttgcataac cccgtataaa   3540
ctagccccga acgctcaagt cccaatactc tggcgttac tttgctgcat taagccgacg   3600
agggcagatg acaccttgca agtgctgaat tacctgtgga acaacaatca aaactttttc   3660
tggatgcaga cgcttatccc acttgcgcg cttattgtat gcatgcgcat gctgcgctgc   3720
ttattttgct gtgggccggc tttttttactt gtctgcggcg ccttgggcgc cgcagcgtac   3780
gaacacacag cagtgatgcc gaacaaggtg gggatcccgt acaaagcttt agtcgaacgc   3840
ccaggttatg cacccgttca cctacagata cagctggtta ataccaggat aattccatca   3900
actaacctgg agtacatcac ctgcaagtat aagacaaaag tgccttctcc agtagtgaaa   3960
tgctgcggtg ccactcaatg tacctccaaa ccccatcctg actatcagtg tcaggtgttt   4020
acaggtgttt acccattcat gtggggagga gcctactgct ctgcgacac tgaaaacct   4080
cagatgagcg aggcgtatgt agagcgctcg gaagagtgct ctattgacca cgcaaaagct   4140
tataaagtac acacaggcac tgttcaggca atggtgaaca taacttatgg gagcgtcagc   4200
tggagatctg cagatgttta cgtcaatggt gaaactcccg cgaaataggg agatgccaaa   4260
ctcatcatag gtccactgtc atctgcgtgg tccccattcg ataacaaggt ggtggttcat   4320
gggcatgaag tgtataatta cgactttcct gagtacggca ccggcaaagc aggctctttt   4380
ggagacctgc aatcacgcac atcaaccagc aacgatctgt acgcaaacac caacttgaag   4440
ctacaacgac cccaggctgg tatcgtgcac acacctttca cccaggcgcc ctccggcttc   4500
gaacgatgga aaaggacaa agggcaccg ttgaacgacg tagccccgtt tggctgttcg   4560
attgccctgg agccgctccg tgcagaaaat tgtgcagtgg gaagcatccc tatatctata   4620
gatataccgg atgcggcttt taccagaata tctgaaacac cgacagtctc agacctggaa   4680
tgcaaaatta cggagtgtac ttatgcctcc gatttcggtg gtatagccac cgttgcctac   4740
aaatccagta agcaggaaa ctgtccaatt cattctccat caggtgttgc agtattaaa   4800
gaatgacg tcactcttgc tgagagcgga tcatttacat tccacttctc cactgcaaac   4860
atccatcctg ctttaagct gcaggtctgc actagtgcag ttacctgcaa aggagattgt   4920
aagccaccga agaccacat cgtcgattat ccagcacaac atactgaatc ctttacgtcg   4980
gcgatatccg ccactgcgtg gtcgtggcta aaagtgctgg taggaggaac atcagcattt   5040
atcgttctgg ggcttattgc tacagcagtg gttgccctag ttctgttctt ccatagacat   5100
taatctagac caggccctgg atccagatct gctgtgcctt ctagttgcca gccatctgtt   5160
gtttgcccct ccccgtgcc ttccttgacc ctgaaggtg ccactcccac tgtccttttcc   5220
taataaatg aggaaattgc atcgcattgt ctgagtaggt gtcattctat tctgggggt   5280
ggggtgggc aggacagcaa gggggaggat tgggaagaca atagcaggca tgctgggat   5340
gcggtgggct ctatgggtac ccaggtgctg aagaattgac ccggttcctc ctgggccaga   5400
aagaagcagg cacatccct tctctgtgac cacgccccg gttcttagtt   5460
ccagccccac tcataggaca ctcatagctc aggagggctc cgccttcaat cccaccgct   5520
aaagtacttg gagcggtctc tccctccctc atcagcccac caaaccaaac ctagcctcca   5580
agagtgggaa gaaattaaag caagataggc tattaagtgc agagggagag aaaatgcctc   5640
caacatgtga ggaagtaatg agagaaatca tagaatttta aggccatgat ttaaggccat   5700
catggcctta atcttccgct tcctcgctca ctgactcgct gcgctcggtc gttcggctgc   5760
```

```
ggcgagcggt atcagctcac tcaaaggcgg taatacggtt atccacagaa tcagggata   5820
acgcaggaaa gaacatgtga gcaaaaggcc agcaaaaggc caggaaccgt aaaaaggccg   5880
cgttgctggc gtttttccat aggctccgcc cccctgacga gcatcacaaa aatcgacgct   5940
caagtcagag gtggcgaaac ccgacaggac tataaagata ccaggcgttt cccccctggaa  6000
gctccctcgt gcgctctcct gttccgaccc tgccgcttac cggatacctg tccgcctttc   6060
tcccttcggg aagcgtggcg ctttctcata gctcacgctg taggtatctc agttcggtgt   6120
aggtcgttcg ctccaagctg ggctgtgtgc acgaaccccc cgttcagccc gaccgctgcg   6180
ccttatccgg taactatcgt cttgagtcca acccggtaag acacgactta tcgccactgg   6240
cagcagccac tggtaacagg attagcagag cgaggtatgt aggcggtgct acagagttct   6300
tgaagtggtg gcctaactac ggctacacta gaagaacagt atttggtatc tgcgctctgc   6360
tgaagccagt taccttcgga aaaagagttg gtagctcttg atccggcaaa caaaccaccg   6420
ctggtagcgg tggttttttt gtttgcaagc agcagattac gcgcagaaaa aaggatctc   6480
aagaagatcc tttgatcttt tctacggggt ctgacgctca gtggaacgaa aactcacgtt   6540
aagggatttt ggtcatgaga ttatcaaaaa ggatccttt ctagatcctt ttaaattaaa   6600
aatgaagttt taaatcaatc taaagtatat atgagtaaac ttggtctgac agttaccaat   6660
gcttaatcag tgaggcacct atctcagcga tctgtctatt tcgttcatcc atagttgcct   6720
gactcggggg ggggggggcgc tgaggtctgc ctcgtgaaga aggtgttgct gactcatacc   6780
aggcctgaat cgccccatca tccagccaga aagtgaggga gccacggttg atgagagctt   6840
tgttgtaggt ggaccagttg gtgattttga acttttgctt tgccacggaa cggtctgcgt   6900
tgtcgggaag atgcgtgatc tgatccttca actcagcaaa agttcgattt attcaacaaa   6960
gccgccgtcc cgtcaagtca gcgtaatgct ctgccagtgt tacaaccaat taaccaattc   7020
tgattagaaa aactcatcga gcatcaaatg aaactgcaat ttattcatat caggattatc   7080
aataccatat ttttgaaaaa gccgtttctg taatgaagga gaaaactcac cgaggcagtt   7140
ccataggatg caagatcct ggtatcggtc tgcgattccg actcgtccaa catcaataca   7200
acctattaat ttcccctcgt caaaaataag gttatcaagt gagaaatcac catgagtgac   7260
gactgaatcc ggtgagaatg gcaaaagctt atgcatttct ttccagactt gttcaacagg   7320
ccagccatta cgctcgtcat caaaatcact cgcatcaacc aaaccgttat tcattcgtga   7380
ttgcgcctga gcgagacgaa atacgcgatc gctgttaaaa ggacaattac aaacaggaat   7440
cgaatgcaac cggcgcagga acactgccag cgcatcaaca atattttcac ctgaatcagg   7500
atattcttct aatacctgga atgctgtttt cccggggatc gcagtggtga gtaaccatgc   7560
atcatcagga gtacggataa aatgcttgat ggtcgtggaa ggcataaatt ccgtcagcca   7620
gtttagtctg accatctcat ctgtaacatc attggcaacg ctaccttgc catgtttcag   7680
aaacaactct ggcgcatcgg gcttcccata caatcgatag attgtcgcac ctgattgccc   7740
gacattatcg cgagcccatt tacccata taaatcagca tccatgttgg aatttaatcg   7800
cggcctcgag caagacgttt cccgttgaat atgctcata acaccctg tattactgtt   7860
tatgtaagca gacagtttta ttgttcatga tgatatattt ttatcttgtg caatgtaaca   7920
tcagagattt tgagacacaa cgtggctttc ccccccccc cattattgaa gcatttatca   7980
gggttattgt ctcatgagcg gatacatatt tgaatgtatt tagaaaaata aacaaatagg   8040
ggttccgcgc acatttcccc gaaaagtgcc acctgacgtc taagaaacca ttattatcat   8100
gacattaacc tataaaata ggcgtatcac gaggcccttt cgtc                    8144

SEQ ID NO: 11          moltype = DNA   length = 8156
FEATURE                Location/Qualifiers
misc_feature           1..8156
                       note = Description of Artificial Sequence: Synthetic
                       polynucleotide
source                 1..8156
                       mol_type = other DNA
                       organism = synthetic construct
SEQUENCE: 11
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataattat tacattttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaataggga cttttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agttttttt ggcaccaaaa tcaacgggac tttccaaaat gtcgtaacaa   840
ctccgcccca ttgacgcaaa tgggcggtag cgtgtacggt gggaggtct atataagcag   900
agctcgttta gtgaaccgtc agatcgcctg gagacgccat ccacgctgtt ttgacctcca   960
tagaagacac cgggaccgat ccagcctcca tcggctcgca tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctaggacc ggagccgcag  1140
cttttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgccaccatg  1380
aatagaggat tctttaacat gctcggccgc cgccccccac tgccatgttg  1440
aggccgcgga gaaggaggca ggcggccccg atgcctgccc gcaaccccgct ggcttctcaa  1500
atccagcaac tgaccacagc cgtcagtgcc ctagtcattg acaggcaac tagacctcaa  1560
ccccccacgtc cacgccgcc accgcgcag aagaagcagg cgccaagca accaccgaag  1620
ccgaagaaac caaaaacgca ggagaagaag aagaagcaac ctgcaaaacc caaacccgga  1680
aagagacagc gcatggcact taagttggag gccgacagat tgttcgacgt caagaacgag  1740
```

```
gacggagatg tcatcgggca cgcactggcc atggaaggaa aggtaatgaa acctctgcac  1800
gtgaaaggaa ccatcgacca ccctgtgcta tcaaagctca aatttaccaa gtcgtcagca  1860
tacgacatgg agttcgcaca gttgccagtc aacatgagaa gtgaggcatt cacctacacc  1920
agtgaacacc ccgaaggatt ctataactgg caccacggag cggtgcagta tagtggaggt  1980
agatttacca tccctcgcgg agtaggaggc agaggagaca gcggtcgtcc gatcatggat  2040
aactccggtc gggttgtcgc gatagtcctc ggtggcgctg atgaaggaac acgaactgcc  2100
ctttcggtcg tcacctggaa tagtaaaggg aagacaatta agacgacccc ggaagggaca  2160
gaagagtggt ccgcagcacc actggtcacg gcaatgtgtt tgctcggaaa tgtgagcttc  2220
ccatgcgaac gcccgcccac atgctatacc cgcgaacctt ccagagccct cgacatcctt  2280
gaagagaacg tgaaccatga ggcctacgat accctgctca atgccatatt gcggtgcgga  2340
tcgtctggca gaagcaaaag aagcgtcatt gacgactttta ccctgaccag ccctacttg   2400
ggcacatgct cgtactgcca ccatactgta ccgtgcttca gccctgttaa gatcgagcag  2460
gtctgggacg aagcggacga taacaccata cgcatacaga cttccgccca gtttggatac  2520
gaccaaagcg gagcagcaag cgcaaacaag taccgctaca tgtcgcttaa gcaggatcac  2580
accgttaaag aaggcaccat ggatgacatc aagattagca cctcaggacc gtgtagaagg  2640
cttagctaca aaggatactt tctcctcgca aaatgccctc caggggacag cgtaacggtt  2700
agcatagtga gtagcaactc agcaacgtca tgtacactgg cccgcaagat aaaaccaaaa  2760
ttcgtgggac gggaaaaata tgatctacct cccgttcacg gtaaaaaaat tccttgcaca  2820
gtgtacgacc gtctgaaaga aacaactgca ggctacatca ctatgcacag gccgagaccg  2880
cacgcttata catcctacct ggaagaatca tcagggaaag tttacgcaaa gccgccatct  2940
gggaagaaca ttacgtatga gtgcaagtgc ggcgactaca agaccggaac cgtttcgacc  3000
cgcaccgaaa tcactggttg caccgccatc aagcagtgcg tcgcctataa gagcgaccaa  3060
acgaagtggg tcttcaactc accggacttg atcagacatg acgaccacac ggcccaaggg  3120
aaaattgcatt tgcctttcaa gttgatcccg agtacctgca tggtccctgt tgcccacgcg  3180
ccgaatgtaa tacatggctt taaacacatc agcctccaat tagatacaga ccacttgaca  3240
ttgctcacca ccaggagact aggggcaaac ccggaaccaa gcccactgca gatcgtcgga  3300
aagacggtca gaaacttcac cgtcgaccga gatggcctgg aatacatatg gggaaatcat  3360
gagccagtga gggtctatgc ccaagagtca gcaccaggag accctcacgg atggccacac  3420
gaaatagtac agcattacta ccatcgccat cctgtgtaca ccatcttagc cgtcgcatca  3480
gctaccgtgg cgatgatgat tggcgtaact gttgcagtgt tatgtgcctg taaagcgcgc  3540
cgtgagtgcc tgacgccata cgccctggcc ccaaacgccg taatcccaac ttcgctggca  3600
ctcttgtgct gcgttaggtc ggccaatgct gaaacgttca ccgagaccat gagttacttg  3660
tggtcgaaca gtcagccgtt cctctgggtc cagttgtgca tacctttggc cgcttttcatc  3720
gttctaatgc gctgctgctc ctgctgcctg ccttttttag tggttgccgg cgcctacctg  3780
gcgaaggtag acgcctacga acatgctacc actgttccaa atgtgccaca gataccgtat  3840
aaggcacttg ttgaaaggc agggtatgcc ccgctcaatt tggagatcac tgtcatgtcc  3900
tcggaggttt tgccttccac caaccaagag tacattacct gcaaattcac cactgtggtc  3960
ccctccccaa aaatcaaatg ctgcggctcc ttggaatgtc agccggccgc tcatgcagac  4020
tataccgtca aggtcttcgg agggtctac ccctttatgt gggaggagc gcaatgtttt  4080
tgcgacagtg agaacagcca gatgagtgag gcgtacgtcg aattgtcagc agattgcgcg  4140
tctgaccacg cgcaggcgat taaggtgcac actgccgcga tgaaagtagg actgcgtatt  4200
gtgtacggga acactaccag tttcctagat gtgtacgtga acggagtcac accaggaacg  4260
tctaaagact tgaaagtcat agctggacca atttcagcat cgtttacgcc attcgatcat  4320
aaggtcgtta tccatcgcgg cctggtgtac aactatgact tccccggaata tggagcgatg  4380
aaaccaggag cgtttggaga cattcaagct acctccttga ctagcaagga tctcatcgcc  4440
agcacagaca ttaggctact caagccttcc gccaagaacg tgcatgtccc gtacacgcag  4500
gcctcatcag gatttgagat gtggaaaaac aactcaggcc gccactgca ggaaaccgca  4560
cctttcgggt gtaagattgc agtaaatccg ctccgagcgg tggactgttc atacgggaac  4620
attcccattt ctattgacat cccgaacgct gcctttatca ggacatcaga tgcaccactg  4680
gtctcaacag tcaaatgtga agtcagtgag tgcacttatt cagcagactt cggcgggatg  4740
gccaccctgc agtatgtatc cgaccgcgaa ggtcaatgcc ccgtacattc gcattcgaac  4800
acagcaactc tccaagagtc gacagtacat gtcctggaga aaggagcggt gacagtacac  4860
tttagcaccg cgagtccaca ggcgaacttt atcgtatcgc tgtgtgggaa gaagacaaca  4920
tgcaatgcag aatgtaaacc accagctgac catatcgtga gcaccccgca caaaatgac  4980
caagaatttc aagccgccat ctcaaaaaca tcatgaggt ggctgtttgc ccttttcggc  5040
ggcgcctcgt cgctattaat tataggactt atgattttg cttgcagcat gatgctgact  5100
agcacacgaa gatgatctag accaggccct ggatccagat ctgctgtgcc ttctagttgc  5160
cagccatctg ttgtttgccc ctcccccgtg ccttccttga ccctggaagg tgccactccc  5220
actgtccttt cctaataaaa tgaggaaatt gcatcgcatt gtctgagtag tgtgcattct  5280
attctggggg gtggggtggg gcaggacagc aagggggagg attgggaaga caatagcagg  5340
catgctgggg atgcggtggg ctctatgggt acccaggtgc tgaagaattg acccggttcc  5400
tcctgggcca gaaagaagca ggcacatccc cttctctgtg acacccctg tccacgcccc  5460
tggttcttag ttcagcccc actcatagga cactcatagc tcaggagggc tccgccttca  5520
atcccacccg ctaaagtact tggagcggtc tctccctccc tcatcagcc accaaaccaa  5580
acctagcctc caagagtggg aagaaattaa agcaagatag gctattaagt cagagggag  5640
agaaaatgcc tccaacatgt gaggaagtaa tgagagaaat catgaatttt taaggccatg  5700
atttaaggcc atcatggcct taatcttccg cttcctcgct cactgactcg ctgcgctcgg  5760
tcgttcggct gcggcgagcg gtatcagctc actcaaaggc ggtaatacgg ttatccacag  5820
aatcagggga taacgcagga aagaacatgt gagcaaaagg ccagcaaaag gccaggaacc  5880
gtaaaaaggc cgcgttgctg gcgttttttcc ataggctccg ccccccctgac gagcatcaca  5940
aaaatcgacg ctcaagtcag aggtggcgaa acccgacagg actataaaga taccaggcgt  6000
ttcccccctga agctccctc gtgcgctctc ctgttccgac cctgccgctt accggatacc  6060
tgtccgcctt tctcccttcg ggaagcgtgg cgctttctca tagctcacgc tgtaggtatc  6120
tcagttcggt gtaggtcgtt cgctccaagc tgggctgtgt gcacgaaccc ccgttcagc  6180
ccgaccgctg cgccttatcc ggtaactatc gtcttgagtc caacccggta agacacgact  6240
tatcgccact ggcagcagcc actggtaaca ggattagcag agcgaggtat gtaggcggtg  6300
ctacagagtt cttgaagtgg tggcctaact acggctacac tagaagaaca gtatttggta  6360
tctgcgctct gctgaagcca gttaccttcg gaaaaagagt tggtagctct tgatccggca  6420
aacaaaccac cgctggtagc ggtggttttt ttgtttgcaa gcagcagatt acgcgcagaa  6480
```

```
aaaaaggatc tcaagaagat cctttgatct tttctacggg gtctgacgct cagtggaacg   6540
aaaactcacg ttaagggatt ttggtcatga gattatcaaa aaggatcttc acctagatcc   6600
ttttaaatta aaaatgaagt tttaaatcaa tctaaagtat atatgagtaa acttggtctg   6660
acagttacca atgcttaatc agtgaggcac ctatctcagc gatctgtcta tttcgttcat   6720
ccatagttgc ctgactcggg ggggggggc gctgaggtct gcctcgtgaa gaaggtgttg   6780
ctgactcata ccaggcctga atcgcccat catccagcca gaaagtgagg gagccacggt   6840
tgatgagagc tttgttgtag gtggaccagt tggtgatttt gaacttttgc tttgccacgg   6900
aacggtctgc gttgtcggga agatgcgtga tctgatcctt caactcagca aaagttcgat   6960
ttattcaaca aagccgccgt cccgtcaagt cagcgtaatg ctctgccagt gttacaacca   7020
attaaccaat tctgattaga aaaactcatc gagcatcaaa tgaaactgca atttattcat   7080
atcaggatta tcaataccat attttttgaaa aagccgtttc tgtaatgaag gagaaaactc   7140
accgaggcag ttccatagga tggcaagatc ctggtatcgg tctgcgattc cgactcgtcc   7200
aacatcaata caacctatta atttccctc gtcaaaaata aggttatcaa gtgagaaatc   7260
accatgagtg acgactgaat ccggtgagaa tggcaaaagc ttatgcattt cttttccagac  7320
ttgttcaaca ggccagccat tacgctcgtc atcaaaatca ctcgcatcaa ccaaaccgtt   7380
attcattcgt gattgcgcct gagcgagacg aaatacgcga tcgctgttaa aaggacaatt   7440
acaaacagga atcgaatgca accggcgcag gaacactgcc agcgcatcaa caatatttc   7500
acctgaatca ggatattctt ctaataccta gaatgctgtt ttcccgggga tcgcagtggt   7560
gagtaaccat gcatcatcag gagtacggat aaaatgcttg atggtcggaa gaggcataaa   7620
ttccgtcagc cagtttagtc tgaccatctc atctgtaaca tcattggcaa cgctaccttt   7680
gccatgtttc agaaacaact ctggcgcatc gggcttccca tacaatcgat agattgtcgc   7740
acctgattgc ccgacattat cgcgagccca tttatacca taaaatcag catccatgtt   7800
ggaatttaat cgcggcctcg agcaagacgt ttccgttga atatggctca taacacccct   7860
tgtattactg tttatgtaag cagacagttt tattgttcat gatgatatat ttttatcttg   7920
tgcaatgtaa catcagagat tttgagacac aacgtggctt tccccccccc cccattattg   7980
aagcatttat caggtgtatt gtctcatgag cggatacata tttgaatgta tttagaaaaa   8040
taaacaaata ggggttccgc gcacatttcc ccgaaaagtg ccacctgacg tctaagaaac   8100
cattattatc atgacattaa cctataaaaa taggcgtatc acgaggccct ttcgtc       8156

SEQ ID NO: 12            moltype = DNA  length = 8180
FEATURE                  Location/Qualifiers
misc_feature             1..8180
                         note = Description of Artificial Sequence: Synthetic
                         polynucleotide
source                   1..8180
                         mol_type = other DNA
                         organism = synthetic construct
SEQUENCE: 12
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacattttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggga cttttccattg acgtcaatgg gtggagtatt tacggtaaac   540
tgcccacttg gcagtacatc aagtgtatca tatgccaagt acgccccta ttgacgtcaa   600
tgacggtaaa tggcccgcct ggcattatgc ccagtacatg accttatggg acttttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctcca tcggctcgta tctctccttc acgcgcccgc  1020
cgccctacct gaggccgcca tccacgccgg ttgagtcgcg ttctgccgcc tcccgcctgt  1080
ggtgcctcct gaactgcgtc cgccgtctag gtaagtttaa agctcaggtc gagaccgggc  1140
ctttgtccgg cgctcccttg gagcctacct agactcagcc ggctctccac gctttgcctg  1200
accctgcttg ctcaactcta gttaacggtg gagggcagtg tagtctgagc agtactcgtt  1260
gctgccgcgc gcgccaccag acataatagc tgacagacta acagactgtt cctttccatg  1320
ggtcttttct gcagtcaccg tcgtcgacac gtgtgatcag atatcgcggc cgccaccatg  1380
aattacatcc ctacgcaaac gttttacggc cgccggtggc cccgcgccc ggcggcccgt  1440
ccttggccgt tgcaggccac tccggtggct cccgtcgtcc ccgacttcca ggcccagcag  1500
atgcagcaaa ctcatcagcg cgtaaatgcg ctgacaatga gacgaacgc aattgctcct  1560
gctaggcctc ccaaaccaaa gaagaagaag acaaccaaac caaagccgaa aacgcagccc  1620
aagaagatca acgaaaaac gcagcagcaa aagaagaaag acaagcaagc cgacaagaag  1680
aagaagaaac ccgaaaaag agaaagaatg tgcatgaaga ttgaaaatga ctgtatcttc  1740
gaagtcaaac acgaaggaaa ggtcactggg tacgcctgcc tggtgggcga caaagtcatg  1800
aaacctgccc acgtgaaagg agtcatcgac aacgcggacc tggcaaagct agcttttcaag  1860
aaatcgagca agtatgacct tgagtgtgcc cagataccag ttcacatgag gtcggatgcc  1920
tcaaagtaca cgcatgagaa gcccgaggga cactataact ggaccacgg ggctgttcag  1980
tacagcggag gtaggttcac tataccgaca ggagcgggca aacgggagaa cagtggccgg  2040
cccatctttg acaacaaggg gagggtagtc gctatcgtcc tgggcgggc caacgaggc   2100
tcacgcacag cactgtcggt ggtcacctgg aacaaagata tggtgactag agtgaccct   2160
gaggggtccg aagagtggtc cgccccgctg attactgcca tgtgtgtcct tgccaatgct  2220
accttccgt gcttccagcc cccgtgtgta ccttgctgct atgaaaacaa cgcagaggcc  2280
acactacgga tgctcgagga taacgtggat aggccagggt actacgacct ccttcaggca  2340
gccttgacgt gccgaaacgg aacaagacac cggcgcagcg tgtcgcaaca cttcaacgtg  2400
tataaggcta cacgccctta catcgcgtac tgcgccgact gcggagcagg gcactcgtgt  2460
```

```
catagccccg tagcaattga agcggtcagg tccgaagcta ccgacgggat gctgaagatt   2520
cagttctcgg cacaaattgg catagataag agtgacaatc atgactacac gaagataagg   2580
tacgcagacg ggcacgccat tgagaatgcc gtccggtcat cttttgaaggt agccacctcc   2640
ggagactgtt tcgtccatgg cacaatggga catttcatac tggcaaagtg cccaccgggt   2700
gaattcctgc aggtctcgat ccaggacacc agaaacgcgg tccgtgcctg cagaatacaa   2760
tatcatcatg accctcaacc ggtgggtaga gaaaaattta caattagacc acactatgga   2820
aaagagatcc cttgcaccac ttatcaacag accacagcgg agaccgtgga ggaaatcgac   2880
atgcatatgc cgccagatac gccggacagg acgttgctat cacagcaatc tggcaatgta   2940
aagatcacag tcggaggaaa gaaggtgaaa tacaactgga cctgtggaac cggaaaacgtt   3000
ggcactacta attcggacat gacgatcaac acgtgtctaa tagagcagtg ccacgtctca   3060
gtgacggacc ataagaaatg gcagttcaac tcacctttcg tcccgagagc cgacgaaccg   3120
gctagaaaag gcaaagtcca tatcccattc ccgttggaca acatcacatg cagagttcca   3180
atggcgcgcg aaccaaccgt catccacggc aaaagagaag tgacactgca ccttcaccca   3240
gatcatccca cgctctttc ctaccgcaca ctgggtgagg acccgcagta tcacgaggaa   3300
tgggtgacag cggcggtgga acggaccata cccgtaccag tggacgggat ggagtaccac   3360
tggggaaaca acgacccagt gaggctttgg tctcaactca ccactgaagg gaaaccgcac   3420
ggctggccgc atcagatcgt acagtactac tatgggcttt accggccgc tacagtatcc   3480
gcggtcgtcg ggatgagctt actggcgttg atatcgatct tcgcgtcgtg ctacatgctg   3540
gttgcggccc gcagtaagtg cttgacccct tatgctttaa caccaggagc tgcagttccg   3600
tggacgctgg ggatactctg ctgcgccccg cgggcgcacg cagctagtgt ggcagagact   3660
atggcctact tgtgggacca aaaccaagcg ttgttctggt tggagtttgc ggcccctgtt   3720
gcctgcatcc tcatcatcac gtattgcctc agaaacgtgc tgtgttgctg taagagcctt   3780
tcttttttag tgctactgag cctcgggca accgccagag cttacgaaca ttcgacagta   3840
atgccgaacg tggtggggtt cccgtataag gctcacattg aaaggccagg atatagcccc   3900
ctcactttgc agatgcaggt tgttgaaacc agcctcgaac caacccttaa tttggaatac   3960
ataacctgtg agtacaagac ggtctcccg tcgccgtacg tgaagtgctg cggcgcctca   4020
gagtgctcca ctaaagagaa gcctgactac caatgcaagg tttacacagg cgtgtacccg   4080
ttcatgtggg gagggcata ttgcttctgc gactcagaaa acacgcaact cagcgaggcg   4140
tacgtcgatc gatcggacgt atgcaggcat gatcacgcat ctgcttacaa agcccataca   4200
gcatcgctga aggccaaagt gagggttatg tacggcaacg taaaccagac tgtggatgtt   4260
tacgtgaacg gagaccatgc cgtcacgata gggggtactc agttcatatt cgggccgctg   4320
tcatcggcct ggaccccgtt cgacaacaag atagtcgtgt acaaagacga agtgttcaat   4380
caggacttcc cgccgtacgg atctgggcaa ccagggcgct tcggcgacat ccaaagcaga   4440
acagtggaga gtaacgacct gtacgcgaac acggcactga agctggcacg cccttcaccc   4500
ggcatggtcc atgtaccgta cacacagaca ccttcagggt tcaaatattg gctaaaggaa   4560
aaagggacag ccctaaatac gaaggctcct tttggctgcc aaatcaaaac gaaccctgtc   4620
agggccatga actgcgccgt gggaaacatc cctgtctcca tgaatttgcc tgacagcgcc   4680
tttacccgca ttgtcgaggc gccgaccatc attgacctga cttgcacagt ggctacctgt   4740
acgcactcct cggatttcgg cggcgtcttg acactgacgt acaagaccaa caagaacgg   4800
gactgctctg tacactcgca ctctaacgta gctactctac aggaggccac agcaaaagtg   4860
aagacagcag gtaaggtgac cttacacttc tccacggcaa gcgcatcacc ttcttttgtg   4920
gtgtcgctat gcagtgctag ggccacctgt tcagcgtcgt gtgagccccc gaaagaccac   4980
atagtcccat atgcggctag ccacagtaac gtagtgtttc cagacatgtc gggcaccgca   5040
ctatcatggg tgcagaaaat ctcggtggt ctgggggcct tcgcaatcgg cgctatcctg   5100
gtgctggttg tggtcacttg cattgggctc cgcagataat ctagaccagg ccctggatcc   5160
agatctgctg tgccttctag ttgccagcca tctgttgttt gcccctcccc cgtgccttcc   5220
ttgaccctgg aaggtgccac tcccactgtc ctttcctaat aaaatgagga aattgcatcg   5280
cattgtctga gtaggtgtca ttctattctg gggggtgggg tgggcagga cagcaagggg   5340
gaggattggg aagacaatag caggcatgct ggggatgcgg tgggctctat gggtacccag   5400
gtgctgaaga attgacccgg ttcctcctgg gccagaaaga agcaggcaca tccccttctc   5460
tgtgcacaca cctgtccacg cccctggttc ttagttccag ccccactcat aggacactca   5520
tagctcagga gggctccgcc ttcaatccca cccgctaaag tacttggagc ggtctctccc   5580
tccctcatca gcccaccaaa ccaaacctag cctccaagag tgggaagaaa ttaaagcaag   5640
ataggctatt aagtgcagag ggagagaaaa tgcctccaac atgtgaggaa gtaatgagag   5700
aaatcataga atttttaaggc catgatttaa ggccatcatg gccttaatct tccgcttcct   5760
cgctcactga ctcgctgcgc tcggtcgttc ggctgcggcg agcggtatca gctcactcaa   5820
aggcggtaat acgttatccc acagaatcag gggataacgc aggaaagaac atgtgagcaa   5880
aaggccagca aaaggccagg aaccgtaaaa aggccgcgtt gctggcgttt ttccataggc   5940
tccgccccc tgacgagcat cacaaaaatc gacgctcaag tcagaggtgg cgaaaccgac   6000
aggactata aagataccag gcgtttcccc ctggaagctc cctcgtgcgc tctcctgttc   6060
cgaccctgcc gcttaccgga tacctgtccg cctttctccc ttcgggaagc gtggcgcttt   6120
ctcatagctc acgctgtagg tatctcagtt cggtgtaggt cgttcgctcc aagctgggct   6180
gtgtgcacga accccccgtt cagcccgacc gctgcgcctt atccggtaac tatcgtcttg   6240
agtccaaccc ggtaagacag acttatcgc cactggcagc agccactggt aacaggatta   6300
gcagagcgag gtatgtaggc ggtgctacag agttcttgaa gtggtggcct aactacggct   6360
acactagaag aacagtattt ggtatctgcg ctctgctgaa gccagttacc ttcggaaaaa   6420
gagttggtag ctcttgatcc ggcaaacaaa ccaccgctgg tagcggtggt ttttttgttt   6480
gcaagcagca gattacgcgc agaaaaaaag gatcctcaaga agatcctttg atcttttcta   6540
cggggtctga cgctcagtgg aacgaaaact cacgttaagg gattttggtc atgagattat   6600
caaaaaggat cttcacctag atccttttaa attaaaaatg aagttttaaa tcaatctaaa   6660
gtatatatga gtaaacttgg tctgacagtt accaatgctt aatcagtgag gcacctatct   6720
cagcgatctg tctatttcgt tcatccatag ttgcctgact cggggggggg gggcgctgag   6780
gtctgcctcg tgaagaaggt gttgctgact cataccaggc ctgaatcgcc ccatcatcca   6840
gccagaaagt gagggagcca cggttgatga gagctttgtt gtaggtggac cagttggtga   6900
ttttgaactt ttgctttgcc acggaacggt ctgcgttgtc gggaagatgc gtgatctgat   6960
ccttcaactc agcaaaagtt cgatttattc aacaaagccg ccgtcccgtc aagtcagcgt   7020
aatgctctgc cagtgttaca accaattaac caattctgat tagaaaaact catcgagcat   7080
caaatgaaac tgcaatttat tcatatcagg attatcaata ccatattttt gaaaagccg   7140
tttctgtaat gaaggagaaa actcaccgag gcagttccat aggatggcaa gatcctggta   7200
```

```
tcggtctgcg attccgactc gtccaacatc aatacaacct attaatttcc cctcgtcaaa    7260
aataaggtta tcaagtgaga aatcaccatg agtgacgact gaatccggtg agaatggcaa    7320
aagcttatgc atttctttcc agacttgttc aacaggccag ccattacgct cgtcatcaaa    7380
atcactcgca tcaaccaaac cgttattcat tcgtgattgc gcctgagcga gacgaaatac    7440
gcgatcgctg ttaaaaggac aattacaaac aggaatcgaa tgcaaccggc gcaggaaacc    7500
tgccagcgca tcaacaatat tttcacctga atcaggatat tcttctaata cctggaatgc    7560
tgttttcccg gggatcgcag tggtgagtaa ccatgcatca tcaggagtac ggataaaatg    7620
cttgatggtc ggaagaggca taaattccgt cagccagttt agtctgacca tctcatctgt    7680
aacatcattg gcaacgctac ctttgccatg tttcagaaac aactctggcg catcgggctt    7740
cccatacaat cgatagattg tcgcacctga ttgcccgaca ttatcgcgag cccatttata    7800
cccatataaa tcagcatcca tgttggaatt taatcgcggc ctcgagcaag acgtttcccg    7860
ttgaatatgc tcataacac cccttgtatt actgtttatg taagcagaca gttttattgt    7920
tcatgatgat atattttat cttgtgcaat gtaacatcag agattttgag acacaacgtg    7980
gctttccccc cccccccatt attgaagcat ttatctcgtc tattgtctca tgagcggata    8040
catatttgaa tgtatttaga aaaataaaca aataggggtt ccgcgcacat ttccccgaaa    8100
agtgccacct gacgtctaag aaaccattat tatcatgaca ttaacctata aaaataggcg    8160
tatcacgagg ccctttcgtc                                                8180

SEQ ID NO: 13         moltype = DNA   length = 8377
FEATURE               Location/Qualifiers
misc_feature          1..8377
                      note = Description of Artificial Sequence: Synthetic
                      polynucleotide
source                1..8377
                      mol_type = other DNA
                      organism = synthetic construct
SEQUENCE: 13
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcagattgc    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctccctg gagcctacct agactcgtcc gctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtctttct gcagtcaccg tcgtcgacac gtgtgatcag atatcgcggc cgcatgtttc   1380
ccatgcaatt caccaactca gcctatcgcc agatggagcc catgtttgca ccgggttcgg   1440
gaggacaagt acagccgtac cggccgcgca ctaagcgccg ccaggagccg caagtcggca   1500
acgccgccat tactgccctc gcgaaccaga tgagtgcgct ccagttgcag gtagctggac   1560
ttgccggcca ggcaagggtg gaccgccgtg ggccaagacg tgttcagaag aacaagcaga   1620
agaagaagaa ctcttccaac ggagaaaaac ccaaagagaa gaagaagaac caaaaacac    1680
aggagaagaa gggaagcggt ggcgaaaaag tcaagaagac taggaaccga cccgggaagg   1740
aggtaaggat ctccgtaaag tgtcccgac agagcacctt ccccgtgtac cacgaaggtg   1800
ctatatccgg ctacgctgtg ctgattggat ctcgcgtatt caagccggca cacgtgaagg   1860
gtaagatcga ccaccctgaa ctggcacga tcaagttcca ggtcgccgag gacatggacc   1920
tcgaagcagc tgcgtacccg aagagcatgc gagaccaagc gctgaacca gcgaccatga   1980
tggacagagt gtacaactgg gagtatggca ctatcagagt ggaggataat gtcataatcg   2040
acgcaagcgg taggggcaag ccgggtgaca gtggcagggc catcaccgac aactcgggaa   2100
aggttgttgg tattgtcctc ggaggaggac ccgatgcgag gcgcacacgc ctctccgtga   2160
tagggttcga caagaagatg aaggctaggg agatcgccta cagtgatgcc atacccttgga  2220
cacgcgctcc ggccctcctg ctgctgccta tggttattgt ctgcacctac aattccaaca   2280
ccttcgattg ctcaaaaccg tcctgccagg actgctgcat tactgctgaa ccagagaagg   2340
ccatgaccat gctgaaggac aatctgaacg acccgaacta ctgggaccta ctcattgctg   2400
tcaccacctg tggctccgcc cggagaaga gggctgtgtc tacgtcgcct gccgccttt    2460
acgacacaca gatcctcgcc gcccacgcag ctgcctcccc atacagggcg tactgcccg    2520
attgtgacgg aacagcgtgt atctcgccga tagccatcga cgaggtggtg agcagtggca   2580
gcgaccacgt cctccgcatg cgggttggtt tcaatcgggg agtgaccgct aagggtgtg    2640
cggcgggtga aacctctctg cgatacctgg aagggacgg gaaggttcac gccgcagaca   2700
acacgcgact cgtggtgcgc acgactgcaa agtgcgacgt gctgcaggcc actggccact   2760
acatcctggc caactgccca gtgggggaga gcctaaccgt ctggatgcga    2820
cccggcatca atgcaccacg gtttctcgaac accaagtaac ggagaagttc accagagaac   2880
gcagcaaggg ccaccatctg tccgacatga ccaagaaatg caccagattt tccactacac   2940
caaaaaagtc cgccctctac ctcgttgatg tgtatgacgc tctgccgatt tctgtagaga   3000
ttagcaccgt cgtaacatgc agcgacagcc agtgcacagt gagggtgcca cctggtacca   3060
cagtgaaatt cgacaagaaa tgcaagagcg ctgactcggc aaccgtcact ttcaccagcg   3120
```

```
actcccagac gtttacgtgt gaggagccag tcctaacggc tgccagtatc acccagggca   3180
agccacacct cagatcggca atgttgccta gcggaggcaa ggaagtgaaa gcaaggatcc   3240
cgttcccgtt cccgccggaa accgcaactt gcagagtgag tgtagcccca ctgccgtcga   3300
tcacctacga ggaaagcgat gtcctgctag ccggtaccgc aaaataccct gtgctgctaa   3360
ccacacggaa ccttggtttc catagcaacg ccacatccag atggatccag ggcaagtacc   3420
tgcgccgcat cccggtcacg cctcaaggga tcgagctaac atggggaaac aacgcgccga   3480
tgcacttttg gtcatccgtc aggtacgcat ccggggacgc tgatgcgtac ccctgggaac   3540
ttctggtgta ccacaccaag caccatccag agtacgcgtg ggcgtttgta ggagttgcat   3600
gcggcctgct ggctatcgca gcgtgcatgt ttgcgtgcgc atgcagcagg gtgcggtact   3660
ctctggtcgc caacacgttc aactcgaacc caccaccatt gaccgcactg actgcagcac   3720
tgtgttgcat accaggggct cgcgcggacc aaccctactt ggacatcatt gcctacttgt   3780
ggaccaacag caaagtggcc ttcgggctac aatttgcggc gcccgtggcc tgtgtgctca   3840
tcattacata cgcccttagg cactgcagat tgtgctgcaa gtctttttta ggggtaagag   3900
ggtggtcagc cctgctggtc atccttgcgt atgtacagag ctgcaagagc tacgaacaca   3960
ccgtggtggt cccaatggat ccaagagccc cgtcgtacga agcagtgata aaccggaatg   4020
ggtatgatcc attgaagctg accatctcag tgaatttcac cgtcatctca ccaactacgg   4080
ctctggaata ttggacctgc gcaggagtcc ccatcgtcga gccgcccat gtgggctgct   4140
gcacgtcggt gtcctgcccc tctgacctct ctacgctgca tgcgtttact ggcaaagctg   4200
tctccgacgt gcactgcgat gtgcacacaa acgtgtaccc cttgttgtgg ggcgcggctc   4260
actgcttctg ttccaccgag aatacacagg tcagcgctgt ggcagccacc gtttctgagt   4320
tctgtgccca ggactcagag cgtgccgaag cgttcagcgt acacagcagc tcagtcaccg   4380
ctgaggtcct ggtgacgctt ggtgaagtgg tgacggcagt ccagtttac gtggacgtgg   4440
taacatcagc caggggcact gacctcaaga tcgtggctgg accaataaca accgactact   4500
ccccattcga tcgcaaagta gtcccgcatc gcgaagaggt ctataactat gactggcctc   4560
cttacgggge tggccgacca ggcacattcg gagacattca agctaggtca accaactatg   4620
tcaaacccaa cgatctgtat ggggacatcg gaattgaagt actgcagccg actaacgacc   4680
acgtacatgt ggcttacacg tatacgacct ctggggttact gcgttggctg caggacgctc   4740
cgaaaccact cagtgtcaca gcaccgcacg gttgtaagat cagtgccaat ccgctcctgg   4800
ccctcgattg tggggttggt gccgtcccca tgtccatcaa cattccggac gcgaagttta   4860
cccgcaaatt aaaggatccg aaaccatcgg ccctgaaatg cgtggtggac agctgcgagt   4920
acggggtgga ctacggggc gccgccacga tcacctacga ggggcacgag gccgggaagt   4980
gcgggattca ttccctgaca ccaggagtcc ccctgagaac atcggtggtt gaagtggttg   5040
ctggcgccaa taccgtcaaa acgaccttct cctcacccac gcccgaggtt gcactcgagg   5100
tagagatctg ttcggcaata gtgaagtgcg ctggtgagtg cactccaccg aaggaacatg   5160
tggtcgcaac caggcctcgc catggcagcg accctggagg ctacatctcc gggccccgcaa   5220
tgcgctgggc cggagggatt gtagggaccc tagtggtcct gttccttatc cttgccgtca   5280
tctactgcgt ggtgaagaag tgccgctcca aaagaatccg gatagtcaag agctaatcta   5340
gaccaggccc tggatccaga tctgctgtgc cttctagttg ccagccatct gttgtttgcc   5400
cctccccgt gccttccttg accctggaag gtgccactcc cactgtcctt tcctaataaa   5460
atgaggaaat tgcatcgcat tgtctgagta ggtgtcattc tattctgggg ggtgggtgg   5520
ggcaggacag caaggggag gattgggaag acaatagcag gcatgctggg gatgcggtgg   5580
gctctatggg tacccaggtg ctgaagaatt gacccggttc tcctgggcc agaaagaagc   5640
aggcacatcc ccttctctgt gacacaccct gtccacgccc ctggttctta gttccagccn   5700
cactcatagg acactcatag ctcaggaggg ctccgccttc aatcccaccc gctaaagtac   5760
ttggagcggt ctctccctcc ctcatcagcc caccaaacca aacctagcct ccaagagtgg   5820
gaagaaatta aagcaagata ggctattaag tgcagaggga gagaaaatgc ctccaacatg   5880
tgaggaagta atgagagaaa tcatagaatt ttaaggccat gatttaaggc catcatggcc   5940
ttaatcttcc gcttcctcgc tcactgactc gctgcgctcg gtcgttcggc tgcggcgagc   6000
ggtatcagct cactcaaagg cggtaatacg gttatccaca gaatcagggg ataacgcagg   6060
aaagaacatg tgagcaaaag gccagcaaaa ggccaggaac cgtaaaaagg ccgcgttgct   6120
ggcgtttttc cataggctcc gccccctga cgagcatcac aaaaatcgac gctcaagtca   6180
gaggtggcga aacccgacag gactataaag ataccaggcg tttccccctg gaagctccct   6240
cgtgcgctct cctgttccga ccctgccgct taccggatac ctgtccgcct ttctcccttc   6300
gggaagcgtg gcgctttctc atagctcacg ctgtaggtat ctcagttcgg tgtaggtcgt   6360
tcgctccaag ctgggctgtg tgcacgaacc ccccgttcag cccgaccgct gcgccttatc   6420
cggtaactat cgtcttgagt ccaacccggt aagacacgac ttatcgccac tggcagcagc   6480
cactggtaac aggattagca gagcgaggta tgtaggcggt gctacagagt tcttgaagtg   6540
gtggcctaac tacggctaca ctagaagaac agtatttggt atctgcgctc tgctgaagcc   6600
agttaccttc ggaaaaagag ttggtagctc ttgatccggc aaacaaacca ccgctggtag   6660
cggtggtttt tttgtttgca agcagcagat tacgcgcaga aaaaaaggat ctcaagaaga   6720
tcctttgatc ttttctacgg ggtctgacgc tcagtggaac gaaaactcac gttaagggat   6780
tttggtcatg agattatcaa aaaggatctt cacctagatc cttttaaatt aaaaatgaag   6840
ttttaaatca atctaaagta tatatgagta aacttggtct gacagttacc aatgcttaat   6900
cagtgaggca cctatctcag cgatctgtct atttcgttca tccatagttg cctgactcgg   6960
ggggggggg cgctgaggtc tgcctcgtga agaaggtgtt gctgactcat accaggcctg   7020
aatcgcccca tcatccagcc agaaagtgag ggagccacgg ttgatgagag ctttgttgta   7080
ggtggaccag ttggtgattt tgaactttg ctttgccacg aacggtctg cgttgtcggg   7140
aagatgcgtg atctgatcct tcaactgcagc aaaagttcga tttattcaac aaagccgccg   7200
tcccgtcaag tcagcgtaat gctctgccag tgttacaaca aattaaccaa ttctgattag   7260
aaaaactcat cgagcatcaa atgaaactgc aatttattca tatcaggatt atcaatacca   7320
tattttgaa aaagccgttt ctgtaatgaa ggagaaaact caccgaggca gttccatagg   7380
atggcaagat cctggtatcg gtctgcgatt ccgactcgtc caacatcaat acaacctatt   7440
aatttcccct cgtcaaaaat aaggttatca agtgagaaat caccatgagt gacgactgaa   7500
tccggtgaga atggcaaaag cttatgcatt tctttccaaa cttgttcaac aggccagcca   7560
ttacgctcgt catcaaaatc actcgcatca accaaaccgt tattcattcg tgattgcgcc   7620
tgagcgagac gaaatacgcg atcgctgtta aaaggacaat tacaaacagg aatcgaatgc   7680
aaccggcgca ggaacactgc cagcgcatca acaatatttt cacctgaatc aggatattct   7740
tctaatacct ggaatgctgt tttcccgggg atcgcagtgg tgagtaacca tgcatcatca   7800
ggagtacgga taaaatgctt gatggtcgga agaggcataa attccgtcag ccagtttagt   7860
```

```
ctgaccatct catctgtaac atcattggca acgctacctt tgccatgttt cagaaacaac   7920
tctggcgcat cgggcttccc atacaatcga tagattgtcg cacctgattg cccgacatta   7980
tcgcgagccc atttataccc atataaatca gcatccatgt tggaatttaa tcgcggcctc   8040
gagcaagacg tttcccgttg aatatggctc ataacacccc ttgtattact gtttatgtaa   8100
gcagacagtt ttattgttca tgatgatata ttttatctt gtgcaatgta acatcagaga    8160
ttttgagaca caacgtggct ttccccccc ccccattatt gaagcattta tcagggttat    8220
tgtctcatga gcggatacat atttgaatgt atttagaaaa ataaacaaat aggggttccg   8280
cgcacatttc cccgaaaagt gccacctgac gtctaagaaa ccattattat catgacatta   8340
acctataaaa ataggcgtat cacgaggccc tttcgtc                            8377

SEQ ID NO: 14          moltype = DNA   length = 8179
FEATURE                Location/Qualifiers
misc_feature           1..8179
                       note = Description of Artificial Sequence: Synthetic
                       polynucleotide
source                 1..8179
                       mol_type = other DNA
                       organism = synthetic construct
SEQUENCE: 14
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga cagattgta ctgagagtgc     180
accatatgcg gtgtgaaata ccgcacagat gcgtaaggag aaaataccgc atcagattgc    240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaatagggg ctttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctccccttg gagcctacct agactcggcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacac gtgtgatcag atatcgcggc cgcatgaatt   1380
acataccaac ccagactttt tacggacgcc gttggcggcc tcgccggccg ttccgtccat   1440
ggcaggtgcc gatgcagccg cacctacta tggttacacc catgctgcaa gcaccggacc    1500
tacaggctca acagatgcaa caactgatca gcgcagtctc tgcactaacc accaaacaga   1560
atgtaaaagc accaaagggg caacggaaac agaaacagca gaaccaaag gaaagaaggg    1620
aaaaacagaa gaaaaagccg acgcnnaaga agaagcagca gcagaaacca aaaccacagg   1680
ctaagaagaa gaaaccaggg agaagagaaa gaatgtgcat gaagatcgag aatgactgca   1740
tattcgaggt caaactggac ggcaaggtta ccggctatgc gtgcctagtc ggagataagg   1800
tcatgaagcc ggctcacgtt aaaggcacaa ttgataaccc agaccttgcg aagttgactt   1860
acaagaaatc cagtaagtat gacctcgaat gcgcccagat cccagtgcac atgaagtccg   1920
acgcctccaa gtacacacat gaaaagcccg aaggtcatta caattggcac catgagcag   1980
tgcagtacag cgnnggaagg tttaccatcc ccacaggcgc cggcaaacca ggagatagcg   2040
gtaggcctat ttttgacaac aaaggcgag tngtggccat cgtgttaggc ggggccaacg    2100
aaggtgcccg cactgcgctg tctgtggtga cgtggacaaa agacatggtc actcgggtaa   2160
cgccagaagg aaccgaagag tggtctgccg cgctgatgat gtgtatcctt gccaacacct   2220
cttccccatg ctcgtcacct ccctgctacc cctgctgcta cgaaaaacag ccagaacaga   2280
cactgcggat gctggaagac aacgtgaata gacctgggta ctatgagtta ctggaagcgt   2340
ccatgacatg cagaaacaga tcacgccacc gccgcagtgt aatagagcac ttcaatgtgt   2400
ataaggctac tagaccgtac ttagcnnact gcgctgactg cggggacggg tacttctgct   2460
atagcccggt tgctatcgag aagatccgag atgaggcgtc tgatggcatg ctcaagatcc   2520
aagtctccgc ccaaataggt ctggacaagg caggtaccca cgcccacacg aagatgcgat   2580
atatggctgg tcatgatgtt caggaatcta agagagattc cttgagggtg tatacgtccg   2640
cagcgtgctc tatacatggg acgtgggac acttcatcgt cgcacactgt ccaccaggcg   2700
actacctcaa ggnttcgttc gaggacgcaa attcacacgt gaaggcatgt aaggtccaat   2760
acaagcacga cccattgccg gtgggtagag agagtttgt ggttagacca cactttggcg     2820
tagagctgcc atgcacctca taccagctga caacggctcc caccgacgag gagattgaca   2880
tgcatacacc gccagatata ccggatcgca ccctgctatc acagcaggcg ggcaacgtca   2940
aaataacagc aggcggcagg actatcaggt acaattgtac ctgcggcccgt gacaacgtag   3000
gcactaccag tactgacaag accatcaaca catgcaagat agaccaatgc catgctgccg   3060
ttaccagcca tgacaaatgg naatttacct ctccatttgt tccagggct gatcagacag    3120
ccaggaaagg caaagtgcat gttccattcc ctttgactaa cgtcacctgc cgagtgccgt   3180
tggcacgagc gccggatgtc acctatgta agaggaggt gaccctaaga ttacacccag     3240
atcatccgac gcncttctcc tataggagtt taggacccgt accgcactca tacggaggat   3300
gggttgacaa gttctctgag cgcatcatcc cagtgacgga agaaggatt gagtaccagt     3360
ggggtaacaa cccgccggtc cgcctgtggg cgcaactgac gactgagggt aaacccccatg   3420
gctgccaca tgaaatcatt cagtactatt atggactata ccccgccgcc actattgccg    3480
cagtatccgg ggcgagtctg atggcctcc taactctagc ggccacatgc tgcatgctgg    3540
ccaccgcgag gagaaagtgc ctaacaccgt acgctttgac gccaggagcg gtggtaccgt   3600
```

```
tgacattggg gctgcttnnn tgcgcaccga gggcgaacgc agcatcattt gctgagacta 3660
tggcctatct gtgggacgag aacaaaaccc tcttttggat ggaatnnnnn nnnnnnnnnn 3720
nngcgcttgc tttgctggca tgctgtatca aaagccgat ctgctgttgt aagccatttt 3780
cttttttagt gttactgagc ctgggagcct ccgcaaaagc ttatgagcac acagccacaa 3840
ttccgaacgt ggtggggttc ccgtataagg ctcacattga aaggaatnnn ttctcgccca 3900
tgactctgca gcttgaagtg gtgganncaa gcttgaacc cacacttaac ctggagtaca 3960
ttacctgcga atacaagacg gtggtcccctt cgccatttat caaatgttgc ggaacatcag 4020
aatgctcatc taaagagcag ccagactacc aatgcaaggt gtacacgggt gtataccctt 4080
tcatgtgggg tggagcttac tgtttctgcg actccgagaa cacgcagctt agcgaggcct 4140
atgtcgacag gtcagacgtt tgcaaacatg atcatgcatt ggcctacaag gcacacacgg 4200
cctctctaaa agcaacaatc aggatcagct acggcaccat caaccagacc accgaggcct 4260
tcgtcaatgc agaacacgcg gtcaacgtgg gcggaagcaa gttcatcttt ggaccgatct 4320
caacagcttg gtcaccgttc gacaataaaa ttgtcgtgta taaagatgat gtctacaacc 4380
aggacttccc accctacgga tcaggccagc cgggnagatc cggagacatc cagagcagga 4440
cagtggagag caaagacttg tatgctaata cggccctaaa actctcaaga ccatcacccg 4500
gggttgtgca tgtgccatac acgcagacac catccggatt taagtattgg ctgaaggaga 4560
aaggatcttc attgaataca aaggccccctt ttggctgcaa gataaagacc aatccagtca 4620
gagctatgga ttgtgcagtt ggcagtatac ctgtgtcgat gacataccct gacagtgcat 4680
tcacacgagt ggtagatgcc ccggctgtaa cagacctgag ctgccaggta gctgtctgta 4740
cacactcctc cgatttcgga nnngttgcca cattgtctta caagacggac aaacccggca 4800
agtgcgccgt tcactcacat tccaacgtcg caacgttgca agaggcgacg gtggatgtca 4860
aggaggatgg caaggtcaca gtgcacttttt ctnnnnnngtc cgcctccccg gcattcaaag 4920
tgtccgtctg tgacgcaaaa acaacgtgca cggcggcgtg cgagcctccg aaagaccaca 4980
tcgtccctta tggggcgagc cataacaacc aggtctttcc ggacatgtca ggaactgcga 5040
tgacgtgggt acagaggatg gccagtgggt taggtgggct ggccctcatc gcggtggttg 5100
tgctgtctt ggtaacctgc ataacaatgc gtcggtaatc tagaccaggc cctggatcca 5160
gatctgctgt gccttctagt tgccagccat ctgttgtttg cccctccccc gtgccttcct 5220
tgaccctgga aggtgccact cccactgtcc tttcctaata aaatgaggaa attgcatcgc 5280
attgtctgag taggtgtcat tctattctgg ggggtgggt ggggcaggac agcaaggggg 5340
aggattggga agacaatagc aggcatgctg gggatgcgt gggctctatg ggtacccaga 5400
tgctgaagaa ttgacccggt tcctcctggg ccagaaagaa gcaggcacat cccccttctct 5460
gtgacacacc ctgtccacgc ccctggttct tagttccagc cccactcata ggacactcat 5520
agctcaggag ggctccgcct tcaatcccac ccgctaaagt acttggagcg gtctctcccct 5580
ccctcatcag cccaccaaac caaacctagc ctccaagagt gggaagaaat taaagcaaga 5640
taggctatta agtgcagagg gagagaaaat gcctccaaca tgtgaggaag taatgagaga 5700
aatcatagaa ttttaaggcc atgatttaag gccatcatgg ccttaatctt ccgcttcctc 5760
gctcactgac tcgctgcgct cggtcgttcg gctgcgcga gcggtatcag ctcactcaaa 5820
ggcggtaata cggttatcca cagaatcagg ggataacgca ggaaagaaca tgtgagcaaa 5880
aggccagcaa aaggccagga accgtaaaaa ggccgcgttg ctggcgtttt tccataggct 5940
ccgcccccct gacgagcatc acaaaaatcg acgctcaagt cagaggtggc gaaacccgac 6000
aggactataa agataccagg cgtttcccccc tggaagctcc ctcgtgcgct ctcctgttcc 6060
gaccctgccg cttaccggat acctgtccgc ctttctcccct tcgggaagcg tggcgcttttc 6120
tcatagctca cgctgtaggt atctcagttc ggtgtaggtc gttcgctcca agctgggctg 6180
tgtgcacgaa ccccccgttc agcccgaccg ctgcgcctta ccggtaact atcgtcttga 6240
gtccaacccg gtaagacacg acttatcgcc actggcagca gccactggta acaggattag 6300
cagagcgagg tatgtaggcg gtgctacaga gttcttgaag tggtggccta actacggcta 6360
cactagaaga acagtatttg gtatctgcgc tctgctgaaga ccagttacct tcggaaaaag 6420
agttggtagc tcttgatccg gcaaacaaac caccgctggt agcggtggtt ttttttgtttg 6480
caagcagcag attacgcgca gaaaaaaagg atctcaagaa gatcctttga tcttttctac 6540
ggggtctgac gctcagtgga acgaaaactc acgttaaggg attttggtca tgagattatc 6600
aaaaaggatc ttcacctaga tccttttaaa ttaaaaatga agttttaaat caatctaaag 6660
tatatatgag taaacttggt ctgacagtta ccaatgctta atcagtgagg cacctatctc 6720
agcgatctgt ctatttcgtt catccatagt tgcctgactc ggggggggggg ggcgctgagg 6780
tctgcctcgt gaagaaggtg ttgctgactc ataccaggcc tgaatcgccc catcatccag 6840
ccagaaagtg agggagccac ggttgatgag agctttgttg taggtggcac agttggtgat 6900
tttgaacttt tgctttgcca cggaacggtc tgcgttgtcg ggaagatgcg tgatctgatc 6960
cttcaactca gcaaaagttc gatttattca acaaagccgc cgtcccgtca agtcagcgta 7020
atgctctgcc agtgttacaa ccaattaacc aattctgatt agaaaaactc atcgagcatc 7080
aaatgaaact gcaatttatt catatcagga ttatcaatac catattttttg aaaaagccgt 7140
ttctgtaatg aaggagaaaa ctcaccgagg cagttccata ggatggcaag atcctggtat 7200
cggtctgcga ttccgactcg tccaacatca atacaaccta ttaatttccc ctcgtcaaaa 7260
ataaggttat caagtgagaa atcaccatga gtgacgactg aatccggtga atgatggcaaa 7320
agcttatgca tttctttcca gacttgttca acaggccagc cattacgctc gtcatcaaaa 7380
tcactcgcat caaccaaacc gttattcatt cgtgattgcg cctgagcgag acgaaatacg 7440
cgatcgctgt taaaaggaca attcaaaaca ggaatcgaat gcaaccggcg caggaacact 7500
gccagcgcat caacaatatt ttcacctgaa tcaggatatt cttctaatac ctggaatgct 7560
gttttcccgg ggatcgcagt ggtgagtaac catgcatcat caggagtacg gataaaatgc 7620
ttgatggtcg gaagaggcat aaattccgtc agccagttta gtctgaccat ctcatctgta 7680
acatcattgg caacgctacc tttgccatgt ttcagaaaca actctcggcg catcgggcttc 7740
ccatacaatc gatagattgt cgcacctgat tgcccgacat tatcgcgagc ccatttatac 7800
ccatataaat cagcatccat gttggaattt aatcgcggcc tcgagcaaga cgtttcccgt 7860
tgaatatggc tcataacacc ccttgtatta ctgtttatgt aagcagacag ttttattgtt 7920
catgatgata tatttttatc ttgtgcaatg taacatcaga gattttgaga cacaacgtgg 7980
ctttccccccc ccccccatta ttgaagcatt tatcagggtt attgtctcat gagcggatac 8040
atatttgaat gtatttagaa aaataaacaa ataggggttc cgcgcacatt tccccgaaaa 8100
gtgccacctg acgtctaaga aaccattatt atcatgacat taacctataa aataggcgt 8160
atcacgaggc cctttcgtc                                                8179

SEQ ID NO: 15        moltype = DNA   length = 8145
```

```
FEATURE                 Location/Qualifiers
misc_feature            1..8145
                        note = Description of Artificial Sequence: Synthetic
                        polynucleotide
source                  1..8145
                        mol_type = other DNA
                        organism = synthetic construct SEQUENCE: 15
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcagattgg   240
ctattggcca ttgcatacgt tgtatccata tcataatatg tacattata ttggctcatg    300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagga cttttccattg acgtcaatgg gtggagtatt tacggtaaac    540
tgcccacttg gcagtacatc aagtgtatca tatgccaagt acgccccta ttgacgtcaa     600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcagtaaa agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc   1020
cgccctacct gaggccgcca tccacgccgg ttgagtcgcg ttctgccgcc tcccgcctgt   1080
ggtgcctcct gaactgcgtc cgccgtctag gtaagtttaa agctcaggtc gagaccgggc   1140
ctttgtccgg cgctcccttg gagcctacct agactcagcc ggctctccac gctttgcctg   1200
accctgcttg ctcaactcta gttaacggtg gagggcagtg tagtctgagc agtactcgtt   1260
gctgccgcgc gcgccaccag acataatagc tgacagacta acagactgtt cctttccatg   1320
ggtcttttct gcagtcaccg tcgtcgacca ccatggagtt cataccagca caaacttact   1380
acaatagaag ataccagcct agaccctgga ctcaacgccc tactatccag gtgatcaggc   1440
caaaaccacg ccgaagaagg cctgcaggac aactcgcaca actgatatcc gcagtcagca   1500
gactagcact gcgtacagtt ccccagaaac cacgccggac ccgaaaaatt aagaagcaaa   1560
agcaagtaaa gcaagaacaa cagagtacta cgaaccagaa gaaaaaggcg ccgaaacaaa   1620
agcagaccca aaagaaaaag agaccaggac gaagggaaag gatgtgcatg aagattgaaa   1680
atgactgcat cttcgaagtc agacatgaag gaaaagtaac ggggtatgca tgcctagtag   1740
gtgataaggt aatgaaacca gcacacgtga aggaactact tgacaacgca gacctagcga   1800
agttggcgtt caaaagatca tccaaatatg atctagagtg gcacagata ccagtgcaca    1860
tgaaatcgga cgcctcaaag ttcacccatg aaaaaccaga aggtattac aactggcatc     1920
acggagcagt acagtattct ggagggaggt tcacgatccc tacaggcgca ggaaagcctg   1980
gggacagcgg aagaccaatc tttgacaaca aggggcgtgt cgtggctatt gttctaggcg   2040
gagcaaacga aggaaccagg acagcactat ctgtagtgac ttggaataaa gacatagtca   2100
caaaaatcac accagagggg tcagttgaat ggagccttgc cctccctgtc atgtgcctgt   2160
tggcaaatac aaccttccca tgttcccaac cgccttgcgc gccgtgctgc tacgaaaaga   2220
aaccggaaga aaccttgaga atgctggagg acaacgtcat gcaaccagga tattaccagt   2280
tactcgattc agcattggcc tgctcacaac gtcgtcaaaa acgtaatgca agagaaaact   2340
tcaatgtcta caaagtcact aggccgtact tagcccactg tcctgactgc ggggagggac   2400
actcatgcca cagcccaata gcattagaac ggatcagaag tgaggcaaca gatggtaccct   2460
tgaaaatcca ggtatctctg caaatcgaa taaagacaga cgacagccac gattggacga     2520
agctacggta tatggatagc catacacctg tggatgcaga tcgatccggg ttgttttgta    2580
gaacgtcagc accgtgcacc atcacggaa cgatgggaca tttcatacta gcacgctgtc    2640
cgaaggaga gacgctgacg gtaggatttg tagacagtag aaggatcagt cacacgtgca     2700
tgcacccgtt ccgccacgag ccaccgctga tagggagaga gaagtttcac tcccgcccgc   2760
agcatggcaa agaactacct tgcagtacat acgtccatac cacagcggca actgctgagg   2820
aaatagaagt gcatatgccg ccagataccc ctgactacac gctgatgaca cagcaagcgg   2880
gaaacgttaa gatcacagtt gacggccaga cggtacgata caagtgcaaa tgtgacggct   2940
ccaatgaagg attaataacc gctgacaaag tcataaataa ctgcaaagta gaccaatgcc   3000
acacagcggt tacaaaccac aagaaatggc aatacaattc accgctgacc ccgcggaact   3060
ccgaacaagg agatagaaaa ggtaagatcc atatcccatt tccactggtg aacaccaacct   3120
gcagggtacc aaaagcaaga aatccgactg tcacatacgg taaaaacaga gtcactctgc    3180
tgttacatcc agaccaccca acactccttt cgtaccgcgc catgggaagg atcccggatt   3240
accatgaaga gtggataaca aacaagaagg aaataagtat cacagtacca gcagaaggct   3300
tagaggttac gtggggtaat aatgacccat acaaatattg gccccaactg tctacaaatg   3360
gtactgcgca cgggcaccca catgaaataa tcctctatta ctatgagctg taccagggtt   3420
ccacaattgc tgtactagct gctgcttcta tcgtaataac atctttggta ggtctatcat   3480
taggcatgtg catatgcgcg agacgcaggt gcatcacgcc atatgagctg actccaggag   3540
ctaccatccc attcctccta ggtgtactat gctgtgccag gactgcaaaa gcagcatcgt   3600
actacgaagc tgcaacatac ctctggaatg agcaacaacc attattttgg ttacagctc    3660
taatccctct gtcagctgca attgttgtgt gtaattgcct aaaacttta ccatgctgct    3720
gcaaaacatt gactttttta gccgtcatga gcatcggtgc ccgcactgtg accgcgtacg    3780
agcacgcaac agtgatcccg aacacggtgg gagtaccgtg taagactctt gttagcagac   3840
cagggtacag ccctatggtc ttagaaatgg agctacagtc ggtcactctg gaaccagcat   3900
tatccttgga ttacattacg tgtgagtata aacaatcac cgtccccgtg tacgtaaaat    3960
gctgtggtac agctgaatgt aaggccaaga cctgccagca ttataactgc aaagtattca   4020
caggcgtcta cccattatat gggggaggag catactgctt ctgtgacgca gagaacacac   4080
agctcagcga ggcacacgtt gagaaatcag aatcatgcaa aactgagttt gcatcagcct   4140
acagagccca cacagcttca gtatcagcta aactacgtgt cttttaccaa gggaataata   4200
tcaccgtgtc tgcatacgcc aatggtgatc atgcagttac ggtggaagac gcgaagtttg   4260
```

```
tcatcggtcc actatcgtcc gcctggtcac catttgataa taagatcgtg gtgtacaaag    4320
gcgaagtcta caatatggac tatccacctt tcggcgcagg gaggccagga cagttcggtg    4380
acatccagag ccgcacgcca gacagcaagg acgtctatgc gaatacgcag ttaatactgc    4440
aaagaccagc ggcaggagca atacacgtgc cttactccca ggcaccttcg ggctttaagt    4500
actggctcaa ggaaaaaggg gcatcattgc agcatactgc accatttggc tgtcagatag    4560
caacaaaccc ggtaagagca gtgaactgtg cagtgggcaa cataccagtc tccattgaca    4620
tcccagatgc agctttcacc agggtcactg acgctcctttc catcacagac atgtcctgcg    4680
aagtagcttc gtgtacccat tcatctgatt ttggaggtgc cgcagtcata aagtacacag    4740
ctagtaaaaa aggaaaatgc gccgtgcact ctgtaacaaa tgcggtcact atccgcgaac    4800
ctaacgtaga tgtcaaggga acagcacaat tgcaaattgc cttctcgacc gcactagcta    4860
gtgcggaatt caaggtgcag atctgctcca cactggtaca ctgctcagcg acgtgccatc    4920
ctcctaaaga ccatatagtc aattacccgt cacctcacac cacactagga gtgcaggaca    4980
tttcaacgac agctatgtct tgggtccaga agattacagg aggagtggga ctcgtggttg    5040
ctatagctgc tttgatcta atattagttc tctgcgtatc atttagcaga cactaagcgg    5100
ccgctctaga ccaggccctg gatccagatc tgctgtgcct tctagttgcc agccatctgt    5160
tgtttgcccc tcccccgtgc cttccttgac cctggaaggt gccactccca ctgtcctttc    5220
ctaataaaat gaggaaattg catcgcattg tctgagtagg tgtcattcta ttctgggggg    5280
tggggtgggg caggacagca agggggagga ttgggaagac aatagcaggc atgctgggga    5340
tgcggtgggc tctatgggta cccaggtgct gaagaattga cccggttcct cctgggccag    5400
aaagaagcag gcacatcccc ttctctgtga cacaccctgt ccacgcccct ggttcttagt    5460
tccagcccca ctcataggac actcatagct caggagggcc ccgccttcaa tcccacccgc    5520
taaagtactt ggagcggtct ctccctcct catcagccca ccaaaccaaa cctagcctcc    5580
aagagtggga agaaattaaa gcaagatagg ctattaagtg cagagggaga gaaatgcct    5640
ccaacatgtg aggaagtaat gagagaaatc atagaatttt aaggccatga tttaaggcca    5700
tcatggcctt aatcttccgc ttcctcgctc actgactcgc tgcgctcggt cgttcggctg    5760
cggcgagcgg tatcagctca ctcaaaggcg gtaatacgg atccacaga atcagggat    5820
aacgcaggaa agaacatgtg agcaaaaggc cagcaaaagg ccaggaaccg taaaaaggcc    5880
gcgttgctgg cgtttttcca taggctccgc cccctgacg agcatcacaa aaatcgacgc    5940
tcaagtcaga ggtggcgaaa cccgacagga ctataaagat accaggcgtt ccccctgga    6000
agctccctcg tgcgctctcc tgttccgacc ctgccgctta ccggatacct gtccgccttt    6060
ctcccttcgg gaagcgtggc gctttctcat agctcacgct gtaggtatct cagttcggtg    6120
taggtcgttc gctccaagct gggctgtgtg cacgaaccc cgttcagcc cgaccgctgc    6180
gccttatccg gtaactatcg tcttgagtcc aacccggtaa gacacgactt atcgccactg    6240
gcagcagcca ctggtaacag gattagcaga gcgaggtatg taggcggtgc tacagagttc    6300
ttgaagtggt ggcctaacta cggctacact agaagaacag tatttggtat ctgcgctctg    6360
ctgaagccag ttaccttcgg aaaaagagtt ggtagctctt gatccggcaa acaaaccacc    6420
gctggtagcg gtggtttttt tgtttgcaag cagcagatta cgcgcagaaa aaaggatct    6480
caagaagatc ctttgatctt ttctacgggg tctgacgctc agtggaacga aaactcacgt    6540
taaggattt tggtcatgag attatcaaaa aggatcttca cctagatcct tttaaattaa    6600
aaatgaagtt ttaaatcaat ctaaagtata tatgagtaaa cttggtctga cagttaccaa    6660
tgcttaatca gtgaggcacc tatctcagcg atctgtctat ttcgttcatc catagttgcc    6720
tgactcgggg ggggggggcg ctgaggtctg cctcgtgaag aaggtgttgc tgactcatac    6780
caggcctgaa tcgccccatc atccagccag aaagtgaggg agccacggtt gatgagagct    6840
ttgttgtagg tggaccagtt ggtgattttg aacttttgct ttgccacgga acggtctgcg    6900
ttgtcgggaa gatgcgtgat ctgatccttc aactcagcaa aagttcgatt tattcaacaa    6960
agccgccgtc ccgtcaagtc agcgtaatgc tctgccagtg ttacaaccaa ttaaccaatt    7020
ctgattagaa aaactcatcg agcatcaaat gaaactgcaa tttattcata tcaggattat    7080
caataccata tttttgaaaa agccgtttct gtaatgaagg agaaaactca ccgaggcagt    7140
tccataggat ggcaagatcc tggtatcggt ctgcgattcc gactcgtcca acatcaaatac   7200
aacctattaa tttcccctcg tcaaaaataa ggttatcaag tgagaaatca ccatgagtga    7260
cgactgaatc cggtgagaat ggcaaaagct tatgcatttc tttccagact tgttcaacag    7320
gccagccatt acgctcgtca tcaaaatcac tcgcatcaac caaaccgtta ttcattcgtg    7380
attgcgcctg agcgagacga aatacgcgat cgctgttaaa aggacaatta caaacaggaa    7440
tcgaatgcaa ccggcgcagg aacactgcca gcgcatcaac aatattttca cctgaatcag    7500
gatattcttc taatacctgg aatgctgttt tcccggggat cgcagtggtg agtaaccatg    7560
catcatcagg agtacggata aaatgcttga tggtcggaag aggcataaat tccgtcagcc    7620
agtttagtct gaccatctca tctgtaacat cattggcaac gctacctttg ccatgtttca    7680
gaaacaactc tggcgcatcg ggcttcccat acaatcgata gattgtcgca cctgattgcc    7740
cgacattatc gcgagcccat ttatacccat ataaatcagc atccatgttg gaatttaatc    7800
gcggcctcga gcaagacgtt tcccgttgaa tatggctcat aacacccctt gtattactgt    7860
ttatgtaagc agacagtttt attgttcatg atgatatatt tttatcttgt gcaatgtaac    7920
atcagagatt ttgagacaca acgtggcttt ccccccccc ccattattga agcatttatc    7980
agggttattg tctcatgagc ggatacatat ttgaatgtat ttagaaaaat aaacaaatag    8040
gggttccgcg cacatttccc cgaaaagtgc cacctgacgt ctaagaaacc attattatca    8100
tgacataac ctataaaaat aggcgtatca cgaggccctt tcgtc                    8145
```

SEQ ID NO: 16        moltype = DNA  length = 8132
FEATURE              Location/Qualifiers
misc_feature       1..8132
                      note = Description of Artificial Sequence: Synthetic
                      polynucleotide
source               1..8132
                      mol_type = other DNA
                      organism = synthetic construct
SEQUENCE: 16

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
```

```
ctattggcca ttgcatacgt tgtatccata tcataaatgt tacatttata ttggctcatg  300
tccaacatta ccgccatgtt gacattgatt attgactagt tattaatagt aatcaattac  360
ggggtcatta gttcatagcc catatatgga gttccgcgtt acataactta cggtaaatgg  420
cccgcctggc tgaccgccca acgaccccg cccattgacg tcaataatga cgtatgttcc  480
catagtaacg ccaatagga cttttccattg acgtcaatgg gtggagtatt tacggtaaac  540
tgcccacttg gcagtacatc aagtgtatca tatgccaagt acgccccta ttgacgtcaa  600
tgacggtaaa tggcccgcct ggcattatgc ccagtacatg accttatggg actttcctac  660
ttggcagtac atctacgtat tagtcatcgc tattaccatg gtgatgcggt tttggcagta  720
catcaatggg cgtggatagc ggtttgactc acggggattt ccaagtctcc accccattga  780
cgtcaatggg agtttgtttt ggcaccaaaa tcaacgggac tttccaaaat gtcgtaacaa  840
ctccgcccca ttgacgcaaa tgggcggtag gcgtgtacgg tgggaggtct atataagcag  900
agctcgttta gtgaaccgtc agatcgcctg gagacgccat ccacgctgtt ttgacctcca  960
tagaagacac cgggaccgat ccagcctcca tcggctcgca tctctccttc acgcgcccgc 1020
cgccctacct gaggccgcca tccacgccgg ttgagtcgcg ttctgccgcc tcccgcctg  1080
ggtgcctcct gaactgcgtc cgccgtctag gtaagtttaa agctcaggtc gagaccgggc 1140
ctttgtccgg cgctcccttg gagcctacct agactcagcc ggctctccac gctttgcctg 1200
accctgcttg ctcaactcta gttaacggtg gagggcagtg tagtctgagc agtactcgtt 1260
gctgccgcgc gcgccaccag acataatagc tgacagacta agagactgtt ccttttccatg 1320
ggtcttttct gcagtcaccg tcgtcgacac gtgtgatcag atatcgcggc cgccaccatg 1380
gacttcctac caactcaagt gttctatggc agacgctgga gaccacgaat gccgccacgc 1440
ccttggagac cacgcatgcc tacaatgcag agaccagacc aacaggcccg acaaatgcag 1500
caattgattg cagcggttag cacgcttgcc ctgaggcaga atgcagccgc ccctcagcgt 1560
ggaaagaaga agcagccacg cagaaagaaa ccaaaaccgc agcccgagaa accaaagaag 1620
caagaacaga agccgaagca aaagaaggcc cctaaacgaa agcagggag aagagaacgc 1680
atgtgcatga agattgagca tgattgcatc ttcgaggtta agcacgaagg taaagtcacg 1740
ggttacgcct gccttgtcgg tgacaaggta atgaagccga cacacgttcc cggggtgata 1800
gacaatgcag atcttgcacg cctgtcgtac aagaaatcca gtaagtacga tctggaatgt 1860
gcacaaatac ccgtggctat gaagtcagat gcttcgaagt acaccatga gaaacccgag 1920
ggtcattaca actggcacta cggcgccgtc cagtacacgg gaggaagatt cacggtgccc 1980
acaggagtgg gtaagcctgg cgacacggt cggcccatct ttgacaacaa agggccggtc 2040
gtcgcaatag tgctgggagg agccaacgaa ggtaccagaa ccgcccttc cgttgtgaca 2100
tggaataaag acatggtcac gaagattaca cctgaaggca ctgtggagtg ggcagcctcg 2160
acagtgacga ccatgtgtct tttgacaaat atatccttcc catgttcca accgagctgt 2220
gcaccgtgct gctatgaaaa ggggcctgag ccgacgctga ggatgctgga ggagaacgta 2280
aattcagaag gatattacga cctgctgcac gctgccgtgt actgtagaaa cagttcaagg 2340
tcgaagagaa gcactgcaaa tcattttaat gcgtataagt tgacccgtcc atatgtggct 2400
tactgcgcag actgcggtat gggtcattct tgccacagcc cagccatgat cgaaaatatt 2460
caggcggatg caacagatgg cacgctaaaa attcagtttg cttcccaaat tggcctgacc 2520
aaaacggaca cgcacgatca cacaaagatt agatatgctg aaggacacga cattgcagag 2580
gctgccagat caacccttaa ggtacacagt agcagtgagt gcacggtaac cggcacaatg 2640
ggacacttta tcctgccaa atgtccacct ggcgaacgaa tcagtgtctc atttgttgat 2700
tcgaaaaacg aacaccggac ctgccggata gcctaccacc atgaacagag gttaataggg 2760
cgagaaagat tcacggttgcg accgcatcat ggaattgaac taccttgcac cacttatcaa 2820
ttgactaccg ccgaaacctc tgaagaaatt gatatgcaca tgccgccgga cattccggat 2880
agaactatcc tttcccaaca atcaggaaat gttaagataa cggtgaatgg acgaaccgtc 2940
aggtacagct cttcttgcgg ttcccaagcc gtcgggacaa caaccacaga caagaccatt 3000
aatagctgta ccgttgacaa atgtcaggct tacgtcacga gccacacaaa atggcaaattc 3060
aattcacctt ttgtcccacg tcggatgcaa gcagagcgca agggcaaagt gcatatcccc 3120
tttccccctta ttaacaccac ctgccgtgta ccgctggctc ccgaggccct tgttaggagc 3180
ggtaaacgcg aagctacact ttcattgcac cctatccacc ccacattgct aagttacaga 3240
acatttggag cggagcgggt cttttgacgag cagtggatca ccgcccagac ggaggtaacg 3300
atcccggtac ctgtggaggg agtgagtac cagtggggca accataaacc tcaacgtttt 3360
gtggtcgcac tgacgactga aggcaaagca catggatggc ctcatgaaat tattgaatac 3420
tactacggac tgcatcctac gacaaccatt gtcgtggtga ttcgtgtctc agtggtggta 3480
cttctgtcat tcgccgcctc ggtctcatg tgcgtggtag cacgaaccaa atgtctgaca 3540
ccatatgcac tcacgccggg agctgttgtt cctgttacca ttggggtgct gtgttgcgca 3600
ccgaaagcac atgcagccag tttcgcagaa ggtatggcct atctgtggga taacaatcag 3660
tcgatgttct ggatggagct gaccggacca ttggccctcc ttattctggc tacatgctgc 3720
gcccgatcac tgctttcctg ctgcaagggg tctttttag tcgcaatgag catcgggagt 3780
gccgttgcca gtgcttacga gcacacggca attattccga accaagtggg attcccgtat 3840
aaggctcatg ttgcgcgtga aggttacagt cctttgaccc tgcagatgca ggtgatagag 3900
accagccttg agcaaacact caacctggag tatatcactt gcgattacaa aacaaaagtt 3960
ccatcaccat acgtaaagtg ctgcggcacg gcagaatgcc gcacacagga caagcctgag 4020
tacaaatgtc agtgttcac aggtgtgtat actttttatg gggaggtgc atactgtttt 4080
tgtgattcgg agaacacaca gatgagcgaa gcctacgtgg agcgcgctga cgtgtgtaaa 4140
cacgaccacg cagctgccta ccgtcccac accgcatccc ttagagcaaa aattaaggtg 4200
acatacggta ctgtgaacca gacagttgag gcgtatgtga acggtgacca tgccgtaacg 4260
attgccggaa caaaatttat tttggggcca gtgtcaacgc cttggacacc gttcgataca 4320
aaaattctgg tttacaaagg ggagttatac aatcaggact tcccacgtta tggtgccggg 4380
cagcctggaa gatttgggga cattcagagc cggacgctgg atagtcgaga cctatatgcc 4440
aacacgggcc tcaagctggc acgaccggca gccggcaaca ttcacgtccc ctatacccag 4500
actccatctg gctttaaaac atggcaaaaa gacagggact caccgcttaa cgccaaggcg 4560
cctttttggat gcataatcca gacaaatccg gtccgagcca tgaactgcgc cgtcggcaac 4620
atacccgtt cgatggatat cgccgacagc ggcctccaga gattgaccga cgccgctgta 4680
atctctgagt tgacgtgcac tgtgtctaca tgcacgcact catcggattt tggcgggatc 4740
gctgtacttt cctacaaggt ggaaaatca ggcaggtgcg acatccattc acattcaaac 4800
gtcgcggtac tccaggaagt ttccatcgag acagaaggtc gatcagtgat ccacttctca 4860
accgcatcag cctccccttc cttcgtagtt tctgtttgta gttcgcgtgc tacgtgcaca 4920
gcgaaatgtg aaccaccgaa agaccacgtt gttacatatc cagcaaatca taacggggta 4980
```

```
actttgccag acttatctag cactgccatg acgtgggcac aacatcttgc cggcggagtt   5040
gggttgctga tagctctggc cgtgctaatt ctggtaatag ttacttgtgt gactttgaga   5100
aggtaaggat ccagatctgc tgtgccttct agttgccagc catctgttgt ttgccctcc    5160
cccgtgcctt ccttgaccct ggaaggtgcc actcccactg tcctttccta ataaaatgag   5220
gaaattgcat cgcattgtct gagtaggtgt cattctattc tggggggtgg ggtggggcag   5280
gacagcaagg gggaggattg ggaagacaat agcaggcatg ctggggatgc ggtgggctct   5340
atgggtaccc aggtgctgaa gaattgaccc ggttcctcct gggccagaaa gaagcaggca   5400
catcccttc tctgtgacac accctgtcca cgccctggt tcttagttcc agccccactc     5460
ataggacact catagctcag gagggctccg ccttcaatcc cacccgctaa agtacttgga   5520
gcggtctctc cctccctcat cagcccacca aaccaaacct agcctccaag agtgggaaga   5580
aattaaagca agataggcta ttaagtgcag agggagagaa aatgcctcca acatgtgagg   5640
aagtaatgag agaaatcata gaattttaag gccatgattt aaggccatca tggccttaat   5700
cttccgcttc ctcgctcact gactcgctgc gctcggtcgt tcggctgcgg cgagcggtat   5760
cagctcactc aaaggcggta atacggttat ccacagaatc aggggataac gcaggaaaga   5820
acatgtgagc aaaaggccag caaaaggcca ggaaccgtaa aaaggccgcg ttgctggcgt   5880
ttttccatag gctccgcccc cctgacgagc atcacaaaaa tcgacgctca agtcagaggt   5940
ggcgaaaccc gacaggacta taaagatacc aggcgtttcc ccctggaagc tccctcgtgc   6000
gctctcctgt tccgaccctg ccgcttaccg gatacctgtc cgcctttctc ccttcgggaa   6060
gcgtggcgct ttctcatagc tcacgctgta ggtatctcag ttcggtgtag gtcgttcgct   6120
ccaagctggg ctgtgtgcac gaaccccccg ttcagcccga ccgctgcgcc ttatccggta   6180
actatcgtct tgagtccaac ccggtaagac acgacttatc gccactggca gcagccactg   6240
gtaacaggat tagcagagcg aggtatgtag gcggtgctac agagttcttg aagtggtggc   6300
ctaactacgg ctacactaga agaacagtat ttggtatctg cgctctgctg aagccagtta   6360
ccttcggaaa aagagttggt agctcttgat ccggcaaaca aaccaccgct ggtagcggtg   6420
gtttttttgt ttgcaagcag cagattacgc gcagaaaaaa aggatctcaa gaagatcctt   6480
tgatcttttc tacggggtct gacgctcagt ggaacgaaaa ctcacgttaa gggattttgg   6540
tcatgagatt atcaaaaagg atcttcacct agatcctttt aaattaaaaa tgaagtttta   6600
aatcaatcta aagtatatat gagtaaactt ggtctgacag ttaccaatgc ttaatcagtg   6660
aggcacctat ctcagcgatc tgtctatttc gttcatccat agttgcctga ctcgggggg    6720
ggggcgctg aggtctgcct cgtgaagaag gtgttgctga ctcataccag gcctgaatcg    6780
ccccatcatc cagccagaaa gtgagggagc cacggttgat gagagctttg ttgtaggtgg   6840
accagttggt gattttgaac ttttgctttg ccacggaacg gtctgcgttg tcgggaagat   6900
gcgtgatctg atccttcaac tcagcaaaag ttcgatttat tcaacaaagc cgccgtcccg   6960
tcaagtcagc gtaatgctct gccagtgtta caaccaatta accaattctg attagaaaaa   7020
ctcatcgagc atcaaatgaa actgcaattt attcatatca ggattatcaa taccatattt   7080
ttgaaaagc cgtttctgta atgaaggaga aaactcaccg aggcagttcc ataggatggc    7140
aagatcctgg tatcggtctg cgattccgac tcgtccaaca tcaatacaac ctattaattt   7200
cccctcgtca aaaataaggt tatcaagtga gaaatcacca tgagtgacga ctgaatccgg   7260
tgagaatggc aaaagcttat gcatttcttt ccagacttgt tcaacaggcc agccattacg   7320
ctcgtcatca aaatcactcg catcaaccaa accgttattc attcgtgatt gcgcctgagc   7380
gagacgaaat acgcgatcgc tgttaaaagg acaattacaa acaggaatcg aatgcaaccg   7440
gcgcaggaac actgccagcg catcaacaat attttcacct gaatcaggat attcttctaa   7500
tacctggaat gctgttttcc cggggatcgc agtggtgagt aaccatgcat catcaggagt   7560
acggataaaa tgcttgatgg tcggaagagg cataaattcc gtcagccagt ttagtctgac   7620
catctcatct gtaacatcat tggcaacgct acctttgcca tgtttcagaa acaactctgg   7680
cgcatcgggc ttcccataca atcgatagat tgtcgcacct gattgcccga cattatcgcg   7740
agcccattta taccatata aatcagcatc catgttggaa tttaatcgcg gcctcgagca   7800
agacgtttcc cgttgaatat ggctcataac accccttgta ttactgttta tgtaagcaga   7860
cagttttatt gttcatgatg atatattttt atcttgtgca atgtaacatc agagattttg   7920
agacacaacg tggctttccc ccccccca ttattgaagc atttatcagg gttattgtct     7980
catgagcgga tacatatttg aatgtatta gaaaaataaa caaatagggg ttccgcgcac    8040
atttcccga aaagtgccac ctgacgtcta agaaaccatt attatcatga cattaaccta   8100
taaaaatagg cgtatcacga ggccctttcg tc                                 8132
```

```
SEQ ID NO: 17           moltype = DNA   length = 8134
FEATURE                 Location/Qualifiers
misc_feature            1..8134
                        note = Description of Artificial Sequence: Synthetic
                        polynucleotide
source                  1..8134
                        mol_type = other DNA
                        organism = synthetic construct
SEQUENCE: 17
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaatagggα ctttccattg acgtcaatgg gtggagtatt tacggtaaac   540
tgcccacttg gcagtacatc aagtgtatca tatgccaagt acgccccta ttgacgtcaa    600
tgacggtaaa tggcccgcct ggcattatgc ccagtacatg accttatgg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
```

```
                                           -continued
tagaagacac cgggaccgat ccagcctcca tcggctcgca tctctccttc acgcgcccgc    1020
cgccctacct gaggccgcca tccacgccgg ttgagtcgcg ttctgccgcc tcccgcctgt    1080
ggtgcctcct gaactgcgtc cgccgtctag gtaagtttaa agctcaggtc gagaccgggc    1140
ctttgtccgg cgctcccttg gagcctacct agactcagcc ggctctccac gctttgcctg    1200
accctgcttg ctcaactcta gttaacggtg gagggacgta tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgctctagac    1380
caggccctgg atccatggat ttcatcccca cccaaacctt ctatggtaga cgatggagac    1440
cagcaccagt ccagagatac ataccccaac cccaaccacc agcgcctcca cgccgtagga    1500
gaggaccatc tcaactccaa cagcttgtgg ctgcattggg cgcactagct ctacaaccca    1560
agcagaaaca aaaagagca cagaagaagc caagaagac accaccacca aaaccaaaaa    1620
agacccagaa gcctaagaaa ccaacccaaa agaagaagtc caaacccggc aaacgtatgc    1680
gtaactgcat gaagatcgag aatgactgca tctttccggt gatgctcgat ggaaaggtta    1740
acggctacgc ttgcttagtg ggggataaag tcatgaaacc agctcatgtg aagggcacga    1800
tcgacaatcc agaactagcc aaattgacat tcaagaaatc tagcaagtat gatctagaat    1860
gtgctcaagt gccggtatgc atgaaatcag acgcatccaa gttcacccat gagaaaccag    1920
aaggacatta caactggcac catggggcag tgcaatttag caatggtagg tttaccattc    1980
cgacgggctc tggcaaacct ggagacagtg gtaggcctat ttttgacaat accggcaagg    2040
tagtagccat agtgctggga ggtgcaaatg aaggggcccg gacagcccta tccgtggtca    2100
cctgaataa ggatatggtg acccgcataa cacctgaaga atcagtggag tggtcggcgg    2160
ccgcactgna tataacagca ctatgtgtcc tccagaactt atcgttcccg tgtgatgcac    2220
caccatgtgc accatgctgt tacgaaaaag accctgcagg gacccaaga ttgctgtctg    2280
accactacta ccaccccaag tattatgaat tacttgactc gacgatgcac tgcccacaag    2340
gaaggagacc taaggtct gttgcgcatt tcgaagccta caaggctacg agaccgtata    2400
tagggtggtg cgcagattgt ggactggcag gatcatgccc atccctgtg agcatcgagc    2460
acgtctggag tgatgccgac gacggcgtac tgaagatcca agtgtccata cagatcgatg    2520
tagctaaaag caatactatt aaccacgcta agatacgtta catgggtgcc aatgagtac    2580
aggaggctga acgctctacc ctaagtgtat ccacaacagc accatgtgac atcttggcga    2640
ccatgggcca tttcatcttg gcccgctgcc gacccggcag tcaagttgaa gtatcactaa    2700
gcaccgatcc aaagctgcta tgccgtacac cattctcccca caagcccagg tttattggca    2760
atgaaaagtc cccagcaccc accgggcaca gacccgaat tccctgcaaa acttactccc    2820
atcagacaga cttaacgaga gaagagatta caatgcatgt accgccggat gtccccatcc    2880
aagggctagt gtccaataca ggtaagtcgt actcattaga cccaaagacg aagaccatca    2940
agtacaaatg cacttgcggc gagactgtaa aagaaggtac tgctacgaac aaaatcacac    3000
tgttcaattg tgacaccgcc ccaaagtgta ttacatatgc agtggataac acagtgtggc    3060
agtacaactc ccaatacgtg cccaggtccg aagttacgga ggtgaaagga aagatccatg    3120
tgccttttcc tctgaccgac agcacgtgtg cagtcagcgt agcacctgaa ccgcaagtga    3180
catacagact gggggaagtg gagttccact tccaccctat gtaccccacc ctcttcca    3240
ttaggagcct cggaaaggat ccgagccaca gtcaagaatg gatagataca cccatgagca    3300
agacaatcca agttggggca gaaggcgtgg agtatgtctg gggaaacaac aacccggtac    3360
gactatgggc acagaagagc tcatcgagca gcgcgcatgg taaccctatt agcatagtct    3420
cacattacta tgacctgtac ccttactgga ccatcacagt actagcgagt ctaggcttgc    3480
taatagtgat tagttccggt ttttcatgct tttgtgttc agtcgctcga accaaatgcc    3540
ttacacccta tcaattagca ccaggcgccc aattacccac atttatagca ctccttttgct    3600
gcgctaagtc tgcacgcgca gacactttag atgattttc ctacctgtgg accaacaacc    3660
aagccatgtt ttggctccaa ctggcatctc cggttcagc gttcttgtgc ttatcctatt    3720
gctgtagaaa tctagcatgc tgtatgaaga tttttttagg gataagcgc ctgtgtgtaa    3780
ttgccacgca ggcctacgag cactcaacca cgatgccgaa tcaggtggga ataccgttta    3840
aagccttgat agagcgacca ggttacgcag gcctcccgct atctttagta gtgattaagt    3900
cagaattagt cccctcatta gttcaggatt atattacctg caactacaag actgtggtcc    3960
cgtctccgta cattaaatgt tgcggaggcg ctgagtgttc acacaaaaat gaagcggact    4020
ataagtgctc ggtgttcaca ggcgtgtacc cgtttatgtg gggaggcgcc tactgcttcc    4080
gtgacaccga aaacagtcag atgagtgaag tatacgtaac cagaggagaa tcatgcgagg    4140
ctgaccatgc catcgcttat caggtacaca cagcatcgct taaggcacaa gtaatgatat    4200
cgattggaga actgaaccaa accgtcgacg tgtttgtcaa cggagacagt ccagccagaa    4260
tccaacaatc aaagttcata cttgggccga tatccagtgc ctggtctcct tttgatcaca    4320
aggtgatcgt atacagggat gaggtgtaca atgaagacta cgcaccgtac ggatccggcc    4380
aagcaggcag gttcggagac atccaaagta gaactgttaa cagcactgat gtctatgcca    4440
acaccaattt gaagcttaaa agaccggctt caggcaatgt tcatgtacca tacacgcaaa    4500
cccccttcggg ttttctcgtac tggaaaaaag agaagggagt accattgaat cgaaacgccc    4560
cttttggctg tatcatcaaa gtcaatccag tacgtgctga aaactgcgta tatggcaaca    4620
taccgatcag tatggatatt gcggacgcgc acttcacaag gatcgatgaa tcccgtctg    4680
tgtccttgaa ggcgtgtgaa gtgcagtcct gcacttattc atcggatttt ggcggagtag    4740
cgagcatttc ctacacatct aataaggtag gtaagtgtgc cattcacagc cactcgaact    4800
ccgcaacgat gaaggattct gtgcaggatg tccaggaaag cggcgccttg tcgctttttct    4860
ttgcgacttc ctctgtcgag ccgaacttcg tggtccaagt gtgtaacgcg cggatcactt    4920
gccatgctaa gtgtgaacca ccgaaagacc acatcgtacc atacgcagcc aaacacaacg    4980
acgccgagtt tccatccatc tctactacag cttggcaatg gttggcacac accacctcag    5040
ggcactcac catacttgtg gtagctatta gtcgttgt tgtagtatcc attgtagtat    5100
gtgcaagaca ctagagatct gctgtgcctt ctagttgcca gccatctgtt gttttgccct    5160
ccccccgtgcc ttccttgacc ctgaaggtg ccactcccac tgtcctttcc taataaatg    5220
aggaaattgc atcgcattgt ctgagtaggt gtcatttctat tctgggggt ggggtggggc    5280
aggacagcaa gggggaggat tgggaagaca atagcaggca tgctgggat gcggtgggct    5340
ctatgggtac ccaggtgctg aagaattgac ccggttcctc ctgggccaga aagaagcagg    5400
cacatcccct tctctgtgac acaccctgtc cacgccctg gttcttagtt ccagcccac    5460
tcataggaca ctcatagctc aggagggctc cgccttcaat cccacccgct aaagtacttg    5520
gagcggtctc tccctccctc atcagcccac caaaccaaac ctagcctcca agagtgggaa    5580
gaaattaaag caagataggc tattaagtgc agagggagag aaaatgcctc caacatgtga    5640
ggaagtaatg agagaaatca tagaatttta aggccatgat ttaaggccat catggcctta    5700
```

```
atcttccgct tcctcgctca ctgactcgct gcgctcggtc gttcggctgc ggcgagcggt    5760
atcagctcac tcaaaggcgg taatacggtt atccacagaa tcaggggata acgcaggaaa    5820
gaacatgtga gcaaaaggcc agcaaaaggc caggaaccgt aaaaaggccg cgttgctggc    5880
gttttttccat aggctccgcc cccctgacga gcatcacaaa aatcgacgct caagtcagag    5940
gtggcgaaac ccgacaggac tataaagata ccaggcgttt ccccctggaa gctccctcgt    6000
gcgctctcct gttccgaccc tgccgcttac cggatacctg tccgcctttc tcccttcggg    6060
aagcgtggcg ctttctcata gctcacgctg taggtatctc agttcggtgt aggtcgttcg    6120
ctccaagctg ggctgtgtgc acgaaccccc cgttcagccc gaccgctgcg ccttatccgg    6180
taactatcgt cttgagtcca acccggtaag acacgactta tcgccactgg cagcagccac    6240
tggtaacagg attagcagag cgaggtatgt aggcggtgct acagagttct tgaagtggtg    6300
gcctaactac ggctacacta agaacagt atttggtatc tgcgctctgc tgaagccagt    6360
taccttcgga aaaagagttg gtagctcttg atccggcaaa caaaccaccg ctggtagcgg    6420
tggttttttt gtttgcaagc agcagattac gcgcagaaaa aaggatctc aagaagatcc    6480
tttgatcttt tctacggggt ctgacgctca gtggaacgaa aactcacgtt aagggattt    6540
ggtcatgaga ttatcaaaaa ggatcttcac ctagatcctt ttaaattaaa aatgaagttt    6600
taaatcaatc taaagtatat atgagtaaac ttggtctgac agttaccaat gcttaatcag    6660
tgaggcacct atctcagcga tctgtctatt tcgttcatcc atagttgcct gactcggggg    6720
gggggggcgc tgaggtctgc ctcgtgaaga aggtgttgct gactcatacc aggcctgaat    6780
cgccccatca tccagccaga aagtgaggga gccacggttg atgagagctt tgttgtaggt    6840
ggaccagttg gtgattttga acttttgctt tgccacggaa cggtctgcgt tgtcgggaag    6900
atgcgtgatc tgatccttca actcagcaaa agttcgattt attcaacaaa gccgccgtcc    6960
cgtcaagtca gcgtaatgct ctgccagtgt tacaaccaat taaccaattc tgattagaaa    7020
aactcatcga gcatcaaatg aaactgcaat ttattcatat caggattatc aataccatat    7080
ttttgaaaaa gccgtttctg taatgaagga gaaaactcac cgaggcagtt ccataggatg    7140
gcaagatcct ggtatcggtc tgcgattccg actcgtccaa catcaataca acctattaat    7200
ttccctcgt caaaaataag gttatcaagt gagaaatcac catgagtgac gactgaatcc    7260
ggtgagaatg gcaaaagctt atgcatttct ttccagactt gttcaacagg ccagccatta    7320
cgctcgtcat caaaatcact cgcatcaacc aaaccgttat tcattcgtga ttgcgcctga    7380
gcgagacgaa atacgcgatc gctgttaaaa ggacaattac aaacaggaat cgaatgcaac    7440
cggcgcagga acactgccag cgcatcaaca atattttcac ctgaatcgcc atattcttct    7500
aatacctgga atgctgtttt cccggggatc gcagtggtga gtaaccatgc atcatcagga    7560
gtacggataa aatgcttgat ggtcggaaga ggcataaatt ccgtcagcca gtttagtctg    7620
accatctcat ctgtaacatc attggcaacg ctaccttgc catgtttcag aaacaactct    7680
ggcgcatcgg gcttcccata caatcgatag attgtcgcac ctgattgcc gacattatcg    7740
cgagccattt tatacccata taaatcagca tccatgttgg aatttaatcg cggcctcgag    7800
caagacgttt cccgttgaat atggctcata cacccccttg tattactgtt tatgtaagca    7860
gacagtttta ttgttcatga tgatatattt ttatcttgtg caatgtaaca tcagagattt    7920
tgagacacaa cgtggctttc ccccccccc cattattgaa gcatttatca gggttattgt    7980
ctcatgagcg gatacatatt tgaatgtatt tagaaaaata aacaaatagg ggttccgcgc    8040
acatttcccc gaaaagtgcc acctgacgtc taagaaacca ttattatcat gacattaacc    8100
tataaaaata ggcgtatcac gaggcccttt cgtc                                8134

SEQ ID NO: 18         moltype = DNA   length = 8153
FEATURE               Location/Qualifiers
misc_feature          1..8153
                      note = Description of Artificial Sequence: Synthetic
                      polynucleotide
source                1..8153
                      mol_type = other DNA
                      organism = synthetic construct
SEQUENCE: 18
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcagattgg    240
ctattggcca ttgcatacgt tgtatccata tcataatatg tacatttata ttggctcatg    300
tccaacatta ccgccatgtt gacattgatt ttgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
catagtaacg ccaataggga ctttccattg acgtcaatgg gtggagtatt tacggtaaac    540
tgcccacttg gcagtacatc aagtgtatca tatgccaagt acgccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctcca tcggctcgca tctctccttc acgcgcccgc    1020
cgccctacct gaggccgcca tccacgccgg ttcctgccgc ctgtcctgcg cctgcgcctg   1080
ggtgcctcct gaactgcgtc cgccgtctag gtaagtttaa agctcaggtc gagaccgggc    1140
ctttgtccgg cgctccctg gagcctacct agactcagcc ggctctccac gctttgcctg    1200
accctgcttg ctcaactcta gttaacggtg gagggcagtg tagtctgagc agtactcgtt    1260
gctgccgcgc gcgccaccag acataatagc tgacagacta acagactgtt cctttccatg    1320
ggtcttttct gcagtcaccg tcgtcgacac gtgtgatcag atatcgcggc cgcaccatg    1380
aactctgtct tttacaatcc gtttggccga ggtgcctacg ctcaacctcc aatagcatgg    1440
aggcaagac gtagggctgc acctgcgcct cgaccatccg ggttgactac ccagatccaa    1500
cagctcacta gggctgttag agctttggtg ctggacaatg ctacacgtcg ccagcgcccg    1560
gctcctcgca cgcgcccgag gaagccgaag actcaaaaac ctaagccgaa gaagcaaaac    1620
cagaaaccac cacaacagca gaagaaaggg aaaaatcagc cccaacaacc gaagaaaccg    1680
```

```
aagcccggta aacgacacgc taccgccctg aaatttgaag ccgaccgcac atttgtcggg   1740
aagaatgaag acggcaagat tatgggatac gccgttgcca tggaagggaa agtgataaaa   1800
ccactacatg taaaaggaac cattgaccac ccggccctag cgaaacttaa attcactaaa   1860
tcttcttctt acgacatgga gtttgctaaa ctaccgaccg aaatgaaaag cgacgcattc   1920
gggtatacaa cggaacaccc cgaagtattt tacaactggc atcacggagc tgtccaattt   1980
tccggcggaa ggttcaccat ccctacagga gtcggaggcc ccggagatag cggaaggcct   2040
atactggata actccggaaa agtggtagcc atagtcctag gaggagctaa tgaagtgcca   2100
ggaacggcac tttctgttgt cacctggaat aagaagggag ccgctattaa aaccaccac    2160
gaagatactg tagagtggtc gcgggctatt accgctatgc gcatcctgca gaacgtcaca   2220
ttcccatgtg accgaccgcc aacttgctat aatcgtaatc ctgacttgac cctaaccatg   2280
ttggaaacaa atgtcaatca cccttcgtac gacgttctgc tggacgctgc tctgaggtgc   2340
cccacgagac ggcacgtcag atcaacgccc accgatgact tcactctcac agcaccgtac   2400
ctcggcttgt gtcacagatg taagacgatg gaaccatgct acagccctat aaaaatcgaa   2460
aaagtgtggg atgatgccga tgacggagtt ctccgtatac aagtaagtgc ccagttaggg   2520
tacaacaggg cgggcactgc agctagcgcc cgactccggt tcatgggcgg aggagtgcct   2580
ccggaaatcc aggagggagc aattgcagat tttaaggtct tcacgtccaa accatgttta   2640
cacctatcac ataaaggata ctttgtcatt gtcaagtgcc ctcctggtga tagtattaca   2700
acatcattga aagtgcatgg ctcggatcaa acctgcacaa ttccaatgcg agtaggttac   2760
aagttcgtag gcagggaaaa atatactctg ccaccaatgc atgggacaca aatacccttg   2820
cttacctacg aaaggacacg agagaaaagt gcaggatacg tgaccatgca tcgtcccgga   2880
caacaatcca taaccatgct gatggaagag agcgagggg aggtgtacgt acaaccgacc    2940
agtgggcgaa acgtcaccta cgagtgtaaa tgcggagact ttaaaactgg gactgtcact   3000
gcgcgcacta aaatagacgg ctgtacagaa aggaaacaat gcattgcgat ttctgccgac   3060
cacgtcaaat gggtgtttaa ctccctgac ttgatcaggc ataccgacca cacagcccaa    3120
gggaagttgc atataccatt cccgctacag caggctcaat gtacagtacc actggcgcac   3180
cttccaggcg ttaagcatgc ttatccagt atgtctcatg cactgcacgc tgagcatcct    3240
acattgctta ctaccgcca tcttggagaa aatcctcagc ccactgcaga atggattgtc    3300
gggagtgtaa ctcgaaactt ctccataacc atacaagggt tcgagtatac ttggggaaat   3360
cagaaaccgg tccgagtgta cgcgcaggaa tcggcacctg gcaatcctca tggctggcca   3420
catgaaatcg tacgccatta ctaccacctc tatcccttct acaccgttac agtgctgagc   3480
ggcatgggac tggccatatg cgctggctta gtgatcagta ttttatgctg ctgcaaagca   3540
agaagggatt gcctaacacc ttaccaactg gccccgaacg ctaccgtacc atttctggta   3600
acattgtgtt gctgttccca acggacttca gcggatgaat ttaccgatac catggggtac   3660
ctatgccaac acagtcaaac aatgttctgg atacaattgg tcataccttt agcagcagtg   3720
ataactttgg ttagatgttg ctcctgctgt ctacctttt tattggttgc cagtcctcca    3780
aacaaagcgg acgcctacga acatacgatc actgtcccaa atgcgccgtt gaactcgtat   3840
aaagcactag tggaacggcc tgggtatgcc cccttgaatc ttgaagtcat ggtcatgaac   3900
acccagatca taccatcggt taaacgtgaa tacattacct gcaggtacca caccgttgtt   3960
ccttcaccgc agattaaatg ttgcgaactc gcgaatgcc cgaaaggtga aaaagcagac    4020
tatacctgca aggtgttcac tggtgtgtac ccatttctgt ggggaggagc acagtgtttt   4080
tgcgactccg aaaacagtca gcttagcgac aagtacgtcg aactgtcaac agattgtcgc   4140
acagaccatg ccgaggcggt cagagtacac acggcttcgg tgaaatcaca gctccgaata   4200
acctacggga actccacagc acaagtagac gtatttgtca acggtgtgac tccagccagg   4260
agcaaagaca tgaaattgat agccggccca ttatctacta cattttcccc gtttgataat   4320
aaggtcatta tatatcatgg gaaagtctat aactatgact tccggaatt tggggccgga   4380
acacctggag ctttcggaga tgtccaagcg tcatccacca ccggatcaga tctattagca   4440
aacacagcaa ttcatttgca gaggccggaa gccagaaaca tacacgtcc gtacacccaa   4500
gctccaagcg ggttcgaatt ctggaagaat aacagcggtc agcctttatc tgacactgcc   4560
cctttcggat gcaaagtcaa tgtcaacccg ctacgtgcag acaagtgtgc cgtgggatca   4620
ctcccgatat ccgtggatat accggacgct gcatttacac gcgtatccga gcccctgcca   4680
tcactgctta agtgcaccgt tactagttgc acatactcta cagactatgg cggagtgctc   4740
gtgttgacat acgagtcgga tcgcgcgggg caatgcgctg tacactgca ttcatcaaca    4800
gcggtactgc gagacccatc ggtatacgtc gagcaaaaag gggagactac acttaaattt   4860
agtacgcgtt ccttgcaggc agacttgag gtatcgatgt gcggaacgag aaccacttgc    4920
catgcccaat gtcaaccacc aacggaacac gtaatgaaca gaccccagaa gtcgactcca   4980
gacttctcct cagcgatatc caaaacatca tggaactgga ttacagcgct tatgggggga   5040
atttccagta tagctgctat agccgcaatt gtgctggtca tagcattagt atttacagca   5100
caacacagat gatctagacc aggccctgga tccagatctg ctgtgccttc tagttgccag   5160
ccatctgttg tttgccccctc cccgtgcct tccttgaccc tggaaggtgc cactcccact    5220
gtcctttcct aataaaatga ggaaattgca tcgcattgtc tgagtaggtg tcattctatt   5280
ctgggggtg gggtggggca ggacagcaag ggggaggatt gggaagacaa tagcaggcat    5340
gctggggatg cggtgggctc tatgggtacc caggtgctga agaattgacc cggttcctcc   5400
tgggccagaa agaagcaggc acatcccctt ctctgtgaca caccctgtcc acgccctgg    5460
ttcttagttc cagccccact cataggcacg tcatagctca ggagggctcc gccttcaagt   5520
ccacccgcta aagtacttgg agcggtctct ccctccctca tcagcccacc aaaccaaacc   5580
tagcctccaa gagtgggaag aaattaaagc aagataggct attaagtgca gagggagaga   5640
aaatgcctcc aacatgtgag gaagtaatga gagaaatcat agaattttaa ggccatgatt   5700
taaggccatc atggccttaa tcttccgctt cctcgctcac tgactcgctg cgctcggtcg   5760
ttcggctgcg gcgagcggta tcagctcact caaaggcggt aatacggtta tccacagaat   5820
caggggataa cgcaggaaag aacatgtgag caaaaggcca gcaaaggcc aggaaccgta     5880
aaaaggccgc gttgctggcg ttttccata ggctccgccc cctgacgag catcacaaaa     5940
atcgacgctc aagtcagagg tggcgaaacc cgacaggact ataagatac caggcgtttc    6000
cccctggaag ctccctcgtg cgctctcctg ttccgaccct gccgcttacc ggatacctgt   6060
ccgcctttct cccttcggga agcgtggcgc tttctcatag ctcacgctgt aggtatctca   6120
gttcggtgta ggtcgttcgc tccaagctgg gctgtgtgca cgaaccccc gttcagcccg    6180
accgctgcgc cttatccggt aactatcgtc ttgagtccaa cccggtaaga cgacttat     6240
cgccactggc agcagccact ggtaacagga ttagcagagc gaggtatgta ggcggtgcta   6300
cagagttctt gaagtggtgg cctaactacg gctacactag aagaacagta tttggtatct   6360
gcgctctgct gaagccagtt accttcggaa aaagagttgg tagctcttga tccggcaaac   6420
```

```
aaaccaccgc tggtagcggt ggttttttg tttgcaagca gcagattacg cgcagaaaaa 6480
aaggatctca agaagatcct ttgatctttt ctacggggtc tgacgctcag tggaacgaaa 6540
actcacgtta agggattttg gtcatgagat tatcaaaaag gatcttcacc tagatccttt 6600
taaattaaaa atgaagtttt aaatcaatct aaagtatata tgagtaaact tggtctgaca 6660
gttaccaatg cttaatcagt gaggcaccta tctcagcgat ctgtctattt cgttcatcca 6720
tagttgcctg actcgggggg gggggcgct gaggtctgcc tcgtgaagaa ggtgttgctg 6780
actcatacca ggcctgaatc gccccatcat ccagccagaa agtgagggag ccacggttga 6840
tgagagcttt gttgtaggtg gaccagttgg tgattttgaa cttttgcttt gccacggaac 6900
ggtctgcgtt gtcgggaaga tgcgtgatct gatccttcaa ctcagcaaaa gttcgattta 6960
ttcaacaaag ccgccgtccc gtcaagtcag cgtaatgctc tgccagtgtt acaaccaatt 7020
aaccaattct gattagaaaa actcatcgag catcaaatga aactgcaatt tattcatatc 7080
aggattatca ataccatatt tttgaaaaag ccgtttctgt aatgaaggag aaaactcacc 7140
gaggcagttc cataggatgg caagatcctg gtatcggtct gcgattccga ctcgtccaac 7200
atcaatacaa cctattaatt tcccctcgtc aaaaataagg ttatcaagtg agaaatcacc 7260
atgagtgacg actgaatccg gtgagaatgg caaaagctta tgcatttctt tccagacttg 7320
ttcaacaggc cagccattac gctcgtcatc aaaatcactc gcatcaacca aaccgttatt 7380
cattcgtgat tgcgcctgag cgagacgaaa tacgcgatcg ctgttaaaag gacaattaca 7440
aacaggaatc gaatgcaacc ggcgcaggaa cactgccagc gcatcaacaa tatttcacc 7500
tgaatcagga tattcttcta atacctggaa tgctgttttc ccggggatcg cagtggtgag 7560
taaccatgca tcatcaggag tacggataaa atgcttgatg gtcggaagag gcataaattc 7620
cgtcagccag tttagtctga ccatctcatc tgtaacatca ttggcaacgc taccttgcc 7680
atgtttcaga aacaactctg gcgcatcggg cttcccatac aatcgataga ttgtcgcacc 7740
tgattgcccg acattatcgc gagcccattt atacccatat aaatcagcat ccatgttgga 7800
atttaatcgc ggcctcgagc aagacgtttc ccgttgaata tggctcataa cacccctgt 7860
attactgttt atgtaagcag acagttttat tgttcatgat gatatatttt tatccttgtc 7920
aatgtaacat cagagatttt gagacacaac gtggctttcc ccccccccc attattgaag 7980
catttatcag ggttattgtc tcatgagcgg atacatattt gaatgtattt agaaaaataa 8040
acaaataggg gttccgcgca catttccccg aaaagtgcca cctgacgtct aagaaaccat 8100
tattatcatg acattaacct ataaaaatag gcgtatcacg aggccctttc gtc 8153
```

```
SEQ ID NO: 19         moltype = DNA   length = 2964
FEATURE               Location/Qualifiers
misc_feature          1..2964
                      note = Description of Artificial Sequence: Synthetic
                      polynucleotide
source                1..2964
                      mol_type = other DNA
                      organism = synthetic construct
SEQUENCE: 19
atgagcctcg ccctcccggt cttgtgcctg ttggcaaaca ctacattccc ctgctctcag   60
ccgccttgca caccctgctg ctacgaaaag gaaccggaaa gcaccttgcg catgcttgag  120
gacaacgtga tgagacccgg atactaccag ctactaaaag catcgctgac ttgctctccc  180
caccgccaag gacgcagtac taaggacaat tttaatgtct ataaagccac aagaccatat  240
ctagctcatt gtcctgactg cggagaaggg cattcgtgcc acagccctat cgcattggag  300
cgcatcagaa atgaagcaac ggacggaacg ctgaaaatcc aggtctcttt gcagatcggg  360
ataaagacag atgacagcca cgattggacc aagctgcgct atatggatag ccatacgcca  420
gcggacgcgg agcgagccgg attgcttgta aggacttcag caccgtcgac gatcaccggg  480
accatgggac actttattct cgcccgatgc ccgaaaggag agacgctgac agtgggattt  540
acggacagca gaaagatcag ccacacatgc acacacccgt tccatcatga accacctgtg  600
ataggtaggg agaggttcca ctctcgacca caacatggta aagagttacc ttgcagcacg  660
tacgtgcaga gcaccgctgc cactgctgag gagatagagt tgcatatgcc cccagatact  720
cctgaccgca cgctgatgac gcagcagtct ggcaacgtga gatcacagt taatgggcag  780
acggtgcggt acaagtgcaa ctgccgtgg tcaaacgagg gactgacaac cacagacaaa  840
gtgatcaata actgcaaaat tgatcagtgc catgctgcag tcactaatca aagaattgg   900
caatacaact cccctttagt cccgcgcaac gctgaactcg gggaccgtaa aggaaagatc  960
cacatcccat tccattggc aaacgtgact tgcagagtgc caaaagcaag aaacccccta 1020
gtaacttacg gaaaaaacca agtcaccatg ctgctgtatc ctgaccatcc gacactcttg 1080
tcttaccgta acatgggaca ggaaccaaat taccacgagg agtgggtgac acacaagaag 1140
gaggttacct tgaccgtgcc tactgagggt ctggaggtca cttggggcaa caacgaacca 1200
tacaagtact ggccgcagat gtctacgaac ggtactgctc atgtccaccc acatgagata 1260
atcttgtact attatgagct gtaccccact atgactgtag tcattgtgtc ggtgcctcg  1320
ttcgtgcttc tgtcgatggt gggcacagca gtgggaatgt gtgtgtgcgc acggcgcaga 1380
tgcattacac catatgaatt aacaccagga gccactgttc ccttcctgct cagcctgcta 1440
tgctgcgtca gaacgaccaa ggcggccaca tattacgagg ctgccgcata tctatggaac 1500
gaacagcagc ccctgttctg gttgcaggct cttatcccgc tggccgcctt gatcgtcctg 1560
tgcaactgtc tgaaactctt gccatgctgc tgtaagacc tggcttttt agccgtaatg 1620
agcatcggtg cccacactgt gagcgcgtac gaacacgtaa cagtgatccc gaacacggtg 1680
ggagtaccgt ataagactct tgtcaacaga ccggttaca gccccatggt gttggagatg 1740
gagctacaat cagtcacctt ggaaccaaca ctgtcacttg actacatcac gtgcgagtac 1800
aaaactgtca tccctccccc gtacgtgaag tgctgtggta cagcagagtg caaggacaag 1860
agcctaccag actacagctg caaggtcttt actggagtct acccatttat gtggggcggc 1920
gcctactgct tttgcgacgc cgaaaatacg caattgagcg aggcacatgt agagaaatct 1980
gaatcttgca aaacagagtt tgcatcggcc tacagagccc acaccgcatc ggcgtcggcg 2040
aagctccgcg tcctttacca aggaaacaac attgcctacg taacggtgac 2100
catgccgtca cagtaaagga cgccaagttt gtcgtgggcc caatgtcctc cgcctggaca 2160
ccttttgaca caaaatcgt ggtgtacaaa gcgacgtct acaacatgga ctacccacct 2220
tttgcgcag aagaccagg acaatttggt gacattcaaa gtcgtacacc ggaaagtaaa 2280
gacgtttatg ccaacactca gttggtacta cagaggccag cagcaggcac ggtacatgta 2340
ccatactctc aggcaccatc tggcttcaag tattggctga aggaacgagg agcatcgcta 2400
```

```
cagcacacgg caccgttcgg ttgccagatt gcgacaaacc cggtaagagc tgtaaattgc 2460
gctgtgggga acataccaat ttccatcgac ataccggatg cggcctttac tagggttgtc 2520
gatgcaccct ctgtaacgga catgtcatgc gaagtaccag cctgcactca ctcctccgac 2580
tttgggggcg tcgccatcat caaatacaca gctagcaaga aggtaaatg tgcagtacat 2640
tcgatgacca acgccgttac cattcgagaa gccgacgtag aagtagaggg gaactcccag 2700
ctgcaaatat ccttctcaac agccctggca agcgccgagt ttcgcgtgca agtgtgctcc 2760
acacaagtac actgcgcagc cgcatgccac cctccaaagg accacatagt caattaccca 2820
gcatcacaca ccaccctttgg ggtccaggat atatccacaa cggcaatgtc ttgggtgcag 2880
aagattacgg gaggagtagg attaattgtt gctgttgctg ccttaattt aattgtggtg 2940
ctatgcgtgt cgtttagcag gcac                                    2964
```

SEQ ID NO: 20          moltype = DNA   length = 2964
FEATURE                Location/Qualifiers
misc_feature           1..2964
                       note = Description of Artificial Sequence: Synthetic
                       polynucleotide
source                 1..2964
                       mol_type = other DNA
                       organism = synthetic construct SEQUENCE: 20
```
atgagtcttg ccatcccagt tatgtgcctg ttggcaaaca ccacgttccc ctgctcccag   60
ccccccttgca cgccctgctg ctacgaaaag gaaccggaag aaaccctacg catgcttgag  120
gacaacgtca tgagacctgg gtactatcag ctgctacaag catccttaac atgttctccc  180
caccgccagc gacgcagcac caaggacaac ttcaatgtct ataaagccac aagaccatac  240
ttagctcact gtcccgactg tggagaaggg cactcgtgcc atagtcccgt agcactagaa  300
cgcatcagaa atgaagcgac agacgggacg ctgaaaatcc aggtctcctt gcaaatcgga  360
ataaagacgg atgacagcca cgattggacc aagctgcgtt atatggacaa ccacatgcca  420
gcagacgcag agagggcggg gctatttgta agaacatcag caccgtgtac gattactgga  480
acaatgggac acttcatcct ggcccgatgt ccaaaagggg aaactctgac ggtgggattc  540
actgacagta ggaagattag tcactcatgt acgcacccat ttccaccacga cccctcctgtg 600
ataggtcgga aaaaattcca ttcccgaccg cagcacggta aagagctacc ttgcagcacg  660
tacgtgcaga gcaccgccgc aactaccgag gagataggg tacacatgcc cccagacacc  720
cctgatcgca cattaatgtc acaacagtcc ggcaacgtaa agatcacagt caatggccag  780
acggtgcggt acaagtgtaa ttgccggtggc tcaaatgaag gactaacaac tacagacaaa  840
gtgattaata actgcaaggt tgatcaatgt catgccgcgt tcaccaatca caaaagtgg   900
cagtataact cccctctggt cccgcgtaat gctgaacttg gggaccgaaa aggaaaaatt  960
cacatcccgt ttcgctggc aaatgtaaca tgcagggtgc ctaaagcaag gaaccccacc  1020
gtgacgtacg ggaaaaacca agtcatcatg ctactgtatc ctgaccaccc aaacactcctg 1080
tcctaccgga atatgggaga agaaccaaac tatcaagaag gtgggtgat gcataagaag  1140
gaagtcgtgc taaccgtgcc gactgaaggg ctcgaggtca cgtggggcaa caacgagccg  1200
tataagtatt ggccgcagtt atctacaaac ggtacagccc atggccaccc gcatgagata  1260
attctgtatt attatgagct gtaccccact atgactgtag tagttgtgtc agtggccacg  1320
ttcatactcc tgtcgatggt gggtatggca gcggggatgt gcatgtgtgc acgacgcaga  1380
tgcatcacac cgtatgaact gacaccagga gctaccgtcc cttcctgct tagcctaata  1440
tgctgcatca gaacagctaa agcggccaca taccaagagg ctgcgatata cctgtggaac  1500
gagcagcaac ctttgttttg gctacaagcc cttattccgc tggcagccct gattgttcta  1560
tgcaactgtc tgagactctt accatgctgc tgtaaaacgt tgcttttttt agccgtaatg  1620
agcgtcggtg cccacactgt gagcgcgtac gaacacgtaa cagtgatccc gaacacggtg  1680
ggagtaccgt ataagactct agtcaataga cctggctaca gccccatggt attggagatg  1740
gaactactgt cagtcacttt ggagccaaca ctatcgcttg attacatcac gtgcgagtac  1800
aaaaccgtca tcccgtctcc gtacgtgaag tgctgcggta cagcagagtg caaggacaaa  1860
aacctacctg actacagctg taaggtcttc accggcgtct acccatttat gtggggcggc  1920
gcctactgct tctgcgacgc tgaaaacacg cagttgagcg aagcacacgt ggagaagtcc  1980
gaatcatgca aaacagaatt tgcatcagca tacaggggctc ataccgcatc tgcatcagct  2040
aagctccgcg tcctttacca aggaaataac atcactgtaa ctgcctatgc aaacggcgac  2100
catgccgtca cagttaagga cgccaaattc attgtgggc caatgtcttc agcctggaca  2160
cctttcgaca acaaaattgt ggtgtacaaa ggtgacgtct ataacatgga ctacccgccc  2220
tttggcgcag gaagaccagg acaatttggc gatatccaaa gtcgcaacacc tgagagtaaa  2280
gacgtctatg ctaatacaca actggtactg cagagaccgg ctgtgggtac ggtacacgtg  2340
ccatactctc aggcaccatc tggctttaag tattggcta agaacgcgg tgcggtgcctg  2400
cagcacacag caccattttgg ctgccaaata gcaacaaacc cggtaagagc ggtgaactgc  2460
gccgtaggga acatgcccat ctccatcgac ataccggaaa cggcctttca tagggtcgtc  2520
gacgcgccct ctttaacgga catgtcgtgc gaggtaccag cctgcaccca ttcctcgac   2580
tttgggggcg tcgccattat taaatatgca gccagcagaa aaggcaagtg tgcggtgcag  2640
tcgatgacta acgccgtcac tattcggaaa gctgagatag aagttgaagg gaattctcag  2700
ctgcaaatct cttctcgac ggccttagcc agcgccgaat tcgcgtaca agtctgttct  2760
acacaagtac actgtgcagc cgagtgccac ccccgaagg accacatagt caactacccg   2820
gcgtcacata ccaccctcgg ggtccaggac atctccgcta cggcgatgtc atgggtgcag  2880
aagatcacgg gaggtgtggg actggttgtt gctgttgccg cactgattct aatcgtggtg  2940
ctatgcgtgt cgttcagcag gcac                                    2964
```

SEQ ID NO: 21          moltype = DNA   length = 783
FEATURE                Location/Qualifiers
misc_feature           1..783
                       note = Description of Artificial Sequence: Synthetic
                       polynucleotide
source                 1..783
                       mol_type = other DNA
                       organism = synthetic construct

```
SEQUENCE: 21
atggagttca tcccgacgca aactttctat aacagaaggt accaacccg accctgggcc    60
ccacgccca caattcaagt aattagacct agaccacgtc cacagaggca ggctgggcaa   120
ctcgcccagc tgatctccgc agtcaacaaa ttgaccatgc gcgcggtacc tcaacagaag   180
cctcgcagaa atcggaaaaa caagaagcaa aggcagaaga agcaggcgcc acaaaacgac   240
ccaaagcaaa agaagcaacc accacaaaag aagccggctc aaaagaagaa gaaaccaggc   300
cgtagggaga gaatgtgcat gaaaattgaa aatgattgca tcttcgaagt caagcatgaa   360
ggcaaagtga tgggctacgc atgcctggtg ggggataaag taatgaaacc agcacatgtg   420
aagggaacta tcgacaatgc cgatctggct aaactggcct ttaagcggtc gtctaaatac   480
gatcttgaat gtgcacagat accggtgcac atgaagtctg atgcctcgaa gtttacccac   540
gagaaacccg aggggtacta taactggcat cacggagcag tgcagtattc aggaggccgg   600
ttcactatcc cgacgggtgc aggcaagccg ggagacagcg gcagaccgat cttcgacaac   660
aaaggacggg tggtggccat cgtcctagga ggggccaacg aaggtgcccg cacggccctc   720
tccgtggtga cgtggaacaa agacatcgtc acaaaaatta cccctgaggg agccgaagag   780
tgg                                                                783

SEQ ID NO: 22          moltype = DNA   length = 783
FEATURE                Location/Qualifiers
misc_feature           1..783
                       note = Description of Artificial Sequence: Synthetic
                       polynucleotide
source                 1..783
                       mol_type = other DNA
                       organism = synthetic construct
SEQUENCE: 22
atggagttca tcccaaccca aacttttac aataggaggt accagcctcg accctggact    60
ccgcgccta ctatccaagt catcaggccc agaccgcgcc ctcagaggca agctgggcaa   120
cttgcccagc tgatctcagc agttaataaa ctgacaatgc gcgcggtacc acaacagaag   180
ccacgcagga atcggaagaa taagaagcaa agcaaaaac aacaggcgcc acaaacaac    240
acaaatcaaa agaagcagcc acctaaaaag aaaccggctc aaaagaaaaa gaagccgggc   300
cgcagagaga ggatgtgcat gaaaatcgaa aatgattgta ttttcgaagt caagcacgaa   360
ggtaaggtaa caggttacgc gtgcctggtg ggggacaaag taatgaaacc agcacacgta   420
aagggggacca tcgataacgc ggacctggcc aaactggcct ttaagcggtc atctaagtat   480
gacctttgaat gcgcgcagat acccgtgcac atgaagtccg acgcttcgaa gttcacccat   540
gagaaaccgg aggggtacta caactggcac cacggagcac tacagtactc aggaggccgg   600
ttcaccatcc ctacaggtgc tggcaaacca ggggacagcg gcagaccgat cttcgacaac   660
aagggacgcg tggtggccat agtcttagga ggagctaatg aaggagcccg tacagccctc   720
tcggtggtga cctggaataa agacattgtc actaaaatca ccccgaggg ggccgaagag   780
tgg                                                                783

SEQ ID NO: 23          moltype = DNA   length = 13756
FEATURE                Location/Qualifiers
misc_feature           1..13756
                       note = Description of Artificial Sequence: Synthetic
                       polynucleotide
source                 1..13756
                       mol_type = other DNA
                       organism = synthetic construct
SEQUENCE: 23
atggctgcgt gagacacacg tagcctacca gtttcttact gctctactct gcaaagcaag    60
agattaataa cccatcatgg atcctgtgta cgtggacata gacgctgaca gcgccttttt   120
gaaggccctg caacgtgcgt accccatgtt tgaggtggaa ccaaggcagg tcacaccgaa   180
tgaccatgct aatgctagag cgttctcgca tctagctata aaactaatag agcaggaaat   240
tgaccccgac tcaaccatcc tggatatcgg cagtgcgcca gcaaggagga tgatgtcgga   300
caggagtac cactgcgtct gcccgatgcg cagtgcggaa gatcccgaga gactcgccaa   360
ttatgcgaga aagctagcat ctgccgcagg aaaagtcctg gacagaaaca tctctgaaa    420
gatcggggac ttacaagcag taatggccgt gccagcacg gagacgccaa cattctgctt   480
acacacagac gtctcatgta gacagagagc agacgtcgct atataccaag acgtctatgc   540
tgtacacgca cccacgtcgc tataccacca ggcgattaaa ggggtccgag tggcgtactg   600
ggttgggttc gacacaaccc cgttcatgta caatgccatg gcgggtgcct acccctcata   660
ctcgacaaac tggcagatgc agcaggtact gaaggctaag aacataggat tatgttcaac   720
agacctgacg gaaggtagac gaggcaagtt gtctattatg agagggaaaa agctaaaacc   780
gtgcgaccgt gtgctgttct cagtagggtc aacgctctac ccggaaagcc gcaagctact   840
taagagctgg cacctgccat cggtgttcca tttaaagggc aaactcagct tcacatgccg   900
ctgtgataca gtggtttcgt gtgagggcta cgtcgttaag agaataacga tgagcccagg   960
cctttatgga aaaaccacag ggtatgcggt aaccaccac gcagacgat tcctgatgtg    1020
caagactacc gacacggttg acggcgaaag aatgtcattc tcggtgtgca catacgtgcc   1080
ggcgaccatt tgtgatcaaa tgaccggcat ccttgctaca gaagtcaccg cggaggatgc   1140
acagaagctg ttggtgggtc tgaaccagaa aatagtggtt aacggcagaa cgcaaacggaa   1200
tacgaacacc atgaaaaatt atctgcttcc cgtggtcgcc caagccttca gtaagtgggc   1260
aaaggagtgc cggaaagaca tggaagatga aaaactcctg ggggtcagag aaagaacact   1320
gacctgctgt gtctatgggc cattcaagaa gcagaaaaca cacacggtct acaagaggcc   1380
tgatacccag tcaattcgaa aggttcaggc cgagtttgac agctttgtgg taccgagtct   1440
gtggtcgtcc gggttgtcaa tccctttgag gactagaatc aaatggttgt taagcaaggt   1500
gccaaaaacc gacctgatcc catacagcgg agacgcccga gaagcccggg acgcagaaaa   1560
agaagcagag gaagaacgag aagcagaact gactcgcgaa gccctaccac ctctacaggc   1620
agcacaggaa gatgttcagg tcgaaatcga cgtggaacag cttgaggaca gagccgggc    1680
aggaataata gagactccga gggagagtat caaagttact gccaaccaa cagaccacgt   1740
cgtgggagag tacctggtac tctccccgca gaccgtacta cgtagccaga agctcagtct   1800
```

```
gattcacgct ttggcggagc aagtgaagac gtgcacgcac aacggacgag cagggaggta  1860
tgcggtcgaa gcgtacgacg gccgagtcct agtgccctca ggctatgcaa tctcgcctga  1920
agacttccag agtctaagcg aaagcgcaac gatggtgtat aacgaaagag agttcgtaaa  1980
cagaaagcta caccatattg cgatgcacgg accagccctg aacaccgacg aagagtcgta  2040
tgagctggtg agggcagaga ggacagaaca cgagtacgtc tacgacgtgg atcagagaag  2100
atgctgtaag aaggaagaag ccgcaggact ggtactggtg ggcgacttga ctaatccgcc  2160
ctaccacgaa ttcgcatatg aagggctaaa aatccgccct gcctgccat  acaaaattgc  2220
agtcatagga gtcttcggag taccgggatc tggcaagtca gctattatca agaacctagt  2280
taccaggcag gacctggtga ctagcggaaa gaaagaaaac tgccaagaaa tcaccaccga  2340
cgtgatgaga cagagaggtc tagagatatc tgcacgtacg gttgactcgc tgctcttgaa  2400
tggatgcaac agaccagtcg acgtgttgta cgtagacgag gcgtttgcgt gccactctgg  2460
aacgctactt gctttgatcg ccttggtgag accaaggcag aaagttgtac tttgtggtga  2520
cccgaagcag tgcggcttct tcaatatgat gcagatgaaa gtcaactata atcacaaacat  2580
ctgcacccaa gtgtaccaca aaagtatctc caggcgcagt acactgcctg tgaccgccat  2640
tgtgtcatcg ttgcattacg aaggcaaaat gcgcactacg aatgagtaca acaagccgat  2700
tgtagtggac actacaggct caacaaaacc tgacctgga gacctcgtgt taacgtgctt  2760
cagagggtgg gttaaacaac tgcaaattga ctatcgtgga tacgaggtca tgacagcagc  2820
cgcatcccaa gggttaacca gaaaaggagt ttacgcagtt agacaaaaag ttaatgaaaa  2880
cccgctctat gcatcaacgt cagagcacgt caacgtactc ctaacgcgta cggaaggtaa  2940
actggtatgg aagacacttt ccggcgaccc gtggataaag acgctgcaga acccaccgaa  3000
aggaaacttc aaagcaacta ttaaggagtg ggaggtggag catgcatcaa taatggcggg  3060
catctgcagt caccaaatga ccttcgatac atttccaaaat aaagccaacg tttgttgggc  3120
taagagcttg gtccctatcc tcgaaacagc ggggataaaa ctaaatgata ggcagtggtc  3180
tcagataatt caagccttca aagaagacaa agcatactca cctgaagtag ccctgaatga  3240
aatatgtacg cgcatgtatg gggtggatct agacagcggg ctattttcta aaccgttggt  3300
gtctgtgtat tacgcggata accactggga taataggcct ggagggaaaa tgttcggatt  3360
taaccccgag gcagcatcca ttctagaaag aaagtatcca ttcacaaaag ggaagtggaa  3420
catcaacaag cagatctgcg tgactaccag gaggatagaa gactttaacc ctaccaccaa  3480
catcataccg gccaacagga gactaccaca ctcattagtg gccgaacacc gcccagtaaa  3540
aggggaaaga atggaatggc tggttaacaa gataaacgat caccacgtgc tcctggctag  3600
tggctataac cttgcactgc ctactaagag agtcacttgg gtagcgccgt taggtgtccg  3660
cggagcggac tacacataca acctagagtt gggtctgcca gcaacgcttg gtaggtatga  3720
cctagtggtc ataaacatcc acacaccttt tcgcatacac cattaccaac agtgcgtcga  3780
ccacgcaatg aaactgcaaa tgctcggggg tgactcattg agactgtca aaccggggcgg  3840
ctctctattg atcagagcat atggttacgc agatagaacc agtgaacgag tcatctgcgt  3900
attgggacgc aagtttagat cgtctagagc gttgaaacca ccatgtgtca ccagcaaacac  3960
tgagatgttt ttcctattca gcaactttga caatggcaga aggaatttca caactcatgt  4020
catgaacaat caactgaatg cagccttcgt aggacaggtg acccgagcag gatgtgcacc  4080
gtcgtaccgg gtaaaacgca tggacatcgc gaagaacgat gaagagtgcg tagtcaacgc  4140
cgctaaccct cgcgggttac cgggtggcgg tgtttgcaag gcagtataca aaaaatggcc  4200
ggagtccttt aagaacagtg caacaccagt gggaaccgca aaaacagtta tgtgcgtac  4260
gtatccagta atccacgctg ttggaccaaa cttctctaat tattcggagt ctgaagggga  4320
ccgggaattg gcagctgcct atcgagaagt cgcaaaggaa gtaactaggc tgggagtaaa  4380
tagtgtagct ataccctctcc tctccacagg tgtatactca ggaggaaag acaggctgac  4440
ccagtcactg aaccacctct ttacagccat ggactcgacg gatgcagacg tggtcatcta  4500
ctgccgcgac aaagaatggg agaagaaaat atctgaggcc atacagatgc ggacccaagt  4560
agagctgttc gatgagcaca tctccataga ctgcgatatt gttcgcgtgc accctgacag  4620
cagcttggca ggcagaaaag gatacagcac cacggaaggc gcactgtact catatctaga  4680
agggacccgt tttcatcaga cggctgtgga tatggcggag atacatacta tgtgccaaa  4740
gcaaacagag gccaatgagc aagtctgcct atatgccctg ggggaaagta ttgaatcgat  4800
caggcagaaa tgcccggtgg atgatgcaga cgcatcatct cccccccaaa ctgtcccgtg  4860
cctttgccgt tacgctatga ctccagaacg cgtcaccegg cttcgcatga accacgtcac  4920
aagcataatt gtgtgttctt cgtttcccct cccaaagtac aaaatagaag gagtgcaaaa  4980
agtcaaatgc tctaaggtaa tgctatttga ccacaacgtg ccatcgcgcg taagtccaag  5040
ggaatataga tcttcccagg agtctgcaca ggaggcgagt acaatcacgt cactgacgca  5100
tagtcaattc gacctaagcg ttgatgcgca gatactgccc gtcccgtcag acctggatgc  5160
tgacgcccca gccctagaac cagcactaga cgacggggcg acacacacgc tgccatccac  5220
aaccggaaac cttgcggccg tgtctgattg gtaatgagc accgtacctg tcgcgccgcc  5280
cagaagaagg cgagggagaa acctgactgt gacatgtgac gagagagag ggaatataac  5340
acccatggct agcgtccgat tcttagggc agagctgtgt ccggtcgtac aagaaacagc  5400
ggagacgcgt gacacagcaa tgtctcttca ggcaccaccg agtaccgcca cggaaccgaa  5460
tcatccgccg atctccttcg gagcatcaag cgagacgttc cccattacat tggggacttt  5520
caacgaagga gaaatcgaaa gcttgtcttc tgagctacta actttcggag acttcttacc  5580
aggagaagtg gatgacttga cagacagcga ctggtccacg tgctcagaca cggacgacga  5640
gttaagacta gacagggcag gtgggtatat attctcgtcg gacaccggtc caggtcattt  5700
acaacagaag tcagtacgcc agtcagtgct gccggtgaac accctggagg aagtccacga  5760
ggagaagtgt tacccaccta agctggatga agcaaaggag caactattac ttaagaaact  5820
ccagagagtg cattcatgg ccaacagaag caggtactgc tcgcgcaaag tagaaaacat  5880
gaaagcagca atcatccaga gactaaagag aggctgtaga ctatacttaa tgtcagagac  5940
cccaaaagtc cctacttacc ggactacata tccggcgcct gtgtactcgc tccgatcaa  6000
cgtccgattg tccaatcccg agtccgcagt ggcagcatgc aatgagttct tagctagaaa  6060
ctatccaact gtctcatcat accaaattac cgacgagtat gatgcatatc tagacatggt  6120
ggacgggtcg gagagttgcc tggaccgagc gacattcaat ccgtcaaaac tcaggagcta  6180
cccgaaacag cacgcttacc acgcgccctc catcagaagc gctgtaccgt cccattcca  6240
gaacacacta cagaatgtac tggcagcagc cacgaaaaga aactgcaacg tcacacagat  6300
gagggaatta cccactttgg actcagcagt attcaacgtg gagtgtttca aaaaattcgc  6360
atgcaaccaa gaatactggg aagaatttgc tgccagccct attaggataa caactgagaa  6420
tttagcaacc tatgttacta aactaaaagg gccaaaagca gcagcgctat tcgcaaaaac  6480
ccataatcta ctgccactac aggaagtacc aatggatagg ttcacagtag atatgaaaag  6540
```

```
ggacgtaaag gtgactcctg gtacaaagca tacagaggaa agacctaagg tgcaggttat  6600
acaggcggct gaacccttgg cgacagcata cctatgtggg attcacagag agctggttag  6660
gaggctgaac gccgtcctcc tacccaatgt acatacacta tttgacatgt ctgccgagga  6720
tttcgatgcc atcatagccg cacactttaa gccaggagac actgttttgg aaacggacat  6780
agcctccttt gataagagcc aagatgattc acttgcgctt actgctttga tgctgttaga  6840
ggatttaggg gtggatcact ccctgctgga cttgatagag gctgctttcg gagagatttc  6900
cagctgtcac ctaccgacag gtacgcgctt caagttcggc gccatgatga aatcaggtat  6960
gttcctaact ctgttcgtca acacattgtt aaacatcacc atcgccagcc gagtgctgga  7020
agatcgtctg acaaaatccg cgtgcgcggc cttcatcggc gacgacaaca taatacatg   7080
agtcgtctcc gatgaattga tggcagccag atgtgccact tggatgaaca tggaagtgaa  7140
gatcatagat gcagttgtat ccttgaaagc cccttacttt tgtggagggt ttatactgca  7200
cgatactgtg acaggaacag cttgcagagt ggcagacccg ctaaaaaggc ttttaaact   7260
gggcaaaccg ctagcggcag gtgacgaaca agatgaagat agaagacgag cgctggctga  7320
cgaagtgatc agatggcaac gaacagggct aattgatgag ctggagaaag cggtatactc  7380
taggtacgaa gtgcagggta tatcagttgt ggtaatgtcc atggccacct ttgcaagctc  7440
cagatccaac ttcgagaagc tcagaggacc cgtcataact ttgtacggcg gtcctaaata  7500
ggtacgcact acagctacct attttgcaga agccgacagc aagtatctaa acactaatca  7560
gctacaatgg agttcatccc aacccaaact ttttacaata ggaggtacca gcctcgaccc  7620
tggactccgc gccctactat ccaagtcatc aggcccagac cgcgccctca gaggcaagct  7680
gggcaacttg cccagctgat ctcagcagtt aataaactga caatgcgcgc ggtaccacaa  7740
cagaagccgc gcaggaatcg gaagaataag aagcaaaagc aaaacaaca ggcgccacaa   7800
aacaacacaa atcaaaagaa gcagccacct aaaagaaagc cggctcaaaa gaaaaagaag  7860
ccgggccgca gagagaggat gtgcatgaaa atcgaaaatg attgtatttt cgaagtcaag  7920
cacgaaggta aggtaacagg ttacgcgtgc ctggtggggg acaaagtaat gaaaccagca  7980
cacgtaaagg ggaccatcga taacgcggac ctggccaaac tggcctttaa gcggtcatct  8040
aagtatgcgc ttgaatgcgc gcagatacac gtgcacatga agtccgacgc ttcgaagttc  8100
acccatgaga aaccggaggg gtactacaac tggcaccacg gagcagtaca gtactcagga  8160
ggccggttca ccatccctac aggtgctggc aaaccagggg acagcggcag accgatcttc  8220
gacaacaagg gacgcgtggt ggccatagtc ttaggaggag ctaatgaagg agcccgtaca  8280
gccctctcgg tggtgacctg gaataaagac atttgtcacta aaatcacccc cgagggggcc  8340
gaagagtgga gtcttgccat cccagttatg tgcctgttgg caaacaccac gttccctgc   8400
tcccagcccc cttgcacgcc ctgctgctac gaaaaggaac cggaggaaac cctacgcatg  8460
cttgaggaca acgtcatgag acctgggtac tatcagctgc tacaagcatc cttaacatgt  8520
tctcccacc gccagcgacg cagcaccaag gacaacttca atgtctataa agccacaaga   8580
ccatacttag ctcactgtcc cgactgtgga gaagggcact cgtgccatag tcccgtagca  8640
ctagaacgca tcagaaatga agcgacagac gggacgctga aaatccaggt ctccttgcaa  8700
atcggaataa agacggatga cagccacgat tggaccaagc tgcgttatat ggacaaccac  8760
atgccagcag acgcagagag ggcggggcta tttgtaagaa catcagcacc gtgtacgatt  8820
actggaacaa tgggacactt catcctggcc cgatgtccaa aagggaaac tctgacggtg   8880
ggattcactg acagtaggaa gattagtcac tcatgtacgc acccatttca ccacgaccct  8940
cctgtgatag gtcgggaaaa attccattcc gaccgcagc acgtaaaga gctaccttgc   9000
agcacgtacg tgcagagcac cgccgcaact accgaggaga tagaggtaca catgcccca   9060
gacaccctg atcgcacatt aatgtcacaa cagtccggca acgtaaagat cacagtcaat   9120
ggccagacgg tgcggtacaa gtgtaattgc ggtggctcaa atgaaggact aacaactaca  9180
gacaaagtga ttaataactg caaggttgat caatgtcatg ccgcgtcac caatcacaaa   9240
aagtggcagt ataactcccc tctggtcccg cgtaatgctg aacttgggga ccgaaaagga  9300
aaaattcaca tcccgtttcc gctggcaaat gtaacatgca gtgtgcctaa agcaaggaac  9360
cccaccgtga cgtacgggaa aaaccaagtc atcatgctac tgtatcctga ccacccaaca  9420
ctcctgtcct accggaatat gggagaagaa ccaaactatc aagaagagtg ggtgatgcat  9480
aagaaggaag tcgtgctaac cgtgccgact gaagggctcg aggtcacgtg gggcaacaac  9540
gagccgtata agtattggcc gcagttatct acaaacggta cagcccatgg ccaccgcat   9600
gagataattc tgtattatta tgagctgtac cccactatga ctgtagtagt tgtgtcagtg  9660
gccacgttca tactcctgtc gatggtgggt atggcagcgg gatgtgcat gtgtgcacga    9720
cgcagatgca tcacaccgta tgaactgaca ccaggagcta ccgtcccttt cctgcttagc  9780
ctaatatgct gcatcagaac agctaaagcg gccacatacc aagaggctgc gatatacctg  9840
tggaacgagc agcaaccttt gttttggcta caagccctta ttccgctggc agccctgatt  9900
gttctatgca actgtctgag actcttacca tgctgctgta aaacgttggc ttttttagcc  9960
gtaatgagcg tcggtgccca cactgtgagc gcgtacgaac acgtaacagt gatcccgaac 10020
acggtgggag taccgtataa gactctagtc aatagacctg gctacagccc catggtattg 10080
gagatggaac tactgtcagt cactttggag ccaacactgt cgcttgatta catcacgtgc 10140
gagtacaaaa ccgtcatccc gtctccgtac gtgaagtgct gcggtacagc agagtgcaag 10200
gacaaaaacc tacctgacta cagctgtaag gtcttcaccg cgtctaccc attttatgtg  10260
ggcggcgcct actgcttctg cgacgctgaa aacacgcagt tgagcgaagc acacgtggag 10320
aagtccgaat catgcaaaac agaatttgca tcagcataca ggcgtcatac cgcatctgca 10380
tcagctaagc tccgcgtcct ttaccaagga aataacatca ctgtaactgc ctatgcaaac 10440
ggcgaccatg ccgtcacagt taaggacgcc aaattcattg tggggccaat gtcttcagcc 10500
tggacacctt tcgacaacaa aattgtggtg tacaaaggtg acgtctataa catggactac 10560
ccgccctttg gcgcaggaag accaggacaa tttggcgata tccaaagtcg cacacctgag 10620
agtaaagacg tctatgctaa tacacaactg gtactgcaga gaccggctgt gggtacggta 10680
cacgtgccat actctcaggc accatctggc tttaagtatt ggctaaaaga acgcggggcg 10740
tcgctgcagc acacagcacc atttggctgc caaatagcaa caaacccggt aagagcggtg 10800
aactgcgccg tagggaacat gcccatctcc atcgacatac cggaagcggc cttcactagg 10860
gtcgtcgacg cgccctcttt aacggacatg tcgtgcgagg taccagcctg cacccattcc 10920
tcagactttg ggggcgtcgc cattattaaa tatgcagcca agaaaagg caagtgtgcg  10980
gtgcattcga tgactaacgc cgtcactatt cggaagctg agatagaagt tgaagggaat 11040
tctcagctgc aaatctcttt ctcgacggcc ttagccagcg ccgaattccg cgtacaagtc 11100
tgttctacac aagtacactg tgcagccgag tgccaccccc cgaaggacca catagtcaac 11160
tacccggcgt cacataccac cctcgggggtc caggacatct ccgctacggc gatgtcatgg 11220
gtgcagaaga tcacgggagg tgtgggactg gttgttgctg ttgccgcact gattctaatc 11280
```

```
gtggtgctat gcgtgtcgtt cagcaggcac taacttgaca attaagtatg aaggtatatg  11340
tgtcccctaa gagacacact gtacatagca ataatctat agatcaaagg gctacgcaac   11400
ccctgaatag taacaaaata caaaatcact aaaaattata aaaacagaaa aatacataaa   11460
taggtatacg tgtcccctaa gagacacatt gtatgtaggt gataagtata gatcaaaggg   11520
ccgaataacc cctgaatagt aacaaaatat gaaaatcaat aaaaatcata aaatagaaaa   11580
accataaaca gaagtagttc aaagggctat aaaaccctg aatagtaaca aaacataaaa    11640
ttaataaaaa tcaaatgaat accataattg gcaaacggaa gagatgtagg tacttaagct   11700
tcctaaaagc agccgaactc actttgagaa gtaggcatag cataccgaac tcttccacga   11760
ttctccgaac ccacagggac gtaggagatg ttattttgtt tttaatattt caaaaaaaaa   11820
aaaaaaaaaa aaaaaaaaaa aaaaaaaaaa agcggccgct taattaatcg aggggaatta   11880
attcttgaag acgaaaggc caggtggcac ttttcgggga aatgtgcgcg aaccccctat    11940
ttgtttattt ttctaaatac attcaaatat gtatccgctc atgagacaat aaccctgata   12000
aatgcttcaa taatattgaa aaaggaagag tatgagtatt caacatttcc gtgtcgccct   12060
tattcccttt tttgcggcat tttgccttcc tgtttttgct cacccagaaa cgctggtgaa   12120
agtaaaagat gctgaagatc agttgggtgc acgagtgggt tacatcgaac tggatctcaa   12180
cagcggtaag atccttgaga gttttcgccc cgaagaacgt tttccaatga tgagcacttt   12240
taaagttctg ctatgtggcg cggtattatc ccgtgttgac gccgggcaag agcaactcgg   12300
tcgccgcata cactattctc agaatgactt ggttgagtac tcaccagtca cagaaaagca   12360
tcttacggat ggcatgacag taagagaatt atgcagtgct gccataacca tgagtgataa   12420
cactgcggcc aacttacttc tgacaacgat cggaggaccg aaggagctaa ccgcttttt    12480
gcacaacatg ggggatcatg taactcgcct tgatcgttgg gaaccggagc tgaatgaagc   12540
cataccaaac gacgagcgtg acaccacgat gcctgtagca atggcaacaa cgttgcgcaa   12600
actattaact ggcgaactac ttactctagc ttcccggcaa caattaatag actggatgga   12660
ggcggataaa gttgcaggac cacttctgcg ctcggccctt ccgctggct ggtttattgc     12720
tgataaatct ggagccggtg agcgtgggtc tcgcggtatc attgcagcac tggggccaga   12780
tggtaagccc tcccgtatcg tagttatcta cacgacgggg agtcaggcaa ctatggatga   12840
acgaaataga cagatcgctg agataggtgc ctcactgatt aagcattggt aactgtcaga   12900
ccaagtttac tcatatatac tttagattga tttaaaactt catttttaat ttaaaaggat   12960
ctaggtgaag atccttttg ataatctcat gaccaaaatc ccttaacgtg agttttcgtt    13020
ccactgagcg tcagacccg tagaaaagat caaaggatct tcttgagatc ctttttttct    13080
gcgcgtaatc tgctgcttgc aaacaaaaaa accaccgcta ccagcggtgg tttgtttgcc   13140
ggatcaagag ctaccaactc tttttccgaa ggtaactggc ttcagcagag cgcagatacc   13200
aaatactgtc cttctagtgt agccgtagtt aggccaccac ttcaagaact ctgtagcacc   13260
gcctacatac ctcgctctgc taatcctgtt accagtggct gctgccagtg gcgataagtc   13320
gtgtcttacc gggttggact caagacgata gttaccggat aaggcgcagc ggtcgggctg   13380
aacggggggt tcgtgcacac agcccagctt ggagcgaacg acctacaccg aactgagata   13440
cctacagcgt gagcattgag aaagcgccac gcttcccgaa gggagaaagg cggacaggta   13500
tccggtaagc ggcagggtcg gaacaggaga gcgcacgagg gagcttccag ggggaaacgc   13560
ctggtatctt tatagtcctg tcgggtttcg ccacctctga cttgagcgtc gatttttgtg   13620
atgctcgtca ggggggcgga gcctatggaa aaacgccagc aacgcgagct cgtatgtgaca  13680
tatttgtcgtt agaacgcggc tacaattaat acataacctt atgtatcata cacaatcgat  13740
ttaggtgaca ctatag                                                  13756
```

```
SEQ ID NO: 24           moltype = AA  length = 1248
FEATURE                 Location/Qualifiers
REGION                  1..1248
                        note = Description of Artificial Sequence: Synthetic
                         polypeptide
source                  1..1248
                        mol_type = protein
                        organism = synthetic construct
SEQUENCE: 24
MEFIPTQTFY NRRYQPRPWT PRPTIQVIRP RPRPQRQAGQ LAQLISAVNK LTMRAVPQQK   60
PRRNRKNKKQ KQKQQAPQNN TNQKKQPPKK KPAQKKKKPG RRERMCMKIE NDCIFEVKHE  120
GKVTGYACLV GDKMKPAHV KGTIDNADLA KLAFKRSSKY DLECAQIPVH MKSDASKFTH   180
EKPEGYYNWH HGAVQYSGGR FTIPTGAGKP GDSGRPIFDN KGRVVAIVLG GANEGARTAL  240
SVVTWNKDIV TKITPEGAEE WSLAIPVMCL LANTTFPCSQ PPCTPCCYEK EPEETLRMLE  300
DNVMRPGYYQ LLQASLTCSP HRQRRSTKDN FNVYKATRPY LAHCPDCGEG HSCHSPVALE  360
RIRNEATDGT LKIQVSLQIG IKTDDSHDWT KLRYMDNHMP ADAERAGLFV RTSAPCTITG  420
TMGHFILARC PKGETLTVGF TDSRKISHSC THPFHHDPPV IGREKFHSRP QHGKELPCST  480
YVQSTAATTE EIEVHMPPDT PDRTLMSQQS GNVKITVNGQ TVRYKCNCGG SNEGLTTTDK  540
VINNCKVDQC HAAVTNHKKW QYNSPLVPRN AELGDRKGKI HIPFPLANVT CRVPKARNPT  600
VTYGKNQVIM LLYPDHPTLL SYRNMGEEPN YQEEWVMHKE EVVLTVPTEG LEVTWGNNEP  660
YKYWPQLSTN GTAHGHPHEI ILYYYELYPT MTVVVVSVAT FILLSMVGMA AGMCMCARRR  720
CITPYELTPG ATVPFLLSLI CCIRTAKAAT YQEAAIYLWN EQQPLFWLQA LIPLAALIVL  780
CNCLRLLPCC CKTLAFLAVM SVGAHTVSAY EHVTVIPNTV GVPYKTLVNR PGYSPMVLEM  840
ELLSVTLEPT LSLDYITCEY KTVIPSPYVK CCGTAECKDK NLPDYSCKVF TGVYPFMWGG  900
AYCFCDAENT QLSEAHVEKS ESCKTEFASA YRAHTASASA KLRVLYQGNN ITVTAYANGD  960
HAVTVKDAKF IVGPMSSAWT PFDNKIVVYK GDVYNMDYPP FGAGRPGQFG DIQSRTPESK 1020
DVYANTQLVL QRPAVGTVHV PYSQAPSGFK YWLKERGASL QHTAPFGCQI ATNPVRAVNC 1080
AVGNMPISID IPEAAFTRVV DAPSLTDMSC EVPACTHSSD FGGVAIIKYA ASKKGKCAVH 1140
SMTNAVTIRE AEIEVEGNSQ LQISFSTALA SAEFRVQVCS TQVHCAAECH PPKDHIVNYP 1200
ASHTTLGVQD ISATAMSWVQ KITGGVGLVV AVAALILIVV LCVSFSRH               1248

SEQ ID NO: 25           moltype = AA  length = 1248
FEATURE                 Location/Qualifiers
REGION                  1..1248
                        note = Description of Artificial Sequence: Synthetic
                         polypeptide
```

```
source                    1..1248
                          mol_type = protein
                          organism = synthetic construct
SEQUENCE: 25
MEFIPTQTFY NRRYQPRPWA PRPTIQVIRP RPRPQRQAGQ LAQLISAVNK LTMRAVPQQK    60
PRRNRKNKQ  RQKKQAPQND  PKQKKQPPQK KPAQKKKKPG RRERMCMKIE NDCIFEVKHE  120
GKVMGYACLV GDKVMKPAHV KGTIDNADLA KLAFKRSSKY DLECAQIPVH MKSDASKFTH   180
EKPEGYYNWH HGAVQYSGGR FTIPTGAGKP GDSGRPIFDN KGRVVAIVLG GANEGARTAL   240
SVVTWNKDIV TKITPEGAEE WSLALPVLCL LANTTFPCSQ PPCTPCCYEK EPESTLRMLE   300
DNVMRPGYYQ LLKASLTCSP HRQRRSTKDN FNVYKATRPY LAHCPDCGEG HSCHSPIALE   360
RIRNEATDGT LKIQVSLQIG IKTDDSHDWT KLRYMDSHTP ADAERAGLLV RTSAPCTITG   420
TMGHFILARC PKGETLTVGF TDSRKISHTC THPFHHEPPV IGRERFHSRP QHGKELPCST   480
YVQSTAATAE EIEVHMPPDT PDRTLMTQQS GNVKITVNGQ TVRYKCNCGG SNEGLTTTDK   540
VINNCKIDQC HAAVTNHKNW QYNSPLVPRN AELGDRKGKI HIPFPLANVT CRVPKARNPT   600
VTYGKNQVTM LLYPDHPTLL SYRNMGQEPN YHEEWVTHKK EVTLTVPTEG LEVTWGNNEP   660
YKYWPQMSTN GTAHGHPHEI ILYYYELYPT MTVVIVSVAS FVLLSMVGTA VGMCVCARRR   720
CITPYELTPG ATVPFLLSLL CCVRTTKAAT YYEAAAYLWN EQQPLFWLQA LIPLAALIVL   780
CNCLKLLPCC CKTLAFLAVM SIGAHTVSAY EHVTVIPNTV GVPYKTLVNR PGYSPMVLEM   840
ELQSVTLEPT LSLDYITCEY KTVIPSPYVK CCGTAECKDK SLPDYSCKVF TGVYPFMWGG   900
AYCFCDAENT QLSEAHVEKS ESCKTEFASA YRAHTASASA KLRVLYQGNN ITVAAYANGD   960
HAVTVKDAKF VVGPMSSAWT PFDNKIVVYK GDVYNMDYPP FGAGRPGQFG DIQSRTPESK  1020
DVYANTQLVL QRPAAGTVRVV PYSQAPSGFK YWLKERGASL QHTAPFGCQI ATNPVRAVNC  1080
AVGNIPISID IPDAAFTRVV DAPSVTDMSC EVPACTHSSD FGGVAIIKYT ASKKGKCAVH  1140
SMTNAVTIRE ADVEVEGNSQ LQISFSTALA SAEFRVQVCS TQVHCAAACH PPKDHIVNYP  1200
ASHTTLGVQD ISTTAMSWVQ KITGGVGLIV AVAALILIVV LCVSFSRH                1248

SEQ ID NO: 26             moltype = DNA  length = 36
FEATURE                   Location/Qualifiers
misc_feature              1..36
                          note = Description of Artificial Sequence: Synthetic primer
source                    1..36
                          mol_type = other DNA
                          organism = synthetic construct
SEQUENCE: 26
gctctagaca ccatgagcct cgccctcccg gtcttg                              36

SEQ ID NO: 27             moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 27
tggatcctca ttagtgcctg ctaaacgaca                                     30

SEQ ID NO: 28             moltype = DNA  length = 36
FEATURE                   Location/Qualifiers
misc_feature              1..36
                          note = Description of Artificial Sequence: Synthetic primer
source                    1..36
                          mol_type = other DNA
                          organism = synthetic construct
SEQUENCE: 28
gctctagaca ccatgagtct tgccatccca gttatg                              36

SEQ ID NO: 29             moltype = DNA  length = 30
FEATURE                   Location/Qualifiers
misc_feature              1..30
                          note = Description of Artificial Sequence: Synthetic primer
source                    1..30
                          mol_type = other DNA
                          organism = synthetic construct
SEQUENCE: 29
tggatcctca ttagtgcctg ctgaacgaca                                     30

SEQ ID NO: 30             moltype = DNA  length = 22
FEATURE                   Location/Qualifiers
misc_feature              1..22
                          note = Description of Artificial Sequence: Synthetic primer
source                    1..22
                          mol_type = other DNA
                          organism = synthetic construct
SEQUENCE: 30
aagctccgcg tcctttacca ag                                             22

SEQ ID NO: 31             moltype = DNA  length = 21
FEATURE                   Location/Qualifiers
misc_feature              1..21
```

```
                        note = Description of Artificial Sequence: Synthetic primer
source                  1..21
                        mol_type = other DNA
                        organism = synthetic construct
SEQUENCE: 31
ccaaattgtc ctggtcttcc t                                                       21

SEQ ID NO: 32           moltype = DNA  length = 26
FEATURE                 Location/Qualifiers
misc_feature            1..26
                        note = Description of Artificial Sequence: Synthetic probe
source                  1..26
                        mol_type = other DNA
                        organism = synthetic construct
SEQUENCE: 32
ccaatgtctt cagcctggac accttt                                                  26

SEQ ID NO: 33           moltype = DNA  length = 13826
FEATURE                 Location/Qualifiers
misc_feature            1..13826
                        note = Description of Artificial Sequence: Synthetic
                          polynucleotide
source                  1..13826
                        mol_type = other DNA
                        organism = synthetic construct
SEQUENCE: 33
atggctgcgt gagacacacg tagcctacca gtttcttact gctctactct gcttagcaag     60
agacttgaga acccatcatg gatcccgtgt acgtggacat agacgccgac agcgcctttt    120
taaaggcccct gcagcgtgcg taccccatgt ttgaggtgga accaaggcag gtcacaccga   180
atgaccatgc caatgctaga gcattctcgc atctagctat aaaactaata gagcaggaaa    240
ttgatcccga ctcaaccatc ctggacatag gcagcgcgcc agcaaggagg atgatgtcgg    300
ataggaagta ccactgcgtt tgccctatgc gcagcgcaga agaccctgag agactcgcca    360
actacgcgag aaaactagca tctgccgcag gaaaagtctt ggacagaaac atctccgaaa    420
aaattggaga tctacaagca gtaatggctg taccagacgc agaaacgccc acattctgct    480
tgcacactga cgtctcatgt agacaaaggg cggacgtcgc tatataccag gatgtctacg    540
ccgtgcatgc accaacatcg ctgtaccacc aggcgattaa aggagtccgt gtagcatact    600
ggatagggtt tgatacaacc ccgttcatgt ataatgccat ggcaggtgca taccccctcgt   660
actcgacaaa ctgggcagat gagcaggtgc tgaaggcaaa gaacatagga ttatgttcaa    720
cagacctgac ggaaggtaga cgaggtaaat tgtctatcat gagaggaaaa aagtgaagc     780
catgtgaccg cgtactgttc tcagtcgggt caacgcttta cccggagagc cgtaagcttc    840
ttaagagttg gcacttacct tcagtgttcc atctaaaagg gaagctcagc ttcacgtgcc    900
gctgtgatac agtggtttcg tgtgaaggct atgtcgttaa gagaataacg attagcccgg    960
gcctctacgg taaaaccaca gggtacgcag taacccaacg tgcacgcgga ttcctaatgt   1020
gcaaaacaac cgatacggta gatggcgaga gagtgtcatt ttcggtatgc acgtacgtac   1080
ccgcaaccat ttgtgatcaa atgacaggta ttcttgccac ggaggttaca ccggaggatg   1140
cacagaagct gctggtggga ctgaaccaga ggatagtggt caatggcaga acgcagagga   1200
acagaacac aatgaagaat tacttgcttc ctgtagttgc ccaagccctc agtaagtggg   1260
caaaggaatg ccggaaagat atggaagatg aaaaactttt gggcatcaga gaaaggacac   1320
tgacatgctg ctgcctttgg gcgttcaaga agcagaagac acacgtc tacaagaggc     1380
ctgacactca gtcaattcag aaagtcccag ccgaatttga cagcttttgtg gtaccaagtc   1440
tgtggtcatc tggactgtcg atcccgctac ggaccagaat caagtggctg ctaagcaaga   1500
tgccaaagac tgatttgatc ccttacagcg gtgacgccaa agaagccgc gacgctgaaa    1560
aagaagcaga agaagaacga gaagcggagc taactcgcga ggcactacca ccactacagg   1620
cggcacagga cgacgtccag gtcgaaattg acgtggaaca gctcgaagac agagctgggg   1680
caggaataat tgaaactcca agaggagcta tcaaagtcac tgcccaacca acagaccacg   1740
tcgtgggaga gtacttggta cttttcccgc agaccgtgtt acgaagccag aagctcagcc   1800
tgatccacgc attggcggaa caagtgaaga catgcacaca cagcggacgg gcaggaaggt   1860
acgcggtcga agcatatgac ggcagaatcc ttgtgccctc aggctatgca atatcacctg   1920
aagacttcca gagcctgagc gaaagtgcga cgatggtgta caacgaaagg gagttcgtaa   1980
ataggaaatt acaccatatc gcgttgcacg gaccagccct gaacactgag gaggagtcgt   2040
acgagctggt aagggcagaa aggacagagc atgagtacgt ctatgatgtg gaccaaagaa   2100
ggtgctgcaa gaaagaggag gcagccgggc tggtactggt cggcgacttg accaacccgc   2160
cctaccatga gttcgcatat gaagggctga aatccgccc cgcctgccca tacaagaccg   2220
cagtaatagg ggtcttttga gtgccaggat ccggcaaatc agcaatcatt aagaacctag   2280
ttaccaggca gacctagtg accagtggaa agaaagaaaa ctgccaagaa atctccaccg   2340
acgtgatgcg acagaggaac ctggagatat ctgcacgcac ggtcgactca ctgctctga   2400
acggatgcaa tagaccagtc gacgtgttgt acgtcgacga agcttttgcg tgccattctg   2460
gcacgctact tgctctgata gccttggtga gaccgaggca gaaagtcgtg ctatgcggtg   2520
atcccaaaca gtgcggcttc ttcaatatga tgcagatgaa gttaactac aaccataaca   2580
tctgcaccca agtgtaccat aaaagtattt tccaggcggtg tacactgcct gtgactgcca   2640
ttgtgtcctc gttgcattac gaaggcaaaa tgcgcacaac aaatgagtac aacaagccaa   2700
ttgtagtgga tactacaggc tcgacaaaac ccgaccccgg agaccttgtg ctaacatgtt   2760
tcagagggtg ggttaagcaa ctgcaaattg actatcgtgg acacgaggtc atgacagcag   2820
ctgcatctca ggggctaacc agaaaagggg tctatgccgt caggcaaaaa gttaatgaaa   2880
aacccccttta cgcatcaaca tcagagcacg tgaacgtgct actgacgcgt acggaaggca   2940
aactagtatg gaagacactt tctgagacc atggataaaa gacactgcag aacccgccga   3000
aaggaaattt taaagcaaca attaaggaat gggaagtgga acatgcttca ataatggcgg   3060
gtatctgtaa ccaccaagtg acctttgaca cgttccagaa taaagccaat gtctgctggg   3120
cgaagagctt agtccccatc ctagaaacag cagggataaa attaaacgac aggcagtggt   3180
```

```
cccagataat ccaggctttt aaagaagaca gagcatactc acccgaggtg gccctgaatg 3240
agatatgcac gcgcatgtac gggggtagacc tggacagcgg actgttctct aaaccactgg 3300
tgtccgtgca tcatgcggat aatcactggg acaacaggcc gggagggaag atgttcggat 3360
tcaaccccga agcggcgtcc atactggaga ggaaataccc gtttacaaaa gggaagtgga 3420
ataccaacaa gcaaatctgt gtgactacta ggaggattga agatttaac ccgaaccaca 3480
acattatacc tgccaacagg agattaccgc attcattggt ggccgaacat cgcccgtaa 3540
aaggggagag gatggaatgg ttggtcaaca aaataaatgg ccaccatgtg ctcctggtca 3600
gcggctacaa cctcgttctg cccactaaga gagtcacctg ggtggcgccg ctgggcattc 3660
ggggagctga ctacacatac aacctagagt taggcctacc agcaacgctc ggtagatatg 3720
acctagtgat tataaacatc cacacaccct ttcgcataca tcattaccaa cagtcgtgg 3780
atcacgcaat gaagctgcag atgctcggag gagactccct gagactgctc aagccgggtg 3840
gttcattact gatcagggca tacggctacg cagacagaac aagcgaacga gtagtctgcg 3900
tattgggacg caagtttcga tcatccagag cgttgaaacc gccgtgcgtc actagcaaca 3960
ccgagatgtt tttcttgttc agcaactttg ataacgg caa aaggaacttt acgacgcacg 4020
taatgaacaa ccagctgaat gctgcttttg ttggtcaggc cacccgagca gggtgcgcac 4080
cgtcgtaccg ggttaaacgc atggacatcg caaagaacga tgaagagtgt gtagtcaacg 4140
ccgccaaccc tcgtgggcta ccaggcgatg gcgtctgtaa agcagtatac aaaaaatggc 4200
cggagtcctt caagaacagt gcaacaccag tgggaaccgc aaagacagtc atgtgcggta 4260
catacccggt aatccatgca gtaggaccta atttctcaaa ttactctgag tccgaaggag 4320
accgggaatt ggcagctgct taccgagaag tcgctaagga ggtgactaga ctaggagtaa 4380
acagcgtagc tataccgctc cttttccaccg gtgtgtactc tggagggaaa gacaggctga 4440
ctcagtcact aaaccacctt tttacagcat tagactacac tgatgcagat gtggttatct 4500
actgccgcga caaggagtgg gagaagaaaa tagctgagc catacaaatg aggacccaag 4560
tggaattact agacgaacac atctctgtag actgcgatat catccgagtg caccctgaca 4620
gcagtttggc aggtagaaaa gggtacagca ctacagaagg ttcactgtac tcctacttgg 4680
aagggacacg gttccatcag acggcagtgg acatggcaga agtatacacc atgtggccaa 4740
agcagacgga ggctaatgaa caagtttgct tgtacgcatt gggggaaagt atagaatcaa 4800
tcaggcaaaa gtgcccagtg gatgacgcag atgcatcgtc gccccaaaa accgtcccgt 4860
gcctctgccg ttatgccatg acacccgaac gagtcaccag gcttcgtatg aaccatgtca 4920
caagcataat agtatgctca tcattccccc ttccaaagta taaaatagaa ggagtgcaga 4980
aagtcaagtg ttctaaagtg atgctgttcg accataacgt gccatcacgc gttagtccaa 5040
gggaatataa atcgcctcag gagaccgcac aagaagtaag ttcgaccacg tcactgacgc 5100
acagccaatt cgaccttagc gttgacggtg aggaactgcc cgctccgtct gacttggaag 5160
ctgacgctcc gattccggaa ccaacaccag acgacagagc ggtacttact ttgcctccta 5220
cgattgataa ttttttcggct gtgtcagact gggtaatgaa taccgcgcca gtcgcaccac 5280
ccagaagaag acgtgggaaa aacttgaatg tcacctgcga cgagagaga gggaacgtac 5340
ttcccatggc tagcgttcgg ttcttcagag cggatctgca ctccatcgta caggaaacgg 5400
cagagatacg cgatacggcc gcgtccctcc aggcgcccct gagtgtcgct acagaaccga 5460
atcaactgcc gatctcattt ggagcaccaa acgagactttt cccataacgg ttcggggatt 5520
ttgatgaagg ggagattgaa agcttgtcct ctgagttact gaccttggg gacttctcgc 5580
cgggcgaagt ggatgacctg acagacagcg actggtccac gtgttcagac acggacgacg 5640
aattatgact agatagggca ggtgggtaca tattctcatc tgacaccggc cccggccacc 5700
tgcaacagag gtctgtccgt cagacagtac tgccggtaaa taccttggag gaagttcagg 5760
aggagaaatg ttacccacct aagttggatg aagtgaaaga gcagttgtta cttaagaaac 5820
tccaggaaag tgcgtccatg gctaacagaa gcaggtacca atcccgcaaa gtagagaaca 5880
tgaaagcaac aatagtccaa aggctgaagg gtggttgcaa actttatta atgtcggaga 5940
ccccgaaagt tcctacctac cgaactacat atccggcacc agtgtactca ccccaatca 6000
atatccgact gtccaacccc gagtctgctg tggcagcgtg caatgagttc ctagcaagga 6060
actatccgac agttgcgtcg taccaaatca ccgatgagta cgatgcatac ctagacatgg 6120
tggacgggtc ggaaagttgc cttgaccggg cgacgttcaa cccatcaaag cttagaagtt 6180
atccaaaaca gcactcctac catgcaccca caatcagaag tgccgtacct tccccgtaa 6240
agaacacgct gcagaacgta ctggctgctg ccacgaaaag aaattgcaac gtcacacaga 6300
tgagagaact gcctactttg gattcagcgg tatttaatgt tgagtgcttt aaaaaatttg 6360
cgtgcaatca agaatactgg aaggaatttg ccgccagccc tattaggata acgactgaga 6420
acttgacaac ttatgtcaca aaactaaaag gaccaaaagc agcagcactg tttgccaaga 6480
cacataacct gctaccactg caggaggtgc cgatggacag gtttactgta gacatgaaaa 6540
gggacgtgaa ggtgactccg gggacgaagc acactgagga aagacctaaa gtgcaggtca 6600
tacaggcagc cgaaccttttg gcaacagcat atctgtgtgg gatccacaga gagttggtca 6660
gaaggctgaa tgcagtcctt ctacctaatg tacacacgct gtttgacatg tctgccgagg 6720
actttgacgc cattattgcc gcgcacttca agccggtaca gcccgtattg gaaaccgata 6780
tagcctcctt tgacaagagc caagacgact cattggcgct cactgctcta atgttgctag 6840
aggatttggg ggtggatcat ccctgtttgg acttgataga ggctgccttc gggggagatct 6900
ccagctgcca cctaccgacg gcacccgttt ttaagttcgg cgccatgatg aagtctggta 6960
tgttcctaac cctgttcgtc aacacactgc taaacatcac catcgccagac caacccgaga 7020
aggaccgctt gacaaggtct gcgtgcgcgg cctttcatcgg cgacgacaat ataatacatg 7080
gggttgtctc tgacgaactg atggcagcaa ggtgtgctac atggatgaac atggaagtga 7140
agatcataga tgcggtcgtg tctcagaaag ccccgtactt ctgcgagggg tttatactgt 7200
atgacacagt agcaggcacg gcctgcagag tggcagaccc gctaaagcgg ctgttcaagc 7260
tgggcaaacc gctggcagcg ggagatgaac cagaagacgt gcactggtgc 7320
acgaagtggt tagatggcaa cgaacaggac taactgatga gctagaaaaa gcggtacact 7380
ccaggtgatga agtgcagggc atatctgcg tggtaatgtc tatggccacc tttgcaagct 7440
ctagatctaa ctttgagaag ctcagaggac ccgtcgtaac cctgtacggt ggtcctaaat 7500
aggtacgcac tacagctacc tatttcgtca gaaaccaatc gcagctactt gcatacctac 7560
ccaaattcaat ggagttcatc ccgacgcaaa cttttctaaa gaaggtac caaccccgac 7620
cctgggcccc acgccctaca attcaagtaa ttagacctag accacgtcca cagaggcagg 7680
ctgggcaact cgcccagctg atctccgcag tcaacaaatt gaccatgcgc gcggtacctc 7740
aacagaagcc tcgcagaaat cggaaaaaca agaagcaaag gcagaagaag caggcgccgc 7800
aaaacgaccc aaagcaaaag aagcaaccac cacaaaagaa gccggctcaa aagaagaaga 7860
aaccaggccg tagggagaga atgtgcatga aaattgaaaa tgattgcatc ttcgaagtca 7920
```

```
agcatgaagg caaagtgatg ggctacgcat gcctggtggg ggataaagta atgaaaccag  7980
cacatgtgaa gggaactatc gacaatgccg atctggctaa actggccttt aagcggtcgt  8040
ctaaatacga tcttgaatgt gcacagatac cggtgcacat gaagtctgat gcctcgaagt  8100
ttacccacga gaaacccgag gggtactata actggcatca cggagcagtg cagtattcag  8160
gaggccggtt cactatcccg acgggtgcag gcaagccggg agacagcggc agaccgatct  8220
tcgacaacaa aggacgggtg gtggccatcg tcctaggagg ggccaacgaa ggtgcccgca  8280
cggccctctc cgtggtgacg tggaacaaag acatcgtcac aaaaattacc cctgagggag  8340
ccgaagagtg gagcctcgcc ctcccggtct tgtgcctgtt ggcaaacact acattcccct  8400
gctctcagcc gccttgcaca ccctgctgct acgaaaagga accggaaagc accttgcgca  8460
tgcttgagga caacgtgatg agacccggat actaccagct actaaaagca tcgctgactt  8520
gctctcccca ccgccaaaga cgcagtacta aggacatttt taatgtctat aaagccacaa  8580
gaccatatct agctcattgt cctgactgcg gagaagggca ttcgtgccac agccctatcg  8640
cattggagcg catcagaaat gaagcaacgg acggaacgct gaaaatccag gtctctttgc  8700
agatcgggat aaagacagat gacagccacg atttggaccaa gctgcgctat atggatagcc  8760
atacgccagc ggacgcggag cgagccggat tgcttgtaag gacttcagca ccgtgcacga  8820
tcaccgggac catgggacac tttattctcg cccgatgccc gaaaggagag acgctgcacg  8880
tgggatttac ggacagcaga aagatcagcc acacatgcac acacccgttc catcatgaac  8940
cacctgtgat aggtagggag aggttccact ctcgaccaca acatggtaaa gagttaccct  9000
gcagcacgta cgtgcagagc accgctgcca ctgctgagga gatagaggtg catatgcccc  9060
cagatactcc tgaccgcacg ctgatgacgc agcagtctgg caacgtgaag atcacagtta  9120
atgggcagac ggtgcggtac aagtgcaact gcggtggctc aaacgaggga ctgacaacca  9180
cagacaaagt gatcaataac tgcaaaattg atcagtgcca tgctgcagtc actaatcaca  9240
agaattggca atacaactcc cctttagtcc cgcgcaacgc tgaactcggg gaccgtaaag  9300
gaaagatcca catcccattc ccattggcaa acgtgacttg cagagtgcca aaagcaagaa  9360
accctacagt aacttacgga aaaaaccaag tcaccatgct gctgtatcct gaccatccga  9420
cactcttgtc ttaccgtaac atgggacagg aaccaaatta caccgaggag tgggtgacac  9480
acaagaagga ggttaccttg accgtgccta ctgagggtct ggaggtcact tggggcaaca  9540
acgaaccata caagtactgg ccgcagatgt ctacgaacgg tactgctcat ggtcacccac  9600
atgagataat cttgtactat tatgagctgt accccactat gactgtagtc attgtgtcgg  9660
tggcctcgtt cgtgcttctg tcgatggtgg gcacagcagt gggaatgtgt gtgtgcgcac  9720
ggcgcagatg cattacacca tatgaattaa caccagagc cactgttccc ttcctgctca  9780
gcctgctatg ctgcgtcaga acgaccaagg cggccacata ttacgaggct gcggcatatc  9840
tatgaacga acagcagccc ctgttctggt tgcaggctct tatcccgctg ccgccttga  9900
tcgtcctgtg caactgtctg aaactcttgc catgctgctg taagaccctg gcttttttag  9960
ccgtaatgag catcggtgcc cacactgtga gcgcgtacga acacgtaaca gtgatcccga 10020
acacggtggg agtaccgtat aagtacttg tcaacagacc gggttacagc cccatggtgt 10080
tggagatgga gctacaatca gtcaccttgg aaccaacact gtcacttgac tacatcacgt 10140
gcgagtacaa aactgtcatc ccctcccgt acgtgaagtg ctgtggtaca gcagagtgca 10200
aggacaagag cctaccagac tacagctgca aggtctttac tggagtctac ccatttatgt 10260
ggggcggcgc ctactgcttt tgcgacgccg aaaatacgca attgagcgag gcacatgtag 10320
agaaatctga atcttgcaaa acagagtttg catcggccta cagagcccac accgcatcgg 10380
cgtcggcgaa gctccgcgtc ctttaccaag gaaacaacat taccgtagct gcctacgcta 10440
acggtgacca tgccgtcaca gtaaaggacg ccaagtttgt cgtgggccca atgtcctccg 10500
cctggacacc ttttgacaac aaaatcgtgg tgtacaaagg cgacgtctac aacatggact 10560
acccaccttt tggcgcagga agaccaggac aatttggtga cattcaaagt cgtacaccgg 10620
aaagtaaaga cgtttatgcc aacactcagt tggtactaca gaggccagca gcaggcacgg 10680
tacatgtacc atactctcag gcaccatctg gcttcaagta ttggctgaag gaacgaggag 10740
catcgctaca gcacacggca ccgttcggtt gccagattgc gacaaacccg gtaagagctg 10800
taaattgcgc tgtggggaac atgccaattt ccatcgacat accggatgcg gccttactta 10860
gggttgtcga tgcaccctct gtaacggaca tgtcatgcga agtaccagcc tgcactcact 10920
cctccgactt tgggggcgtc gccatcatca aatacacacg tagcaagaaa tatgatgtgg 10980
cagtacattc gatgaccaac gccgttacca ttcgagaagc cgactagaa gtagaggga 11040
actcccagct gcaaatatcc ttctcaacag ccctggcaag cgccgagttt cgcgtgcaag 11100
tgtgctccac acaagtacac tgcgcagccg catgccaccc tccaaaggac acatagtca 11160
attaccagc atcacacacc ccccttgggg tccaggatat atccacaacg caatgtctt 11220
gggtgcagaa gattacggga ggagtaggat taattgttgc tgttgctgcc ttaattttaa 11280
ttgtggtgct atgcgtgtcg tttagcaggc actaaaccga tgataagca cgaaataact 11340
aaatagcaaa agtagaaagt acataaccag gtatatgtgc cccttaagag gcacaatata 11400
tatagctaag cactattaga tcaaagggct atacaacccc tgaatagtaa caaaacacaa 11460
aaaccaataa aatcataaa agaaaaatc tcataaacag gtataagtgt ccctaagag 11520
acacattgta tgtaggtagt aagtatagat caaagggcta tattaccccc tgaatagtaa 11580
caaaacacaa aaacaataaa aactacaaaa tagaaatct ataaacaaaa gtagttcaaa 11640
gggctacaaa acccctgaat agtaacaaaa cataaatgt aataaaatt aagtgtgtac 11700
ccaaaaagagg tacagtaaga atcagtgaat atcacaattg gcaacgagaa gagacgtagg 11760
tatttaagct tcctaaaagc agccgaactc actttgagac gtaggcatag cataccgaac 11820
tcttccacta ttctccgaac ccacagggac gtaggagatg ttattttgt tttaatattt 11880
caaaaaaaaa aaaaaaaaaa aaaaaaaaaaa aaaaaaaaa agcggccgct taattaatcg 11940
aggggaatta attcttgaag acgaaagggc caggtggcac ttttcgggga aatgtgcgcg 12000
gaacccctat ttgttttattt ttctaaatac attcaaatat gtatccgctc atgagacaat 12060
aaccctgata aatgcttcaa taatattgaa aaaggaagag tatgagtatt caacatttcc 12120
gtgtcgccct tattcccttt tttgcggcat tttgccttcc tgttttttgct cacccagaaa 12180
cgctggtgaa agtaaaagat gctgaagatc agttgggtgc acgagtgggt tacatcgaac 12240
tggatctcaa cagcggtaag atccttgaga gttttcgccc cgaagaacgt tttccaatga 12300
tgagcacttt taaagtcctg ctatgtgggcg cggtattatc ccgtgttgac gccgggcaag 12360
agcaactcgg tcgccgcata cactattctc agaatgactt ggttgagtac tcaccagtca 12420
cagaaaagca tcttacggat ggcatgacag taagagaatt atgcagtgct gccataacca 12480
tgagtgataa cactgcggcc aacttacttc tgacaacgat cggaggaccg aaggagctaa 12540
ccgctttttt gcacaacatg ggggatcatg taactcgcct tgatcgttgg gaaccggagc 12600
tgaatgaagc cataccaaac gacgagcgtg acaccacgat gcctgtagca atggcaacaa 12660
```

-continued

```
cgttgcgcaa actattaact ggcgaactac ttactctagc ttcccggcaa caattaatag  12720
actggatgga ggcggataaa gttgcaggac cacttctgcg ctcggccctt ccggctggct  12780
ggtttattgc tgataaatct ggagccggtg agcgtgggtc tcgcggtatc attgcagcac  12840
tggggccaga tggtaagccc tcccgtatcg tagttatcta cacgacgggg agtcaggcaa  12900
ctatggatga acgaaataga cagatcgctg agataggtgc ctcactgatt aagcattggt  12960
aactgtcaga ccaagtttac tcatatatac tttagattga tttaaaactt cattttttaat 13020
ttaaaaggat ctaggtgaag atccttttttg ataatctcat gaccaaaatc ccttaacgtg  13080
agttttcgtt ccactgagcg tcagaccccg tagaaaagat caaaggatct tcttgagatc  13140
cttttttttct gcgcgtaatc tgctgcttgc aaacaaaaaa accaccgcta ccagcggtgg  13200
tttgtttgcc ggatcaagag ctaccaactc tttttccgaa ggtaactggc ttcagcagag  13260
cgcagatacc aaatactgtc cttctagtgt agccgtagtt aggccaccac ttcaagaact  13320
ctgtagcacc gcctacatac ctcgctctgc taatcctgtt accagtggct gctgccagtg  13380
gcgataagtc gtgtcttacc gggttggact caagacgata gttaccggat aaggcgcagc  13440
ggtcgggctg aacggggggt tcgtgcacac agcccagctt ggagcgaacg acctacaccg  13500
aactgagata cctacagcgt gagcattgag aaagcgccac gcttcccgaa gggagaaagg  13560
cggacaggta tccggtaagc ggcagggtcg gaacaggaga gcgcacgagg gagcttccag  13620
ggggaaacgc ctggtatctt tatagtcctg tcgggtttcg ccacctctga cttgagcgtc  13680
gatttttgtg atgctcgtca ggggggcgga gcctatggaa aaacgccagc aacgcgagct  13740
cgtatggaca tattgtcgtt agaacgcggc tacaattaat acataacctt atgtatcata  13800
cacaatcgat ttaggtgaca ctatag                                       13826
```